(12) United States Patent
Dimasi et al.

(10) Patent No.: US 9,580,509 B2
(45) Date of Patent: Feb. 28, 2017

(54) MULTISPECIFIC AND MULTIVALENT BINDING PROTEINS AND USES THEREOF

(71) Applicant: MedImmune, LLC, Gaithersburg, MD (US)

(72) Inventors: Nazzareno Dimasi, Gaithersburg, MD (US); Ryan Fleming, Gaithersburg, MD (US); Binyam Bezabeh, Gaithersburg, MD (US); Changshou Gao, Gaithersburg, MD (US); Antonio Digiandomenico, Gaithersburg, MD (US); Paul Warrener, Gaithersburg, MD (US); Charles Stover, Gaithersburg, MD (US); Bret Sellman, Gaithersburg, MD (US); Mladen Tomich, Gaithersburg, MD (US); Reena Varkey, Gaithersburg, MD (US); Partha S. Chowdhury, Gaithersburg, MD (US); Ralph Minter, Cambridge (GB); Sandrine Guillard, Cambridge (GB); Steven Rust, Cambridge (GB); Vignesh Venkatraman, Cambridge (GB)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 14/356,434

(22) PCT Filed: Nov. 6, 2012

(86) PCT No.: PCT/US2012/063639
§ 371 (c)(1),
(2) Date: May 6, 2014

(87) PCT Pub. No.: WO2013/070565
PCT Pub. Date: May 16, 2013

(65) Prior Publication Data
US 2014/0302038 A1  Oct. 9, 2014

Related U.S. Application Data

(60) Provisional application No. 61/697,585, filed on Sep. 6, 2012, provisional application No. 61/625,299, filed on Apr. 17, 2012, provisional application No. 61/624,651, filed on Apr. 16, 2012, provisional application No. 61/556,645, filed on Nov. 7, 2011.

(51) Int. Cl.
| | |
|---|---|
| *C07K 16/00* | (2006.01) |
| *C07K 16/12* | (2006.01) |
| *C07K 16/22* | (2006.01) |
| *C07K 16/28* | (2006.01) |
| *C07K 16/46* | (2006.01) |

(52) U.S. Cl.
CPC .......... *C07K 16/2863* (2013.01); *C07K 16/00* (2013.01); *C07K 16/1214* (2013.01); *C07K 16/22* (2013.01); *C07K 16/468* (2013.01); *C07K 2316/52* (2013.01); *C07K 2317/31* (2013.01); *C07K 2317/35* (2013.01); *C07K 2317/524* (2013.01); *C07K 2317/526* (2013.01); *C07K 2317/55* (2013.01); *C07K 2317/56* (2013.01); *C07K 2317/64* (2013.01); *C07K 2317/66* (2013.01); *C07K 2317/73* (2013.01); *C07K 2317/76* (2013.01); *C07K 2317/94* (2013.01)

(58) Field of Classification Search
CPC .... C07K 16/00; C07K 16/1214; C07K 16/22; C07K 16/2863; C07K 16/68; C07K 2317/31; C07K 2317/35; C07K 2317/55; C07K 2317/622; C07K 2317/524; C07K 2317/526; C07K 2317/56; C07K 2317/73; C07K 2317/76; C07K 2317/94; C07K 2317/66; C07K 2316/52; C07K 16/468; C07K 2317/53; C07K 2317/64; C07K 2317/522; C07K 2317/41; A61K 2039/505

See application file for complete search history.

(56) References Cited

U.S. PATENT DOCUMENTS

| | | | |
|---|---|---|---|
| 5,624,821 | A | 4/1997 | Winter et al. |
| 5,714,350 | A | 2/1998 | Co et al. |
| 6,277,375 | B1 | 8/2001 | Ward |
| 6,350,861 | B1 | 2/2002 | Co et al. |
| 6,602,684 | B1 | 8/2003 | Umana et al. |
| 6,737,056 | B1 | 5/2004 | Presta |
| 6,946,292 | B2 | 9/2005 | Kanda et al. |
| 7,064,191 | B2 | 6/2006 | Shinkawa et al. |
| 7,083,784 | B2 | 8/2006 | Dall'Acqua et al. |

(Continued)

FOREIGN PATENT DOCUMENTS

| | | |
|---|---|---|
| WO | WO94/29351 | 12/1994 |
| WO | WO01/77342 | * 10/2001 |

(Continued)

OTHER PUBLICATIONS

Stancovski et al., Proceedings of the National Academy of Science USA 88: 8691-8695, 1991.*

(Continued)

*Primary Examiner* — Phuong Huynh

(57) ABSTRACT

The disclosure generally provides proteins that bind two epitopes (e.g., a first and a second epitope) and that are bivalent for binding to each of the first and second epitopes. The disclosure also provides compositions comprising such proteins, nucleic acid molecules encoding such proteins and methods of making and using such proteins.

18 Claims, 60 Drawing Sheets

(56) References Cited

U.S. PATENT DOCUMENTS

| | | |
|---|---|---|
| 7,183,076 B2 | 2/2007 | Arathoon et al. |
| 7,214,775 B2 | 5/2007 | Hanai et al. |
| 7,217,797 B2 | 5/2007 | Hinton et al. |
| 7,276,585 B2 | 10/2007 | Lazar et al. |
| 7,317,091 B2 | 1/2008 | Lazar et al. |
| 7,355,008 B2 | 4/2008 | Stavenhagen et al. |
| 7,393,683 B2 | 7/2008 | Kanda et al. |
| 7,425,446 B2 | 9/2008 | Kanda et al. |
| 7,504,256 B1 | 3/2009 | Ogawa et al. |
| 7,670,600 B2 | 3/2010 | Dall'Acqua et al. |
| 7,855,275 B2 | 12/2010 | Eigenbrot et al. |
| 8,088,376 B2 | 1/2012 | Chamberlain et al. |
| 2002/0147311 A1 | 10/2002 | Giles et al. |
| 2003/0003097 A1 | 1/2003 | Reff et al. |
| 2003/0157108 A1 | 8/2003 | Presta |
| 2004/0002587 A1 | 1/2004 | Watkins et al. |
| 2005/0215768 A1 | 9/2005 | Armour et al. |
| 2005/0226867 A1 | 10/2005 | Iida et al. |
| 2006/0024298 A1 | 2/2006 | Lazar et al. |
| 2006/0173170 A1 | 8/2006 | Chamberlain et al. |
| 2007/0135620 A1 | 6/2007 | Chamberlain et al. |
| 2007/0224188 A1 | 9/2007 | Allan et al. |
| 2008/0089892 A1 | 4/2008 | Allan et al. |
| 2009/0004179 A1 | 1/2009 | Ravetch et al. |
| 2009/0010921 A1 | 1/2009 | Umana et al. |
| 2009/0155275 A1* | 6/2009 | Wu ................. C07K 16/468 424/136.1 |
| 2011/0033378 A1 | 2/2011 | Dimasi et al. |

FOREIGN PATENT DOCUMENTS

| | | |
|---|---|---|
| WO | WO2007/005786 A2 | 1/2007 |
| WO | WO2009/018386 A1 | 2/2009 |
| WO | WO2009/058379 A2 | 5/2009 |
| WO | WO2009/058492 A2 | 5/2009 |
| WO | WO2011/005481 A1 | 1/2011 |
| WO | WO2011/130324 A1 | 10/2011 |

OTHER PUBLICATIONS

Yu et al., Investigative Ophthalmology & Visual Science 49(2): 522-527, Feb. 2008.*

Jubala et al., Vet Pathol 42: 468-476, 2005.*

Rudikoff et al., Proc. Natl. Acad. Sci. USA 1982 vol. 79 p. 1979.*

Brinkmann, U., et al., "A recombinant immunotoxin containing a disulfide-stabilized Fv fragment," Proceedings of the National Academy of Sciences, vol. 90, No. 16, pp. 7538-7542 (Aug. 15, 1993).

Choi, K.H., et al., "A Tn7-based broad-range bacterial cloning and expression system," Nature Methods, vol. 2, Issue 6, pp. 443-448 (Jun. 2005).

Ferrara, C., et al., "Modulation of therapeutic antibody effector functions by glycosylation engineering: Influence of Golgi enzyme localization domain and co-expression of heterologous β1, 4-N-acetylglucosaminyltransferase III and Golgi α-mannosidase II," Biotechnology and Bioengineering, vol. 93, Issue 5, pp. 851-861 (Apr. 5, 2006).

Cox, K. M., et al., "Glycan optimization of a human monoclonal antibody in the aquatic plant Lemna minor," Nature Biotechnology, vol. 24, Issue 12, pp. 1591-1597 (Dec. 2006).

Davies, J., et al., "Expression of GnTIII in a recombinant anti-CD20 CHO production cell line: Expression of antibodies with altered glycoforms leads to an increase in ADCC through higher affinity for FCγRIII," Biotechnology and Bioengineering, vol. 74, Issue 4, pp. 288-294 (Aug. 20, 2001).

Digiandomenico, A., et al., "Oral Vaccination of BALB/c Mice with Salmonella enterica Serovar Typhimurium Expressing Pseudomonas aeruginosa O Antigen Promotes Increased Survival in an Acute Fatal Pneumonia Model," Infection and Immunity, vol. 72, Issue 12, pp. 7012-7021 (Dec. 2004).

Dimasi, N., et al., "The design and characterization of oligospecific antibodies for simultaneous targeting of multiple disease mediators," The Journal of Molecular Biology, vol. 393, Issue 3, pp. 672-692 (Oct. 2009).

Glockshuber, R., et al., "A Comparison of Strategies to Stabilize Immunoglobulin Fv-Fragments," Biochemistry, vol. 29, No. 6, pp. 1362-1367 (1990).

Kaneko, Y., et al., "Anti-Inflammatory Activity of Immunoglobulin G Resulting from Fc Sialylation," Science, vol. 313, Issue 5787, pp. 670-673 (Aug. 2006).

Luo, D., et al., "Vi-Linker-Vh Orientation-Dependent Expression of Single Chain Fv Containing an Engineered Disulfide-Stabilized Bond in the Framework Regions," The Journal of Biochemistry, vol. 118, Issue 4, pp. 825-831 (1995).

Merchant, A. M., et al., "An efficient route to human bispecific IgG," Nature Biotechnology, vol. 16, Issue 7, pp. 677-681 (Jul. 1998).

Mori, K., et al., "Engineering Chinese hamster ovary cells to maximize effector function of produced antibodies using FUT8 siRNA," Biotechnology and Bioengineering, vol. 88, Issue 7, pp. 901-908 (Dec. 30, 2004).

Reiter, Y., et al., "Engineering antibody Fv fragments for cancer detection and therapy: disulfide-stabilized Fv fragments," Nature Biotechnology, vol. 14, Issue 10, pp. 1239-1245 (Oct. 1996).

Reiter, Y., et al., "Stabilization of the Fv fragments in recombinant immunotoxins by disulfide bonds engineered into conserved framework regions," Biochemistry, vol. 33, Issue 18, pp. 5451-5459 (May 1994).

Scallon, B. J., et al., "Higher levels of sialylated Fc glycans in immunoglobulin G molecules can adversely impact functionality," Molecular Immunology, vol. 44, Issue 7, pp. 1524-1534 (Mar. 2007).

Shields, R. L., et al., "Lack of fucose on human IgG1 N-linked oligosaccharide improves binding to human Fcgamma RIII and antibody-dependent cellular toxicity," The Journal of Biological Chemistry, vol. 277, Issue 30, pp. 26733-26740 (2002).

Shinkawa, T., et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," The Journal of Biological Chemistry, vol. 278, Issue 5, pp. 3466-3473 (2003).

Umana, P., et al., "Engineered glycoforms of an antineuroblastoma IgG1 with optimized antibody-dependent cellular cytotoxic activity," Nature Biotechnology, vol. 17, Issue 2, pp. 176-180 (Feb. 1999).

Young, N. M., et al., "Thermal stabilization of a single-chain Fv antibody fragment by introduction of a disulphide bond," FEBS Letters, vol. 377, Issue 2, pp. 135-139 (Dec. 18, 1995).

Zhu, Z., et al., "Remodeling domain interfaces to enhance heterodimer formation," Protein Science, vol. 6, Issue 4, pp. 781-788 (Apr. 1997).

* cited by examiner

HEAVY CHAIN CONFIGURATION

>DNA: encoding desired VH region          >Protein: desired VH region
>DNA: CH1 constant domain
GCGTCGACCAAGGGCCCATCCGTCTTCCCCCTGGCACCCTCCTCCAAGAGCACCTCTGGGGGCACAGCGGCCCTGGGCTGCCTGGTCAAGGA
CTACTTCCCCGAACCGGTGACGGTGTCCTGGAACTCAGGCGCTCTGACCAGCGGCGTGCACACCTTCCCGGCTGTCCTACAGTCCTCAGGAC
TCTACTCCCTCAGCAGCGTGGTGACCGTGCCCTCCAGCAGCTTGGGCACCCAGACCTACATCTGCAACGTGAATCACAAGCCCAGCAACACC
AAGGTGGACAAGAGAGTT (SEQ ID NO:1)
>Protein: CH1 constant domain
ASTKGPSVFPLAPSSKSTSGGTAALGCLVKDYFPEPVTVSWNSGALTSGVHTFPAVLQSSGLYSLSSVVTVPSSSLGTQTYICNVNHKPSNT
KVDKRV (SEQ ID NO:2)
>DNA: human IgG1 full hinge
GAGCCCAAATCTTGTGACAAAACTCACACATGCCCACCGTGCCCA (SEQ ID NO: 9)
>Protein: human IgG1 full hinge (position 228 as numbered by the EU index is underlined)
EPKSCDKTHTCPP̲CP (SEQ ID NO: 10)

>DNA: human IgG1 upper hinge                    >Protein: human IgG1 upper hinge
GAGCCCAAATCTTGTGACAAAACT (SEQ ID NO:3)        EPKSC̲DKT    (SEQ ID NO:4)
OR
>DNA: modified human IgG1 upper hinge            >Protein: modified human IgG1 upper hinge
GAGCCCAAATCTTGTGGAAAAACT (SEQ ID NO:5)         EPKSCG̲KT (SEQ ID NO:6)
OR
>DNA: short human IgG1 upper hinge               >Protein: short human IgG1 upper hinge
GAGCCCAAATCTTGT (SEQ ID NO:37)                EPKSC (SEQ ID NO:38)

>DNA sequence: linker connecting upper hinge to the N-terminus of scFv
GGCGGAGGGGGATCCGGCGGAGGGGGCTCT (SEQ ID NO:7)
>Protein: linker connecting the upper hinge to the N-terminus of scFv
GGGGSGGGGS (SEQ ID NO:8)

Fig. 2A

>DNA: encoding desired scFv (VH-linker-VL or VL-linker-VH; may include stabilizing disulfide bonds)
>Protein: desired scFv (VH-linker-VL or VL-linker-VH; may include stabilizing disulfide bonds)
>DNA: linker connecting the C-terminus of scFv to the N-terminus of hinge
GGTGGCGGTGGCTCTGGTGGCGGTGGCTCT (SEQ ID NO:7)
>Protein sequence: linker connecting the C-terminus of scFv to the N-terminus of hinge
GGGGSGGGGS (SEQ ID NO:8)

>DNA: hinge variant of human IgG1
GAGCCCAAATCTGTAGACAAAACTCACACATGCCCACCGTGCCCA
(SEQ ID NO:11)
OR
>DNA: lower hinge of human IgG1
TGCCCACCGTGCCCA (SEQ ID NO:13)
OR
>DNA: hinge variant of human IgG1
GACAAAACTCACACATGCCCACCGTGCCCA (SEQ ID NO:39)

>Protein: hinge variant of human IgG1
EPKSVDKTHTCPPCP (SEQ ID NO:12)

>Protein: lower hinge of human IgG1
CPPCP (SEQ ID NO:14)

>Protein: hinge variant of human IgG1
DKTHTCPPCP (SEQ ID NO:40)

Fig. 2B

>DNA: Fc constant domain CH2
GCACCTGAACTCCTGGGGGGACCGTCAGTCTTCCTCTTCCCCCCAAAACCCAAGGACACCCTCATGATCTCCCGGACCCCTG
AGGTCACATGCGTGGTGGTGGACGTGAGCCACGAAGACCCTGAGGTCAAGTTCAACTGGTACGTGGACGGCGTGGAGGTGCA
TAATGCCAAGACAAAGCCGCGGGAGGAGCAGTACAACAGCACGTACCGTGTGGTCAGCGTCCTCACCGTCCTGCACCAGGAC
TGGCTGAATGGCAAGGAGTACAAGTGCAAGGTCTCCAACAAAGCCCTCCCAGCCCCCATCGAGAAAACCATCTCCAAAGCCA
AA (SEQ ID NO:15)

>Protein: Fc constant domain CH2 (positions 234, 235 and 331 are underlined; 239, 330 and 332 are bolded and double underlined; 252, 254 and 256 are enlarged and wavy underlined, all positions numbered as per EU index)
APELLGGPSVFLFPPKPKDTLM̲I̲S̲R̲T̲PEVTCVVVDVSHEDPEVKFNWYVDGVEVHNAKTKPREEQYNSTYRVVSVLTVLHQ
DWLNGKEYKCKVSNKALPAPIEKTISKAK (SEQ ID NO:16)

>DNA: Fc constant domain CH3
GGGCAGCCCCGAGAACCACAGGTCTACACCCTGCCCCCATCCCGGGAGGAGATGACCAAGAACCAGGTCAGCCTGACCTGCC
TGGTCAAAGGCTTCTATCCCAGCGACATCGCCGTGGAGTGGGAGAGCAATGGGCAGCCGGAGAACAACTACAAGACCACGCC
TCCCGTGCTGGACTCCGACGGCTCCTTCTTCCTCTATAGCAAGCTCACCGTGGACAAGAGCAGGTGGCAGCAGGGGAACGTC
TTCTCATGCTCCGTGATGCATGAGGCTCTGCACAACCACTACACGCAGAAGAGCTTAAGCCTGTCTCCGGGTAAA (SEQ ID NO:17)

>Protein: Fc constant domain CH3 (positions 428 and 434 are bolded and underlined, all positions numbered as per EU index)
GQPREPQVYTLPPSREEMTKNQVSLTCLVKGFYPSDIAVEWESNGQPENNYKTTPPVLDSDGSFFLYSKLTVDKSRWQQGNV
FSCSVMHEALHNHYTQKSLSLSPGK (SEQ ID NO:18)

Fig. 2C

```
                                    cleavage can occur at this D
                                              ↓
                            C_H1                      BD
>upper-sequence-IgG-wt      KVDKRVE PKSCDKTHTC--------- XXXXX
>upper-sequence-variant     KVDKRVE PKSCGKT---GGGGSGGGGS XXXXX
>upper-sequence-variant     KVDKRVE PKSC------GGGGSGGGGS XXXXX
                                       ↑
                         This cysteine makes the interchain disulphide
                            bridge with the light chain cysteine
```

---

```
                                              cleavage can occur at this D
                                                         ↓
                              BD                                C_H2
>lower-sequence-IgG-wt       XXXXX----------EPKSCDKTHTCPPCP APELLG
>lower-sequence-variant      XXXXX-GGGGSGGGGSEPKSVDKTHTCPPCP APELLG
>lower-sequence-variant      XXXXXSGGGGSGGGGS---------CPPCP APELLG
>lower-sequence-variant      XXXXX-GGGGSGGGGS-----DKTHTCPPCP APELLG
                               ↑
              The serine insertion can be made in order to introduce a
              Xho I restriction site for directional cloning of any scFv
```

Fig. 2D

>Protein: *chimeric heavy chain having human IgG1 upper hinge and hinge variant of human IgG1 flanking the scFv (VH-linker-VL configuration)*

VARIABLE HEAVY DOMAIN I - ASTKGPSVFPLAPSSKSTSGGTAALGCLVKDYFPEPVTVSWNSGALTSGVHTFPAVLQSSGLY SLSSVVTVPSSSLGTQTYICNVNHKPSNTKVDKRV*EPKSCDKT*GGGGSGGGGS - scFv VH domain II - GGGGSGGGGSGGG GSGGGGS - scFv VL domain II - *GGGGSGGGGSEPKSVDKTHTCPPC*PAPELLGGPSVFLFPPKPKDTLMISRTPEVTCVVV DVSHEDPEVKFNWYVDGVEVHNAKTKPREEQYNSTYRVVSVLTVLHQDWLNGKEYKCKVSNKALPAPIEKTISKAKGQPREPQVYTLPP SREEMTKNQVSLTCLVKGFYPSDIAVEWESNGQPENNYKTTPPVLDSDGSFFLYSKLTVDKSRWQQGNVFSCSVMHEALHNHYTQKSLS LSPGK (SEQ ID NOS: 2, 4, 8, 10, 12, 16, 18 assembled)

>Protein: *chimeric heavy chain having modified human IgG1 upper hinge and lower hinge of human IgG1 flanking the scFv (VH-linker-VL configuration)*

VARIABLE HEAVY DOMAIN I - ASTKGPSVFPLAPSSKSTSGGTAALGCLVKDYFPEPVTVSWNSGALTSGVHTFPAVLQSSGLY SLSSVVTVPSSSLGTQTYICNVNHKPSNTKVDKRV*EPKSCGKT*GGGGSGGGGS - scFv VH domain II - GGGGSGGGGSGGG GSGGGGS - scFv VL domain II - *GGGGSGGGGSCPPC*PAPELLGGPSVFLFPPKPKDTLMISRTPEVTCVVV DVSHEDPEVKFNWYVDGVEVHNAKTKPREEQYNSTYRVVSVLTVLHQDWLNGKEYKCKVSNKALPAPIEKTISKAKGQPREPQVYTLPP SREEMTKNQVSLTCLVKGFYPSDIAVEWESNGQPENNYKTTPPVLDSDGSFFLYSKLTVDKSRWQQGNVFSCSVMHEALHNHYTQKSLS LSPGK (SEQ ID NOS: 2, 6, 8, 10, 14, 16, 18 assembled)

Linker/hinge regions are underlined and italics
Hinge regions are also bolded

Fig. 3

>DNA sequence: human IgG1 upper hinge
GAGCCCAAATCTTGTGACAAAACT (SEQ ID NO:3)

>Protein sequence: human IgG1 upper hinge
EPKSCDKT (SEQ ID NO:4)

>*DNA: modified human IgG1 upper hinge*
*GAGCCCAAATCTTGTGGAAAAACT* (SEQ ID NO:5)

>*Protein: modified human IgG1 upper hinge*
*EPKSCGKT* (SEQ ID NO:6)

>*DNA: short human IgG1 upper hinge*
GAGCCCAAATCTTGT (SEQ ID NO:37)

>*Protein: short human IgG1 upper hinge*
EPKSC (SEQ ID NO:38)

>DNA: poly-glycine-serine linker and human IgG1 hinge domain variant
GGTGGCGGTGGCTCTGGTGGCGGTGGCTCTGAGCCCAAATCT_GTA_GACAAAACTCACACATGCCCACCGTGCCCA
(SEQ ID NOS: 65)

>Protein: poly-glycine-serine linker and human IgG1 hinge domain variant
GGGGSGGGGSEPKSVDKTHTCPPCP (SEQ ID NOS:66)

>*DNA: poly-glycine-serine linker and human IgG1 lower hinge domain*
GGACGCGGAGGATCTGGCGGAGGCGGATCTTGCCCACCGTGCCCA (SEQ ID NOS:67)

>*Protein: poly-glycine-serine linker and human IgG1 lower hinge domain*
GGGGSGGGGSCPPCP (SEQ ID NOS:68)

\>DNA: poly-glycine-serine linker and hinge variant of human IgG1
GGTGGCGGTGGCTCTGGTGGCGGTGGCTCTGACAAAACTCACACATGCCCACCGTGCCCA
(SEQ ID NOS:69)

\>Protein: poly-glycine-serine linker hinge variant of human IgG1
GGGGSGGGGSDKTHTCPPCP (SEQ ID NOS:70)

>DNA sequence: light chain variable domain 1 (Fab) and constant kappa domain (anti-EGFR light chain derived from Panitumumab)
GACATCCAGATGACCCAGAGCCCCAGCAGCCTGAGCGCCAGCGTGGGCGACAGAGTGACCATCACCTGCCAGGCCAGCCAGGACATCAG
CAACTACCTGAACTGGTATCAGCAGAAGCCCGGCAAGGCCCCCAAGCTGCTGATCTACGACGCCAGCAACCTGGAGACAGGCGTGCCCA
GCAGATTCAGCGGCAGCGGCTCCGGCACCGACTTCACCTTCACCATCAGCAGCCTCCAGCCCGAGGATATCGCCACCTACTTTTGCCAG
CACTTCGACCACCTGCCCCTGGCCTTTGGCGGCGGAACAAAGGTGGAGATCAAGCGTACGGTGGCTGCACCATCTGTCTTCATCTTCCC
GCCATCTGATGAGCAGTTGAAATCTGGAACTGCCTCTGTTGTGTGCCTGCTGAATAACTTCTATCCCAGAGAGGCCAAAGTACAGTGGA
AGGTGGATAACGCCCTCCAATCGGGTAACTCCCAGGAGAGTGTCACAGAGCAGGACAGCAAGGACAGCACCTACAGCCTCAGCAGCACC
CTGACGCTGAGCAAAGCAGACTACGAGAAACACAAAGTCTACGCCTGCGAAGTCACCCATCAGGGCCTGAGCTCGCCCGTCACAAAGAG
CTTCAACAGGGGAGAGTGTTAGTGA (SEQ ID NO:19)
>Protein sequence: light chain variable domain 1 (Fab) and constant kappa domain (anti-EGFR light chain derived from Panitumumab)
DIQMTQSPSSLSASVGDRVTITCQASQDISNYLNWYQQKPGKAPKLLIYDASNLETGVPSRFSGSGSGTDFTFTISSLQPEDIATYFCQ
HFDHLPLAFGGGTKVEIKRTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC (SEQ ID NO:20)
>Protein sequence: light chain variable domain 1 (VL) (anti-EGFR light chain derived from Panitumumab)
DIQMTQSPSSLSASVGDRVTITCQASQDISNYLNWYQQKPGKAPKLLIYDASNLETGVPSRFSGSGSGTDFTFTISSLQPEDIATYFCQ
HFDHLPLAFGGGTKVEIK (SEQ ID NO:21)

Fig. 6A

>DNA sequence: VH-CH1 domain of the Fab forming binding unit 1 (anti-EGFR, derived from Panitumumab), connecting linkers as shown in Figure 4 and Figure 5, scFv of binding unit 2 (anti-IGF1R, derived from Dalotuzumab) and Fc (VH and C$_H$1 portions are underlined)

<u>CAGGTGCAGCTCCAGGAGAGCGGCCCTGGCCTGGTGAAGCCCAGCGAGACACTGAGCCTCACCTGCACCGTGTCCGGCGGCAGCCTGTC</u>
<u>CAGCGGCGACTACTACTGGACCTGGATCAGACAGAGCCCCGGCAAGGGCCTGGAGTGGATCGGCCACATCTACTACAGCGGCAACACCA</u>
<u>ACTACAACCCCAGCCTGAAGTCCAGACTGACCATCAGCATCGACACCAGCAAGACCCAGTTCAGCCTGAAGCTGTCCAGCGTGACAGCC</u>
<u>GCCGACACCGCCATCTACTACTGCGTGAGAGACAGAGTGACCGGCGCTTTCGACATCTGGGGCCAGGGCACCATGGTCACCGTGTCCAG</u>
CGCGTCGACCAAGGGACCTAGCGTGTTCCCTCTGGCCCCCAGCAGCAAGTCTACATCTGCCGGAACAGCCGCCCTGGCCTGCCTCGTGA
AGGACTACTTTCCCGAGCCCGTGACCGTGTCCTGGAACAGCGGAGCACTGACAAGCGGCCTGCACACCTTTCCAGCCGTGCTGCAGAGC
AGCGGCCTGTACTCTCTGAGCAGCGTCGTGACAGTGCCCAGCAGCTCTCTGGGCACCCAGACCTACATCTGCAACGTGAACCACAAGCC
CAGCAACACCAAGGTGGACAAGCGGGTGGAACCCAAGAGCTGCGGCAAAACAGCGGCGGAGGATCCGGCGGAGGCGGCTCTGATATCG
TGATGACCCAGAGCCCCCTGAGCCTGCCTGTGACACCTGGCGAACCTGCCAGCATCAGCTGCAGATCCAGCCAGAGCATCGTGCACAGC
AACGCCAACACCTACCTGCAGTGGTATCTGCAGAAGCCCGGCCAGAGCCCTCAGCTGCTCATCTACAAGGTGTCCAACCGGCTGTACGG
CGTGCCCGACAGATTTTCTGGCAGCGGCTCCGGCACCGACTTCACCCTGAAGATCTCCCGGGTGGAAGCCGAGGACGTGGGCGTCTACT
ACTGTTTTCAAGGCAGCCACGTGCCCTGGACCTTCGGCTGTGGCACAAAGGTGGAAATCAAGGGCGGAGGGGGATCTGGGGGCGGAGGC
TCTGGCGGGGGAGGAAGTGGGGGAGGCGGATCTCAGCTGCAGCTGCAGGAATCTGGCCCTGGCCTCGTGAAACCCAGCGAGACACTGAG
CCTGACATGCACCGTGTCCGGCTACAGCATCACCGGCGGCTACCTGTGGAACTGGATCAGACAGCCCCCTGGCAAGTGCCTGGAATGGA
TCGGCTACATCAGCTACGACGGCACCAACAACTACAAGCCCTCCCTGAAGGACAGAGTGACCATCAGCCGGGACACCAGCAAGAACCAG
TTCAGCCTGAAGCTGTCCAGCGTGACAGCCGCCGATACCGCCGTGTACTATTGCGCCAGATACGGCCGGGTGTTCTTCGACTATTGGGG
CCAGGGCACCCTCGTGACTGTGTCATCTGGGGGAGGCGGAAGCGGAGGCGGAGGAAGTTGTCCTCCTTGTCCTGCCCCCGAACTGCTGG
GCGGACCTTCCGTGTTCCTGTTCCCCCCAAAGCCCAAGGACACCCTGATGATCAGCCGGACCCCCGAAGTGACCTGCGTGGTGGTGGAT
GTGTCCCACGAGGACCCTGAAGTGAAGTTCAATTGGTACGTGGACGGCGTGGAAGTGCACAACGCCAAGACCAAGCCTAGAGAGCAACA
GTACAACAGCACCTACCGGGTGGTGTCCGTGCTGACAGTGCTGCACCAGGACTGGCTGAACGGCAAAGAGTACAAGTGCAAAGTCTCCA
ACAAGGCCCTGCCTGCCCCCATCGAGAAAACCATCAGCAAGGCCAAGGGACAGCCCCGCGAGCCCCAAGTGTATACCCTGCCCCCTAGC
CGGGAAGAGATGACCAAGAATCAGGTGTCCCTGACCTGTCTCGTGAAAGGCTTCTACCCCAGCGACATTGCCGTGGAATGGGAGAGCAA
CGGCCAGCCCGAGAACAATTACAAGACCACCCCCCCTGTGCTGGACTCCGACGGCTCATTCTTCCTGTACTCCAAGCTGACCGTCGACA
AGAGCCGGTGGCAGCAGGGCAACGTGTTCAGCTGCTCCGTGATGCACGAGGCCCTGCACAACCACTACACCCAGAAGTCCCTGTCCCTG
AGCCCCGGCAAA (SEQ ID NO:22)

Fig. 6B

>Protein sequence: VH-CH1 domain of the Fab forming binding unit 1 (anti-EGFR, derived from Panitumumab), connecting linkers as shown in Figure 4 and Figure 5, scFv of binding unit 2 (anti-IGF1R, derived from Dalotuzumab) and Fc (VH and C$_H$1 portions are underlined)

<u>QVQLQESGPGLVKPSETLSLTCTVSGGSVSSGDYYWTWIRQSPGKGLEWIGHIYYSGNTNYNPSLKSRLTISIDTSKTQFSLKLSSVIA
ADTAIYYCVRDRVTGAFDIWGQGTMVTVSSASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKRVEPKSCGKT</u>GGGGSGGGGSDIVMTQSPLSLPVTPGEPASISCRSSQSIVHS
NGNTYLQWYLQKPGQSPQLLIYKVSNRLYGVPDRFSGSGSGTDFTLKISRVEAEDVGVYYCFQGSHVPWTFGCGTKVEIKGGGGSGGGG
SGGGGSGGGGSQVQLQESGPGLVKPSETLSLTCTVSGYSITGGYLWNWIRQPPGKCLEWIGYISYDGTNNYKPSLKDRVTISRDTSKNQ
FSLKLSSVTAADTAVYYCARYGRVFFDYWGQGTLVTVSSGGGGSGGGGSCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVDKSRWQQGNVFSCSVMHEALHNHYTQKSLSL
SPGK (SEQ ID NO:23)

>Protein sequence: VH domain of the Fab forming binding unit 1 (anti-EGFR, derived from Panitumumab QVQLQESGPGLVKPSETLSLTCTVSGGSVSSGDYYWTWIRQSPGKGLEWIGHIYYSGNTNYNPSLKSRLTISIDTSKTQFSLKLSSVIA
ADTAIYYCVRDRVTGAFDIWGQGTMVTVSS (SEQ ID NO:24)

>Protein sequence: scFv of binding unit 2 (anti-IGF1R, derived from Dalotuzumab)

DIVMTQSPLSLPVTPGEPASISCRSSQSIVHSNGNTYLQWYLQKPGQSPQLLIYKVSNRLYGVPDRFSGSGSGTDFTLKISRVEAEDVG
VYYCFQGSHVPWTFGCGTKVEIKGGGGSGGGGSGGGGSGGGGSQVQLQESGPGLVKPSETLSLTCTVSGYSITGGYLWNWIRQPPGKCL
EWIGYISYDGTNNYKPSLKDRVTISRDTSKNQFSLKLSSVTAADTAVYYCARYGRVFFDYWGQGTLVTVSS (SEQ ID NO:25)

>Protein sequence: VL domain of binding unit 2 (anti-IGF1R, derived from Dalotuzumab)

DIVMTQSPLSLPVTPGEPASISCRSSQSIVHSNGNTYLQWYLQKPGQSPQLLIYKVSNRLYGVPDRFSGSGSGTDFTLKISRVEAEDVGVYYCFQ
GSHVPWTFGCGTKVEIK (SEQ ID NO:26)

>Protein sequence: VH domain of binding unit 2 (anti-IGF1R, derived from Dalotuzumab)

QVQLQESGPGLVKPSETLSLTCTVSGYSITGGYLWNWIRQPPGKCLEWIGYISYDGTNNYKPSLKDRVTISRDTSKNQFSLKLSSVTAA
DTAVYYCARYGRVFFDYWGQGTLVTVSS (SEQ ID NO:27)

Fig. 6C

>DNA sequence: light chain variable domain 1 (Fab) and constant kappa domain (anti-VEGF) light chain derived from bevacizumab/Avastin)
GACATCCAGATGACCCAGAGCCCCAGCAGCCTGAGCGCCAGCGTGGGCGACAGAGTGACCATCACCTGTAGCGCCAGCCAGGACATCAG
CAACTACCTGAACTGGTATCAGCAGAAGCCCGGCAAGGCCCCCAAGGTGCTGATCTACTTCACCAGCTCCCTGCACAGCGGCGTGCCCA
GCAGATTTTCTGGCAGCGGCAGCGGCACCGACTTCACCCTGACCATCAGCAGCCTGCAGCCCGAGGACTTCGCCACCTACTACTGCCAG
CAGTACAGCACCGTGCCTTCGACCTTCGGCCAGGGCACCAAGGTGGAAATCAAGCGTACGGTGGCTGCACCATCTGTCTTCATCTTCCC
GCCATCTGATGAGCAGTTGAAATCTGGAACTGCCTCTGTTGTGTGCCTGCTGAATAACTTCTATCCCAGAGAGGCCAAAGTACAGTGGA
AGGTGGATAACGCCCTCCAATCGGGTAACTCCCAGGAGAGTGTCACAGAGCAGGACAGCAAGGACAGCACCTACAGCCTCAGCAGCACC
CTCACGCTGAGCAAAGCAGACTACGAGAAACACAAAGTCTACGCCTGCGAAGTCACCCATCAGGGCCTGAGCTCGCCCGTCACAAAGAG
CTTCAACAGGGGAGAGTGT (SEQ ID NO:28)

>Protein sequence: light chain variable domain 1 (Fab) and constant kappa domain (anti-VEGF light chain derived from bevacizumab/Avastin)
DIQMTQSPSSLSASVGDRVTITCSASQDISNYLNWYQQKPGKAPKVLIYFTSSLHSGVPSRFSGSGSGTDFTLTISSLQPEDFATYYCQ
QYSTVPWTFGQGTKVEIKRTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC (SEQ ID NO:29)

>Protein sequence: light chain variable domain 1 (VL) (anti-VEGF light chain derived from bevacizumab/Avastin)
DIQMTQSPSSLSASVGDRVTITCSASQDISNYLNWYQQKPGKAPKVLIYFTSSLHSGVPSRFSGSGSGTDFTLTISSLQPEDFATYYCQ
QYSTVPWTFGQGTKVEIK (SEQ ID NO:30)

Fig. 7A

>DNA sequence: VH-CH1 domain of the Fab forming binding unit 1 (anti-VEGF, derived from bevacizumab/Avastin), connecting linkers as shown in Figure 4 and Figure 5, scFv of binding unit 2 (anti-Ang2, derived from LC06) and Fc (VH and C$_H$1 portions are underlined)

GAGGTGCAGCTGGTGGAAAGCGGCGGAGGACTGGTGCAGCCTGGCGGCAGCCTGAGACTGTCTTGTGCCGCCAGCGGCTACACCTTCAC
CAACTACGGCATGAACTGGGTGCGCCAGGCCCCTGGCAAGGGACTGGAATGGGTGGGATGGATCAACACCTACACCGGCGAGCCCACCT
ACGCCGCCGACTTCAAGCGCCGGTTCACCTTCAGCCTGGACACCAGCAAGAGCACCGCCTACCTGCAGATGAACAGCCTGCGCGCCGAC
GACACCGCCGTGTACTACTGCGCCAAGTACCCCCACTACTACGGCAGCAGCCACTGGTACTTCGACGTGTGGGGCCAGGGCACCCTGGT
GACAGTGTCCAGCGCGTCGACCAAGGGACCTAGCGTGTTCCCTCTGGCCCCCAGCAGCAAGTCTACATCTGGCGGAACAGCCGCCCTGG
GCTGCCTCGTGAAGGACTACTTTCCCGAGCCCGTGACCGTGTCCTGGAACAGCGGAGCACTGACAAGCGGCGTGCACACCTTTCCAGCC
GTGCTGCAGAGCAGCGGCCTGTACTCTCTGAGCAGCGTCGTGACAGTGCCCAGCAGCTCTCTGGGCACCCAGACCTACATCTGCAACGT
GAACCACAAGCCCAGCAACACCAAGGTGGACAAGCGGGTGGAACCCAAGAGCTGCGGCAAAACAGGCGGCGGAGGATCCGGCGAGGCC
GATCTCAGGTGCAGCTGGTCGAAAGCGGCGCTGAAGTGAAGAAACCTGGGGCCAGCGTGAAGGTGTCCTGCAAGGCCAGCGGCTACACC
TTTACCGGCTACTACATGCACTGGGTGCGCCAGGCCCCTGGCCAGTGTCTGGAATGGATGGGCTGGATCAACCCCAACAGCGGCGGCAC
CAACTACGCCCAGAAATTCCAGGGCAGAGTGACCATGACCCGGGACACCAGCATCAGCACCGCCTACATGGAACTGAGCCGGCTGAGAA
GCGACGACACCGCCGTGTACTACTGCGCCAGAAGCCCCAACCCCTACTACTACGACAGCAGCGGCTATTACTACCCTGGGGCCTTCGAC
ATCTGGGGACAGGGCACAATGGTCACCGTGTCTAGCGGAGGGGGAGGATCTGGGGGCGGAGGCTCTGGCGGGGAGGAAGTGCGGGAGC
CGGAAGCCAGCCTGGACTGACACAGCCTCCAAGCGTGTCAGTGGCCCCTGGACAGACCGCCAGAATCACCTGTGGCGGCAACAACATCG
GCAGCAAGAGCGTCCACTGCTATCAGCAGAAGCCCGGACAGGCCCCAGTGCTGGTGGTGTACGACGACAGCGATAGACCCAGCGGCATC
CCCGAGAGATTCAGCGGCAGCAACTCCGGCAATACCGCCACCCTGACCATCAGCAGAGTGGAAGCCGGCGACGAGGCCGACTACTACTG
CCAAGTGTGGGACAGCAGCAGCGACCACTACGTGTTCGGCTGTGGCACCAAAGTGACCGTGCTCGGAGGCGGGGGATCAGGGCGAGGGC
GGTCTTGTCCTCCTTGTCCTGCTCCCAACTGCTGGGCGACCTTCCGTGTTCCTGTTCCCCCCAAAGCCCAAGGACACCCTCATGATC
AGCCGGACCCCCGAAGTGACCTGCGTGGTGGTGGATGTGTCCCACGAGGACCCAGAAGTGAAGTTCAATTGGTACGTGGACGGCGTGGA
AGTGCACAACGCCAAGACCAAGCCTAGAGAGGAACAGTACAACAGCACCTACCGGGTGGTGTCCGTGCTGACAGTGCTGCACCAGGACT
GGCTGAACGGCAAAGAGTACAAGTGCAAGGTGTCCAACAAAGCCCTGCCTGCCCCCATCGAGAAAACCATCTCCAAGGCCAAGGGCCAG
CCCCGCGAGCCTCAAGTGTATACCCTGCCCCCTAGCCGGGAAGAGATGACCAAGAACCAGGTGTCCCTGACCTGTCTCGTGAAAGGCTT
CTACCCCTCCGATATCGCCGTGGAATGGGAGAGCAACGGCCAGCCCGAGAACAACTACAAGACCACCCCCCTGTGCTGGACAGCGACG
GCTCATTCTTCCTGTACTCCAAGCTGACCGTGGACAAGAGCCGGTGGCAGCAGGGCAACGTGTTCAGCTGCAGCGTGATGCACGAGGCC
CTGCACAACCACTACACACAGAAGTCCCTGAGCCTGAGCCCCGGCAAA (SEQ ID NO:31)

Fig. 7B

>Protein sequence: VH-CH1 domain of the Fab forming binding unit 1 (anti-VEGF, derived from bevacizumab/Avastin), connecting linkers as shown in Figure 4 and Figure 5, scFv of binding unit 2 (anti-Ang2, derived from LC06) and Fc (VH and $C_H1$ portions are underlined)

<u>EVQLVESGGGLVQPGGSLRLSCAASGYTFTNYGMNWVRQAPGKGLEWVGWINTYTGEPTYAADFKRRFTFSLDTSKSTAYLQMNSLRAE
DTAVYYCAKYPHYYGSSHWYFDVWGQGTLVTVSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKRVEPKSC</u>GKTGGGGSGGGGSQVQLVESGAEVKKPGASVKVSCKASGYT
FTGYYMHWVRQAPGQCLEWMGWINPNSGGTNYAQKFQGRVTMTRDTSISTAYMELSRLRSDDTAVYYCARSPNPYYYDSSGYYYPGAFD
IWGQGTMVTVSSGGGGSGGGGSGGGGSGGGGSQPGLIQPPSVSVAPGQTARITCGGNNIGSKSVHWYQQKPGQAPVLVVYDDSDRPSGI
PERFSGSNSGNTATLTISRVEAGDEADYYCQVWDSSSDHYVFGCGTKVTVLGGGGSGGGGSCPPCPAPELLGGPSVFLFPPKPKDTLMI
SRTPEVTCVVVDVSHEDPEVKFNWYVDGVEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVLDSDGSFFLYSKLTVDKSRWQQGNVFSCSVMHEA
LHNHYTQKSLSLSPGK (SEQ ID NO:32)

>Protein sequence: VH domain of the Fab forming binding unit 1 (anti-VEGF, derived from bevacizumab/Avastin)
EVQLVESGGGLVQPGGSLRLSCAASGYTFTNYGMNWVRQAPGKGLEWVGWINTYTGEPTYAADFKRRFTFSLDTSKSTAYLQMNSLRAE
DTAVYYCAKYPHYYGSSHWYFDVWGQGTLVTVSS (SEQ ID NO:33)

>Protein sequence: scFv of binding unit 2 (anti-Ang2, derived from LC06)
QVQLVESGAEVKKPGASVKVSCKASGYTFTGYYMHWVRQAPGQCLEWMGWINPNSGGTNYAQKFQGRVTMTRDTSISTAYMELSRLRSD
DTAVYYCARSPNPYYYDSSGYYYPGAFDIWGQGTMVTVSSGGGGSGGGGSGGGGSGGGGSQPGLIQPPSVSVAPGQTARITCGGNNIGS
KSVHWYQQKPGQAPVLVVYDDSDRPSGIPERFSGSNSGNTATLTISRVEAGDEADYYCQVWDSSSDHYVFGCGTKVTVL (SEQ ID NO:34)

>Protein sequence: VL of binding unit 2 (anti-Ang2, derived from LC06)
QPGLIQPPSVSVAPGQTARITCGGNNIGSKSVHWYQQKPGQAPVLVVYDDSDRPSGIPERFSGSNSGNTATLTISRVEAGDEADYYCQV
WDSSSDHYVFGCGTKVTVL (SEQ ID NO:35)

>Protein sequence: VH of binding unit 2 (anti-Ang2, derived from LC06)
QVQLVESGAEVKKPGASVKVSCKASGYTFTGYYMHWVRQAPGQCLEWMGWINPNSGGTNYAQKFQGRVTMTRDTSISTAYMELSRLRSD
DTAVYYCARSPNPYYYDSSGYYYPGAFDIWGQGTMVTVSS (SEQ ID NO:36)

Fig. 7C

\>DNA sequence: light chain variable domain 1 (Fab) and constant kappa domain (derived from anti-PcrV antibody V2L2)
GCCATCCAGATGACCCACTCTCCATCCTCCCTGTCTGCATCTGTAGGAGACAGAGTCACCATCACTTGCCGGGCAAGTCACGGCATTAG
AAATGATTTAGGCTGGTATCAACAGAAGCCAGGGAAAGCCCCTAAACTCGTGATCTATTCTGCATCCACTTTACAAAGTGGGGTCCCAT
CAAGGTTCAGCGGCAGTGGATCTGGCACAGATTTCACTCTCTCCATCAGCAGCCTGCAGCCTGACGATTTTGCAACTTATTACTGTCTA
CAAGATTACAATTACCCGTGGACGTTCGGCCAAGGGACCAAGGTTGAAATCAAACGTACGGTGGCTGCACCATCTGTCTTCATCTTCCC
GCCATCTGATGAGCAGTTGAAATCTGGAACTGCCTCTGTTGTGTGCCTGCTGAATAACTTCTATCCCAGAGAGGCCAAAGTACAGTGGA
AGGTGGATAACGCCCTCCAATCGGGTAACTCCCAGGAGAGTGTCACAGAGCAGGACAGCAAGGACAGCACCTACAGCCTCAGCAGCACC
CTGACGCTGAGCAAAGCAGACTACGAGAAACACAAAGTCTACGCCTGCGAAGTCACCCATCAGGGCCTGAGCTCGCCCGTCACAAAGAG
CTTCAACAGGGGAGAGTGT (SEQ ID NO:41)
\>Protein sequence: light chain variable domain 1 (Fab) and constant kappa domain (anti-PcrV light chain derived from antibody V2L2)
AIQMTQSPSSLSASVGDRVTITCRASQGIRNDLGWYQQKPGKAPKLVIYSASTLQSGVPSRFSGSGSGTDFTLSISSLQPDDFATYYCL
QDYNYPWTFGQGTKVEIKRTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC (SEQ ID NO:42)
\>Protein sequence: light chain variable domain 1 (VL) anti-PcrV light chain (anti-PcrV light chain derived from antibody V2L2)
AIQMTQSPSSLSASVGDRVTITCRASQGIRNDLGWYQQKPGKAPKLVIYSASTLQSGVPSRFSGSGSGTDFTLSISSLQPDDFATYYCL
QDYNYPWTFGQGTKVEIK (SEQ ID NO:43)

Fig. 8A

>DNA sequence: VH-CH1 domain of the Fab forming binding unit 1 (derived from anti-PcrV antibody V2L2), connecting linkers as shown in Figure 4C and Figure 5C, scFv of binding unit 2 (derived from anti-Psl antibody W4-RAD) and Fc (VH and $C_H1$ portions are underlined)

GAGATGCAGCTGTTGGAGTCTGGGGGAGGCTTGGTACAGCCTGGGGGGTCCCTGAGACTCTCCTGTGCAGCCTCTGGATTCACCTTTAGC
AGCTATGCCATGAACTGGGTCCGCCAGGCTCCACGGGAGGGGCTGGAGTGGGTCTCAGCTATTACTATTAGTGGTATTACCGCATACTAC
ACCGACTCCGTGAAGGGCCGGTTCACCATCTCCAGAGACAATTCCAAGAACACGCTATATCTGCAAATGAACAGCCTGAGGGCCGGGGAC
ACGGCCGTATATTACTGTGCGAAGGAAGAATTTTTACCTGGAACGCACTACTACTACGGTATGGACGTCTGGGGCCAAGGGACCACGGTC
ACCGTCTCCTCAGCgTCgACCAAGGGCCCATCcGTCTTCCCCCTGGCACCCTCCTCCAAGAGCACCTCTGGGGGCACAGCGGCCCTGGGC
TGCCTGGTCAAGGACTACTTCCCCGAACCGGTGACGGTGTCcTGGAACTCAGGCGCtCTGACCAGCGGCGTGCACACCTTCCCGGCTGTC
CTACAGTCCTCAGGACTCTACTCCCTCAGCAGCGTGGTGACCGTGCCCTCCAGCAGCTTGGGCACCCAGACCTACATCTGCAACGTGAAT
CACAAGCCCAGCAACACCAAGGTGGACAAGAGACTTGAGCCCAAATCTTGTGGCGGAGGGGCTCTGGCGGAGGGggatccGAGGTGCAG
CTGTTGGAGTCGGGCCCAGGACTGGTGAAGCCTTCGGAGACCCTGTCCCTCACCTGCAATGTCGCTGGTGGCTCCATCAGTCCTTACTAC
TGGACCTGGATCCGGCAGCCCCCAGGGAAGTGCCTGGAGTTGATTGGTTATATCCACTCCAGTGGGTACACCGACTACAACCCCTCCCTC
AAGAGTCGAGTCACCATATCAGGAGACACGTCCAAGAAGCAGTTCTCCCTGCACGTGAGCTCTGTGACCGCTGCGGACACGGCCGTGTAC
TTCTGTGCGAGAGCCGATTGGGACCTGCTTCATGCTCTTGATATCTGGGGCCAAGGGACCCTGGTCACCGTCTCGAGTGGCGGAGGGGGC
TCTGGGGGAGGGGGCAGCGGCGGCGGAGGATCTCGGGCAGGGGGCAGCGAAATTGTGTTGACACAGTCTCCATCCTCCCTGTCTACATCT
GTAGGAGACAGAGTCACCATCACTTGCCGGGCAAGTCAGAGCATTAGGAGCCATTTAAATTGGTATCAGCAGAAACCAGGGAAAGCCCCT
AAACTCCTGATCTATGGTGCATCCAATTTGCAAAGTGGGGTCCCATCAAGGTTCAGTGGCAGTGGATCTGGGACAGATTTCACTCTCACC
ATTAGTAGTCTGCAACCTGAAGATTTTGCAACTTACTACTGTCAACAGAGTTACAGTTTCCCCCTCACTTTCGGCTGTGGGACCAAGCTG
GAGATCAAAGCGGAGGTGGCTCTGGCGGAGGGggatccGACAAAACTCACACATGCCCACCGTGCCCAGCACCTGAACTCCTGGGGGGA
CCGTCAGTCTTCCTCTTCCCCCCAAAACCCAAGCACACCCTCATGATCTCCCGGACCCCTGAGGTCACATGCGTGGTGGTGCACGTGAGC
CACGAAGACCCTGAGGTCAAGTTCAACTGGTACGTGGACGGCGTGGAGGTGCATAATGCCAAGACAAAGCCGCGGGAGGAGCAGTACAAC
AGCACGTACCGTGTGGTCAGCGTCCTCACCGTCCTGCACCAGGACTGGCTGAATGGCAAGGAGTACAAGTGCAAGGTCTCCAACAAAGCC
CTCCCAGCCCCCATCGAGAAAACCATCTCCAAACCCAAAGGGCAGCCCCGAGAACCACAGGTCTACACCCTGCCCCCATCCCGGGAGGAG
ATGACCAAGAACCAGGTCAGCCTGACCTGCCTGGTCAAAGGCTTCTATCCCAGCGACATCGCCGTGGAGTGGGAGAGCAATGGGCAGCCG
GAGAACAACTACAAGACCACGCCTCCCGTGCTGCACTCCGACGGCTCCTTCTTCCTCTATAGCAAGCTCACCGTGGACAAGAGCAGGTGG
CAGCAGGGGAACGTCTTCTCATGCTCCGTGATGCATGAGGCTCTGCACAACCACTACACGCAGAAGAGCttaagCCTGTCTCCGGGTAAA
(SEQ ID NO: 44)

Fig. 8B

>Protein sequence: VH-CH1 domain of the Fab forming binding unit 1 (derived from anti-PcrV antibody V2L2), connecting linkers as shown in Figure 4C and Figure 5C, scFv of binding unit 2 (derived from anti-Psl antibody W4-RAD) and Fc (VH and $C_H1$ portions are underlined)

<u>EMQLLESGGGLVQPGGSLRLSCAASGFTFSSYAMNWVRQAPGEGLEWVSAITISGITAYYTDSVKGRFTISRDNSKNTLYLQMNSLRAG</u>
<u>DTAVYYCAKEEFLPGTHYYYGMDVWGQGTTVTVSSASTKGPSVFPLAPSSKSTSGGTAALGCLVKDYFPEPVTVSWNSGALTSGVHTFP</u>
<u>AVLQSSGLYSLSSVVTVPSSSLGTQTYICNVNHKPSNTKVDKRVEPKSCGGGGS</u>GGGGSEVQLLESGPGLVKPSETLSLTCNVAGGSIS
PYYWTWIRQPPGKCLELIGYIHSSGYTDYNPSLKSRVTISGDTSKKQFSLHVSSVTAADTAVYFCARADWDLLHALDIWGQGTLVTVSS
GGGGSGGGGSGGGGSGGGGSEIVLTQSPSSLSTSVGDRVTITCRASQSIRSHLNWYQQKPGKAPKLLIYGASNLQSGVPSRFSGSGSGT
DFTLTISSLQPEDFATYYCQQSYSFPLTFGCGTKLEIKGGGGSGGGGSDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDSDGSFFLYSKLTVDKSRWQQGNVFSCSVMHEALHNHYTQK
SLSLSPGK (SEQ ID NO:45)

>Protein sequence: VH domain of the Fab forming binding unit 1 (derived from anti-PcrV antibody V2L2)

EMQLLESGGGLVQPGGSLRLSCAASGFTFSSYAMNWVRQAPGEGLEWVSAITISGITAYYTDSVKGRFTISRDNSKNTLYLQMNSLRAG
DTAVYYCAKEEFLPGTHYYYGMDVWGQGTTVTVSS (SEQ ID NO:46)

>Protein sequence: scFv of binding unit 2 (derived from anti-Psl antibody W4-RAD)

EVQLLESGPGLVKPSETLSLTCNVAGGSISPYYWTWIRQPPGKCLELIGYIHSSGYTDYNPSLKSRVTISGDTSKKQFSLHVSSVTAAD
TAVYFCARADWDLLHALDIWGQGTLVTVSSGGGGSGGGGSGGGGSGGGGSEIVLTQSPSSLSTSVGDRVTITCRASQSIRSHLNWYQQK
PGKAPKLLIYGASNLQSGVPSRFSGSGSGTDFTLTISSLQPEDFATYYCQQSYSFPLTFGCGTKLEIK (SEQ ID NO:47)

>Protein sequence: VL of binding unit 2 (derived from anti-Psl antibody W4-RAD)

EIVLTQSPSSLSTSVGDRVTITCRASQSIRSHLNWYQQKPGKAPKLLIYGASNLQSGVPSRFSGSGSGTDFTLTISSLQPEDFATYYCQ
QSYSFPLTFGCGTKLEIK (SEQ ID NO:48)

>Protein sequence: VH of binding unit 2 (derived from anti-Psl antibody W4-RAD)

EVQLLESGPGLVKPSETLSLTCNVAGGSISPYYWTWIRQPPGKCLELIGYIHSSGYTDYNPSLKSRVTISGDTSKKQFSLHVSSVTAAD
TAVYFCARADWDLLHALDIWGQGTLVTVSS (SEQ ID NO:49)

Fig. 8C

| Test molecule | Transient expression after 10 days using 293 cells (mg/L) |
|---|---|
| biMab-EI(PaniX/Dalo) | 20 |
| biMab-VA(Ava/LC06) | 130 |

Fig. 9

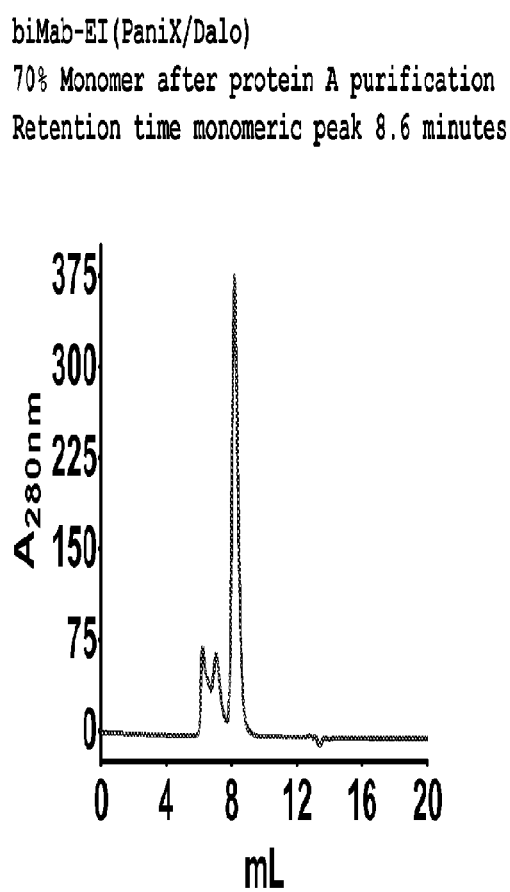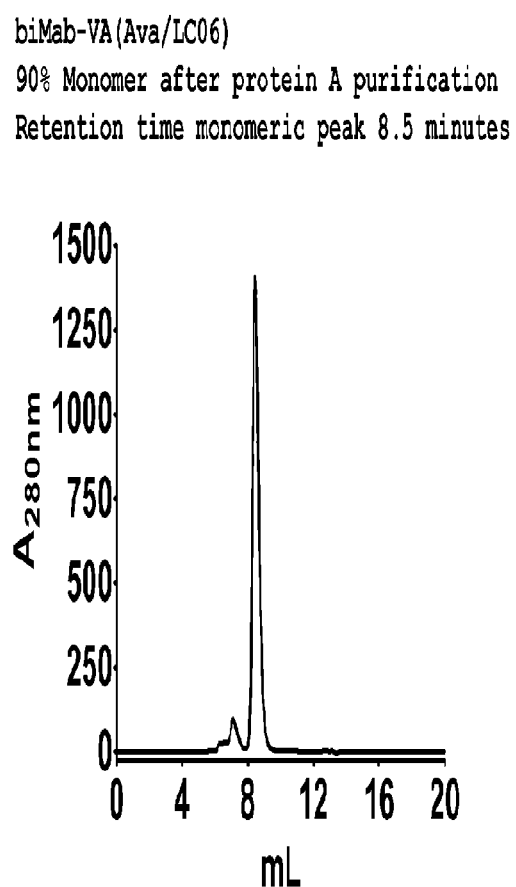
Fig. 10

| Test molecule immobilized using amine coupling chemistry | Human FcRn $K_D$ (µM) |
|---|---|
| biMab-EI (PaniX/Dalo) | 0.93 |
| biMab-VA (Ava/LC06) | 0.68 |
| PaniX (anti-EGFR) | 0.84 |

Fig. 15

| Test molecule | Initial concentration (mg/mL) | Monomer content at initial concentration (%) |
|---|---|---|
| biMab-EI(PaniX/Dalo) | 0.54 | 99 |
| biMab-VA(Ava/LC06) | 1.84 | 99 |

| Test molecule | Final concentration (mg/mL) | Monomer content at final concentration (%) |
|---|---|---|
| biMab-EI(PaniX/Dalo) | 25 | 99 |
| biMab-VA(Ava/LC06) | 25 | 99 |

Buffer: 25 mM Histidine-HCl pH 6.0

Fig. 19

Percent protection against lethal pneumonia in mice challenged with P. aeruginosa strain 6206 (O11-ExoU+)

| Antibody | Antibody concentration (mg/kg) | | | | | | | |
|---|---|---|---|---|---|---|---|---|
|  | 15 | 10 | 5 | 2 | 1 | 0.5 | 0.2 | 0.1 |
| BS2-V2L2[a] | 100 (10) | - | 100 (10) | - | 67 (30) | 40 (30) | - | - |
| BS2-V2L2-2C | - | - | 90 (20) | - | 25 (20) | 0 (20) | 0 (10) | - |
| BS2-W4-RAD-2C | - | - | 70 (10) | - | 10 (10) | 0 (10) | 0 (10) | - |
| BS3-V2L2-2C | - | 80 (10) | 40 (20) | - | 10 (20) | 0 (20) | 0 (20) | - |
| BS4-V2L2-2C | - | - | 100 (50) | - | 88 (60) | 60 (60) | 10 (60) | - |
| V2L2 | - | - | 80 (10) | - | 20 (10) | 10 (10) | 0 (10) | - |
| W4-RAD | 0 (10) | - | 0 (10) | - | 0 (10) | - | - | - |
| Mixture | Antibody concentration (mg/kg for each mAb) | | | | | | | |
|  |  |  | 5 | 2 | 1 | 0.5 | 0.2 | 0.1 |
| W4-RAD + V2L2 |  |  | 100 (10) | 100 (40) | 78 (40) | 15 (40) | - | 3 (40) |

120 hr post-infection (inocula ~1.0e6 CFU/animal)
Parentheses indicate total number of animals
[a] 1mg/kg and 0.5mg/kg includes studies where animals were treated with 1.7 and 0.55mg/kg, respectively

Fig. 24

MULTISPECIFIC AND MULTIVALENT BINDING PROTEINS AND USES THEREOF

CROSS-REFERENCE TO RELATED APPLICATIONS

This application is a U.S. National Stage application of International Application No. PCT/US2012/063639, filed on Nov. 6, 2012, said International Application No. PCT/US2012/063639 claims benefit under 35 U.S.C. §119(e) of the U.S. Provisional application Nos.: 61/697,585, filed Sep. 6, 2012; 61/625,299, filed Apr. 17, 2012; 61/624,651, filed Apr. 16, 2012; and 61/556,645, filed Nov. 7, 2011. Each of the above listed applications is incorporated by reference herein in its entirety for all purposes.

REFERENCE TO SEQUENCE LISTING SUBMITTED ELECTRONICALLY

This application incorporates by reference a Sequence Listing submitted with this application as text file entitled "AEMS_115 WO1_SL" created on Nov. 5, 2012 and having a size of 99.2 kilobytes.

BACKGROUND

Many diseases are caused by or associated with biomolecules, and it is useful to develop disease treatments, therapies, diagnostic reagents, and research reagents that target biomolecules and, optionally, modulate their activities. Agents, including therapeutic, diagnostic, and research agents, that bind to more than one site may be desired, so that a single molecule can bind either to multiple regions of the same target biomolecule, or else to multiple different targets. The approach described herein provides novel bispecific bivalent binding proteins based on a unique core structure which may be adapted to generate binding proteins that bind additional epitopes (i.e., have additional specificities) e.g. trispecific binding proteins, tetraspecific binding proteins, pentaspecific binding proteins.

SUMMARY OF THE DISCLOSURE

The present disclosure generally provides proteins that bind at least two epitopes (e.g., proteins that are, at least, bispecific and bind to a first epitope and a second epitope). Note, however, that the disclosure also provides proteins that, although monospecific, exhibit tetravalency for binding to an epitope (e.g., a first a second binding unit each bind the same epitope).

In one aspect, the disclosure provides a protein comprising a Fab arm that binds to a first epitope, a binding domain (BD) that binds to a second epitope, and an Fc region comprising $C_H2$ and $C_H3$ domains, wherein the BD is interconnected to the Fab arm via a first polypeptide linker (L1) and to the Fc region via a second polypeptide linker (L2), and wherein the protein is bivalent for binding to each of the first and second epitopes.

In certain aspects, L1 and/or L2 comprise a hinge portion and a linker portion. In certain aspects, the linker portion of L1 and/or L2 comprises a Gly-Ser peptide. In certain aspects, neither L1 nor L2 comprise a hinge portion.

In certain aspects, the BD is selected from the group consisting of an scFv, a single domain antibody, a single chain diabody, an antibody mimetic, an antibody variable domain and a receptor binding domain.

In certain aspects, the Fc region is selected from the group consisting of an Fc region from an IgG1, IgG2, IgG3, IgG4, IgA, IgM, IgE and IgD.

In certain aspects, the Fc region is a variant sequence Fc region.

In certain aspects, the protein comprises a chimeric heavy chain comprising the following polypeptide domains, from N-terminus to C-terminus VH1-CH1-L1-BD-L2-Fc; wherein VH1 comprises an amino acid sequence comprising the heavy chain variable domain of the Fab, CH1 comprises an amino acid sequence comprising the heavy chain constant domain 1 of the Fab, L1 comprises an amino acid sequence comprising a first polypeptide linker, BD comprises an amino acid sequence encoding binding unit 2, L2 comprises an amino acid sequence comprising a second polypeptide linker, and Fc comprises an amino acid sequence comprising $C_H2$ and $C_H3$ domains.

In some aspects, BD comprises an scFv.

In some aspects, the scFv comprises, from N-terminus to C-terminus, VH2-polypeptide linker-VL2 or VL2-polypeptide linker-VH2, wherein VH2 comprises an amino acid sequence comprising the heavy chain variable domain of scFv and VL2 comprises an amino acid sequence comprising the light chain variable domain of the scFv. In some aspects the polypeptide linker between VH2 and VL2 comprises a protease cleavage site.

In certain aspects, L1 comprises, from N-terminus to C-terminus, a hinge portion and a linker portion.

In certain aspects, L2 comprises, from N-terminus to C-terminus, a linker portion and a hinge portion.

In some aspects, the Fab arm binds to a first epitope present on a target selected from EGFR, IGFR1, VEGF, Ang2, Psl or PcrV.

In some aspects, the BD binds to a second epitope present on a target selected from EGFR, IGFR1, VEGF, Ang2, Psl or PcrV.

In some aspects, the first and second epitopes are different. In other aspects, the first and second epitopes are the same. In certain aspects, the first and second epitopes are located on the same target molecule. In other aspects, the first and second epitopes are located on different target molecules.

In certain aspects, the Fab arm and/or the Fc region further comprises at least one binding unit, wherein the at least one binding unit is interconnected to the Fab arm and/or Fc region via a polypeptide linker.

In some aspects, the at least one binding unit is selected from the group consisting of a Fab arm, an scFv, a single domain antibody, a single chain diabody, an antibody mimetic, an antibody variable domain and a receptor binding domain.

In some aspects, the protein comprises more than two binding units, such as at least three or at least four or at least five binding units.

In certain aspects, the binding units (at least 2, 3, 4, 5, etc) each bind different epitopes. In other aspects, two or more binding units (in a molecule having at least 2, 3, 4, 5, etc.) each bind the same epitope. In some aspects, the protein comprises more than two binding units, and none of binding unit 3, 4, 5, etc. bind the first and/or the second epitope.

The present disclosure also provides a nucleic acid composition comprising a first nucleic acid molecule comprising a first nucleotide sequence and a second nucleic acid molecule comprising a second nucleotide sequence, wherein the first and second nucleic acid molecules encode a protein comprising a Fab arm that binds to a first epitope, a binding domain (BD) that binds to a second epitope, and an Fc region comprising $C_H2$ and $C_H3$ domains, wherein the BD is interconnected to the Fab arm via a first polypeptide linker (L1) and to the Fc region via a second polypeptide linker (L2), and wherein the protein is bivalent for binding to each of the first and second epitopes.

The disclosure contemplates all combinations of any of the foregoing aspects, as well as combinations with any of the aspects set forth in the detailed description and examples.

BRIEF DESCRIPTION OF THE DRAWINGS

For the purpose of illustrating the disclosure, there are depicted in the drawings certain aspects of the disclosure. However, the disclosure is not limited to the precise arrangements and instrumentalities of the aspects depicted in the drawings.

FIGS. 2A-2C provide representative DNA sequences and protein sequences of chimeric heavy chain domains of a representative biMab.

FIG. 2D provides an alignment of the proteins sequences of a wild type hinge region and several representative L1 and L2 variations. The top panel shows representative L1 sequences, the $C_H1$ and BD domains are boxed, the cysteine that makes the interchain disulphide bridge with the light chain and the aspartate residue where undesirable cleavage may occur are indicated with arrows. The bottom panel shows representative L2 sequences, the BD and $C_H2$ domains are boxed, the optional serine insertion (made to introduce an XhoI restriction site for directional cloning) and the aspartate residue where undesirable cleavage may occur are indicated with arrows. Removal of the indicated asparte (e.g., use of linkers lacking this residue or having an amino acid substitution at this position) can reduce undesirable cleavage within the L1 and L2 linkers.

FIG. 3 provides protein sequence of two representative biMabs. Note that actual amino acid sequence is not provided for the following portions of the molecule: VARIABLE HEAVY DOMAIN I; scFv VH domain II; scFv VL domain II. These portions of the molecule will comprise amino acid sequence for the particular binding unit used. The two linker/hinge regions are underlined with the hinge portion bolded.

FIGS. 6A-D show the DNA sequence, protein sequence of light and heavy chains of a representative anti-EGFR/IGF1R biMab (biMab-EI), and a schematic representation of this biMab.

FIGS. 7A-D show the DNA sequence and protein sequence of light and heavy chains of a representative anti-VEGF/Ang2 biMab (biMab-VA), and a schematic representation of this biMab.

FIG. 8A-D show the DNA sequence and protein sequence of light and heavy chains of a representative anti-PcrV/Psl biMab (Bs4-V2L2-2C), and a schematic representation of this biMab.

FIG. 9 shows the transient expression levels, in mg/L, of representative biMabs (e.g., biMab-EI and biMab-VA) after 10 days of transient expression in 293 cells.

FIG. 10 shows size-exclusion chromatograms (SEC-HPLC) for representative biMabs (e.g., biMab-EI and biMab-VA) after protein A purification and dialysis in 25 mM Histidine-HCl pH 6. The chromatogram for biMab-EI is provided on the left and the chromatogram for biMab-VA is provided on the right. Monomeric content (%) after protein A purification and retention time (minutes) are schematically shown on the figure.

FIG. 15 provides $K_D$ values for binding to human FcRn by biMab-EI, biMab-VA and the parental conventional anti-EGFR mAb used in constructing the biMab-EI. KD values were determined by using BIAcore equilibrium binding.

FIG. 19 shows that biMab-EI and biMab-VA can be concentrated without significant monomer loss.

FIG. 24 shows the percent protection against lethal pneumonia in mice treated with the Bs2, Bs3, BiMab, parental antibodies alone and in combination. The mice were treated with different doses of antibody ranging from 0.2 mg/kg to 15 mg/kg. The percent survival is indicated in the table with the number of animals for each comparison indicated in parentheses.

DETAILED DESCRIPTION

Figure 1:
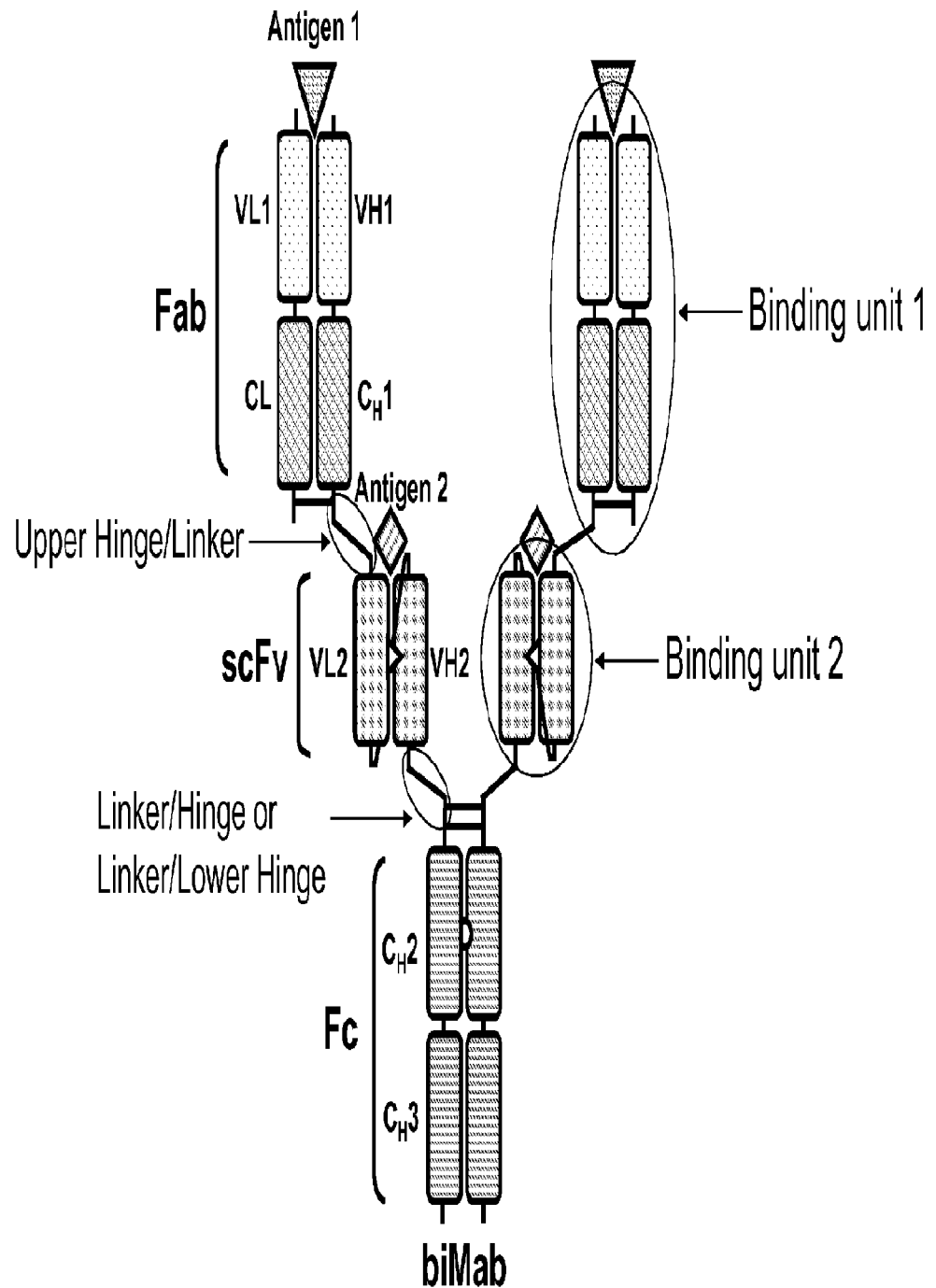
FIG. 1 is a schematic diagram of a representative bispecific polypeptide bivalent for binding to each epitope. This depiction of a bispecific polypeptide bivalent for binding to each epitope is referred to herein as a biMab (bispecific and bivalent protein comprising antibody portions). As depicted, this biMab has two binding units, each of which binds a different epitope. The binding units are labeled on the right side of the figure, but each of the binding units are also present on the left side of the figure (e.g., the molecule is bivalent for binding to each epitope; the molecule is bilaterally symmetric with respect to the binding units and upper and lower linker/hinge regions). The biMab epitopes can be from the same or different target antigen; when the same target is bound then the biMab binding units bind to non-overlapping regions (i.e., different, preferably non-overlapping epitopes).

Before continuing to describe the present disclosure in further detail, it is to be understood that this disclosure is not limited to specific compositions or process steps, as such may vary. It must be noted that, as used in this specification and the appended claims, the singular form "a", "an" and "the" include plural referents unless the context clearly dictates otherwise.

Unless defined otherwise, all technical and scientific terms used herein have the same meaning as commonly understood by one of ordinary skill in the art to which this invention is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this invention.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The numbering of amino acids in the variable domain, complementarity determining region (CDRs) and framework regions (FR), of an antibody follow, unless otherwise indicated, the Kabat definition as set forth in Kabat et al. Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insertion (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence. Maximal alignment of framework residues frequently requires the insertion of "spacer" residues in the numbering system, to be used for the Fv region. In addition, the identity of certain individual residues at any given Kabat site number may vary from antibody chain to antibody chain due to interspecies or allelic divergence.

As used herein, the terms "antibody" and "antibodies", also known as immunoglobulins, encompass monoclonal antibodies (including full-length monoclonal antibodies), polyclonal antibodies, multispecific antibodies formed from at least two different epitope binding fragments (e.g., multispecifc antibodies, e.g., PCT publication WO2009018386, PCT Application No. PCT/US2012/045229, incorporated herein by reference in its entirety), biMabs, human antibodies, humanized antibodies, camelised antibodies, single-chain Fvs (scFv), single-chain antibodies, single domain antibodies, domain antibodies, Fab fragments, F(ab')2 fragments, antibody fragments that exhibit the desired biological activity (e.g. the antigen binding portion), disulfide-linked Fvs (dsFv), and anti-idiotypic (anti-Id) antibodies (including, e.g., anti-Id antibodies to antibodies of the invention), intrabodies, and epitope-binding fragments of any of the above. In particular, antibodies include immunoglobulin molecules and immunologically active fragments of immunoglobulin molecules, i.e., molecules that contain at least one antigen-binding site. Antibodies also include peptide fusions with antibodies or portions thereof such as a protein fused to an Fc domain. Immunoglobulin molecules can be of any isotype (e.g., IgG, IgE, IgM, IgD, IgA and IgY), subisotype (e.g., IgG1, IgG2, IgG3, IgG4, IgA1 and IgA2) or allotype (e.g., Gm, e.g., G1m(f, z, a or x), G2m(n), G3m(g, b, or c), Am, Em, and Km(1, 2 or 3)). Antibodies may be derived from any mammal, including, but not limited to, humans, monkeys, pigs, horses, rabbits, dogs, cats, mice, etc., or other animals such as birds (e.g. chickens).

A. Novel Bispecific Binding Proteins

Adding multiple binding sites to a single binding molecule can greatly enhance the capabilities (e.g. therapeutic, diagnostic, etc) of the molecule. For example, a bispecific antibody may bind to more than one region of the same target biomolecule, conferring greater specificity than a uni-specific polypeptide that binds to only one epitope on a target. Alternately, a bispecific antibody may bind to multiple target biomolecules, such as targets that are present in a complex, or targets for which sequestering and/or clustering is desired. In a third scenario, the same bispecific antibody may perform distinct functions at any given time, depending on the localization and/or expression of its target molecules.

Described herein are novel binding proteins. Exemplary configurations of these novel binding proteins are referred to as "biMabs". Schematic representations of exemplary biMabs, as well as specific examples of particular biMabs are provided herein. More generally, a biMab is polypeptide containing two binding units, each of which binds to an epitope (e.g., binding unit 1 binds to a first epitope and binding unit 2 binds to a second epitope). The basic biMab is bivalent for binding to each of the two epitopes (e.g., the polypeptide comprises two binding unit 1's and two binding unit 2's). Thus, where the binding unit 1 and 2 bind different epitopes, the biMab has the multi-specificity of a conventional bispecific antibody and the bivalency of a conventional antibody molecule. Where binding unit 1 and 2 bind the same epitope the biMab has monospecificity of a conventional antibody but is tetravalent. In addition to binding units, biMabs also include linker polypeptides and an Fc portion. The present disclosure also provides binding proteins which bind to more than two epitopes by the addition of additional binding units to the "core" biMab structure to generate trispecific, tetraspecific, pentaspecific and hexaspecific binding proteins which are bivalent for each epitope (see for example FIGS. 26, 27 and 28). The present disclosure provides binding proteins, such as biMabs, and binding proteins comprising a biMab core. Binding proteins of the disclosure comprise binding units, linker polypeptides and an Fc portion, as described herein. The disclosure also provides nucleic acid molecules encoding such biMabs and methods of producing and using such biMabs. biMabs, binding proteins comprising a biMab core, and the various portions of biMabs are described in greater detail herein.

A biMab, as described herein, comprises two heavy-light chain pairs, wherein the heavy and light chains each comprise a variable region (e.g. VL and VH), which together form a first binding unit, and wherein the heavy chains further comprises a second binding unit (e.g. an scFv). Where the first and second binding units bind different epitopes each heavy-light chain pair is bispecific and the two pairs together are bivalent for each epitope. Where the first and second binding units bind the same epitope each heavy-light chain pair is monospecific and the two pairs together are tetravalent for the epitope. In some aspects, the two heavy-light chain pairs are identical. In some aspects, the two heavy-light chain pairs are not identical.

The domains of the biMabs may be based on immunoglobulin domains. Immunoglobulin molecules such as monoclonal antibodies (mAbs) are widely used as diagnostic and therapeutic agents, and methods for engineering the binding fragments of mAbs are well-known in the art. Monoclonal antibodies, like all immunoglobulin molecules, are made up of peptide subunits. A typical or conventional mAb comprises two heavy chain subunits and two light chain subunits. Each mAb heavy chain contains one variable domain (VH) which contributes to antigen binding, and a constant domain (CH) made up of three or four subregions ($C_H1$, $C_H2$, $C_H3$, $C_H4$). Each mAb light chain contains one variable domain (VL) and one constant domain (CL). There are two isotypes of light chain constant domains, kappa (κ) and lambda (λ), found in mammals. Disulfide bonds join each $C_H1$ domain to one CL domain, and join $C_H2$ domains to one another. Five types of heavy chains (α, δ, ε, γ, and μ) are found in different classes of antibodies (IgA, IgD, IgE, IgG, and IgM). mAb heavy chains have hinge regions which confer structural flexibility and mobility. biMabs of the disclosure may have a similar overall structure to a conventional antibody, but are distinguishable by the presence of an additional binding unit located between a first antigen binding portion and an Fc portion. Thus, unlike conventional antibodies that are bivalent for binding to a single epitope, biMab's are bivalent for binding to two epitopes. However, as described herein, biMab's still maintain numerous desirable properties of conventional antibodies, such as ability to bind FcRn and ability to bind C1q and Fcγ receptors (e.g., indicative of ability to mediate antibody and complement dependent cytotoxicity).

mAb fragments containing only select portions of a mAb molecule, such as Fab, F(ab')₂, Fab', scFv, di-scFv, sdAb fragments, have also been used as diagnostic or therapeutic agents. In addition, specific residues in the variable domains have been altered to improve binding specificity of antibodies and antibody fragments. Other residues not directly involved in antigen binding have been replaced in order to "humanize" regions of non-human antibodies and reduce immunogenicity of the mAb.

Although biMabs differ from conventional antibodies, for example, they are bivalent for binding to two different epitopes (or tetravalent for binding to a single epitope), many of the portions of biMabs are derived from or analogous to portions of conventional antibodies. Any mAb domains and/or fragments known in the art may be used in the biMabs described herein. In particular, the biMab may comprise Fab and/or scFvs fragments, or variants thereof. Exemplary, non-limiting variants of scFvs include but are not limited to tandem di-scFvs, tandem tri-scFvs, diabodies, and tri(a)bodies. Thus, in certain aspects, the disclosure provides a bivalent, multispecific polypeptide comprising a Fab that binds to a first epitope (binding unit 1), an scFv or variant of an scFv that binds to a second epitope (binding unit 2), an Fc comprising at least $C_H2$ and $C_H3$ domains, a polypeptide linker interconnecting binding unit one to binding unit two (L1; upper hinge/linker), and a polypeptide linker interconnecting binding unit 2 to the Fc (L2; linker/lower hinge).

The disclosure relates generally to novel binding proteins of the disclosure, of which biMabs are an illustrative example. Additional examples are binding proteins comprising a biMab core as well as one or more additional binding units (see, e.g., FIGS. 27 and 28) and/or binding proteins comprising an extended biMab core (see, e.g., FIG. 29). It should be understood that whenever biMabs or features of biMabs are described herein, such description applies generally to the novel binding proteins of the disclosure, regardless of whether such binding proteins include two binding units or more than two binding units. Accordingly, the term biMab is exemplary of binding proteins of the disclosure and, where context permits, any such reference to biMab may also be used to describe binding proteins comprising a biMab core.

FIG. 1 shows a schematic diagram of an exemplary biMab of the present disclosure. As shown in FIG. 1, one aspect of a biMab of the disclosure comprises two identical heavy-light chain pairs, wherein each heavy-light chain pair is bispecific and the two identical pairs are together bivalent for each epitope. Each heavy-light chain pair comprises a Fab domain that binds a first epitope (binding unit 1), a binding domain (BD) that binds a second epitope (binding unit 2; depicted as an scFv in FIG. 1), and an Fc region. More specifically, the biMab comprises two chimeric heavy chains, each comprising a heavy chain variable region (VH1), a heavy chain constant region (CH1), a first polypeptide linker (labeled upper hinge/linker in FIG. 1; also referred to herein as L1), a binding domain (BD), a second polypeptide linker (labeled linker/lower hinge in FIG. 1; also referred to herein as L2) and an Fc region comprising a $C_H2$ domain and $C_H3$ domain. The biMab of the disclosure also comprises two conventional antibody light chains, each comprising a light chain variable region (VL1) and light chain constant region (CL). The binding domain (binding unit 2) of the particular biMab illustrated in FIG. 1 is an scFv. However, the binding domain of a biMab according to various aspects of the present disclosure may be any binding domain known in the art.

FIG. 1 provides a useful schematic representation of a biMab, also referred to herein as a biMab "core". FIGS. 2 and 3 provide additional description of the heavy chain of a representative biMab. We refer to the polypeptide chain, as shown in FIG. 1, comprising: a VH1 domain, a CH1 domain, an upper hinge/linker (also referred to herein as L1 or a first polypeptide linker), binding unit 2 (such as VL2 and VH2 of an scFv), a linker/lower hinge (also referred to herein as L2 or a second polypeptide linker), and Fc (such as a $C_H2$ and $C_H3$ domain). Because this heavy chain may include traditional light chain regions, it is referred to herein as a chimeric heavy chain. A biMab comprises two such chimeric heavy chains, and these may be the same or different. Note that the variable heavy chain domain (VH) for binding unit 1 is referred to as VH1. In certain aspects, this is a variable heavy chain of a Fab that binds to a first epitope. Similarly, the variable light chain domain (VL) for binding unit 1 is referred to as VL1. In certain aspects, this is a variable light chain of a Fab that binds to a first epitope. In contrast, the domains for binding unit two are denoted with the number "2", such as VH2 and VL2 for aspects in which binding unit 2 is an scFv that binds to a second epitope.

FIG. 2 provides DNA and amino acid sequence information for several domains used in exemplary biMab chimeric heavy chains. The portions of the chimeric heavy chain are presented in FIGS. 2A-2C. At the top of FIG. 2A, the DNA and protein sequence of the VH1 region is shown schematically. For any particular biMab, this actual sequence would correspond to the VH1 of the particular binding unit one, such as the VH1 for a particular Fab. FIG. 2A then provides the DNA and protein sequence for an exemplary $C_H1$ domain and the full human IgG1 hinge region. This is followed by DNA and amino acid sequences for several exemplary options for polypeptide linker 1 (L1) which interconnects the Fab and the BD in a biMab. L1 may comprise a hinge portion and a linker portion (upper hinge/linker), and this is depicted in FIG. 2A. FIG. 2A first depicts an example of a hinge portion of L1 (denoted as upper hinge, in this case human Ig1 upper hinge). Note that FIG. 2A depicts three possible aspects of a hinge portion for L1, denoted as human IgG1 upper hinge or modified human IgG1 upper hinge. These hinge portions differ in that the modified hinge portion contains a D to G substitution immediately following the cysteine or are lacking the residues after the cysteine. FIG. 2A then depicts the linker portion of L1, here, a $G_4S$ linker. The upper hinge portion and linker portion together form L1. However, in certain aspects, L1 includes only a linker portion or only a hinge portion.

FIG. 2B depicts schematically the DNA and protein sequence of binding unit 2, here an scFv, which may be in VH2-linker-VL2 or VL2-linker-VH2 orientation. For any particular biMab, this sequence would correspond to, for example, the VH2 and VL2 sequences for the particular binding unit 2, as well as the appropriate linker for these VH2 and VL2 domains. It will be appreciated that the hinge and linker portions of L1 may be repeated, such that for example, L1 comprises two hinge portions and two linker portions.

The DNA and amino acid sequence for an exemplary second polypeptide linker (L2; also referred to as linker/lower hinge) is depicted on FIGS. 2A and 2B. The linker portion of L2 is provided on the bottom of FIG. 2B. As depicted, this linker portion is a $G_4S$ linker. The hinge portion of an L2 is depicted on the bottom of FIG. 2B (note, this hinge portion is depicted as lower hinge or hinge variant). FIG. 2B provides three aspects for a hinge portion of L2, hinge variant of human IgG1 and lower hinge of human IgG1. A lower hinge portion and linker portion together form L2 (also referred to as linker/lower hinge). However, in certain aspects, L2 includes only a linker portion or only a hinge portion.

FIG. 2C provides DNA and amino acid sequence for Fc $C_H2$ and $C_H3$ domains. The $C_H2$ and $C_H3$ domains depicted in FIG. 2B are from an IgG1 although a biMab could readily be generated using the Fc from any Ig class, including IgM, IgG, IgD, IgA and IgE, and any isotype, including IgG1, IgG2, IgG3 and IgG4. It will be appreciated that the hinge and linker portions of L2 may be repeated, such that for example, L2 comprises two hinge portions and two linker portions.

Finally, FIG. 2D provides an alignment of the protein sequences of a wild type hinge region and several representative L1 and L2 variations. Indicated is the aspartate where an undesirable cleavage event may occur. In certain aspects this aspartate is not present in L1 and/or L2. In certain aspects, the asparate is replaced with another amino acid residue (e.g., a glycine). In other aspects, the aspartate residue is deleted. Also represented is a variation of L2 that comprises an amino acid insertion (e.g., serine). This amino acid insertion was made in order to introduce a restriction site (e.g., XhoI) into the DNA sequence encoding the linker. It is contemplated that desired restriction sites may be incorporated into any linker present in a binding protein of the invention, in particular to facilitate cloning of binding domains.

FIG. 3 provides another representation of the amino acid sequence of the chimeric heavy chain for an exemplary schematic depiction of a biMab. Of course, it should be understood that the specific sequence for the VH1 (variable heavy chain domain 1 of binding unit 1) and the specific sequence for binding domain 2 (depicted as an svFc in the VH2-linker-VL2 orientation) are not provided. These sequences will depend upon the particular binding units that make up a particular biMab. However, the relative position of the portions of the biMab relative to each other is maintained (e.g., the biMab format is the same—although the particular binding units vary).

In FIG. 3, L1 and L2 are underlined and italicized, and the hinge portions of L1 and L2 are bolded. In the top panel, the hinge portion of L1 corresponds to the human IgG1 upper hinge, whereas in the bottom panel the hinge portion of L1 corresponds to the modified human IgG1 upper hinge. In the top panel, the hinge portion of L2 corresponds to the lower hinge variant of human IgG1, whereas in the bottom panel the hinge portion of L2 corresponds to the lower hinge of human IgG1. In either case, L1 interconnects binding unit 1 to binding unit 2, for example, by interconnecting the VH1 of binding unit 1 to the VH2 of binding unit 2. L2 interconnects binding unit 2 to Fc, for example, by interconnecting the VL2 of binding unit 2 to the $C_H2$ domain of an Fc.

Figure 4A:
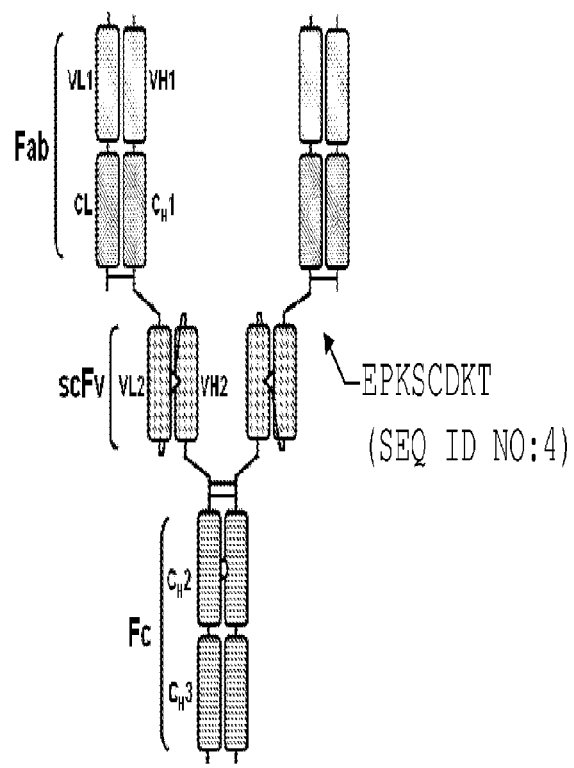
FIG. 4A shows the DNA sequence and protein sequence for the hinge portion of the upper hinge/linker (also referred to as L1) of a representative biMab, as well as a schematic representation of that biMab. The sequence of this hinge portion is depicted on the right hand side of the schematic and is EPKSCDKT (SEQ ID NO:4). The sequence for the linker portion of the upper hinge/linker (L1) is not shown on the schematic.
Figure 4B:
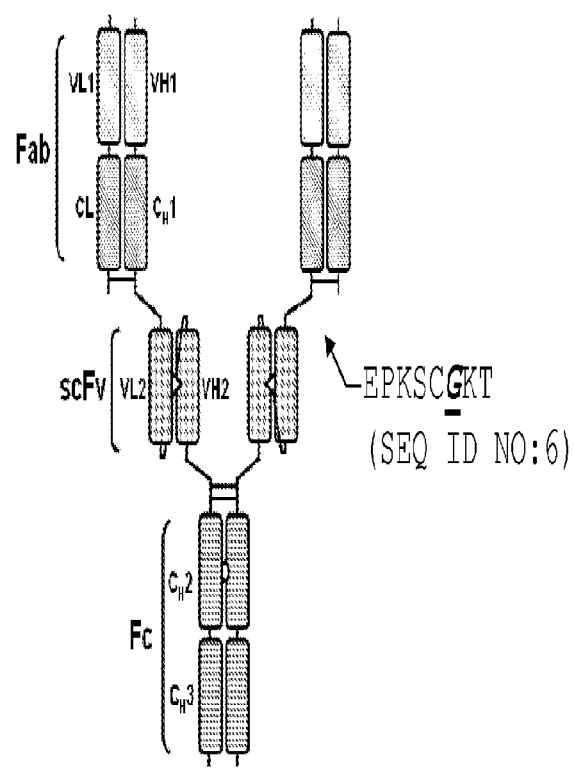
FIG. 4B shows the DNA sequence and protein sequence for the modified hinge portion of the upper hinge/linker (also referred to as L1) of a representative biMab, as well as a schematic representation of that biMab. The sequence of this hinge portion is depicted on the right hand side of the schematic and is EPKSCGKT (SEQ ID NO:6). The residue (G) in this modified upper hinge, which has been modified from the normal IgG1 upper hinge sequence (see also the sequence in FIG. 4A), is shown as underlined, bold and italic. The sequence for the linker portion of the upper hinge/linker (L1) is not shown on the schematic.
Figure 4C:
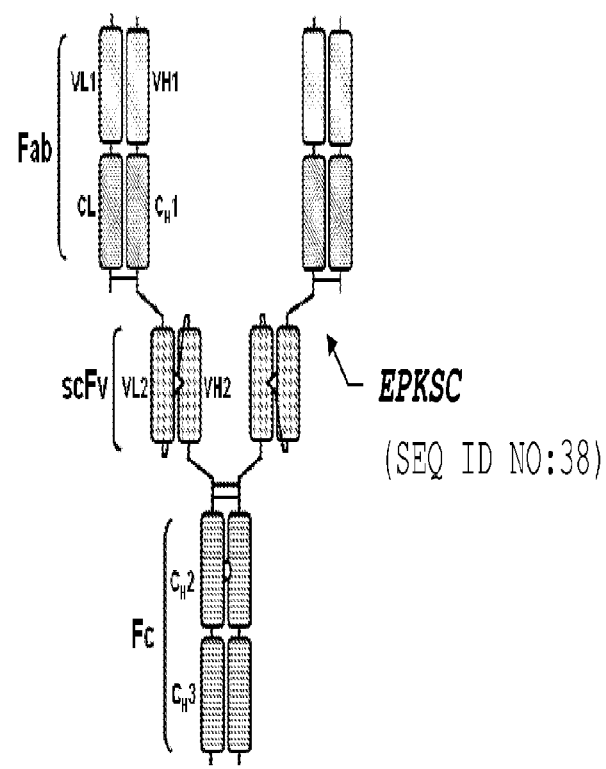
FIG. 4C shows the DNA sequence and protein sequence for the short hinge portion of the upper hinge/linker (also referred to as L1) of a representative biMab, as well as a schematic representation of that biMab. The sequence of this hinge portion is depicted on the right hand side of the schematic and is EPKSC (SEQ ID NO:38). The C-terminal three amino acid residues of the human IgG1 upper hinge are not present in this short upper hinge, which has been modified from the normal IgG1 upper hinge sequence (see also the sequence in FIG. 4A). The sequence for the linker portion of the upper hinge/linker (L1) is not shown on the schematic.
Figure 5A:
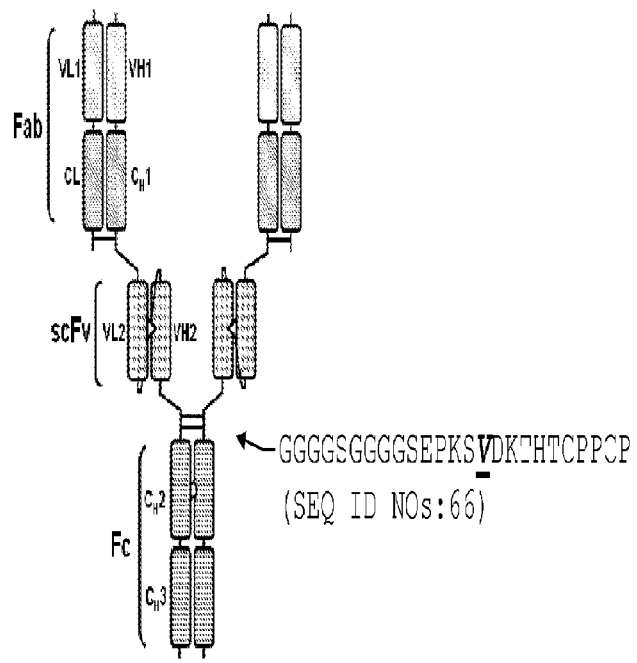
FIG. 5A shows the DNA and protein sequences for both the linker and hinge portions of the linker/lower hinge (also referred to as L2) of a representative biMab, as well as a schematic representation of that biMab. The linker portion is a poly-glycine-serine linker and the hinge portion is a modified hinge. The sequence of this linker/lower hinge is depicted on the right hand side of the schematic. The residue (V) in this modified hinge, which has been modified from the normal IgG1 hinge sequence (see also the alignment in FIG. 2D), is shown as underlined, bold and italic.
Figure 5B:
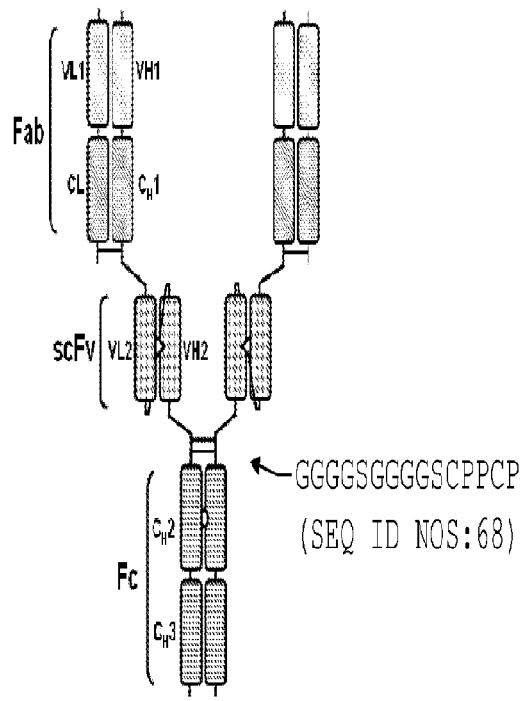
FIG. 5B shows the DNA and protein sequences for both the linker and hinge portions of the linker/lower hinge of a representative biMab (also referred to as L2), as well as a schematic representation of that biMab. The linker portion is a poly-glycine-serine linker and the hinge portion is a shortened hinge. The sequence of this linker/lower hinge is depicted on the right hand side of the schematic. This hinge is a portion of the normal IgG1 hinge sequence (see also the alignment in FIG. 2D).
Figure 5C:
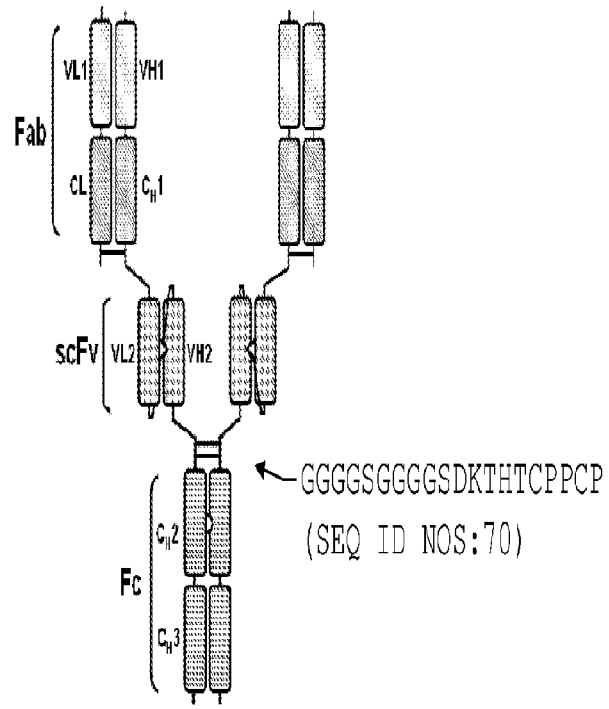
FIG. 5C shows the DNA and protein sequences for both the linker and hinge portions of the linker/lower hinge of a representative biMab (also referred to as L2), as well as a schematic representation of that biMab. The linker portion is a poly-glycine-serine linker and the hinge portion is also a shortened modified hinge. The sequence of this linker/lower hinge is depicted on the right hand side of the schematic. This hinge is a portion of the normal IgG1 hinge sequence (see also the alignment in FIG. 2D).

Further schematic representations of representative biMabs are provided in FIGS. 4 and 5. These figures depict the relative position in the molecule of the hinge portions of L1 and L2. For example, in FIGS. 4A-4C, the relative position of the hinge portion of L1 is depicted. L1 may further include a linker portion, the sequence of which is not shown in FIG. 4A, 4B or 4C. Examples of L1 further comprising a linker portion are provided in SEQ ID NO:62, 63, and 64). Note, however, that when present, the hinge portion of L1 is interconnected directly to binding unit 1 (e.g., is contiguous with a portion of binding unit 1) and the linker portion is interconnected directly to binding unit 2 (e.g., is contiguous with a portion of binding unit 2). Because of this configuration, L1 is also referred to as upper hinge/linker. By way of further example, FIGS. 5A-5C depict the relative position of the hinge portion of L2. L2 may further include a linker portion, the sequence of which is not shown in FIG. 5A, 5B or 5C. Note, however, that when present, the hinge portion of L2 is interconnected directly to the Fc domain (e.g., is contiguous with a portion of an Fc domain) and the linker portion is interconnected directly to binding unit 2 (e.g., is contiguous with a portion of binding unit 2). Because of this configuration, L2 is also referred to as linker/lower hinge.

Having now described the overall biMab format, also referred to herein as the biMab "core". The various portions and exemplary functional properties of biMabs of the disclosure are described in greater detail below. The disclosure contemplates biMabs comprising combinations of any of the aspects, such as aspects describing portions of a molecule or functional features of a molecule, disclosed above or below.

1. Binding Units biMabs of the disclosure comprise at least two binding units (binding unit 1 and binding unit 2). In certain aspects each binding unit binds to a different epitope, either different epitopes located on the same target molecule or epitopes on different targets. Because each binding unit of a biMab is present as a pair (there are two binding unit 1s and two binding unit 2s) biMabs exhibit bivalent binding to each epitope. It will be understood from the teachings herein, that where each binding unit binds the same epitope a biMab will exhibit tetravalent binding to the epitope.

In certain aspects, the first binding unit is a Fab fragment, for example, a Fab fragment of a conventional monoclonal antibody or a recombinantly produced antigen binding fragment comprising a variable light chain (VL1), a constant light chain (CL1), a variable heavy chain (VH1), and a constant heavy chain portion (CH1). Optionally, the light and heavy chains of the Fab may be interconnected via one or more disulphide linkages. The Fab binds to a first epitope.

In certain aspects, the Fab is derived from or based on the sequence of a conventional monoclonal antibody, such as a conventional murine, humanized or human antibody. In certain aspects, biMab containing the Fab derived from or based on the sequence of a conventional monoclonal antibody retains one or more functional activities of the conventional antibody (e.g., retains at least 80% or more (80%, 85%, 90%, 95%, 97%, 98%, 99% or 100%) of a functional activity). For example, in certain aspects, the biMab containing such an Fab retains one or more of the affinity for antigen, inhibitory activity, or cell killing activity of the conventional antibody.

In certain aspects, the Fab binds to epidermal growth factor receptor (EGFR). In certain aspects, the Fab binds to IGFR1. In certain aspects, the Fab binds to VEGF. In certain aspects, the Fab binds to Ang2. In certain aspects, the Fab is derived from or based on the sequence of a conventional monoclonal antibody that binds to any of EGFR, IGFR1, VEGF, Ang2, Psl or PcrV. Exemplary conventional monoclonal antibodies include panitumumab, dalotuzumab, bevacizumab, LC06, W4-RAD or V2L2. For example, in certain aspects, a biMab of the disclosure comprises a Fab as binding unit one, and this Fab comprises 1, 2, 3, 4, 5, or all 6 CDRs of panitumumab, dalotuzumab, bevacizumab or LC06.

In certain aspects, the Fab comprises a light chain portion (VL1 and CL) comprising the amino acid sequence set forth in any of SEQ ID NO: 20, 29 and 42. In certain aspects, the Fab comprises a heavy chain portion (VH1 and $C_H1$) comprising the amino acid sequence underlined in FIG. 6C, 7C or 8C as set forth in any of SEQ ID NO: 23, 32 and 45. In certain aspects, the Fab comprises a variable light chain portion (VL1) comprising the amino acid sequence set forth in SEQ ID NO: 21 and a variable heavy chain portion (VH1) comprising the amino acid sequence set forth in SEQ ID NO: 24. In certain aspects, the Fab comprises a variable light chain portion (VL1) comprising the amino acid sequence set forth in SEQ ID NO: 30 and a variable heavy chain portion (VH1) comprising the amino acid sequence set forth in SEQ ID NO: 33. In certain aspects, the Fab comprises a variable light chain portion (VL1) comprising the amino acid sequence set forth in SEQ ID NO: 43 and a variable heavy chain portion (VH1) comprising the amino acid sequence set forth in SEQ ID NO: 46. In certain aspects, the Fab is encoded by a nucleotide sequence encoding the light chain portion (VL1 and CL) and a nucleotide sequence encoding the heavy chain portion (VH1 and CH1), for example, a nucleotide sequence comprising the nucleic acid sequence set forth in SEQ ID NO: 19 28, 41 and a nucleotide sequence comprising the nucleic acid sequence underlined in FIG. 6A, 7A or 8A as set forth in SEQ ID NO: 22, 29 or 44.

In certain aspects, biMabs of the disclosure comprise binding unit 2 and binding unit two comprises a binding domain that binds a second epitope. Binding domains according to the present disclosure (also referred to as "BDs") include for example, antibody variable regions, antibody fragments, scFvs, single chain diabodies, or other binding domains known in the art. Binding domains also include bispecific single chain diabodies, or single chain diabodies designed to bind two distinct epitopes. Also included are antibody-like molecules or antibody mimetics, for example, but not limited to minibodies, maxybodies, "A" domain oligomers (also known as Avimers) (See for example, US. Patent Application Publication Nos. 2005/0164301, 2005/0048512, and 2004/017576 each of which are incorporated by reference), Fn3 based protein scaffolds (see for example, US Patent Application Publication 2003/0170753 which is incorporated by reference), Ankrin repeats (also known as DARpins), VASP polypeptides, Avian pancreatic polypeptide (aPP), Tetranectin (based on CTLD3), Affililin (based on γB-crystallin/ubiquitin), Knottins, SH3 domains, PDZ domains, Tendamistat, Neocarzinostatin, Protein A domains, Lipocalins, Transferrin, and Kunitz domains that specifically bind epitopes. In one aspect, epitope binding domains useful in the construction of multispecific epitope binding domains of the disclosure are exemplified in WO 2009/058379 and WO 2011/130324 which are hereby incorporated by reference for all purposes.

Moreover, in certain aspects, the BD comprises a ligand binding domain of a receptor or a receptor binding domain of a ligand. For example, the BD comprises a portion of FGF that binds FGFR, a portion of EGF that binds EGFR, a portion of PDGF that binds PDGFR and the like. Alternatively, the BD may comprise a portion of FGFR that binds FGF, a portion of EGFR that binds EGF, a portion of PDGFR that binds PDGF, and the like. The respective binding domains of numerous ligand/receptor pairs are well known in the art, and thus can be readily selected and adapted for use in the biMab format.

Figure 29:
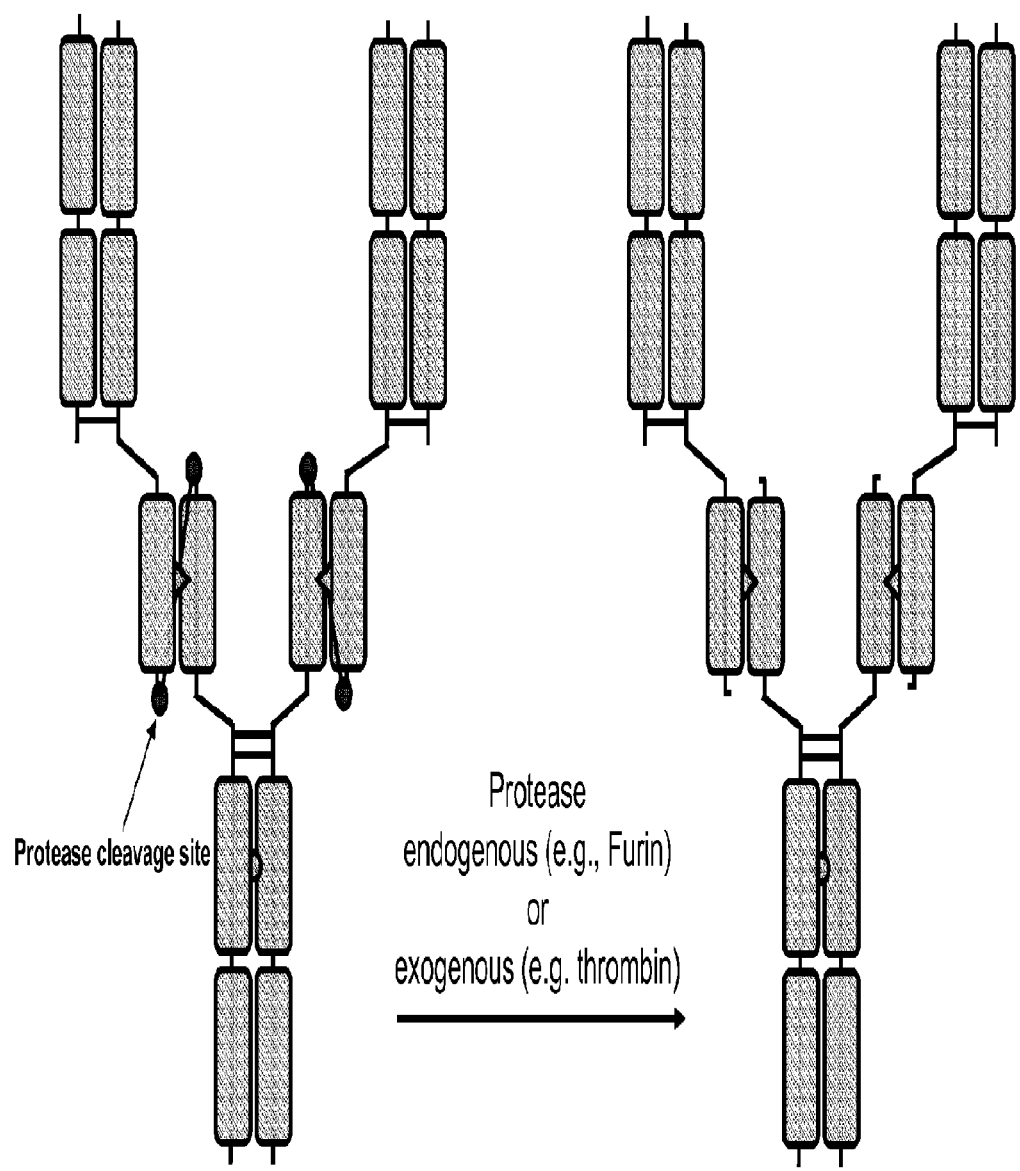
FIG. 29 is a schematic diagram of a representative biMab "core" wherein binding unit 2 is an scFv having a polypeptide linker comprising two protease cleavage sites. The left panel depicts the structure prior to protease cleavage. The right panel depicts the structure post protease treatment, which results in the removal of the linker present between VH2 and VL2 of the scFv. The resulting protein is a disulphide-bridged homodimer, comprising a total of six separate polypeptide chains.

In certain aspects, the binding domain is an scFv. Thus, in certain aspects, binding unit 2 comprises an scFv. It is to be understood that an scFv encompasses a polypeptide chain comprising a variable heavy chain domain (VH) linked to a variable light chain domain (VL) via a flexible polypeptide linker. FIG. 1 shows a schematic of an exemplary biMab, wherein the BD (here, depicted as binding unit 2) is an scFv and the domains are designated as VL2 and VH2. In some aspects the polypeptide linker between VH2 and VL2 comprises a protease cleavage site. FIG. 29 shows a schematic of a representative biMab "core" before and after protease cleavage of the polypeptide linker of an scFv binding domain.

The VH and VL domains of the scFv may be derived from the same or from different antibodies. In some aspects, a VH or VL of the scFv may comprise one or more CDRs which bind to a target of interest, while the remainder of the VH or VL domain is derived from a different antibody or is synthetic. In some aspects, the scFv comprises at least one CDR of an antibody, e.g., an antibody known in the art to bind to a target of interest. In some aspects, the scFv comprises at least two CDRs of a given antibody. In some aspects, the scFv comprises at least three CDRs of a given antibody. In some aspects, the scFv comprises at least four CDRs of a given antibody. In some aspects, the scFv comprises at least five CDRs of a given antibody. In some aspects, the scFv comprises at least six CDRs of a given antibody.

Several methodologies can be used alone or in combination to improve the stability of a biMab comprising an scFv molecule. One potential methodology that can be used, alone or in combination with one or more of the other methodologies described herein, is engineered the length and/or composition of the linker connecting the scFv domains to stabilize the scFv portion.

Another potential methodology that can be used, alone or in combination with one or more of the other methodologies described herein, is by introducing at least two amino acid substitutions (also referred to as modifications or mutations) into the VH and/or VL domains of the scFv so as to promote disulphide bond formation (see for example Brinkmann et al., 1993, PNAS, 90:7538-42; Zhu et al., 1997, Prot. Sci. 6:781-8; Reiter et al., 1994, Biochem. 33:5451-9; Reiter et al., 1996, Nature 14: 1239-45; Luo et al., 1995, J. Biochem. 118:825-31; Young et al., 1995, FEBS Let. 377:135-9; Glockshuber et al., 1990, Biochem. 29:1362-7).

In certain aspects, one mutation is introduced into each of the VH and VL domains of the scFv to promote interchain disulphide bond formation between the VH and VL domains upon expression of a biMab comprising an scFv. In another aspect, the two mutations are introduced in the same domain of the chain. In certain aspect, the two mutations are introduced in different chains. In certain aspects, multiple pairs of two mutations are introduced to promote formation of multiple disulphide bonds. In certain aspects, a cysteine is introduced to promote the disulphide bond formation. Exemplary amino acids that may be mutated to cysteine include amino acids 43, 44, 45, 46, 47, 103, 104, 105, and 106 of VH2 and amino acids 42, 43, 44, 45, 46, 98, 99, 100, and 101 of VL2. The foregoing numbering is based on Kabat numbering identifying the position relative only to the VH2 and VL2 of the scFv (and not relative to the position of the amino acid in the full length sequence of the biMab or SEQ ID NOS: provided herein). Exemplary combinations of amino acid positions which may be mutated to cysteine residues include: VH44-VL100, VH105-VL43, VH105-VL42, VH44-VL101, VH106-VL43, VH104-VL43, VH44-VL99, VH45-VL98, VH46-VL98, VH103-VL43, VH103-VL44, and VH103-VL45. In some aspects, amino acid 44 of VH and amino acid 100 of VL are mutated to cysteines.

A further potential methodology that can be used, alone or in combination with one or more of the other methodologies described herein, is selecting the order of the domains of the scFv. In certain aspects, the orientation of the VH domain relative to the VL domain is optimized for stability. In certain aspects, the scFv is in the VH-linker-VL orientation. In certain aspects, the scFv is in the VL-linker-VH orientation. The orientation of the domains in the scFv also determines how the scFv interconnects to the Fab portion and the Fc portion of the biMab. This is described in more detail below in the context of polypeptide linkers. Briefly, however, given that the BD, for example an scFV, is interconnected to the Fab by a polypeptide linker (L1) and interconnected to the Fc by a polypeptide linker (L2), the order of domains determines which portion of the scFv is interconnected to L1 and which portion of the scFv is interconnected to L2.

An additional methodology that can be used, alone or in combination with one or more of the methodologies described herein, is by introducing one or more stabilizing mutations by mutating one or more surface residues of the scFv. In some aspects, one, two, three, four, five, six, or more than six residues are mutated in one or both of the VH and/or VL domain of the scFv. In certain aspects, changes are made in only the VH domain of the scFv. In certain aspects, changes are made in only the VL domain of the scFv. In certain aspects, changes are made in both the VH and VL domains of the scFv. The same number of changes may be made in each domain or a different number of changes may be made in each domain. In certain aspects, one or more of the changes is a conservative amino acid substitution from the residue present in the unmodified, parent scFv. In other aspects, one or more of the changes is a non-conservative amino acid substitution from the residue present in the unmodified, parent scFv. When multiple substitutions are made, either in one or both of the VH or VL domains of the scFv, each substitution is independently a conservative or a non-conservative substitution. In certain aspects, all of the substitutions are conservative substitutions. In certain aspects, all of the substitutions are non-conservative. In certain aspects, at least one of the substitutions is conservative. In certain aspects, at least one or the substitutions is non-conservative.

Yet a further methodology that can be used, alone or in combination with one or more of the additional methodologies described herein, is by introducing one or more substitutions by mutating one or more residues present in the VH and/or VL domain of the scFv to match the most frequent residue at said particular position of a consensus sequence of VH and/or VL domain of known antibodies. In certain aspects, substitutions are introduced at one, two, three, four, five, six, or more than six positions in one or both of the VH domain and/or the VL domain of the scFv. The same number of changes may be made in each domain or a different number of changes may be made in each domain. In certain aspects, one or more of the changes in sequence match that of a given consensus is a conservative amino acid substitution from the residue present in the unmodified VH and/or VL sequence. In other aspects, one or more of the changes represent a non-conservative amino acid substitution from the residue present in the unmodified VH and/or VL sequence. When multiple substitutions are made, either in one or both of the VH or VL domain of the scFv, each substitution is independently a conservative or a non-conservative substitution. In certain aspects, all of the substitutions are conservative substitutions. In certain aspects, all of the substitutions are non-conservative substitutions. In certain aspects, at least one of the substitutions is conservative. In certain aspects, at least one or the substitutions is non-conservative.

It should be noted that any of the modifications described as useful for modifying or stabilizing the scFv portion can be applied to modify the Fab portion. For example, the variable domains of the Fab portion of a biMab can be modified to improve stability, antigen binding and the like. Moreover, either the Fab or scFv portion can be modified to reduce immunogenicity.

In certain aspects, binding unit 2 (the BD) is an scFv, for example, an scFv derived from a conventional monoclonal antibody comprising a variable light chain (VL2) and a variable heavy chain (VH2) interconnected by a flexible linker, such as a glycine-serine linker. Optionally, the variable light and variable heavy chains of the scFv may be further interconnected via one or more disulphide linkages, and as described above, may include one or more mutations or variations. The scFv binds to a second epitope. In certain aspects the second epitope is different from the first epitope bound by binding unit 1. In other aspects the second epitope is the same as the first epitope bound by binding unit 1. In certain aspects, the scFv is derived from or based on the sequence of a conventional monoclonal antibody, such as a conventional murine, humanized or human antibody. In certain aspects, biMab containing the scFv derived from or based on the sequence of a conventional monoclonal antibody retains one or more functional activities of the conventional antibody (e.g., retains at least 80% or more (80%, 85%, 90%, 95%, 97%, 98%, 99% or 100%) of a functional activity). For example, in certain aspects, the biMab containing such an scFv retains one or more of the affinity for antigen, inhibitory activity, or cell killing activity of the conventional antibody.

In certain aspects, the scFv binds to epidermal growth factor receptor (EGFR). In certain aspects, the scFv binds to IGFR1. In certain aspects, the scFv binds to VEGF. In certain aspects, the scFv binds to Ang2. In certain aspects, the scFv is derived from or based on the sequence of a conventional monoclonal antibody that binds to any of EGFR, IGFR1, VEGF, Ang2, Psl or PcrV. Exemplary conventional monoclonal antibodies include panitumumab, dalotuzumab, bevacizumab or LC06. For example, in certain aspects, a biMab of the disclosure comprises an scFv as binding unit two, and this scFv comprises 1, 2, 3, 4, 5, or all 6 CDRs of panitumumab, dalotuzumab, bevacizumab or LC06.

In certain aspects, the scFv comprises a variable light chain portion (VL2) comprising the amino acid sequence set forth in any of SEQ ID NO: 26, 35 and 48. In certain aspects, the scFv comprises a variable heavy chain portion (VH2)

comprising the amino acid sequence set forth in any of SEQ ID NO: 27, 36, 49. In certain aspects, the scFv comprises the amino acid sequence set forth in any of SEQ ID NO: 25, 34 and 47. See FIGS. 6B, 6C, 7B, 7C, 8B and 8C.

The disclosure contemplates that, in certain aspects, a biMab of the disclosure comprises any of the binding unit is and binding unit 2s described herein, including any combination of a binding unit 1 and a binding unit 2 described herein. For example, in certain aspects, the disclosure provides a polypeptide comprising a Fab that binds to a particular target (e.g., that binds to an epitope on a particular target), such as a Fab comprising a particular amino acid sequence or encoded by a particular nucleotide sequence and/or an scFv that binds to a particular target (e.g., that binds to an epitope on a particular target), such as an scFv comprising a particular amino acid sequence or encoded by a particular nucleotide sequence.

As described in detail above, binding unit 1 and binding unit 2 are interconnected via linker polypeptide 1 (L1; also referred to as upper hinge/linker). Generally, the linkage is via the chimeric heavy chain of the biMab, such that the interconnection is via the heavy chain $C_H1$ domain of binding unit 1 (VH1, such as VH1 of a Fab) and a portion of binding unit 2 (e.g., if binding unit 2 is an scFv, the interconnection is via the VH2 or VL2 of the scFv). L1 can vary in length and sequence, and exemplary L1 configurations are described herein. The disclosure contemplates biMabs comprising any combination of binding units and linker polypeptides, including any combination of the specific binding units that bind desired target(s) and specific L1 and L2 polypeptide linkers described herein.

2. Fc Region

As used herein, "Fc region" encompasses domains derived from the constant region of an immunoglobulin, preferably a human immunoglobulin, including a fragment, analog, variant, mutant or derivative of the constant region. Suitable immunoglobulins include IgG1, IgG2, IgG3, IgG4, and other classes such as IgA, IgD, IgE and IgM. The Fc region may be a native sequence Fc region or an altered Fc region. The Fc region of an immunoglobulin generally comprises two constant domains, a $C_H2$ domain and a $C_H3$ domain, and optionally comprises a $C_H4$ domain. biMabs of the disclosure include an Fc region comprising a $C_H2$ domain and a $C_H3$ domain. In certain aspects, a biMab of the disclosure includes an Fc domain of the same class as the hinge portions of one or both of L1 or L2.

a. Altered Fc Regions

Altered Fc regions (also referred to herein as "variant Fc regions") may be used to alter the effector function and/or half life of a biMab of the disclosure. One or more alterations may be made in the Fc region in order to change functional and/or pharmacokinetic properties of molecules. Such alterations may result in a decrease or increase of C1q binding and complement dependent cytotoxicity (CDC) or of FcγR binding, for IgG, and antibody-dependent cellular cytotoxicity (ADCC), or antibody dependent cell-mediated phagocytosis (ADCP). The present disclosure encompasses biMabs wherein changes have been made to fine tune the effector function, either by enhancing or diminishing function or providing a desired effector function. Accordingly, in one aspect of the disclosure, the biMabs comprise a variant Fc region (i.e., Fc regions that have been altered as discussed below). biMabs comprising a variant Fc region are also referred to here as "Fc variant biMabs." As used herein "native" refers to the unmodified parental sequence and the biMab comprising a native Fc region is herein referred to as a "native Fc biMab". Fc variant biMabs can be generated by numerous methods well known to one skilled in the art. Non-limiting examples include, isolating antibody coding regions (e.g., from hybridoma) and making one or more desired substitutions in the Fc region. Alternatively, the antigen-binding portion (e.g., variable regions) of a biMab may be subcloned into a vector encoding a variant Fc region. In one aspect, the variant Fc region exhibits a similar level of inducing effector function as compared to the native Fc region. In another aspect, the variant Fc region exhibits a higher induction of effector function as compared to the native Fc. In another aspect, the variant Fc region exhibits lower induction of effector function as compared to the native Fc. Some specific aspects of variant Fc regions are detailed infra. Methods for measuring effector function are well known in the art.

In general, the effector function is modified through changes in the Fc region, including but not limited to, amino acid substitutions, amino acid additions, amino acid deletions and changes in post translational modifications to Fc amino acids (e.g. glycosylation). The methods described below may be used to fine tune the effector function of a biMab of the disclosure, a ratio of the binding properties of the Fc region for the FcR (e.g., affinity and specificity), resulting in a biMab with the desired properties.

It is understood that the Fc region as used herein includes the polypeptides comprising the constant region of an antibody molecule, excluding the first constant region immunoglobulin domain. Thus Fc refers to the last two constant region immunoglobulin domains of IgA, IgD, and IgG, and the last three constant region immunoglobulin domains of IgE and IgM, and, optionally, all or a portion of the flexible hinge N-terminal to these domains. For IgA and IgM, Fc may include the J chain. For IgG, Fc comprises immunoglobulin domains Cgamma2 and Cgamma3 (Cγ2 and Cγ3) and optionally a portion of the lower hinge between Cgamma1 (Cγ1) and Cgamma2 (Cγ2). Although the boundaries of the Fc region may vary, as used herein the human IgG heavy chain Fc region comprises residues A231 to its carboxyl-terminus, wherein the numbering is according to the EU index as set forth in Kabat. Fc may refer to this region in isolation, or this region in the context of an antibody, antibody fragment, or Fc fusion protein. Polymorphisms have been observed at a number of different Fc positions, including but not limited to positions 270, 272, 312, 315, 356, and 358 of IgG1 as numbered by the EU index, and thus slight differences between the presented sequence and sequences in the prior art may exist.

In one aspect, the present disclosure encompasses Fc variant biMabs which have altered binding properties for an Fc ligand (e.g., an Fc receptor, C1q) relative to a native Fc biMab. Examples of binding properties include but are not limited to, binding specificity, equilibrium dissociation constant ($K_d$), dissociation and association rates ($k_{off}$ and $k_{on}$ respectively), binding affinity and/or avidity. It is known in the art that the equilibrium dissociation constant ($K_d$) is defined as $k_{off}/k_{on}$. In certain aspects, a biMab comprising an Fc variant region with a low $K_d$ may be more desirable than a biMab with a high $K_d$. However, in some instances the value of the $k_{on}$ or $k_{off}$ may be more relevant than the value of the $K_d$. One skilled in the art can determine which kinetic parameter is most important for a given application. For example, a modification that reduces binding to one or more positive regulator (e.g., FcγRIIIA) and/or enhanced binding to an inhibitory Fc receptor (e.g., FcγRIIB) would be suitable for reducing ADCC activity. Accordingly, the ratio of binding affinities (e.g., the ratio of equilibrium dissociation constants ($K_d$)) for different receptors can indicate if the ADCC activity of an Fc variant biMab of the disclosure is enhanced or decreased. Additionally, a modification that reduces binding to C1q would be suitable for reducing or eliminating CDC activity.

In one aspect, Fc variant biMabs exhibit altered binding affinity for one or more Fc receptors including, but not limited to FcRn, FcγRI (CD64) including isoforms FcγRIA, FcγRIB, and FcγRIC; FcγRII (CD32 including isoforms FcγRIIA, FcγRIIB, and FcγRIIC); and FcγRIII (CD16, including isoforms FcγRIIIA and FcγRIIIB) as compared to a native Fc biMab.

In certain aspects, an Fc variant biMab has increased affinity for an Fc ligand. In other aspects, an Fc variant biMab has decreased affinity for an Fc ligand relative to a native Fc biMab.

In a specific aspect, an Fc variant biMab has enhanced binding to the Fc receptor FcγRIIIA In another specific aspect, an Fc variant biMab has enhanced binding to the Fc receptor FcγRIIB. In a further specific aspect, an Fc variant biMab has enhanced binding to both the Fc receptors FcγRIIIA and FcγRIIB. In certain aspects, Fc variant biMabs that have enhanced binding to FcγRIIIA do not have a concomitant increase in binding the FcγRIIB receptor as compared to a native Fc biMab. In a specific aspect, an Fc variant biMab has reduced binding to the Fc receptor FcγRIIIA In a further specific aspect, an Fc variant biMab has reduced binding to the Fc receptor FcγRIIB. In another specific aspect, and Fc variant biMab has enhanced binding to the Fc receptor FcRn. In still another specific aspect, an Fc variant biMab exhibiting altered affinity for FcγRIIIA and/or FcγRIIB has enhanced binding to the Fc receptor FcRn. In yet another specific aspect, an Fc variant biMab exhibiting altered affinity for FcγRIIIA and/or FcγRIIB has altered binding to C1q relative to a native Fc biMab.

In another aspect, Fc variant biMabs exhibit increased or decreased affinities to C1q relative to a native Fc biMab. In still another specific aspect, an Fc variant biMab exhibiting altered affinity for C1q has enhanced binding to the Fc receptor FcRn. In yet another specific aspect, an Fc variant biMab exhibiting altered affinity for C1q has altered binding to FcγRIIIA and/or FcγRIIB relative to a native Fc biMab.

It is well known in the art that antibodies are capable of directing the attack and destruction of targeted antigen through multiple processes collectively known in the art as antibody effector functions. One of these processes, known as "antibody-dependent cell-mediated cytotoxicity" or "ADCC" refers to a form of cytotoxicity in which secreted Ig bound onto Fc gamma receptors (FcγRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins. Specific high-affinity IgG antibodies directed to the surface of target cells "arm" the cytotoxic cells and are required for such killing. Lysis of the target cell is extracellular, requires direct cell-to-cell contact, and does not involve complement. Another process encompassed by the term effector function is complement-dependent cytotoxicity (hereinafter referred to as "CDC") which refers to a biochemical event of antibody-mediated target cell destruction by the complement system. The complement system is a complex system of proteins found in normal blood plasma that combines with antibodies to destroy pathogenic bacteria and other foreign cells. Still another process encompassed by the term effector function is antibody dependent cell-mediated phagocytosis (ADCP) which refers to a cell-mediated reaction wherein nonspecific cytotoxic cells that express one or more effector ligands recognize bound antibody on a target cell and subsequently cause phagocytosis of the target cell.

It is contemplated that Fc variant biMabs are characterized by in vitro functional assays for determining one or more FcγR mediated effector cell functions. In certain aspects, Fc variant biMabs have similar binding properties and effector cell functions in in vivo models (such as those described and disclosed herein) as those in in vitro based assays. However, the present disclosure does not exclude Fc variant biMabs that do not exhibit the desired phenotype in in vitro based assays but do exhibit the desired phenotype in vivo.

The serum half-life of proteins comprising Fc regions may be increased by increasing the binding affinity of the Fc region for FcRn. The term "antibody half-life" as used herein means a pharmacokinetic property of an antibody that is a measure of the mean survival time of antibody molecules following their administration. Antibody half-life can be expressed as the time required to eliminate 50 percent of a known quantity of immunoglobulin from the patient's body (or other mammal) or a specific compartment thereof, for example, as measured in serum, i.e., circulating half-life, or in other tissues. Half-life may vary from one immunoglobulin or class of immunoglobulin to another. In general, an increase in antibody (or biMab) half-life results in an increase in mean residence time (MRT) in circulation for the biMab administered.

The increase in half-life allows for the reduction in amount of drug given to a patient as well as reducing the frequency of administration. To increase the serum half life of a biMab, one may incorporate a salvage receptor binding epitope into the biMab (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule. Alternatively, biMabs of the disclosure with increased half-lives may be generated by modifying amino acid residues identified as involved in the interaction between the Fc and the FcRn receptor (see, for examples, U.S. Pat. Nos. 6,821,505 and 7,083,784; and WO 09/058492). In addition, the half-life of biMabs of the disclosure may be increased by conjugation to PEG or albumin by techniques widely utilized in the art.

In one aspect, the present disclosure provides Fc variants, wherein the Fc region comprises a modification (e g, amino acid substitutions, amino acid insertions, amino acid deletions) at one or more positions selected from the group consisting of 221, 225, 228, 234, 235, 236, 237, 238, 239, 240, 241, 243, 244, 245, 247, 250, 251, 252, 254, 255, 256, 257, 262, 263, 264, 265, 266, 267, 268, 269, 279, 280, 284, 292, 296, 297, 298, 299, 305, 308, 313, 316, 318, 320, 322, 325, 326, 327, 328, 329, 330, 331, 332, 333, 334, 339, 341, 343, 370, 373, 378, 392, 416, 419, 421, 428, 433, 434, 435, 436, 440, and 443 as numbered by the EU index as set forth in Kabat. Optionally, the Fc region may comprise a modification at additional and/or alternative positions known to one skilled in the art (see, e.g., U.S. Pat. Nos. 5,624,821; 6,277,375; 6,737,056; 7,083,784; 7,317,091; 7,217,797; 7,276,585; 7,355,008; 2002/0147311; 2004/0002587; 2005/0215768; 2007/0135620; 2007/0224188; 2008/0089892; WO 94/29351; and WO 99/58572). Additional, useful amino acid positions and specific substitutions are exemplified in Tables 2, and 6-10 of U.S. Pat. No. 6,737,056; the tables presented in FIG. 41 of US 2006/024298; the tables presented in FIGS. 5, 12, and 15 of US 2006/235208; the tables presented in FIGS. 8, 9 and 10 of US 2006/0173170 and the tables presented in FIGS. 8-10, 13 and 14 of WO 09/058492.

In a specific aspect, the present disclosure provides an Fc variant, wherein the Fc region comprises at least one substitution selected from the group consisting of 221K, 221Y, 225E, 225K, 225W, 228P, 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235E, 235F, 236E, 237L, 237M, 237P, 239D, 239E, 239N, 239Q, 239F, 239T, 239H, 239Y, 240I, 240A, 240T, 240M, 241W, 241 L, 241Y, 241E, 241R. 243W, 243L 243Y, 243R, 243Q, 244H, 245A, 247L, 247V, 247G, 250E, 250Q, 251F, 252L, 252Y, 254S, 254T, 255L, 256E, 256F, 256M, 257C, 257M, 257N, 262I, 262A, 262T, 262E, 263I, 263A, 263T, 263M, 264L, 264I, 264W, 264T, 264R, 264F, 264M, 264Y, 264E, 265A, 265G, 265N, 265Q, 265Y, 265F, 265V, 265I, 265L, 265H, 265T, 266I, 266A, 266T, 266M, 267Q, 267L, 268E, 269H, 269Y, 269F, 269R, 270E, 280A, 284M, 292P, 292L, 296E, 296Q, 296D, 296N, 296S, 296T, 296L, 296I, 296H, 296G, 297S, 297D, 297E, 298A, 298H, 298I, 298T, 298F, 299I, 299L, 299A, 299S, 299V, 299H, 299F, 299E, 305I, 308F 313F, 316D, 318A, 318S, 320A, 320S, 322A, 322S, 325Q, 325L, 325I, 325D, 325E, 325A, 325T, 325V, 325H, 326A, 326D, 326E, 326G, 326M, 326V, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 331G, 331A, 331L, 331M, 331F, 331W, 331K, 331Q, 331E, 331S, 331V, 331I, 331C, 331Y, 331H, 331R, 331N, 331D, 331T, 332D, 332S, 332W, 332F, 332E, 332N, 332Q, 332T, 332H, 332Y, 332A, 333A, 333D, 333G, 333Q, 333S, 333V, 334A, 334E, 334H, 334L, 334M, 334Q, 334V, 334Y, 339T, 370E, 370N, 378D, 392T, 396L, 416G, 419H, 421K, 428L, 428F, 433K, 433L, 434A, 424F, 434W, 434Y, 436H, 440Y and 443W as numbered by the EU index as set forth in Kabat. Optionally, the Fc region may comprise additional and/or alternative amino acid substitutions known to one skilled in the art including, but not limited to, those exemplified in Tables 2, and 6-10 of U.S. Pat. No. 6,737,056; the tables presented in FIG. 41 of US 2006/024298; the tables presented in FIGS. 5, 12, and 15 of US 2006/235208; the tables presented in FIGS. 8, 9 and 10 of US 2006/0173170 and the tables presented in FIGS. 8, 9 and 10 of WO 09/058492.

In a specific aspect, the present disclosure provides an Fc variant biMab, wherein the Fc region comprises at least one modification (e.g., amino acid substitutions, amino acid insertions, amino acid deletions) at one or more positions selected from the group consisting of 228, 234, 235 and 331 as numbered by the EU index as set forth in Kabat. Position 228 is underlined in SEQ ID NO:10 in FIG. 2A and positions 234, 235 and 331 are underlined in SED ID NO:16 in FIG. 2C. In one aspect, the modification is at least one substitution selected from the group consisting of 228P, 234F, 235E, 235F, 235Y, and 331S as numbered by the EU index as set forth in Kabat.

In another specific aspect, the present disclosure provides an Fc variant biMab, wherein the Fc region is an IgG4 Fc region and comprises at least one modification at one or more positions selected from the group consisting of 228 and 235 as numbered by the EU index as set forth in Kabat. In still another specific aspect, the Fc region is an IgG4 Fc region and the non-naturally occurring amino acids are selected from the group consisting of 228P, 235E and 235Y as numbered by the EU index as set forth in Kabat.

In another specific aspect, the present disclosure provides an Fc variant biMab, wherein the Fc region comprises at least one non-naturally occurring amino acid at one or more positions selected from the group consisting of 239, 330 and 332 as numbered by the EU index as set forth in Kabat. Positions 239, 330 and 332 are shown in bold and are doubled underlined in SEQ ID NO:16 in FIG. 2C. In one aspect, the modification is at least one substitution selected from the group consisting of 239D, 330L, 330Y, and 332E as numbered by the EU index as set forth in Kabat. See, U.S. Pat. No. 7,317,091, incorporated herein by referenced in its entirety.

In a specific aspect, the present disclosure provides an Fc variant biMab, wherein the Fc region comprises at least one non-naturally occurring amino acid at one or more positions selected from the group consisting of 252, 254, and 256 as numbered by the EU index as set forth in Kabat. Positions 252, 254, 256 are shown larger and wavy underlined in SEQ ID NO:16 in FIG. 2C. In one aspect, the modification is at least one substitution selected from the group consisting of 252Y, 254T and 256E as numbered by the EU index as set forth in Kabat. See, U.S. Pat. No. 7,083,784, incorporated herein by reference in its entirety.

In certain aspects, the present disclosure provides an Fc variant biMab, wherein the Fc region comprises a non-naturally occurring amino acid at position 428 as numbered by the EU index as set forth in Kabat. In one aspect, the modification at position 428 is selected from the group consisting of 428T, 428L, 428F, and 428S as numbered by the EU index as set forth in Kabat. See, U.S. Pat. No. 7,670,600, incorporated herein by reference in its entirety. In another aspect, an Fc variant biMab may further comprises a non-naturally occurring amino acid at position 434 as numbered by the EU index as set forth in Kabat. In one aspect, the modification at position 434 is selected from the group consisting of 434A, 434S, and 434F as numbered by the EU index as set forth in Kabat. In other aspects, the present disclosure provides an Fc variant biMab, wherein the Fc region comprises a non-naturally occurring amino acid at positions 428 and 434 as numbered by the EU index as set forth in Kabat. In a specific aspect, the Fc region comprises 428L, 434S. See, U.S. Pat. No. 8,088,376. Positions 428 and 434 are bolded and underlined in SEQ ID NO:18 in FIG. 2C In certain aspects, the effector functions elicited by IgG antibodies strongly depend on the carbohydrate moiety linked to the Fc region of the protein (Claudia Ferrara et al., 2006, Biotechnology and Bioengineering 93:851-861). Thus, glycosylation of the Fc region can be modified to increase or decrease effector function (see for examples, Umana et al, 1999, Nat. Biotechnol 17:176-180; Davies et al., 2001, Biotechnol Bioeng 74:288-294; Shields et al, 2002, J Biol Chem 277:26733-26740; Shinkawa et al., 2003, J Biol Chem 278:3466-3473; U.S. Pat. Nos. 6,602,684; 6,946,292; 7,064,191; 7,214,775; 7,393,683; 7,425,446; 7,504,256; U.S. Publication. Nos. 2003/0157108; 2003/0003097; 2009/0010921; POTELLIGENT™ technology (Biowa, Inc. Princeton, N.J.); GLYCOMAB™ glycosylation engineering technology (GLYCART biotechnology AG, Zurich, Switzerland)). Accordingly, in one aspect the Fc regions of biMabs of the disclosure comprise altered glycosylation of amino acid residues. In another aspect, the altered glycosylation of the amino acid residues results in lowered effector function. In another aspect, the altered glycosylation of the amino acid residues results in increased effector function. In a specific aspect, the Fc region has reduced fucosylation. In another aspect, the Fc region is afucosylated (see for examples, U.S. Patent Application Publication No. 2005/0226867). In one aspect, these biMabs with increased effector function, specifically ADCC, are generated in host cells (e.g., CHO cells, *Lemna minor*) engineered to produce highly defucosylated polypeptide with over 100-fold higher ADCC compared to polypeptide produced by the parental cells (Mori et al., 2004, Biotechnol Bioeng 88:901-908; Cox et al., 2006, Nat Biotechnol., 24:1591-7).

Addition of sialic acid to the oligosaccharides on IgG molecules can enhance their anti-inflammatory activity and alter their cytotoxicity (Keneko et al., Science, 2006, 313: 670-673; Scallon et al., Mol. Immuno. 2007 March; 44(7): 1524-34). The studies referenced above demonstrate that IgG molecules with increased sialylation have anti-inflammatory properties whereas IgG molecules with reduced sialylation have increased immunostimulatory properties (e.g., increase ADCC activity). Therefore, a biMab can be modified with an appropriate sialylation profile for a particular application (US Publication No. 2009/0004179 and International Publication No. WO 2007/005786).

In one aspect, the Fc regions of biMabs of the disclosure comprise an altered sialylation profile compared to the native Fc region. In one aspect, the Fc regions of biMabs of the disclosure comprise an increased sialylation profile compared to the native Fc region. In another aspect, the Fc regions of biMabs of the disclosure comprise a decreased sialylation profile compared to the native Fc region.

In one aspect, the Fc variants of the present disclosure may be combined with other known Fc variants such as those disclosed in Ghetie et al., 1997, Nat Biotech. 15:637-40; Duncan et al, 1988, Nature 332:563-564; Lund et al., 1991, J. Immunol 147:2657-2662; Lund et al, 1992, Mol Immunol 29:53-59; Alegre et al, 1994, Transplantation 57:1537-1543; Hutchins et al., 1995, Proc Natl. Acad Sci USA 92:11980-11984; Jefferis et al, 1995, Immunol Lett. 44:111-117; Lund et al., 1995, Faseb J 9:115-119; Jefferis et al, 1996, Immunol Lett 54:101-104; Lund et al, 1996, J Immunol 157:4963-4969; Armour et al., 1999, Eur J Immunol 29:2613-2624; Idusogie et al, 2000, J Immunol 164: 4178-4184; Reddy et al, 2000, J Immunol 164:1925-1933; Xu et al., 2000, Cell Immunol 200:16-26; Idusogie et al, 2001, J Immunol 166:2571-2575; Shields et al., 2001, J Biol Chem 276:6591-6604; Jefferis et al, 2002, Immunol Lett 82:57-65; Presta et al., 2002, Biochem Soc Trans 30:487-490); U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 7,122,637; 7,183,387; 7,332,581; 7,335,742; 7,371,826; 6,821,505; 6,180,377; 7,317,091; 7,355,008; U.S. Patent publication 2004/0002587; and International Patent publication WO 99/58572. Other modifications and/or substitutions and/or additions and/or deletions of the Fc domain will be readily apparent to one skilled in the art.

It is notable that polypeptides presented in the biMab format comprising a native Fc retain the ability to bind FcRn and C1q and to mediate ADCC, as shown in the examples. Thus, in certain aspects, a biMab retains the ability to bind FcRn and/or C1q and/or one or more Fcgamma receptors (FcγRs). For example, in certain aspects, a biMab retains at least 70%, 75%, 80%, 85%, 90%, 95%, 96%, 97%, 98%, 99%, or 100% of the ability to bind FcRn and/or C1q and/or one or more FcγRs, as compared to a conventional antibody that binds to one of the epitopes to which the biMab binds. In certain aspects, a biMab is generated from the binding domains of one or two conventional antibodies, and the comparison of activity is made to one or both of those conventional antibodies.

Altered Fc regions may also be used to generate heavy chain heterodimers, resulting in biMabs comprising two different heavy-light chain pairs. To facilitate the formation of heterodimers the interface between a pair of Fc regions is engineered to maximize the percentage of heterodimers which are recovered from recombinant cell culture. In certain aspects, the interface comprises at least a part of the CH3 domain. In this method, a "protrusion" is generated by replacing one or more, small amino acid side chains from the interface of the first antibody molecule with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers. CH3 modifications include, for example, Y407V/T366S/L368A on one heavy chain and T366W on the other heavy chain; S354C/T366W on one heavy chain and Y349C/Y407V/T366S/L368A on the other heavy chain. Additional modifications resulting in a protrusion on one chain and a cavity on the other are described in U.S. Pat. No. 7,183,076; and Merchant et al., 1998, Nat. Biotech 16:677-681. Other modifications which may be used to generate heterodimers include but are not limited to those which alter the charge polarity across the Fc dimer interface such that co-expression of electrostatically matched Fc regions results in heterodimerization. Modifications which alter the charge polarity include, but are not limited to, those presented in the Table 1 below (also see, WO 2007/147901; Gunasekaran et al., 2010, JBC 285: 19637-46). In addition, Davis et al. (2010, Prot. Eng. Design & Selection 23:195-202) describe a heterodimeric Fc platform using strand-exchanged engineered domain (SEED) CH3 regions which are derivatives of human IgG and IgA CH3 domains (also, see WO 2007/110205).

TABLE 1

CH3 modifications for heterodimerization

| Modification(s) in Fc region of one heavy chain | Modification(s) in Fc region of other heavy chain |
| --- | --- |
| K370E/D399K/K439D | D356K/E357K/K409D |
| K409D | D399K |
| K409E | D399K |
| K409E | D399R |
| K409D | D399R |
| D339K | E356K |
| D399K/E356K | K409D/K392D |
| D399K/E356K | K409D/K439D |
| D399K/E357K | K409D/K370D |
| D399K/E356K/E357K | K409D/K392D/K370D |
| D399K/E357K | K409D/K392D |
| K392D/K409D | D399K |
| K409D/K360D | D399K |

3. Glycosylation

In addition to the ability of glycosylation to alter the effector function of polypeptides, modified glycosylation in the variable region can alter the affinity of the antibody (or biMab) for a target antigen. In one aspect, the glycosylation pattern in the variable region of the present biMabs is modified. For example, an aglycoslated biMab can be made (i.e., the biMab lacks glycosylation). Glycosylation can be altered to, for example, increase the affinity of the biMab for a target antigen. Such carbohydrate modifications can be accomplished by, for example, altering one or more sites of glycosylation within the biMab sequence. For example, one or more amino acid substitutions can be made that result in elimination of one or more variable region framework glycosylation sites to thereby eliminate glycosylation at that site. Such aglycosylation may increase the affinity of the biMab for antigen. Such an approach is described in further detail in U.S. Pat. Nos. 5,714,350 and 6,350,861. One or more amino acid substitutions can also be made that result in elimination of a glycosylation site present in the Fc region (e.g., Asparagine 297 of IgG). Furthermore, aglycosylated biMabs may be produced in bacterial cells which lack the necessary glycosylation machinery.

4. Polypeptide Linkers

Figure 26:
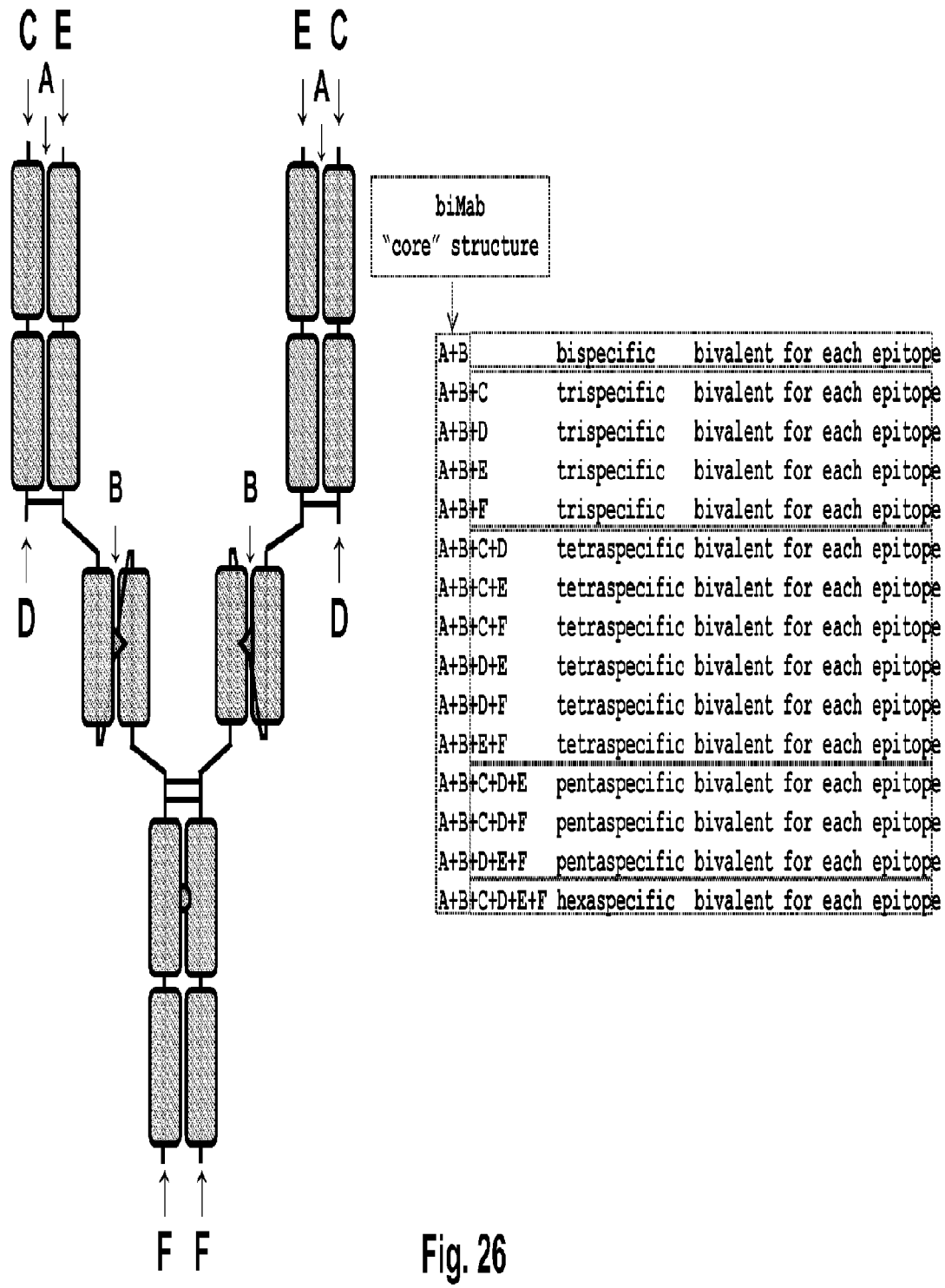
FIG. 26 illustrates multispecific binding units that can be generated using the biMab "core" structure as a base. As schematically illustrated, the biMab "core" structure is made of binding units A and B (also see FIG. 1). Using the A+B "core" structure, other binding units can be linked at each terminal end of the polypeptides that make up the A+B "core," specifically at positions C, D, E and F. Thus, using the biMab core as base structure, trispecific binding units (A+B+C; A+B+D; A+B+E; A+B+F); tetraspecific binding units (A+B+C+D; A+B+C+E; A+B+C+F; A+B+D+E; A+B+D+F; A+B+E+F); pentaspecific binding units (A+B+C+D+E; A+B+C+D+F; A+B+D+E+F); and hexaspecific binding units (A+B+C+D+E+F) can be generated. As indicated in the Table, all the binding proteins are bivalent for each epitope. Binding units B, C, D, E, and F can be any binding moiety, for example, antibody fragments (such as scFv in any possible domain orientation and with any linker length and composition); single antibody domains (such as VH or VL); antibody mimetics, such as polypeptide scaffolds that mimic the binding structure of an antibody; protein domains, such as immunologic mediators (e.g., cytokines); ligand binding domains; and macromolecular toxins. The binding units B, C, D, E, and F can be linked using genetic methods or by in vitro chemical- or protein-mediated conjugation methods. The linker connecting the units B, C, D, E, and F can be but not limited to (GGGGS) repeats. Site-specific protease cleavage sites can be engineered in or around the linkers if the release of the units B, C, D, E, and F is needed (see for e.g., FIG. 29). The various binding units (A, B, C, D, E, and F) may bind epitopes from the same or different target antigens; when the same target is bound then the binding units bind to non-overlapping regions (i.e., different, preferably non-overlapping epitopes). It will be understood based on the teachings herein that the valency of any of the above binding proteins can be increased by the incorporation of binding units that bind the same epitope. For example, but not by way of limitation, the addition of the same binding unit at C and D will result in a binding molecule that is bivalent for the different epitopes bound by A and B and will be tetravalent for the epitope bound by the binding units at C and D (which bind the same epitope).
Figure 27A:
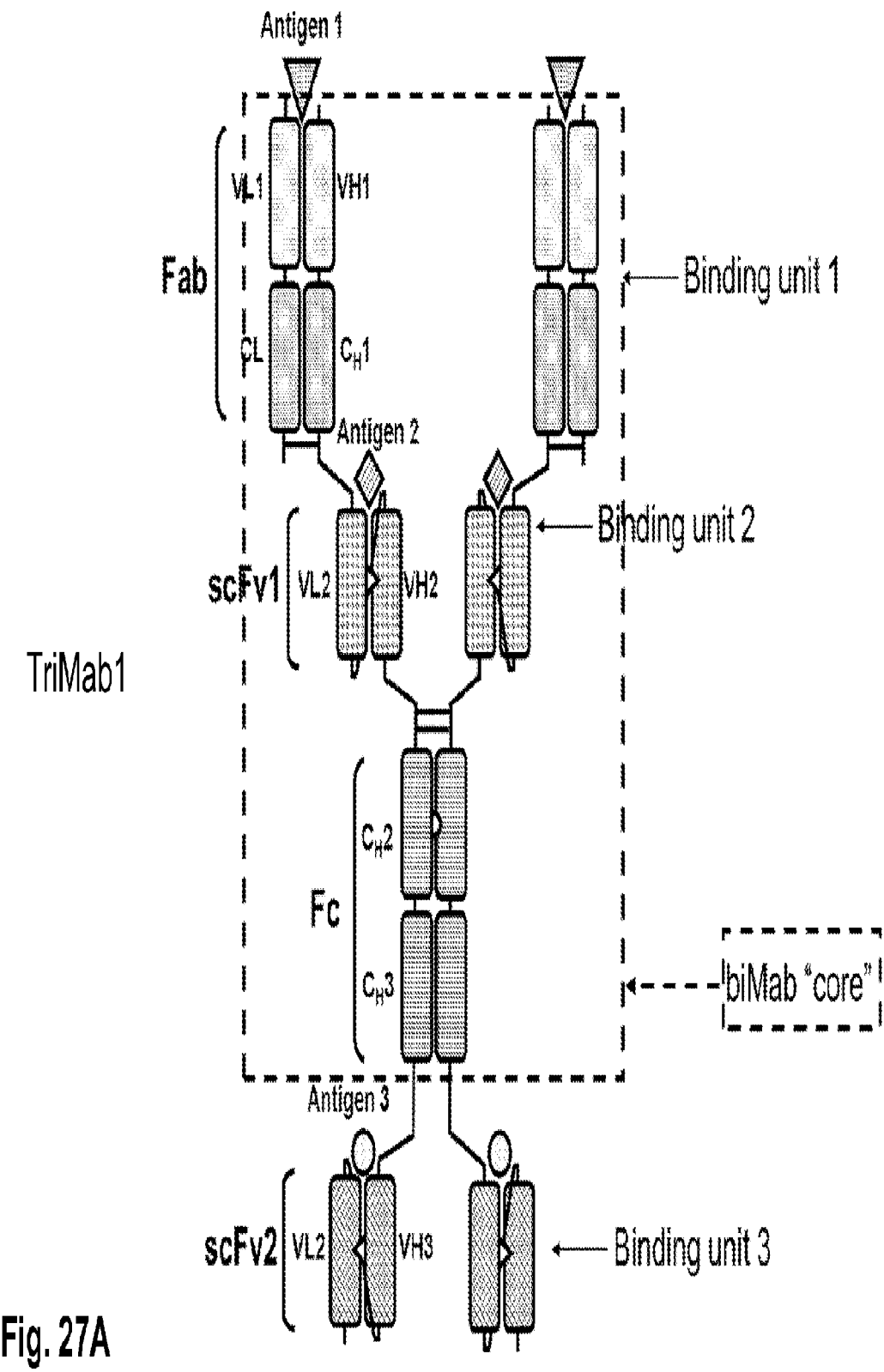
FIG. 27 illustrates several multispecific binding units that can be generated by linking additional scFv units to the biMab "core" structure (indicated by the dashed box) as described in FIG. 26. Trispecific binding units A+B+F (TriMab1); A+B+C (TriMab2); A+B+E (TriMab3); and A+B+D (TriMab4) are illustrated in Panels A, B, C and D, respectively. Tetraspecific binding units (A+B+C+D (TetraMab1) and A+B+D+E (TetraMab2) are illustrated in Panels E and F, respectively. Pentaspecific binding units A+B+C+D+E (PentaMab1); A+B+C+D+F (PentaMab2); and A+B+D+E+F PentaMab3) are illustrated in Panels G, H and I, respectively. The hexaspecific binding unit A+B+C+D+E+F is illustrated in Panel J.
Figure 27B:
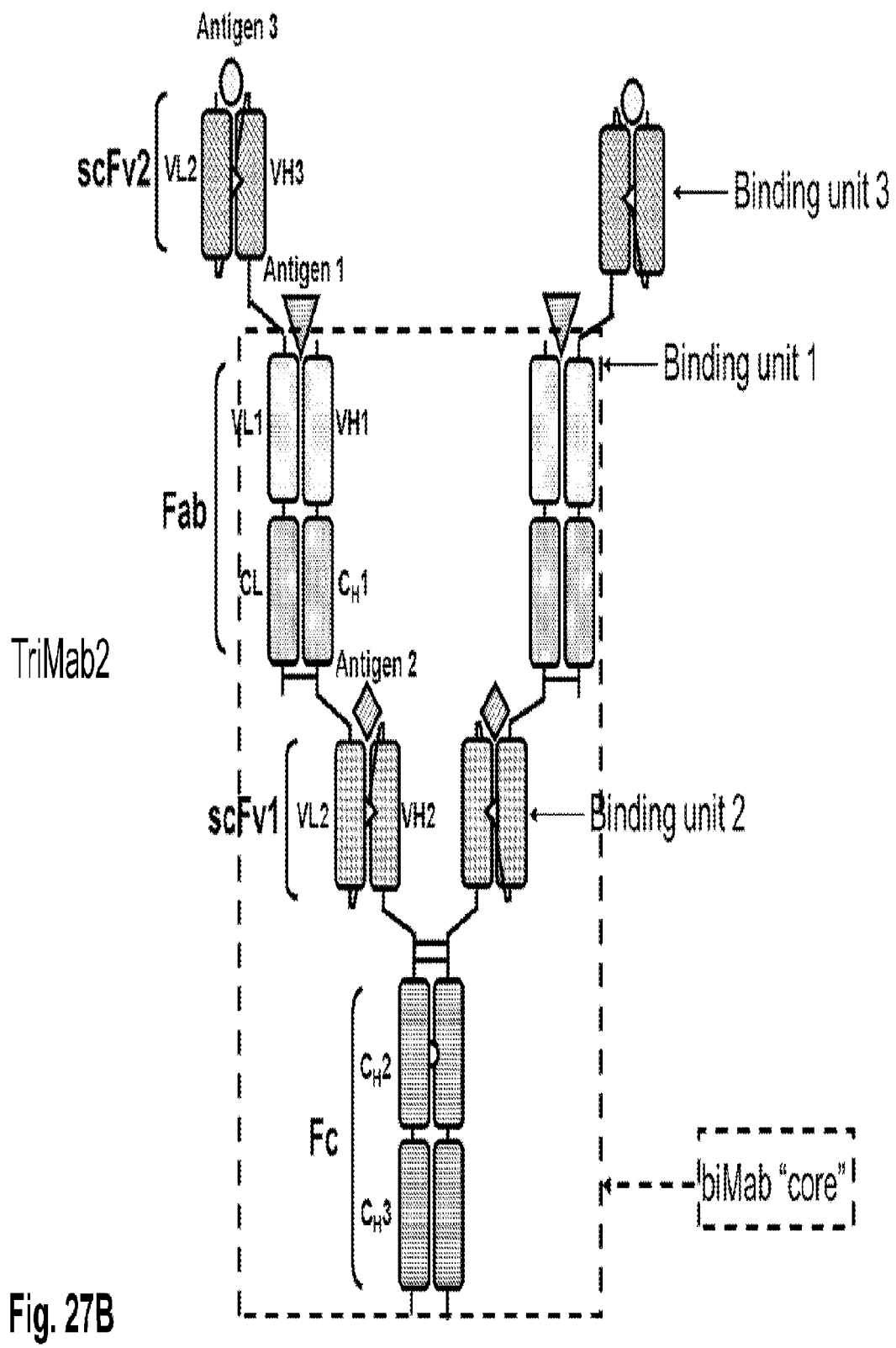
Figure 27C:
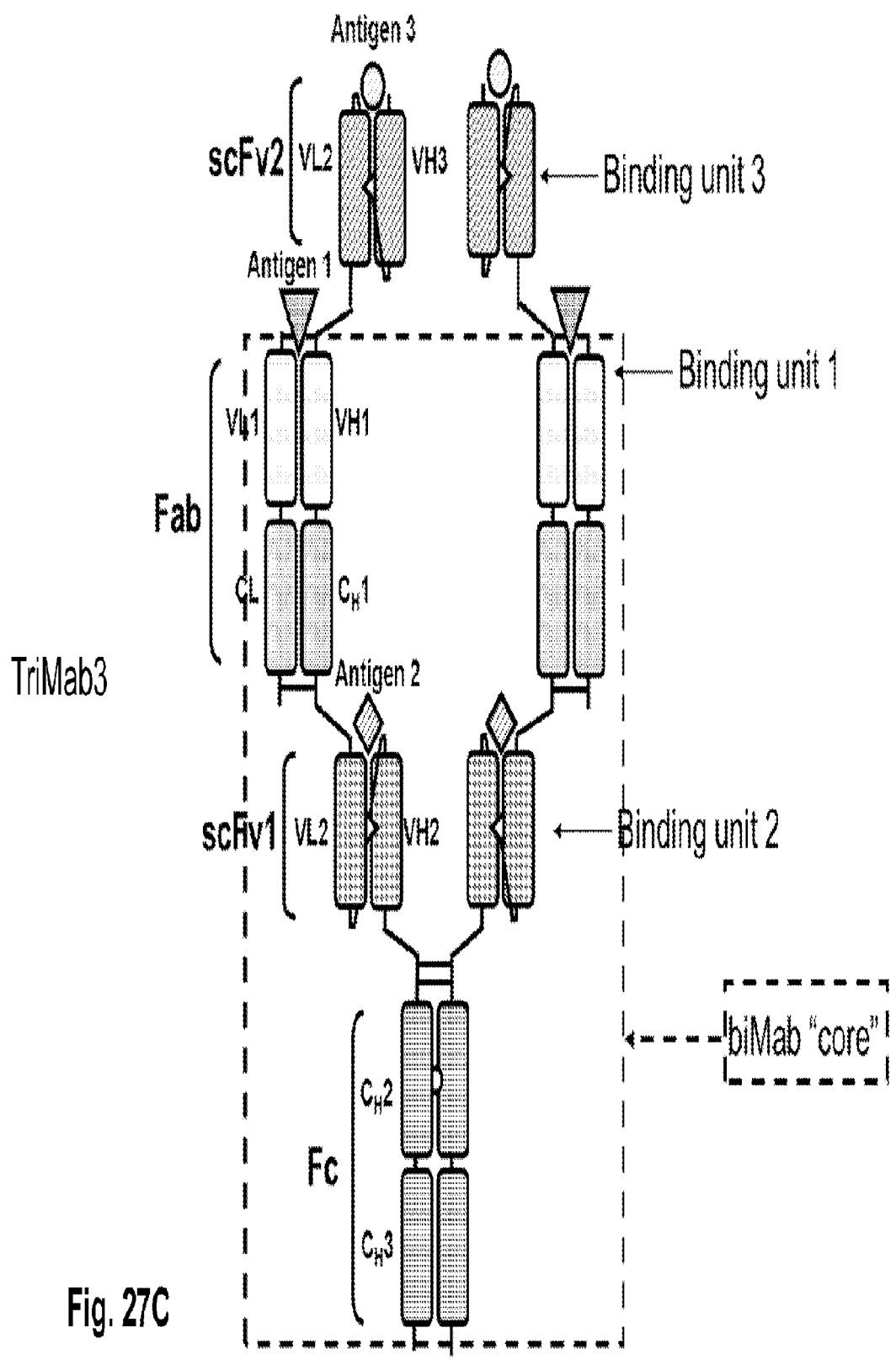
Figure 27D:
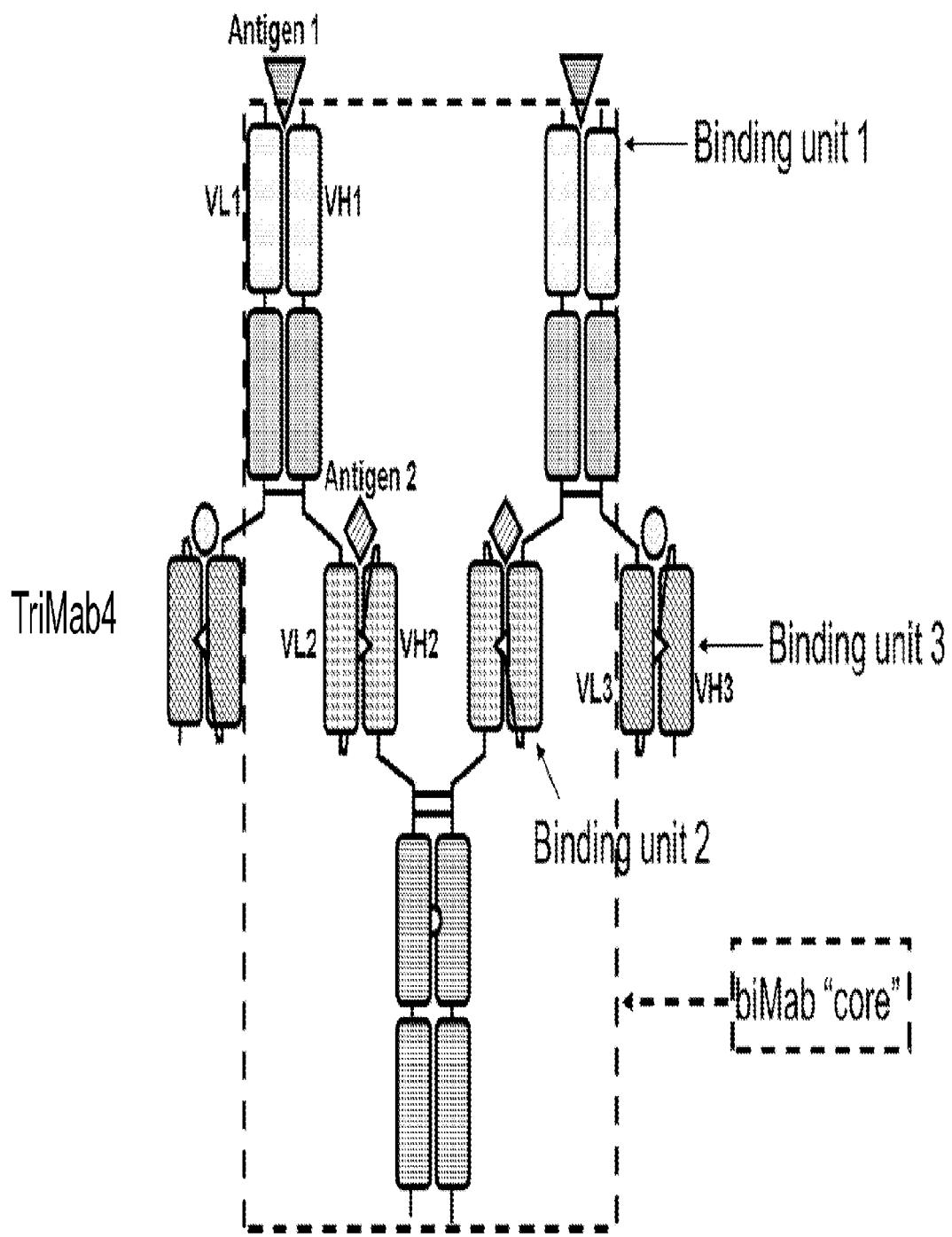
Figure 27E:
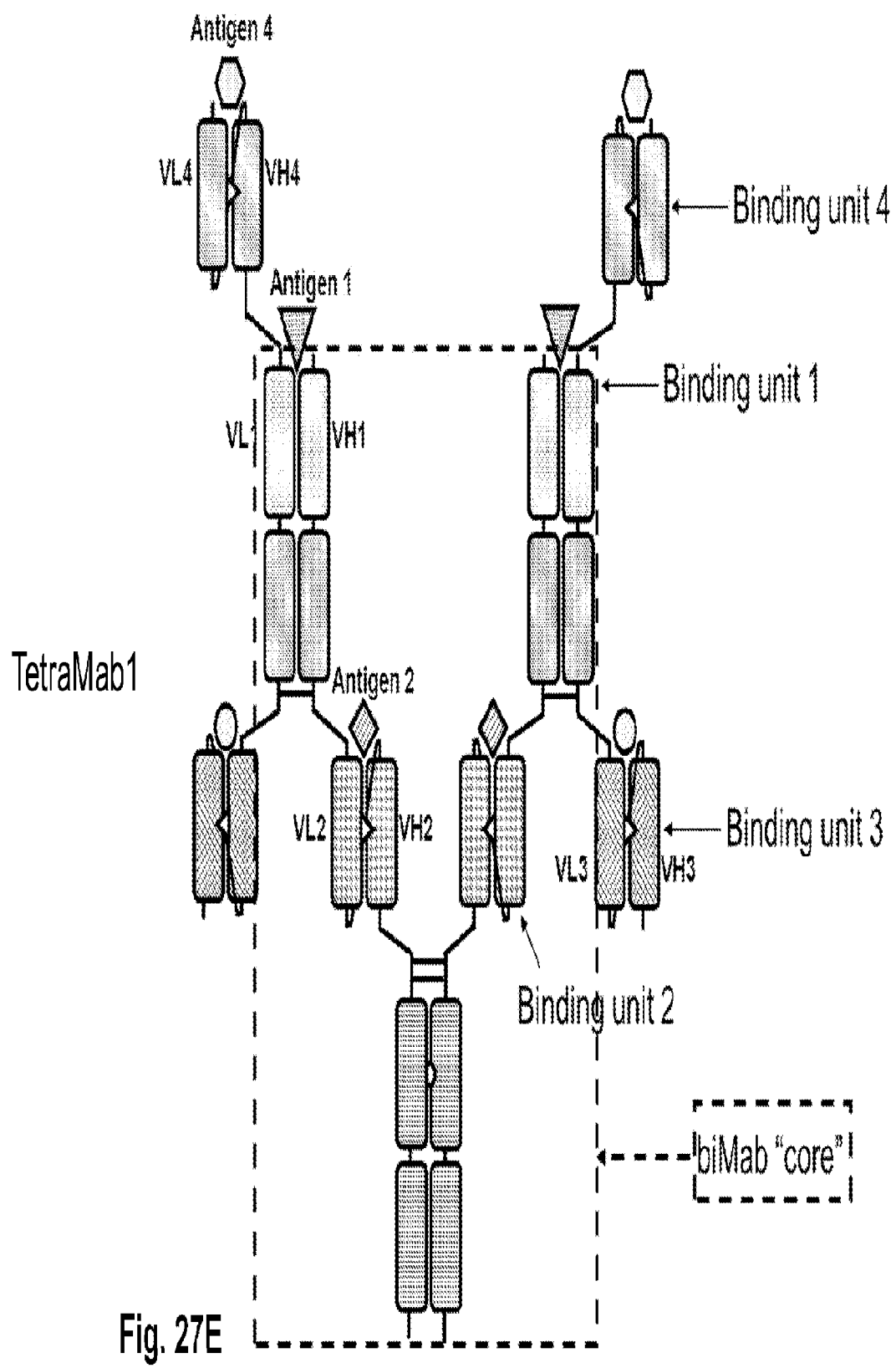
Figure 27F:
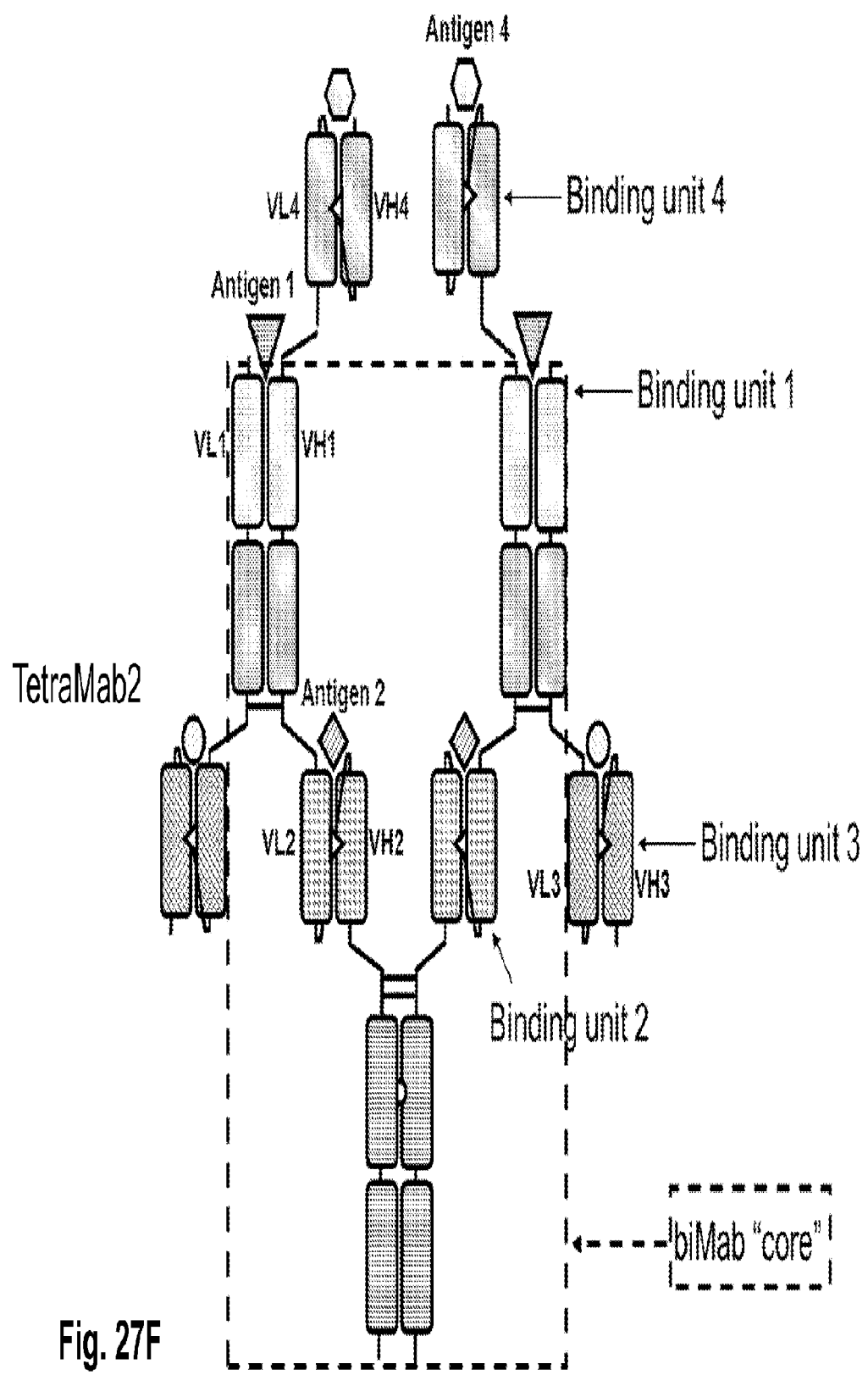
Figure 27G:
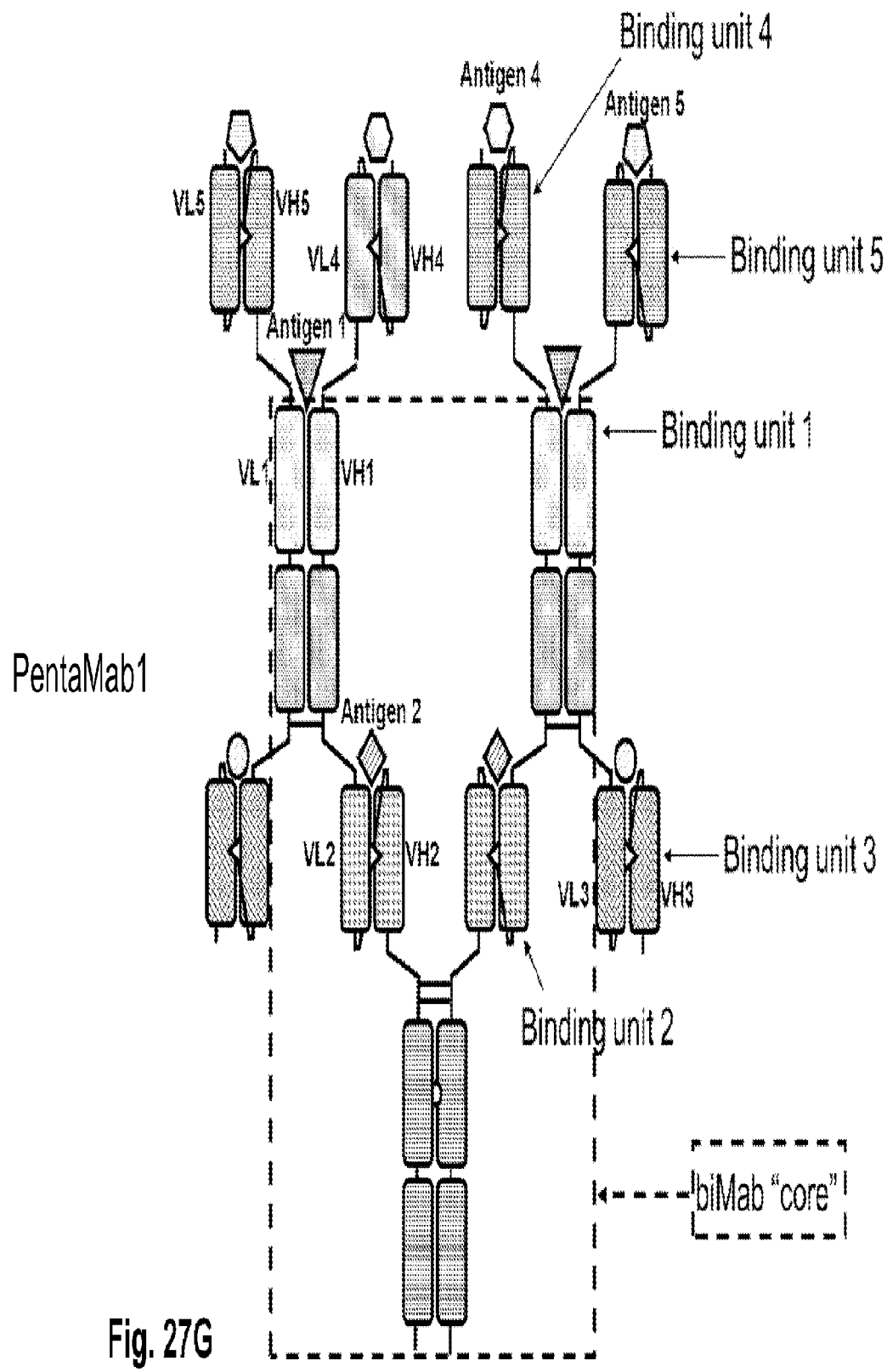
Figure 27H:
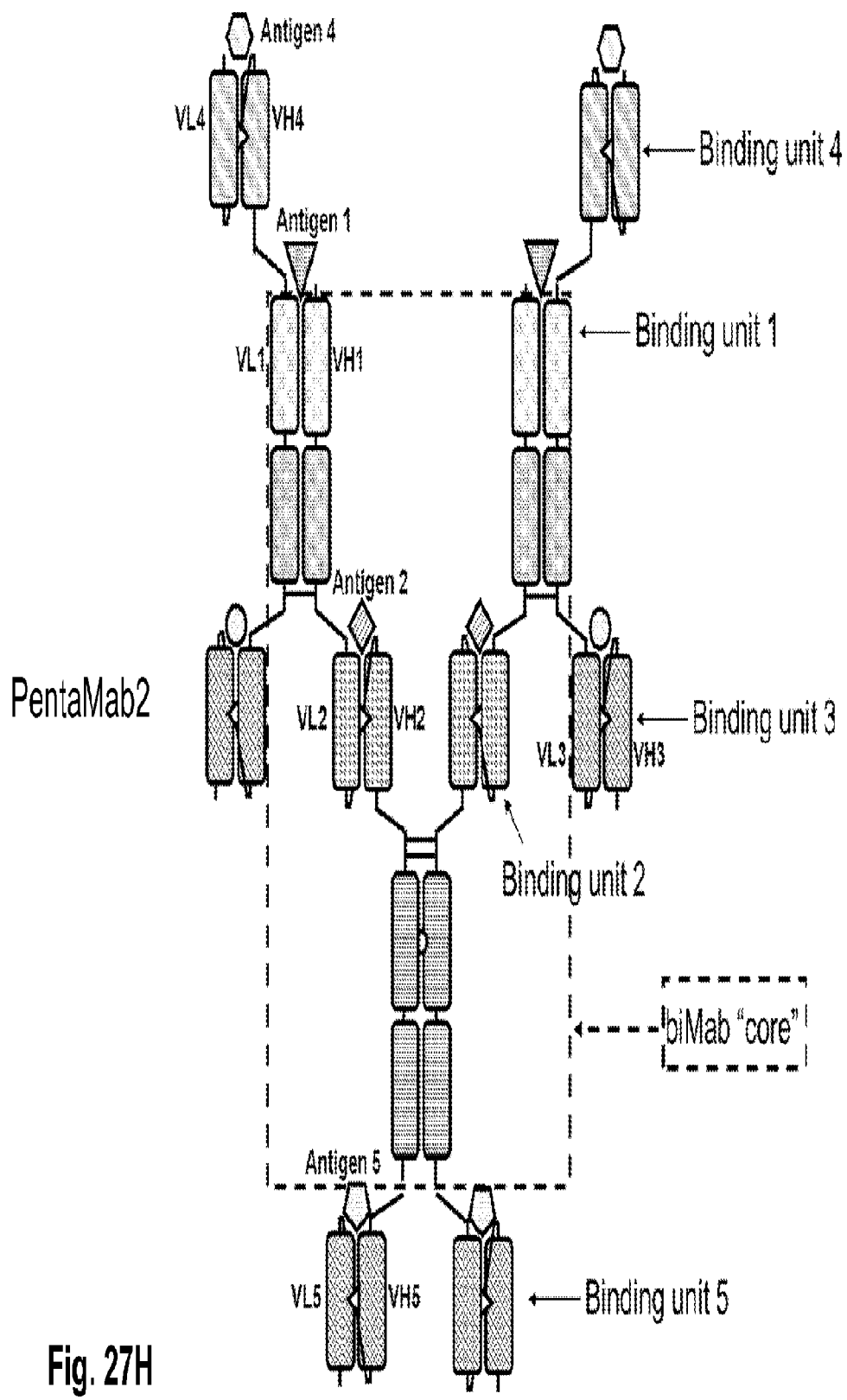
Figure 27I:
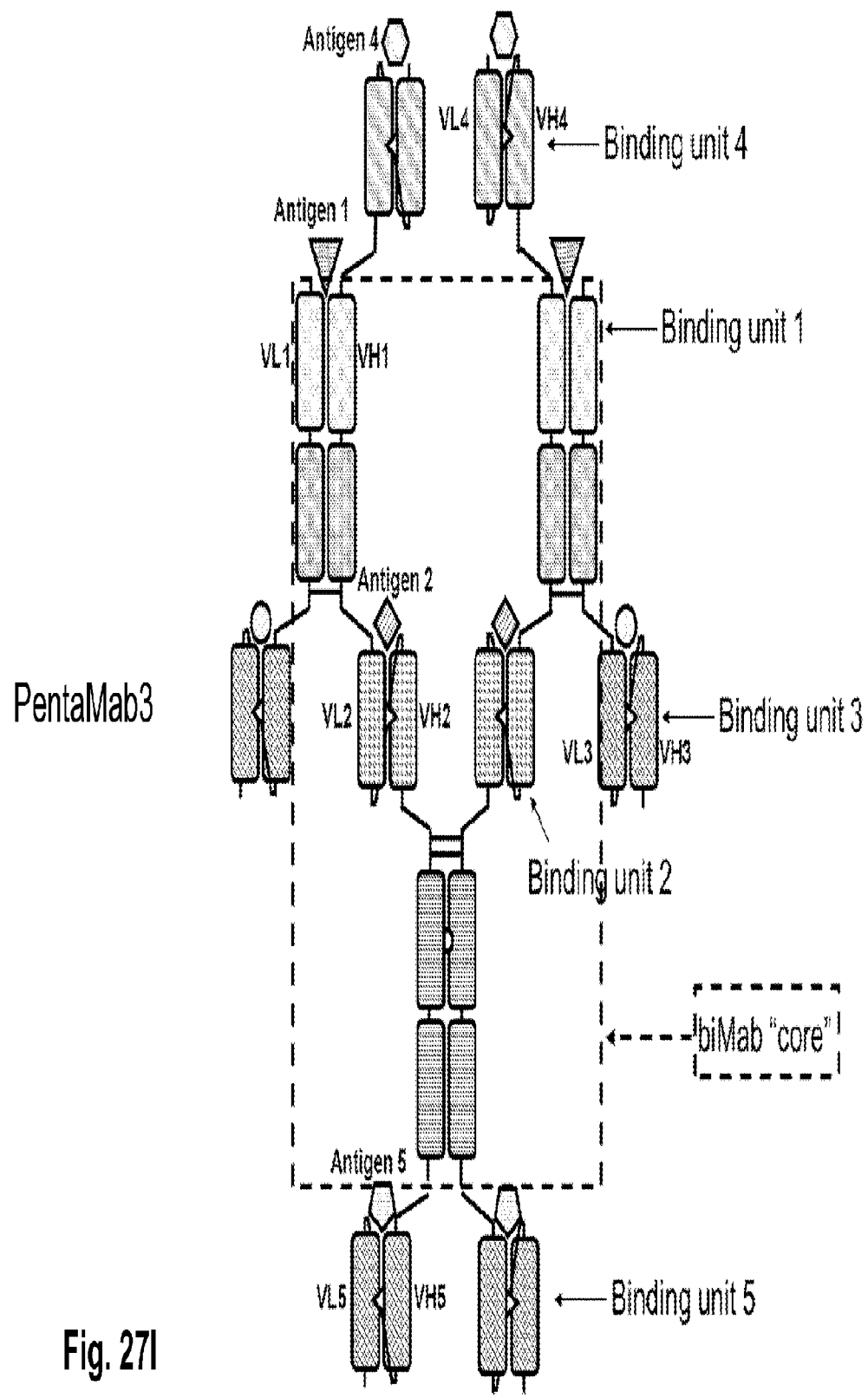
Figure 27K:
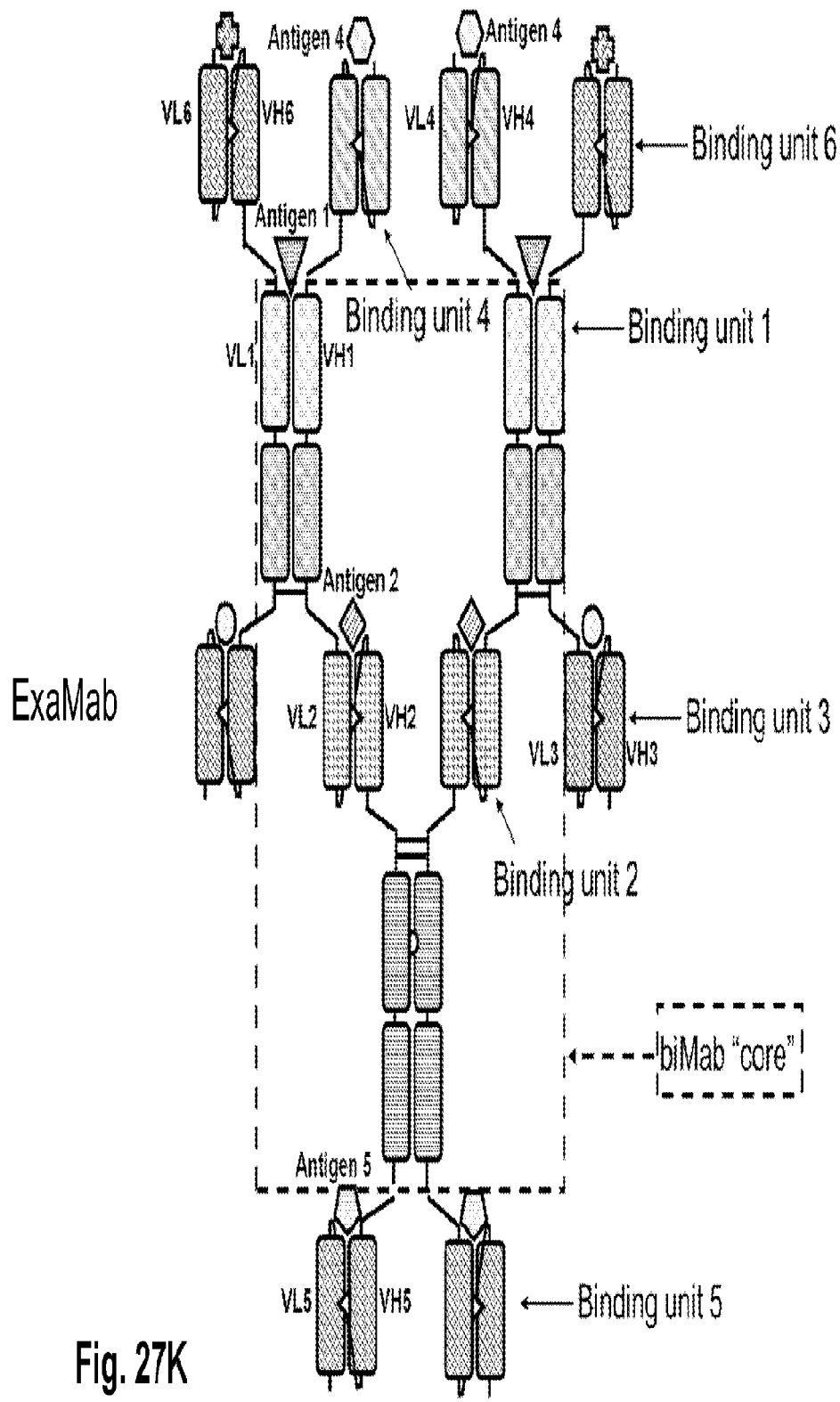
Figure 28:
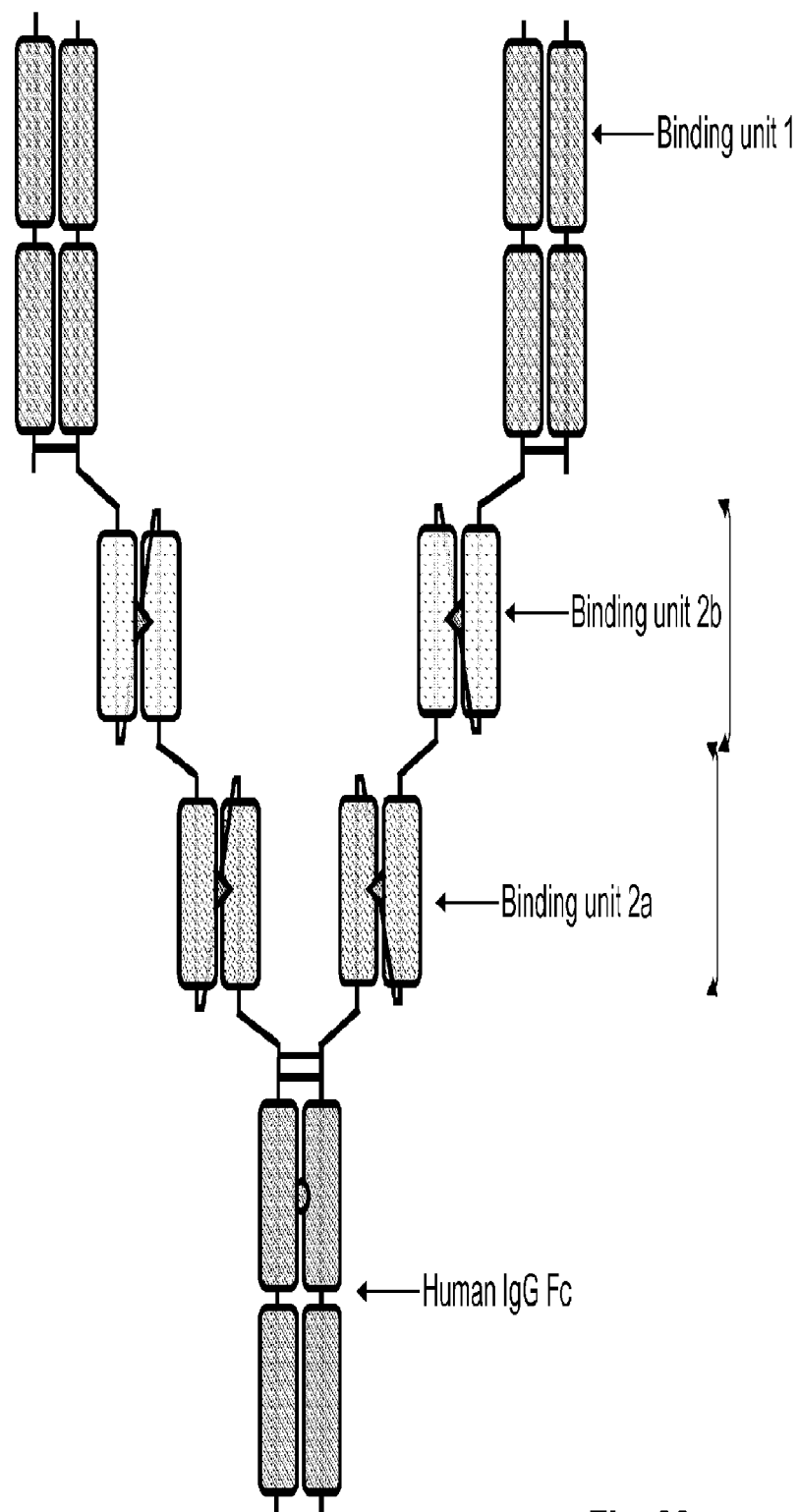
FIG. 28 is a schematic diagram of a representative extended biMab "core" having two tandem binding units, 2a and 2b (depicted here as scFvs) inserted at the hinge region of a human IgG. This figure is for illustration purpose only and is not intended to limit the number or type of binding units which may be inserted at the hinge. The binding units inserted at the hinge can be any binding moiety, for example, antibody fragments (such as scFv in any possible domain orientation and with any linker length and composition); single antibody domains (such as VH or VL); antibody mimetics, such as polypeptide scaffolds that mimic the binding structure of an antibody; protein domains, such as immunologic mediators (e.g., cytokines); ligand binding domains; and macromolecular toxins. The intra-molecular and/or inter-molecular linkers connecting the binding units present in the hinge can be but not limited to (GGGGS) repeats. Site-specific protease cleavage sites can be engineered in or around the linkers if the release of the units B, C, D, E, and F is needed (see for e.g., FIG. 29). Where the binding unit is an scFv they may be present in any given orientation and may comprise mutations to change the chemicophysical properties of the scFv domains. The various binding units may bind epitopes from the same or different target antigens; when the same target is bound then the binding units bind to non-overlapping regions (i.e., different, preferably non-overlapping epitopes). It will be understood based on the teachings herein that the valency of any of the above binding proteins can be increased by the incorporation of binding units that bind the same epitope. For example, but not by way of limitation, the addition of the same binding unit at 2a and 2b will result in a binding molecule that is bivalent for the different epitopes bound by binding units 1 and binding units 2a/2b and will be tetravalent for the epitope bound by the binding units at 2a and 2b (which bind the same epitope).

Linkers may be used to join domains/regions of the biMab chimeric heavy chain into a contiguous molecule. As described above, a biMab includes at least two linker polypeptides, L1 and L2. Additionally, a biMab may include additional linkers, such as a flexible linker interconnecting the variable heavy and light chains of an scFv. Additionally, a biMab may include additional linkers, such as a flexible linker interconnecting the variable heavy and light chains of an scFv and other linkers that connect other binding units to the biMab core structure. Examples of additional binding units connected to the biMab core structure are depicted in FIGS. 26-28.

An exemplary, non-limiting example of a linker is a polypeptide chain comprising at least 4 residues. Portions of such linkers may be flexible, hydrophilic and have little or no secondary structure of their own (linker portions or flexible linker portions). Linkers of at least 4 amino acids may be used to join domains and/or regions that are positioned near to one another after the molecule has assembled. Longer linkers may also be used. Thus, linkers may be approximately 1, 2, 3, 4, 5, 6, 7, 8, 9, 10, 11, 12, 13, 14, 15, 16, 17, 18, 19, 20, 25, 30, 35, 40, 45, 50, residues. Linkers may also be, for example, from about 100-175 residues. When multiple linkers are used to interconnect portions of the molecule, the linkers may be the same or different (e.g., the same or different length and/or amino acid sequence).

Linkers may be cleavable linkers, which contain at least one bond that can be selectively cleaved by a cleavage reagent. Cleavable linkers may be used to facilitate removal of all or a portion of the linker sequence. Linkers may be engineered to contain protease cleavage sites, so that cleavage occurs in the middle of the linker or in at least one end of the linker. For example, thrombin sites may be engineered at each of the two flanking ends of a linker. Depending on the type of linker used, cleavage may also be mediated by agents such as TCEP, TFA, and DTT. Linkers may be designed so that cleavage reagents remove all residues from the linker from the cleavage product. Other exemplary non-limiting linkers include prodrug linkers whose bonds can be selectively cleaved under in vivo conditions, for example, in the presence of endogenous enzymes or other endogenous factors, or simply in aqueous fluids present in the body or in cells of the body. When biMabs contain more than one polypeptide linker, each of the linkers may be different, or at least one of the linkers may be different from the others. In some aspects a biMab comprises cleavable linker. In a specific aspect, the biMab comprises an scFv, wherein the scFv comprises a cleavable linker between VH2 and VL2.

The linker(s) facilitate formation of the desired structure. Linkers may comprise (Gly-Ser)$_n$ residues, with some Glu or Lys residues dispersed throughout to increase solubility. Alternatively or additionally linkers may not comprise any Serine residues, such linkers may be preferable where the linker is subject to O-linked glycosyation. In some aspects, linkers may contain cysteine residues, for example, if dimerization of linkers is used to bring the domains of the biMab into their properly folded configuration. In some aspects, the biMab comprises at least two polypeptide linkers that join domains of the polypeptide. In other aspects, the biMab comprises at least three polypeptide linkers. In other aspects the biMab comprises four or more polypeptide linkers.

In some aspects, the polypeptide linker comprises 1-50 residues, 1-25 residues, 25-50 residues, or 30-50 residues. In some aspects, the polypeptide linker comprises a portion of an Fc moiety. For example, in some aspects, the polypeptide linker can comprise a portion of immunoglobulin hinge domain of an IgG1, IgG2, IgG3, and/or IgG4 antibody. In some aspects, the polypeptide linker comprises a portion of a mutated immunoglobulin hinge domain of an IgG1, IgG2, IgG3 and/or IgG4. In some aspects, the polypeptide linker comprises at least 5, 7, 8, or 15 amino acid residues of an immunoglobulin hinge region/domain of an IgG1, IgG2, IgG3, and/or IgG4 antibody. In some aspects, the polypeptide linker comprises at least 5, 7, 8, or 15 amino acid residues of a modified immunoglobulin hinge region/domain of an IgG1, IgG2, IgG3, and/or IgG4 antibody.

The polypeptide linker may comprise all, or a portion of a hinge region that naturally comprises three cysteines. In certain aspects, the selected hinge region is truncated or otherwise altered or substituted relative to the complete and/or naturally-occurring hinge region such that only one or two of the cysteine residues remain. Similarly, in certain other aspects, the polypeptide linker may comprise a mutated or otherwise altered portion of a hinge region in which the number of cysteine residues is reduced by amino acid substitution or deletion, for example a mutated or otherwise altered hinge region containing zero, one or two cysteine residues as described herein.

A mutated or otherwise altered hinge domain may thus be derived or constructed from (or using) a wild-type immunoglobulin hinge domain that contains one or more cysteine residues. In certain aspects, a mutated or otherwise altered portion of a hinge region may contain zero or only one cysteine residue, wherein the mutated or otherwise altered hinge region is or has been derived from a wild type immunoglobulin hinge region that contains, respectively, one or more or two or more cysteine residues. In the mutated or otherwise altered portion of a hinge region, the cysteine residues of the wild-type immunoglobulin hinge region are preferably deleted or substituted with amino acids that are incapable of forming a disulfide bond. In some aspects, a mutated or otherwise altered portion of a hinge region is or has been derived from a human IgG wild-type hinge region, which may include any of the four human IgG isotype subclasses, IgG1, IgG2, IgG3 or IgG4.

In some aspects, the polypeptide linker comprises a portion of a hinge region comprising the cysteine residue that forms a disulfide bond with an immunoglobulin light chain (EU residue 220). In some aspects, the polypeptide linker comprises an altered portion of a hinge region comprising an amino acid substitution at EU residue C220. In some aspects, the polypeptide linker comprises the amino acid substitution C220V.

In some aspects, the polypeptide linker comprises an amino acid substitution that prevents hinge-related spontaneous self-cleavage. In some aspects, the polypeptide linker comprises an amino acid substitution at position at EU position D221. In some aspects, the polypeptide linker comprises the amino acid substitution D221G. In some aspects, the polypeptide linker lacks the amino acid D221.

In some aspects, the polypeptide linker comprises or consists of a gly-ser linker. As used herein, the term "gly-ser linker" refers to a peptide that consists of glycine and serine residues. An exemplary gly-ser linker comprises an amino acid sequence of the formula $(Gly_4Ser)n$, wherein n is a positive integer (e.g., 1, 2, 3, 4, 5, 6, 7, 8, 9 or 10). A preferred gly-ser linker is $(Gly_4Ser)_2$ and $(Gly_4Ser)_4$. Another exemplary gly-ser linker is $(Gly_4Ser)_3$. In yet other aspects, two or more gly-ser linker are incorporated in series in a polypeptide linker. In some aspects, the polypeptide linker comprises at least a portion of a hinge region (e.g., derived from an IgG1, IgG2, IgG3, or IgG4 molecule) and a series of gly-ser amino acid residues (e.g., a gly-ser linker such as $(Gly_4Ser)n$).

In certain aspects, L1 and/or L2 include both a hinge portion and a linker portion, such as a linker portion comprising a gly-ser linker. In other aspects, L1 and/or L2 include only a hinge portion or only a linker portion, such as a gly-ser linker. In other aspects, L1 and L2 include a gly-ser linker portion. In certain aspects, the gly-ser linker portion of L1 and L2 is the same length, whereas in other aspects, the gly-ser linker portion of L1 and L2 are different lengths. When a biMab comprises an scFv, the heavy and light chains of the scFv may be connected by a flexible linker. This flexible linker generally does not include a hinge portion, but rather, is a gly-ser linker or other flexible linker. The length and amino acid sequence of a flexible linker interconnecting domains of an scFv may be readily selected and optimized.

In some aspects, the polypeptide linker (particularly L1 and/or L2) comprises a gly-ser or all gly linker and a portion or modified portion of a hinge domain. In some aspects, the polypeptide linker (L1) connecting the Fab domain to the binding domain (BD; binding unit 2) of the biMab comprises the amino acid sequence EPKSCDKTGGGGSGGGGS (SEQ ID NO: 63) or EPKSCGKTGGGGSGGGGS (SEQ ID NO: 64) or EPKSCGGGGSGGGGS (SEQ ID NO: 65). In some aspects the polypeptide linker (L2) connecting the binding domain and the binding domain to the Fc domain of the biMab comprises the amino acid sequence GGGGSGGGGSEPKSVDKTHTCPPCP (SEQ ID NO: 67) or GGGGSGGGGSCPPCP (SEQ ID NO:69) or GGGGSGGGGSDKTHTCPPCP (SEQ ID NO: 70).

Regardless of the polypeptide linker used to interconnect binding unit 1 to binding unit 2 and binding unit 2 to Fc (e.g., L1 and L2), the biMab may optionally comprise additional polypeptide linkers. The lengths and sequence of such additional polypeptide linkers are independently selected. For example, the biMab may further comprise a flexible polypeptide linker interconnecting the variable heavy and light chains of a scFv. This flexible polypeptide linker may comprise a gly-ser linker. Generally, this linker does not include a hinge portion.

5. Specific Configuration of biMabs

The biMabs of the present disclosure comprise two heavy-light chain pairs. The polypeptide sequence of the biMab chimeric heavy chain may comprise a polypeptide sequence comprising an antibody heavy chain variable domain (VH1), a polypeptide sequence comprising an antibody heavy chain constant domain 1 (CH1), a polypeptide sequence comprising a first polypeptide linker (L1), a polypeptide sequence comprising a binding domain (BD1), a polypeptide sequence comprising a second polypeptide linker (L2), and a polypeptide sequence comprising an Fc domain. In some aspects, the Fc domain comprises a $C_H2$ domain and a $C_H3$ domain. Thus, a biMab chimeric heavy chain may comprise polypeptide sequences in the following orientation from N-terminus to C-terminus: VH1-$C_H$1-L1-BD-L2-$C_H$2-$C_H$3. The polypeptide sequence of the biMab light chain may comprise a light chain variable domain (VL1) and a light chain constant domain (CL). Thus, a biMab light chain may comprise polypeptide sequence in the following orientation from N-terminus to C-terminus: VL1-CL1. Note that VH1, VL1, and CL1 are used to denote portions of binding unit 1 that binds the first epitope. BD is used to denote portions of binding unit 2 that binds the second epitope. In certain aspects, one or more additional binding units (e.g., scFvs) are present at the N-terminal and/or C-terminal ends of the biMab core, see for example FIGS. 26 and 27. In other aspects, one or more additional binding units (e.g., scFvs) are present within the hinge. Thus, a biMab heavy chain may comprise an extended core and have polypeptide sequences in the following orientation from N-terminus to C-terminus: VH1-$C_H$1-L1-(BD)$_n$-L2-$C_H$2-$C_H$3 where n>1. An exemplary biMab having an extended core is provided in FIG. 28.

In the aspects where the binding domain is an scFv, the biMab chimeric heavy chain may comprise a polypeptide sequence comprising an antibody heavy chain variable domain (VH1), a polypeptide sequence comprising an antibody heavy chain constant domain 1 (CH1), a polypeptide sequence comprising a first polypeptide linker (L1), a polypeptide sequence comprising an antibody light chain variable domain (VL2), a polypeptide sequence comprising a flexible linker, a polypeptide sequence comprising an antibody heavy chain variable domain (VH2), a polypeptide sequence comprising a second polypeptide linker (L2), and a polypeptide sequence comprising an antibody Fc domain. Thus, the chimeric heavy chain of a biMab comprising an scFv as the BD may comprise a polypeptide sequences in the following orientation from N-terminus to C-terminus: VH1-CH1-L1-VL2-L3-VH2-L2-Fc. The chimeric heavy chain is a polypeptide chain comprising an amino acid sequence (e.g., the amino acid sequence of each of the polypeptide domains). Alternatively, a chimeric heavy chain of a biMab comprising an scFv as the binding domain may comprise a polypeptide sequence in the following orientation from N-terminus to C-terminus: VH1-CH1-L1-VH2-L3-VL2-L2-Fc. The chimeric heavy chain is a polypeptide chain comprising an amino acid sequence (e.g., the amino acid sequence of each of the polypeptide domains). Note that VH1, VL1, and CL1 are used to denote portions of binding unit 1, with VH1 and VL1 denoting that portion that binds the first epitope. VH2 and VL2 is used to denote portions of binding unit 2 that bind the second epitope. In certain aspects, additional scFv binding domains are present at the N-terminal and/or C-terminal ends of the polypeptides that make up the biMab core, see for example FIG. 26-27 (depicting the biMab core further comprising binding unit 3 and/or 4 and/or 5). In certain aspects, more than one scFv binding domains are present within the biMab core, see for example FIG. 28 (depicting an extended biMab core comprising binding units 2a and 2b). Each additional scFv comprises an antibody heavy chain variable region denoted as VH3, VH4, VH5, and a corresponding antibody light chain variable region denoted as VL3, VL4, VL5.

6. Labels, Conjugates and Moieties biMabs of the disclosure may be conjugated to labels for the purposes of diagnostics and other assays wherein the biMabs and/or its associated targets(s) may be detected. Labels include, without limitation, a chromophore, a fluorophore, a fluorescent protein, a phosphorescent dye, a tandem dye, a particle, a hapten, an enzyme and a radioisotope.

In certain aspects, the biMabs are conjugated to a fluorophore. The choice of the fluorophore attached to the biMabs will determine the absorption and fluorescence emission properties of the conjugated biMabs. Physical properties of a fluorophore label that can be used for a biMabs and biMab-bound ligands include, but are not limited to, spectral characteristics (absorption, emission and stokes shift), fluorescence intensity, lifetime, polarization and photo-bleaching rate, or combination thereof. All of these physical properties can be used to distinguish one fluorophore from another, and thereby allow for multiplexed analysis. Other desirable properties of the fluorescent label may include cell permeability and low toxicity, for example if labeling of the biMab is to be performed in a cell or an organism (e.g., a living animal).

In certain aspects, an enzyme is a label and is conjugated to a biMab. Enzymes are desirable labels because amplification of the detectable signal can be obtained resulting in increased assay sensitivity. The enzyme itself does not produce a detectable response but functions to break down a substrate when it is contacted by an appropriate substrate such that the converted substrate produces a fluorescent, colorimetric or luminescent signal. Enzymes amplify the detectable signal because one enzyme on a labeling reagent can result in multiple substrates being converted to a detectable signal. The enzyme substrate is selected to yield the preferred measurable product, e.g. colorimetric, fluorescent or chemiluminescence. Such substrates are extensively used in the art and are well known by one skilled in the art and include for example, oxidoreductases such as horseradish peroxidase and a substrate such as 3,3'-diaminobenzidine (DAB); phosphatase enzymes such as an acid phosphatase, alkaline and a substrate such as 5-bromo-6-chloro-3-indolyl phosphate (BCIP); glycosidases, such as beta-galactosidase, beta-glucuronidase or beta-glucosidase and a substrate such as 5-bromo-4-chloro-3-indolyl beta-D-galactopyranoside (X-gal); additional enzymes include hydrolases such as cholinesterases and peptidases, oxidases such as glucose oxidase and cytochrome oxidases, and reductases for which suitable substrates are known.

Enzymes and their appropriate substrates that produce chemiluminescence are suitable for some assays. These include, but are not limited to, natural and recombinant forms of luciferases and aequorins. Chemiluminescence-producing substrates for phosphatases, glycosidases and oxidases such as those containing stable dioxetanes, luminol, isoluminol and acridinium esters are additionally useful.

In another aspect, haptens such as biotin, are also utilized as labels. Biotin is useful because it can function in an enzyme system to further amplify the detectable signal, and it can function as a tag to be used in affinity chromatography for isolation purposes. For detection purposes, an enzyme conjugate that has affinity for biotin is used, such as avidin-HRP. Subsequently a peroxidase substrate is added to produce a detectable signal.

Haptens also include hormones, naturally occurring and synthetic drugs, pollutants, allergens, affector molecules, growth factors, chemokines, cytokines, lymphokines, amino acids, peptides, chemical intermediates, nucleotides and the like.

In certain aspects, fluorescent proteins may be conjugated to the biMabs as a label. Examples of fluorescent proteins include green fluorescent protein (GFP) and the phycobiliproteins and the derivatives thereof. The fluorescent proteins, especially phycobiliprotein, are particularly useful for creating tandem dye labeled labeling reagents. These tandem dyes comprise a fluorescent protein and a fluorophore for the purposes of obtaining a larger stokes shift wherein the emission spectra is farther shifted from the wavelength of the fluorescent protein's absorption spectra.

In certain aspects, the label is a radioactive isotope. Examples of suitable radioactive materials include, but are not limited to, iodine ($^{121}$I, $^{123}$I, $^{125}$I, $^{131}$I) carbon ($^{14}$C), sulfur ($^{35}$S), tritium ($^{3}$H), indium ($^{111}$In, $^{112}$In, $^{113}$mIn, $^{115}$mIn,), technetium ($^{99}$Tc, $^{99}$mTc), thallium ($^{201}$Ti), gallium ($^{68}$Ga, $^{67}$Ga), palladium ($^{103}$Pd), molybdenum ($^{99}$Mo), xenon ($^{135}$Xe), fluorine ($^{18}$F), $^{153}$SM, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh and $^{97}$Ru.

In some aspects, drugs may be conjugated to the biMabs. For example, a biMab comprising an scFv may be conjugated to a cytotoxic drug. In this example, the scFv may bind to a target antigen on a cell surface, and the cytotoxic drug is then delivered to the cell. In some aspects, the biMab conjugate is internalized, which releases the cytotoxic drug to the cell. Any cytotoxic drug known in the art may be conjugated to a biMab. Some antibody conjugates are already approved by the FDA or are currently undergoing clinical trials.

In certain features, drugs and other molecules may be targeted to biMab via site-specific conjugation. For example, biMabs may comprise cysteine engineered domains (including cysteine(s) engineered into a binding unit and/or Fc domain), which result in free thiol groups for conjugation reactions. In certain aspects, a biMab is engineered to incorporate specific conjugation sites. FIG. 225 is a schematic representation of a biMab modified for drug conjugation. In some aspects, the present disclosure provides an Fc variant biMab, wherein the Fc region comprises an amino acid substitution at one or more of positions 239, 282, 289, 297, 312, 324, 330, 335, 337, 339, 356, 359, 361, 383, 384, 398, 400, 440, 422, and 442, as numbered by the EU index. In some aspects, the Fc region comprises substitutions at one or more of the following groups of positions: a) 289 and 440; b) 330 and 440; c) 339 and 440; d) 359 and 440; e) 289 and 359; f) 330 and 359; g) 339 and 359; h) 289 and 339; i) 330 and 339; j) 289 and 330; k) 339 and 442; l) 289, 339, and 442; m) 289, 330, and 339; n) 330, 339, and 442; and o) 289, 330, and 442. In other aspects, the present disclosure provides a biMab, wherein the CH1 domain of the Fab arm comprises a substitution at one or more of positions 131, 132, 134, 135, 136 and 139, as numbered by the EU index. In one aspect the substitution comprises a substitution to an amino acid chosen from cysteine, lysine, tyrosine, histidine, selenocysteine, and selenomethionine. In a specific aspect, the substitution is a cysteine. Methods for generating stable cysteine engineered antibodies are described in U.S. Pat. No. 7,855,275, U.S. 20110033378 and WO 2011/005481, the contents of which are incorporated herein by reference in their entirety.

7. Exemplary Targets

In some aspects, specific pairs of molecules are targeted by biMabs (e.g., binding unit 1 binds one of the targets and binding unit 2 binds the other target). A biMab of the disclosure may be capable of binding pairs of cytokines selected from, for example, IL-1α and IL-1β; IL-12 and IL-18; TNFα and IL-23; TNFα and IL-13; TNF and IL-18; TNF and IL-12; TNF and IL-1beta; TNF and MIF; TNF and IL-17; and TNF and IL-15; TNF and VEGF; VEGFR and EGFR; IL-13 and IL-9; IL-13 and IL-4; IL-13 and IL-5; IL-13 and IL-25; IL-13 and TARC; IL-13 and MDC; IL-13 and MIF; IL-13 and TGF-β; IL-13 and LHR agonist; IL-13 and CL25; IL-13 and SPRR2a; IL-13 and SPRR2b; IL-13 and ADAMS; TNFα and PGE4; IL-13 and PED2; TNF and PEG2.

In certain aspects, biMabs of the disclosure may be capable of binding pairs of targets selected from, for example, CD138 and CD20; CD138 and CD40; CD19 and CD20; CD20 and CD3; CD38 and CD138; CD38 and CD20; CD38 and CD40; CD40 and CD20; CD-8 and IL-6; CSPGs and RGM A; CTLA4 and BTNO2; IGF1 and IGF2; IGF1/2 and ErbB2; IGFR and EGFR; ErbB2 and ErbB3; ErbB2 and CD64; IL-12 and TWEAK; IL-13 and IL-1β; MAG and RGM A; NgR and RGM A; NogoA and RGM A; OMGp and RGM A; PDL-1 and CTLA4; RGM A and RGM B; Te38 and TNFα; TNFα and Blys; TNFα and CD-22; TNFα and CTLA-4; TNFα and GP130; TNFα and IL-12p40; and TNFα and RANK ligand.

In some aspects, biMabs of the disclosure may be capable of binding one, two or more cytokines, cytokine-related proteins, and cytokine receptors selected from among, for example, BMP1, BMP2, BMP3B (GDF10), BMP4, BMP6, BMP8, CSF1 (M-CSF), CSF2 (GM-CSF), CSF3 (G-CSF), EPO, FGF1 (αFGF), FGF2 (βFGF), FGF3 (int-2), FGF4 (HST), FGF5, FGF6 (HST-2), FGF7 (KGF), FGF9, FGF10, FGF11, FGF12, FGF12B, FGF14, FGF16, FGF17, FGF19, FGF20, FGF21, FGF23, IGF1, IGF2, IFNα1, IFNα2, IFNα4, IFNα5, IFNα6, IFNα7, IFNβ1, IFNγ, IFNω1, FIL1 FIL1 (EPSILON), FIL1 (ZETA), IL1α, IL1β, IL2, IL3, IL4, IL5, IL6, IL7, IL8, IL9, IL10, IL11, IL12A, IL12B, IL13, IL14, IL15, IL16, IL17, IL17B, IL18, IL19, IL20, IL22, IL23, IL24, IL25, IL26, IL27, IL28A, IL28B, IL29, IL30, PDGFA, PDGFB, TGFA, TGFB1, TGFB2, TGFB3, LTA (TNF-β), LTB, TNF (TNF-α), TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TNFSF10 (TRAIL), TNFSF11 (TRANCE), TNFSF12 (APO3L), TNFSF13 (April), TNFSF13B, TNFSF14 (HVEM-L), TNFSF15 (VEGI), TNFSF18, FIGF (VEGFD), VEGF, VEGFB, VEGFC, IL1R1, IL1R2, IL1RL1, IL1RL2, IL2RA, IL2RB, IL2RG, IL3RA, IL4R, IL5RA, IL6R, IL7R, IL8RA, IL8RB, IL9R, IL10RA, IL10RB, IL11RA, IL12RB1, IL12RB2, IL13RA1, IL13RA2, IL15RA, IL17R, IL18R1, IL20RA, IL21R, IL22R, IL1HY1, IL1RAP, IL1RAPL1, IL1RAPL2, IL1RN, IL6ST, IL18BP, IL18RAP, IL22RA2, AIF1, HGF, LEP (leptin), PTN, and THPO.

In further aspects, biMabs of the disclosure may be capable of binding one or more chemokines, chemokine receptors, and chemokine-related proteins selected from among, for example, CCL1 (I-309), CCL2 (MCP-1/MCAF), CCL3 (MIP-1a), CCL4 (MIP-1b), CCL5 (RANTES), CCL7 (MCP-3), CCL8 (mcp-2), CCL11 (eotaxin), CCL13 (MCP-4), CCL15 (MIP-1d), CCL16 (HCC-4), CCL17 (TARC), CCL18 (PARC), CCL19 (MIP-3b), CCL20 (MIP-3a), CCL21 (SLC/exodus-2), CCL22 (MDC/STC-1), CCL23 (MPIF-1), CCL24 (MPIF-2/eotaxin-2), CCL25 (TECK), CCL26 (eotaxin-3), CCL27 (CTACK/ILC), CCL28, CXCL1 (GRO1), CXCL2 (GRO2), CXCL3 (GRO3), CXCL5 (ENA-78), CXCL6 (GCP-2), CXCL9 (MIG), CXCL10 (IP 10), CXCL11 (I-TAC), CXCL12 (SDF1), CXCL13, CXCL14, CXCL16, PF4 (CXCL4), PPBP (CXCL7), CX3CL1 (SCYD1), SCYE1, XCL1 (lymphotactin), XCL2 (SCM-1b), BLR1 (MDR15), CCBP2 (D6/JAB61), CCR1 (CKR1/HM145), CCR2 (mcp-1RB/RA), CCR3 (CKR3/CMKBR3), CCR4, CCR5 (CMKBR5/ChemR13), CCR6 (CMKBR6/CKR-L3/STRL22/DRY6), CCR7 (CKR7/EBI1), CCR8 (CMKBR8/TER1/CKR-L1), CCR9 (GPR-9-6), CCRL1 (VSHK1), CCRL2 (L-CCR), XCR1 (GPR5/CCXCR1), CMKLR1, CMKOR1 (RDC1), CX3CR1 (V28), CXCR4, GPR2 (CCR10), GPR31, GPR81 (FKSG80), CXCR3 (GPR9/CKR-L2), CXCR6 (TYMSTR/STRL33/Bonzo), HM74, IL8RA (IL8Ra), IL8RB (IL8Rb), LTB4R (GPR16), TCP10, CKLFSF2, CKLFSF3, CKLFSF4, CKLFSF5, CKLFSF6, CKLFSF7, CKLFSF8, BDNF, C5R1, CSF3, GRCC10 (C10), EPO, FY (DARC), GDF5, HIF1A, IL8, PRL, RGS3, RGS13, SDF2, SLIT2, TLR2, TLR4, TREM1, TREM2, and VHL.

In further aspects, biMabs of the disclosure may be capable of binding one or more cancer antigen selected from among, for example, 707-AP, ALK, AFP, AKAP-4, ANHYDRASE IX, ART-4, B7H3, BAGE, b-catenin-mutated, Bcr-ab1, BORIS, CAMEL, CAP-1, CASP-8, CDC27 mutated, CDK4 mutated, CEA, CT, CYCLIN B1, Cyp-B, CYP1B1, DAM-6/MAGE-B2, DAM-10/MAGE-B1, EGFRvIII, ELF2M, EPCAM, EPHA2, EPHA4, ERG, ETV6-AML1, FAP, FLUCOSYL, G250, GAGE, GD2, GD3, GLOBOH, GM1, GM3, GnT-V, Gp100, HAGE, HER2, HER3, HER4, HLA-A*0201-R170I, HPV-E6, HPV-E7, HSP70-2M, HST-2, HTERT, iCE, KIAA0205, LAGE, LCK, LDLR/FUT, LMP2, LUGUMAIN, MAD-CT1, MAD-CT2, MAGE, MAGE-A1, MAGE-A3, MART1, MC1R, MESOTHELIN, ML-IAP, MUC1, MUM-1, -2, -3, MYCN, NA17, NA88-A, NY-ESO-1, P15, p190 minor bcr-ab1, P53, PAGE4, PAP, PAXS, PDGFR B, PLAC1, Pml/RARa, POLYSIALIC ACID, PR1, PRAME, PSA, PSCA, PSMA, RAGE, RAS-MUTANT, RGSS, RHOC, RU1, RU2, SAGE, SART-1, SART-3, SSX2, STN, SURVIVIN, TEL/AML1, TIE2, TPI mutated, TRP-1, TRP-2, TRP-2/INT2, VEGFR2, WT1 and XAGE1.

Other biMabs may be capable of binding cell surface proteins selected from among, for example, integral membrane proteins including ion channels, ion pumps, G-protein coupled receptors, structural proteins, adhesion proteins such as integrins, transporters, membrane-bound enzymes, proteins involved in accumulation and transduction of energy and lipid-anchored proteins including G proteins and some membrane-anchored kinases. biMabs may also be capable of binding enzymes such as kinases, proteases, lipases, phosphatases, fatty acid synthetases, digestive enzymes such as pepsin, trypsin, and chymotrypsin, lysozyme, and polymerases. biMabs may also be capable of binding to receptors such as hormone receptors, lymphokine receptors, monokine receptors, growth factor receptors, G-protein coupled receptors, and more.

In further aspects, biMabs of the disclosure may be capable of binding one or more infectious agent (e.g., bacteria, virus). Infectious bacteria include, but are not limited to, gram negative and gram positive bacteria. Gram positive bacteria include, but are not limited to *Pasteurella* species, *Staphylococci* species, and *Streptococcus* species. Gram negative bacteria include, but are not limited to, *Escherichia coli*, *Pseudomonas* species, and *Salmonella* species. Specific examples of infectious bacteria include but are not limited to: *Helicobacter pyloris, Borrelia burgdorferi, Legionella pneumophilia, Mycobacteria* sps (e.g., *M. tuberculosis, M. avium, M. intracellulare, M. kansasii, M. gordonae), Staphylococcus aureus, Pseudomonas aeruginosa, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic species), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae,*

Clostridium perfringens, Clostridium tetani, Enterobacter aerogenes, Klebsiella pneumoniae, Pasturella multocida, Bacteroides sp., Fusobacterium nucleatum, Streptobacillus moniliformis, Treponema pallidum, Treponema pertenue, Leptospira, Rickettsia, and Actinomyces israelli. Viruses include, but are not limited to, enteroviruses, rotaviruses, adenovirus, hepatitis virus. Specific examples of viruses that have been found in humans include but are not limited to: Retroviridae (e.g., human immunodeficiency viruses (HIV); Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arenaviridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papillomaviruses, polyoma viruses); Adenoviridae (most adenoviruses); Herpesviridae (herpes simplex virus (HSV) 1 and 2, varicella zoster virus, cytomegalovirus (CMV)); Poxviridae (variola viruses, vaccinia viruses, pox viruses); Iridoviridae (e.g., African swine fever virus); and unclassified viruses (e.g., the etiological agents of spongiform encephalopathies, the agent of delta hepatitis, the agents of non-A, non-B hepatitis; Norwalk and related viruses, and astroviruses).

In certain aspects, a biMab of the disclosure binds two different epitopes on the same target (e.g., binding unit 1 binds a first epitope on a target and binding unit 2 binds a second epitope on the same target).

In certain aspects, a biMab of the disclosure binds to EGFR and IGFR1. In certain aspects, binding unit 1 binds to EGFR and binding unit 2 binds to IGFR1. In other aspects, binding unit 1 binds to IGFR1 and binding unit 2 binds to EGFR. In other aspects, a biMab of the disclosure binds to VEGF and Ang2. In certain aspects, binding unit 1 binds to VEGF and binding unit 2 binds to Ang2. In other aspects, binding unit 1 binds to Ang2 and binding unit 2 binds to VEGF.

In some aspects, the multimeric nature of the biMabs of the disclosure confers the ability to target labels or therapeutics to a specific cell type or molecular target. For example, one functional domain in a biMab may bind to a target at the surface of a cell, while another functional domain in the same biMabs binds to a hapten or labeling agent useful for detection. Similarly, one functional domain may bind to a cellular target while a second functional domain binds to a toxin. Because both binding reactions are mediated through a single molecule, the toxin may be placed in the proximity of the cellular target, where it affects a cytotoxic function.

B. Nucleic Acid Molecules Encoding biMabs

The present disclosure provides nucleic acid molecules that encode biMabs. One aspect of the disclosure provides nucleic acid molecules encoding any of the biMabs of the disclosure. A nucleic acid molecule may encode a heavy chain and/or light chain of the biMab.

In some aspects, a nucleic acid molecule encoding a heavy chain of the biMab is a contiguous nucleic acid molecule comprising a nucleic acid portion comprising a nucleotide sequence encoding a VH1 domain; a nucleic acid portion comprising a nucleotide sequence encoding a $C_H1$ domain; a nucleic acid portion comprising a nucleotide sequence encoding a binding domain (BD) that binds a second epitope; a nucleic acid portion comprising a nucleotide sequence encoding an Fc domain, wherein the nucleic acid molecule further comprises at least one nucleic acid portion comprising a nucleotide sequence that encodes a polypeptide linker. In some aspects, a nucleic acid portion comprising a nucleotide sequence encoding a CH1 domain is linked to a nucleic acid portion comprising a nucleotide sequence encoding a binding domain (BD) via a nucleic acid portion comprising a nucleotide sequence encoding a first polypeptide linker (L1). In some aspects, a nucleic acid portion comprising a nucleotide sequence encoding a binding domain (BD) is linked to a nucleic acid portion comprising a nucleotide sequence encoding an Fc region via a nucleic acid portion comprising a nucleotide sequence encoding a second polypeptide linker (L2).

In some aspects, the binding domain (BD) is an scFv, wherein the nucleic acid portion encoding the scFv comprises a nucleotide sequence encoding a VL2 domain and a nucleotide sequence encoding a VH2, and wherein the nucleotide sequence encoding the VL2 domain is linked to the nucleotide sequence encoding the VH2 domain via a nucleotide sequence encoding a flexible polypeptide linker.

In some aspects, a contiguous a nucleic acid molecule encoding a heavy chain of the biMab further comprises a nucleic acid portion encoding a binding unit linked to the 5' end of a nucleic acid portion comprising a nucleotide sequence encoding a VH1 domain and/or a nucleic acid portion encoding a binding unit linked to the 3' end of a nucleic acid portion comprising a nucleotide sequence encoding an Fc region. In certain aspects, a nucleic acid portion encoding a binding unit is linked to a nucleic acid portion comprising a nucleotide sequence encoding a VH1 domain via a nucleic acid portion comprising a nucleotide sequence encoding a polypeptide linker. In certain other aspects, a nucleic acid portion comprising a nucleotide sequence encoding an Fc region is linked to a nucleic acid portion encoding a binding unit via a nucleic acid portion comprising a nucleotide sequence encoding a polypeptide linker.

In some aspects, a nucleic acid molecule encodes a light chain of the biMab. The nucleic acid encoding a light chain of the biMab may comprise a nucleic acid portion comprising a nucleotide sequence encoding a VL1 domain, and a nucleic acid portion comprising a nucleotide sequence encoding a CL domain.

In some aspects, a nucleic acid molecule encoding a light chain of the biMab further comprises a nucleic acid portion encoding a binding unit linked to the 5' end of a nucleic acid portion comprising a nucleotide sequence encoding a VL1 domain and/or a nucleic acid portion encoding a binding unit linked to the 3' end of a nucleic acid portion comprising a nucleotide sequence encoding a CL domain. In certain aspects, a nucleic acid portion encoding a binding unit is linked to a nucleic acid portion comprising a nucleotide sequence encoding a VL1 domain via a nucleic acid portion comprising a nucleotide sequence encoding a polypeptide linker. In certain other aspects, a nucleic acid portion comprising a nucleotide sequence encoding a CL domain is linked to a nucleic acid portion encoding a binding unit via a nucleic acid portion comprising a nucleotide sequence encoding a polypeptide linker. Another aspect of the disclosure provides a vector comprising a nucleic acid molecule or molecules as described herein, wherein the vector encodes a biMab as described herein.

A further aspect provides a host cell transformed with any of the nucleic acid molecules as described herein. In another aspect of the disclosure there is provided a host cell comprising the vector comprising nucleic acid molecules as described herein. In one aspect the host cell may comprise more than one vector.

The disclosure contemplates nucleic acid molecules encoding any biMab of the disclosure, as well as either the light or chimeric heavy chain of a biMab. For example, the disclosure contemplates a nucleic acid molecule comprising a nucleotide sequence encoding a biMab light chain (e.g., VL1+CL of a binding unit 1, such as a Fab that binds a first epitope) and/or a nucleotide sequence encoding a biMab chimeric heavy chain (e.g., VH1+CH1+L1+BD+L2+Fc). The disclosure further contemplates nucleic acid molecules encoding any biMab of the disclosure further comprising additional binding units. For example, a nucleic acid molecule comprising a nucleotide sequence encoding a biMab light chain further comprising an additional binding unit (e.g., binding unit 2+VL1+CL of a binding unit 1) and/or a nucleotide sequence encoding a biMab chimeric heavy chain further comprising an additional binding unit (e.g., binding unit 4+VH1+CH1+L1+BD+L2+Fc).

C. Methods for Producing biMabs

The present disclosure provides methods for producing biMabs. In certain aspects, the recombinant nucleic acids may be operably linked to one or more regulatory nucleotide sequences in an expression construct. The nucleic acid sequences encoding the biMab light and chimeric heavy chains can be cloned in the same expression vector in any orientation (e.g., light chain in front of the heavy chain or vice versa) or can be cloned in two different vectors. If expression is carried out using one vector, the two coding genes can have their own genetic elements (e.g., promoter, RBS, leader, stop, polyA, ect) or they can be cloned with one single set of genetic elements, but connected with a cistron element. Regulatory nucleotide sequences will generally be appropriate for a host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome.

In certain aspects, the expression vector contains a selectable marker gene to allow the selection of transformed host cells. Selectable marker genes are well known in the art and will vary with the host cell used. In certain aspects, this disclosure relates to an expression vector comprising a nucleotide sequence encoding a polypeptide and operably linked to at least one regulatory sequence. Regulatory sequences are art-recognized and are selected to direct expression of the encoded polypeptide. Accordingly, the term regulatory sequence includes promoters, enhancers, and other expression control elements. Exemplary, non-limiting regulatory sequences are described in Goeddel; *Gene Expression Technology: Methods in Enzymology*, Academic Press, San Diego, Calif. (1990). It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

The present disclosure further pertains to methods of producing a biMab of the disclosure. For example, a host cell transfected with one or more than one expression vectors encoding a biMab (e.g., a single vector encoding the chimeric heavy and the light chain or two vectors, one encoding the chimeric heavy chain and one encoding the light chain) can be cultured under appropriate conditions to allow expression of the polypeptide to occur. The biMab may be secreted and isolated from a mixture of cells and medium containing the polypeptide. Alternatively, the biMab may be retained in the cytoplasm or in a membrane fraction and the cells harvested, lysed and the protein isolated. A cell culture includes host cells, media and other byproducts. Suitable media for cell culture are well known in the art. biMabs can be isolated from cell culture medium, host cells, or both using techniques known in the art for purifying proteins, including ion-exchange chromatography, gel filtration chromatography, ultrafiltration, electrophoresis, and immunoaffinity purification. In certain aspects, the biMab is made as a fusion protein containing a domain which facilitates its purification.

A recombinant nucleic acid can be produced by ligating the cloned gene, or a portion thereof, into a vector suitable for expression in either prokaryotic cells, eukaryotic cells (yeast, avian, insect or mammalian), or both. Expression vehicles for production of a recombinant polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*. In certain aspects, mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

Techniques for making fusion genes are well known. Essentially, the joining of various nucleic acid fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another aspect, the fusion gene can be synthesized by conventional techniques including automated DNA synthesizers. Alternatively, PCR amplification of gene fragments can be carried out using anchor primers which give rise to complementary overhangs between two consecutive nucleic acid fragments which can subsequently be annealed to generate a chimeric gene sequence (see, for example, *Current Protocols in Molecular Biology*, eds. Ausubel et al., John Wiley & Sons: 1992).

In some aspects, an expression vector expressing any of the nucleic acids described above may be used to express biMabs in a host cell. For example, a biMab may be expressed in bacterial cells such as *E. coli*, insect cells (e.g., using a baculovirus expression system), yeast, or mammalian cells. Other suitable host cells are known to those skilled in the art.

Once the expression vector is transferred to a host cell by conventional techniques, the transfected cells are then cultured by conventional techniques to produce an antibody. Thus, the disclosure includes host cells containing a polynucleotide encoding biMab or fragments thereof, operably linked to a heterologous promoter. In certain aspects, both the chimeric heavy chain and the light chain may be co-expressed (from the same or different vectors) in the host cell for expression of the entire biMab. In certain aspects, both the heavy and light chains of the biMab are expressed from a single promoter. In certain aspects, the heavy and light chains of the biMab are expressed from multiple promoters. In certain aspects, the heavy and light chains of the biMab are encoded on a single vector. In certain aspects, the heavy and light chains of the biMab are encoded on multiple vectors.

Mammalian cell lines available as hosts for expression of recombinant antibodies are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Different host cells have characteristic and specific mechanisms for the post-translational processing and modification of proteins and gene products. Appropriate cell lines or host systems can be chosen to ensure the correct modification and processing of the antibody or portion thereof expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, HsS78T, HTB2, BT2O and T47D, NS0 (a murine myeloma cell line that does not endogenously produce any functional immunoglobulin chains), SP20, CRL7O3O and HsS78Bst cells. In one aspect, human cell lines developed by immortalizing human lymphocytes can be used to recombinantly produce monoclonal antibodies. In one aspect, the human cell line PER.C6. (Crucell, Netherlands) can be used to recombinantly produce monoclonal antibodies.

Additional cell lines which may be used as hosts for expression of recombinant antibodies include, but are not limited to, insect cells (e.g. Sf21/Sf9, *Trichoplusia ni* Bti-Tn5b1-4) or yeast cells (e.g. *S. cerevisiae, Pichia*, U.S. Pat. No. 7,326,681; etc), plants cells (US20080066200); and chicken cells (WO2008142124).

In certain aspects, biMabs of the disclosure are stably expressed in a cell line. Stable expression can be used for long-term, high-yield production of recombinant proteins. For example, cell lines which stably express the antibody molecule may be generated. Host cells can be transformed with an appropriately engineered vector comprising expression control elements (e.g., promoter, enhancer, transcription terminators, polyadenylation sites, etc.), and a selectable marker gene. Following the introduction of the foreign DNA, cells may be allowed to grow for 1-2 days in an enriched media, and then are switched to a selective media. The selectable marker in the recombinant plasmid confers resistance to the selection and allows cells that stably integrated the plasmid into their chromosomes to grow and form foci which in turn can be cloned and expanded into cell lines. Methods for producing stable cell lines with a high yield are well known in the art and reagents are generally available commercially.

In certain aspects, biMabs of the disclosure are transiently expressed in a cell line. Transient transfection is a process in which the nucleic acid introduced into a cell does not integrate into the genome or chromosomal DNA of that cell. It is in fact maintained as an extrachromosomal element, e.g. as an episome, in the cell. Transcription processes of the nucleic acid of the episome are not affected and a protein encoded by the nucleic acid of the episome is produced.

The cell line, either stable or transiently transfected, is maintained in cell culture medium and conditions well known in the art resulting in the expression and production of monoclonal antibodies. In certain aspects, the mammalian cell culture media is based on commercially available media formulations, including, for example, DMEM or Ham's F12. In other aspects, the cell culture media is modified to support increases in both cell growth and biologic protein expression. As used herein, the terms "cell culture medium," "culture medium," and "medium formulation" refer to a nutritive solution for the maintenance, growth, propagation, or expansion of cells in an artificial in vitro environment outside of a multicellular organism or tissue. Cell culture medium may be optimized for a specific cell culture use, including, for example, cell culture growth medium which is formulated to promote cellular growth, or cell culture production medium which is formulated to promote recombinant protein production. The terms nutrient, ingredient, and component are used interchangeably herein to refer to the constituents that make up a cell culture medium.

Once a molecule has been produced, it may be purified by any method known in the art for purification of an immunoglobulin molecule or other multimeric molecules, for example, by chromatography (e.g., ion exchange, affinity, particularly by affinity for the specific antigens Protein A or Protein G, and sizing column chromatography), centrifugation, differential solubility, or by any other standard technique for the purification of proteins. Further, the molecules of the present disclosure or fragments thereof may be fused to heterologous polypeptide sequences (referred to herein as "tags") described above or otherwise known in the art to facilitate purification.

When using recombinant techniques, the molecule can be produced intracellularly, in the periplasmic space, or directly secreted into the medium. If the molecule is produced intracellularly, as a first step, the particulate debris, either host cells or lysed fragments, is removed, for example, by centrifugation or ultrafiltration. Carter et al., *Bio/Technology*, 10:163-167 (1992) describe a procedure for isolating antibodies which are secreted into the periplasmic space of *E. coli*. Where the molecule is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The composition prepared from the cells can be purified using, for example, hydroxylapatite chromatography, hydrophobic interaction chromatography, ion exchange chromatography, gel electrophoresis, dialysis, and/or affinity chromatography either alone or in combination with other purification steps. The suitability of protein A as an affinity ligand depends on the species and isotype of any immunoglobulin Fc domain, if present, in the molecule and will be understood by one of skill in the art. The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Other techniques for protein purification such as fractionation on an ion-exchange column, ethanol precipitation, Reverse Phase HPLC, chromatography on silica, chromatography on heparin, SEPHAROSE chromatography on an anion or cation exchange resin (such as a polyaspartic acid column), chromatofocusing, SDS-PAGE, and ammonium sulfate precipitation are also available depending on the molecule to be recovered.

Following any preliminary purification step(s), the mixture comprising the molecule of interest and contaminants may be subjected to low pH hydrophobic interaction chromatography using an elution buffer at a pH between about 2.5-4.5, and performed at low salt concentrations (e.g., from about 0-0.25 M salt).

A biMab may be made and purified using, for example, any one or combination of techniques set forth above and/or in the Examples. Solely to illustrate, a biMab may be affinity purified using standard protein A affinity chromatography using HiTrap rProteinA FF column that has been equilibrated in PBS 1×. The biMab may be loaded on the column, which may be washed to eliminate contaminants and unbound material. Washing may be done with PBS 1× until the A280 trace reaches baseline. The bound protein may then be eluted in 25 mM glycine pH 2.8. Fractions may be immediately neutralized by addition of 0.1 volumes 1M Tris-HCl buffer pH 8. Fractions may then be analyzed for their biMab content by reading their absorbance at A280. The fractions containing the biMab may be pooled together and dialyzed overnight using a dialysis membrane cutoff of 10,000 kiloDalton (kDa), at 4° C. in 10× volume of PBS 1×. The dialyzed biMab may then be filtered using 0.22 micron filters and analyzed by reducing and non-reducing SDS-PAGE, for example a 4-12% Nupage gel run in MOPS buffer.

Following protein A purification, the biMab may be analyzed by analytical size-exclusion chromatography in order to determine the molecular weight (MW, Dalton) and the monomeric content of constructs. SEC-HPLC may be carried out using a TSK-GEL G3000SWXL column (Tosoh Bioscience LLC, Montgomeryville, Pa.), which separates globular proteins with MW that range from approximately 10 to 500 kDa, with a buffer containing 100 mM sodium phosphate, pH 6.8, and at a flow rate of 1 ml/min.

Regardless of how a biMab is purified, to confirm functional binding of the biMabs of the disclosure, binding assays may be performed (before and/or after purification). For example, dual ELISA assays may be used. In some aspects, a first antigen is coated on a well, and binding to this antigen immobilizes the biMab. A tagged second antigen is added to the well, and detected. Only bispecific molecules that are both immobilized via binding to the first antigen and also bound to the second antigen will be detected.

D. Pharmaceutical Formulations

In certain aspects, the disclosure provides pharmaceutical compositions. Such pharmaceutical compositions may be compositions comprising a nucleic acid molecule that encodes a biMab. Such pharmaceutical compositions may also be compositions comprising a biMab, or a combination of biMabs, and a pharmaceutically acceptable excipient. In certain aspects, the pharmaceutical compositions of the disclosure are used as a medicament.

In certain aspects, a biMab or a combination of biMabs (or nucleic acid molecules encoding a biMab or a combination of biMabs) may be formulated with a pharmaceutically acceptable carrier, excipient or stabilizer, as pharmaceutical compositions. In certain aspects, such pharmaceutical compositions are suitable for administration to a human or non-human animal via any one or more route of administration using methods known in the art. As will be appreciated by the skilled artisan, the route and/or mode of administration will vary depending upon the desired results. The term "pharmaceutically acceptable carrier" means one or more non-toxic materials that do not interfere with the effectiveness of the biological activity of the active ingredients. Such preparations may routinely contain salts, buffering agents, preservatives, compatible carriers, and optionally other therapeutic agents. Such pharmaceutically acceptable preparations may also contain compatible solid or liquid fillers, diluents or encapsulating substances which are suitable for administration into a human. Other contemplated carriers, excipients, and/or additives, which may be utilized in the formulations described herein include, for example, flavoring agents, antimicrobial agents, sweeteners, antioxidants, antistatic agents, lipids, protein excipients such as serum albumin, gelatin, casein, salt-forming counterions such as sodium and the like. These and additional known pharmaceutical carriers, excipients and/or additives suitable for use in the formulations described herein are known in the art, e.g., as listed in "Remington: The Science & Practice of Pharmacy", 21$^{st}$ ed., Lippincott Williams & Wilkins, (2005), and in the "Physician's Desk Reference", 60$^{th}$ ed., Medical Economics, Montvale, N.J. (2005). Pharmaceutically acceptable carriers can be selected that are suitable for the mode of administration, solubility and/or stability desired or required.

The formulations described herein comprise active agents in a concentration resulting in a w/v appropriate for a desired dose. In certain aspects, the active agent is present in a formulation at a concentration of about 1 mg/ml to about 200 mg/ml, about 1 mg/ml to about 100 mg/ml, about 1 mg/ml to about 50 mg/ml, or about 1 mg/ml to about 25 mg/ml. In certain aspects, the active agent is present at a concentration of about 25 mg/ml. In certain aspects, the concentration of the active agent in a formulation may vary from about 0.1 to about 100 weight %. In certain aspects, the concentration of the active agent is in the range of 0.003 to 1.0 molar.

In one aspect, the formulations of the disclosure are pyrogen-free formulations which are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). In certain specific aspects, the endotoxin and pyrogen levels in the composition are less than 10 EU/mg, or less than 5 EU/mg, or less than 1 EU/mg, or less than 0.1 EU/mg, or less than 0.01 EU/mg, or less than 0.001 EU/mg.

When used for in vivo administration, the formulations of the disclosure should be sterile. The formulations of the disclosure may be sterilized by various sterilization methods, including sterile filtration, radiation, etc. In one aspect, the formulation is filter-sterilized with a presterilized 0.22-micron filter. Sterile compositions for injection can be formulated according to conventional pharmaceutical practice as described in "Remington: The Science & Practice of Pharmacy", $21^{st}$ ed., Lippincott Williams & Wilkins, (2005).

Therapeutic compositions of the present disclosure can be formulated for particular routes of administration, such as oral, nasal, pulmonary, topical (including buccal and sublingual), rectal, vaginal and/or parenteral administration. The phrases "parenteral administration" and "administered parenterally" as used herein refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Formulations of the present disclosure which are suitable for topical or transdermal administration include powders, sprays, ointments, pastes, creams, lotions, gels, solutions, patches and inhalants. The biMabs may be mixed under sterile conditions with a pharmaceutically acceptable carrier, and with any preservatives, buffers, or propellants which may be required (U.S. Pat. Nos. 7,378,110; 7,258,873; 7,135,180; US Publication No. 2004-0042972; and 2004-0042971).

The formulations may conveniently be presented in unit dosage form and may be prepared by any method known in the art of pharmacy. Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient (e.g., "a therapeutically effective amount"). The selected dosage level will depend upon a variety of pharmacokinetic factors including the activity of the particular compositions employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. Suitable dosages may range from about 0.0001 to about 100 mg/kg of body weight or greater, for example about 0.1, 1, 10, or 50 mg/kg of body weight, with about 1 to about 10 mg/kg of body weight being suitable.

Note that the disclosure similarly contemplates that formulations suitable for diagnostic and research use may also be made. The concentration of active agent in such formulations, as well as the presence or absence of excipients and/or pyrogens can be selected based on the particular application and intended use.

E. Uses biMabs, as described herein, may be used to bind targets associated with diseases or disorders, thereby removing or otherwise inhibiting the activity of the targets and treating the diseases or disorders and/or alleviating symptoms thereof. In some aspects, the biMabs of the disclosure may be used for treating a disorder related to angiogenesis, cell proliferation, cell motility, cell invasion, or cell adhesion in a subject, by administering to the subject in need thereof a therapeutically effective dose of a biMab of the disclosure that binds to a target associated with the disease or symptoms of the disorder. For example, aberrant signalling through growth factors and/or growth factor receptors has been shown to contribute to unwanted cell proliferation and cancer. Accordingly, biMabs may be used to treat unwanted cell proliferation and/or cancer associated with growth factor signalling. In particular, the tumor growth curve of a tumor and/or the volume of a tumor may be reduced by administration of a biMab directed to proteins in growth factor signalling pathways. A similar strategy may be used for specific cancers or examples of unwanted cell proliferation associated with other signalling molecules.

An exemplary, non-limiting example of a specific biMab is a bispecific, bivalent molecule that binds EGFR and IGFR. This biMab may be used to treat unwanted cell proliferation and/or cancer associated with EGF and IGF signalling. Another non-limiting exemplary specific biMab is a bispecific, bivalent molecule that binds VEGF and Ang2. This biMab may be used to treat unwanted cell proliferation and/or cancer associated with VEGF and Ang2 signalling. For example, the biMab may be used to inhibit tumor growth and/or decrease the volume of an existing tumor. Similarly, a biMab may be used diagnostically to detect or monitor cells or tumors. Moreover, a biMab may be used in a research context to study, for example, cell growth and survival in wild type or diseased cells and tissues.

In other aspects, the biMabs of the disclosure may be used to treat diseases or disorders caused by an infectious agent such as a virus, bacteria, or parasite. A biMab may be designed to bind to one or more biomolecular targets on an infectious agent, thereby rendering the agent unable to invade and/or infect the host cells. Alternately, a plurality of biMabs may bind to an infectious agent and, like native immunoglobulins, trigger an immune response. Finally, a biMab may be used to bind a target molecule released by an infectious agent, in order to prevent the target from acting on host cells and tissues.

In still other aspects, biMabs of the disclosure may be used to modulate immune responses to antigens such as pollen, plants, insect parts and/or secretions, animal dander, nuts, or self-antigens. biMabs may be engineered to bind biomolecular targets present in these antigens and/or targets that mediate the immune response to these targets, like IgE, anaphylatoxins, or histamine.

biMabs of the disclosure, such as those described herein, may also be used for diagnostic purposes. For example, one or more target biomolecules may be detected in tissues or cells of a subject in order to screen for a disease or disorder associated with changes in expression of the targets. A diagnostic kit may comprise one or more biMabs that bind to target molecules, and a detection system for indicating the reaction of the biMab(s) with the target(s), if any.

The disclosure contemplates numerous uses for biMabs, including therapeutic, diagnostic, and research uses. Diagnostic and research uses may be in vivo or ex vivo. For example, a particular biMab may be used to identify, in cell culture, in tissue biopsy or in an animal or animal model, whether cells or tissue express a particular antigen(s) and whether simultaneously binding of an antibody molecule to both antigens improves detection, alters cell survival or behavior, and the like. Moreover, the activity of biMabs may be compared to the activity of conventional antibodies to evaluate the interactions or roles of multiple targets or multiple signaling pathways in a normal or disease state (e.g., does simultaneous inhibition of two targets have a different effect on cell behavior in comparison to inhibition of each target separately).

F. Kits

Another aspect of the present disclosure is a kit. In one aspect, a kit comprises any of the compositions or pharmaceutical compositions of a nucleic acid, polypeptide, expression vector, or host cell described above, and instructions or a label directing appropriate use or administration. Optionally, a kit may also include one or more containers and/or a syringe or other device to facilitate delivery or use. The disclosure contemplates that all or any subset of the components for conducting research assays, diagnostic assays and/or for administering therapeutically effective amounts may be enclosed in the kit. Similarly, the kit may include instructions for making a polypeptide by, for example culturing a host cell that expresses a nucleic acid that encodes a biMab of the disclosure under suitable conditions. By way of additional example, a kit for therapeutic administration of a biMab of the disclosure may comprise a solution containing a pharmaceutical formulation of the biMab, or a lyophilized preparation of a biMab, and instructions for administering the composition to a patient in need thereof and/or for reconstituting the lyophilized product.

The present disclosure also encompasses a finished packaged and labeled pharmaceutical product. This article of manufacture includes the appropriate unit dosage form in an appropriate vessel or container such as a glass vial or other container that is hermetically sealed. In the case of dosage forms suitable for parenteral administration the active ingredient, e.g., an above-described biMab, is sterile and suitable for administration as a particulate free solution. In certain aspects, the formulation is suitable for intravenous administration, such as for intravenous infusion to a human or animal.

In a specific aspect, the formulations of the disclosure are formulated in single dose vials as a sterile liquid. Exemplary containers include, but are not limited to, vials, bottles, pre-filled syringes, IV bags, blister packs (comprising one or more pills). Optionally associated with such container(s) can be a notice in the form prescribed by a governmental agency regulating the manufacture, use or sale of pharmaceuticals or biological products, which notice reflects approval by the agency of manufacture, use or sale for human diagnosis and/or administration.

As with any pharmaceutical product, the packaging material and container are designed to protect the stability of the product during storage and shipment. Further, the products of the disclosure include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures, etc., and other monitoring information.

A kit for diagnostic assays may comprise a solution containing a biMab or a lyophilized preparation of a biMab of the disclosure, wherein the biMab binds specifically to one or more targets, as well as reagents for detecting such biMabs. The biMabs may be labeled according to methods known in the art and described herein, including but not limited to labels such as small molecule fluorescent tags, proteins such as biotin, GFP or other fluorescent proteins, or epitope sequences such as his or myc. Similarly, primary antibodies used for detecting biMabs may be included in the kit. Primary antibodies may be directed to sequences on the biMabs or to labels, tags, or epitopes with which the biMabs are labeled. Primary antibodies may, in turn, be labeled for detection, or, if further amplification of the signal is desired, the primary antibodies may be detected by secondary antibodies, which may also be included in the kit.

Kits for research use are also contemplated. Such kits may, for example, resemble kits intended for diagnostic or therapeutic uses but further include a label specifying that the kit and its use is restricted to research purposes only.

Exemplary Embodiments

1. A protein, comprising:
   a Fab arm that binds to a first epitope,
   a binding domain (BD) that binds to a second epitope, and
   an Fc region comprising CH2 and CH3 domains;
wherein the BD is interconnected to the Fab arm via a first polypeptide linker (L1) and to the Fc region via a second polypeptide linker (L2); and wherein the protein is bivalent for binding to each of the first and second epitopes.

2. The protein of embodiment 1, wherein the L1 comprises 1-50 amino acid residues.

3. The protein of embodiment 1 or 2, wherein the L2 comprises 1-50 amino acid residues.

4. The protein of any of embodiments 1-3, wherein each of the L1 and the L2 comprises 1-50 amino acid residues.

5. The protein of any of embodiments 1-4, wherein each of the L1 and the L2 comprises 15-30 amino acid residues.

6. The protein of any of embodiments 1-5, wherein the L1 comprises a hinge portion and a linker portion.

7. The protein of any of embodiments 1-6, wherein the L2 comprises a hinge portion and a linker portion.

8. The protein of any of embodiments 1-7, wherein each of the L1 and the L2 comprises a hinge portion and a linker portion.

9. The protein of any of embodiments 1-8, wherein the L1 comprises at least 5 amino acid residues of an antibody hinge region.

10. The protein of any of embodiments 1-9, wherein the L2 comprises at least 5 amino acid residues of an antibody hinge region.

11. The protein of any of embodiments 1-10, wherein the L1 comprises at least 7 amino acid residues of an antibody hinge region.

12. The protein of any of embodiments 1-11, wherein the L2 comprises at least 7 amino acid residues of an antibody hinge region.

13. The protein of any of embodiments 1-12, wherein the L2 comprises at least 12 amino acid residues of an antibody hinge region.

14. The protein of any of embodiments 1-13, wherein the L1 comprises 8 amino acid residues of an antibody hinge region.

15. The protein of any of embodiments 1-14, wherein the L2 comprises 15 amino acid residues of an antibody hinge region.

16. The protein of any of embodiments 1-15, wherein each of the L1 and the L2 comprises all or part of an antibody hinge region or a modified antibody hinge region.

17. The protein of any of embodiments 1-16, wherein the L1 comprises at least 5 amino acid residues of an antibody hinge region, and wherein the hinge region comprises an aspartic acid to glycine substitution at EU position 221.

18. The protein of embodiment 16 or 17, wherein the hinge region comprises a substitution where a cysteine is replaced with another amino acid.

19. The protein of any of embodiments 1-18, wherein the L2 comprises at least 5 amino acid residues of an antibody hinge region, and wherein the hinge region comprises a cysteine to valine substitution at EU position 220.

20. The protein of any of embodiments 1-19, wherein the L1 comprises a linker portion comprising a Gly-Ser peptide.

21. The protein of any of embodiments 1-20, wherein the L2 comprises a linker portion comprising a Gly-Ser peptide.

22. The protein of any of embodiments 1-21, wherein each of the L1 and the L2 comprises a linker portion comprising a Gly-Ser peptide.

23. The protein of any of embodiments 20-22, wherein the Gly-Ser peptide is of the formula (Gly4Ser)n, wherein n is a positive integer selected from the group consisting of 1, 2, 3, 4, 5, 6, 7, 8, 9 and 10.

24. The protein of any of embodiments 1-5, wherein the L1 does not include a hinge portion.

25. The protein of any of embodiments 1-5, wherein the L2 does not include a hinge portion.

26. The protein of any of embodiments 1-5, wherein the L1 and the L2 do not include a hinge portion.

27. The protein of any of embodiments 1-23, wherein the L1 comprises the amino acid sequence EPKSCDKT (SEQ ID NO:4).

28. The protein of any of embodiments 1-23, wherein the L1 comprises the amino acid sequence EPKSCGKT (SEQ ID NO:6).

29. The protein of any of embodiments 1-23, wherein the L1 comprises the amino acid sequence EPKSC (SEQ ID NO:38).

30. The protein of any of embodiments 1-23, 27-29, wherein the L2 comprises the amino acid sequence EPKSVDKTHTCPPCP (SEQ ID NO:12).

31. The protein of any of embodiments 1-23, 27-29, wherein the L2 comprises the amino acid sequence CPPCP (SEQ ID NO:14).

32. The protein of any of embodiments 1-23, 27-29, wherein the L2 comprises the amino acid sequence DKTHTCPPCP (SEQ ID NO:40).

33. The protein of any of embodiments 1-32, wherein the BD is selected from the group consisting of an scFv, a single domain antibody, a single chain diabody, an antibody mimetic, an antibody variable domain, and a receptor binding domain.

34. The protein of embodiment 33, wherein the BD comprises an scFv.

35. The protein of embodiment 34, wherein the scFv comprises a VH domain, a polypeptide linker and a VL domain.

36. The protein of embodiment 35, wherein the Fab domain is interconnected via the L1 to an N-terminus of the VH domain of the scFv.

37. The protein of embodiment 35, wherein the Fab domain is interconnected via the L1 to an N-terminus of the VL domain of the scFv.

38. The protein of embodiment 35 or 37, wherein the Fc region is interconnected via the L2 to a C-terminus of the VH domain of the scFv.

39. The protein of embodiment 35 or 36, wherein the Fc region is interconnected via the L2 to a C-terminus of the VL domain of the scFv.

40. The protein of any of embodiments 35-39, wherein the VL domain of the scFv has a cysteine at Kabat position 100.

41. The protein of any of embodiments 35-40, wherein the VH domain of the scFv has a cysteine at Kabat position 44.

42. The protein of embodiment 33, wherein the antibody mimetic is selected from the group consisting of a minibody, a maxybody, an avimer, an Fn3 based protein scaffold, an ankyrin repeat, a VASP polypeptide, an avian pancreatic polypeptide (aPP), a Tetranectin, an affililin, a knottin, an SH3, a PDZ domain, a protein A domain, a lipocalin, a transferrin, and a kunitz domains.

43. The protein of any of embodiments 1-42, wherein the Fc region is selected from the group consisting of an Fc region from an IgG1, IgG2, IgG3, IgG4, IgA, IgM, IgE, and IgD.

44. The protein of embodiment 43, wherein the Fc region comprises a variant Fc region.

45. The protein of embodiment 43 or 44, wherein the Fc region is aglycosylated.

46. The protein of embodiment 43 or 44, wherein the Fc region is deglycosylated.

47. The protein of embodiment 43 or 44, wherein the Fc region has reduced fucosylation or is afucosylated.

48. The protein of any of embodiments 44-47, wherein the variant Fc region comprises a substitution at position 297.

49. The protein of embodiment 48, wherein the substitution at position 297 is 297Q.

50. The protein of any of embodiments 43-49, wherein the variant Fc region comprises a substitution at one or more of positions 239, 282, 289, 297, 312, 324, 330, 335, 337, 339, 356, 359, 361, 383, 384, 398, 400, 440, 422, and 442, as numbered by the EU index.

51. The protein of any of the preceding embodiments, wherein the CH1 domain of the Fab arm comprises a substitution at one or more of positions 131, 132, 134, 135, 136 and 139, as numbered by the EU index.

52. The protein of embodiment 50 or 51, wherein substitution comprises a substitution to an amino acid chosen from cysteine, lysine, tyrosine, histidine, selenocysteine, and selenomethionine.

53. The protein of embodiment 52, wherein the substitution is a cysteine.

54. The protein of any of embodiments 1-53, wherein the protein comprises a chimeric heavy chain comprising the following polypeptide domains, from N-terminus to C-terminus, VH1-CH1-L1-BD-L2-Fc;

wherein VH1 comprises the heavy chain variable domain of the Fab, CH1 comprises the heavy chain constant domain 1 of the Fab, L1 comprises the first linker polypeptide, BD comprises binding unit 2, L2 comprises the second linker polypeptide, and Fc comprises a CH2 and a CH3 domain.

55. The protein of embodiment 54, wherein BD comprises an scFv.

56. The protein of embodiment 55, wherein the scFv comprising, from N-terminus to C-terminus, VH2-polypeptide linker-VL2 or VL2-polypeptide linker-VH2;

wherein VH2 comprises the heavy chain variable domain of the scFv and VL2 comprises the light chain variable domain of the scFv.

57. The protein of any of embodiments 54-56, wherein the L1 comprises a hinge portion and a linker portion.

58. The protein of any of embodiments 54-57, wherein the L2 comprises a hinge portion and a linker portions.

59. The protein of embodiment 57 or 58, wherein the L1 comprises, from N-terminus to C-terminus, a hinge portion and a linker portion.

60. The protein of any of embodiments 57-59, wherein the L2 comprises, from N-terminus to C-terminus, a linker portion and a hinge portion.

61. The protein of any of embodiments 1-60, wherein the Fab arm binds to a first epitope, and wherein said first epitope is on a target selected from EGFR, IGFR1, VEGF, Ang2, Psl or PcrV.

62. The protein of any of embodiments 1-60, wherein the BD binds to a second epitope, and wherein said second epitope is on a target selected from EGFR, IGFR1, VEGF, Ang2, Psl or PcrV.

63. The protein of embodiment 61 or 62, wherein the Fab arm binds to EGFR.

64. The protein of embodiment 61 or 62, wherein the Fab arm binds to VEGF.

65. The protein of embodiment 61 or 62, wherein the Fab arm binds to PcrV

66. The protein of any of embodiments 61-65, wherein the BD binds to IGFR1.

67. The protein of any of embodiments 61-65, wherein the BD binds to Ang2.

68. The protein of any of embodiments 61-65, wherein the BD binds to Psl

69. The protein of any of embodiments 1-68, wherein the Fab arm comprises a VH1 domain comprising the amino acid sequence set forth in any of SEQ ID NOs: 24, 27, 33, 36, 46 and 49.

70. The protein of any of embodiments 1-69, wherein the Fab arm comprises a VL1 domain comprising the amino acid sequence set forth in any of SEQ ID NOs: 21, 26, 30, 35, 43 and 48.

71. The protein of embodiment 69 or 70, wherein the Fab arm comprises a VH1 domain comprising the amino acid sequence set forth in SEQ ID NO: 24 and a VL1 domain comprising the amino acid sequence set forth in SEQ ID NO: 21.

72. The protein of embodiment 69 or 70, wherein the Fab arm comprises a VH1 domain comprising the amino acid sequence set forth in SEQ ID NO: 33 and a VL1 domain comprising the amino acid sequence set forth in SEQ ID NO: 30.

73. The protein of embodiment 69 or 70, wherein the Fab arm comprises a VH1 domain comprising the amino acid sequence set forth in SEQ ID NO: 46 and a VL1 domain comprising the amino acid sequence set forth in SEQ ID NO: 43.

74. The protein of any of embodiments 1-673, wherein the BD comprises an scFv, and the scFv comprises an amino acid sequence selected from the group consisting of the sequences set forth in SEQ ID NO: 24, 27, 33, 36, 49, 49, 21, 26, 30, 35 43 and 48.

75. The protein of embodiment 74, wherein the scFv comprises the amino acid sequence set forth in SEQ ID NO: 25.

76. The protein of embodiment 74, wherein the scFv comprises the amino acid sequence set forth in SEQ ID NO: 34.

77. The protein of embodiment 74, wherein the scFv comprises the amino acid sequence set forth in SEQ ID NO: 47.

78. The protein of any of embodiments 1-54, wherein the protein comprises a chimeric heavy chain comprising the amino acid sequence set forth in SEQ ID NO: 23 or 32 or 45.

79. The protein of embodiment 78, wherein the protein comprises a light chain comprising the amino acid sequence set forth in SEQ ID NO: 19 or 28 or 41.

80. The protein of any of embodiments 1-79, wherein the first and second epitopes are different.

81. The protein of any of embodiments 1-68, wherein the first and second epitopes are the same.

82. The protein of any of embodiments 1-81, wherein the Fab arm and/or Fc region further comprise at least one binding unit.

83. The protein of embodiment 82, wherein the at least one binding unit is interconnected to the Fab arm and/or Fc via a polypeptide linker.

84. The protein of embodiment 82 or 83, wherein the at least one binding unit is interconnected at the N-terminal and/or C-terminal end of the chimeric heavy chain.

85. The protein of any one of embodiments 82-84, wherein the at least one binding unit is interconnected at the N-terminal and/or C-terminal end of the light chain.

86. The protein of embodiment 84 or 85, wherein the at least one binding unit is interconnected at the N-terminal and/or C-terminal end of the heavy chain, and at least one binding unit is interconnected to the N-terminal and/or C-terminal end of the light chain.

87. The protein of embodiment 84 or 85, wherein at least one binding unit is interconnected at the N-terminal and C-terminal end of the heavy chain, and/or at least one binding unit is interconnected to the N-terminal and C-terminal end of the light chain.

88. The protein of embodiment 84 or 85, wherein at least one binding unit is interconnected at the N-terminal and C-terminal end of the heavy chain, and at least one binding unit is interconnected to the N-terminal and C-terminal end of the light chain.

89. The protein of any of embodiments 1-88, wherein the protein further comprises at least one additional binding unit interconnected between the Fab arm and the Fc region.

90. The protein of embodiment 89, wherein at least one additional binding unit is interconnected between L1 and the BD.

91. The protein of embodiment 89, wherein at least one additional binding unit is interconnected between the BD and L2.

92. The protein of embodiment 90 or 91, wherein at least one additional binding unit is interconnect to the BD by a polypeptide linker.

93. The protein of any of embodiments 82-92, wherein each binding unit is selected from the group consisting of a Fab domain, an scFv, a single domain antibody, a single chain diabody, an antibody mimetic, an antibody variable domain, and a receptor binding domain.

94. The protein of any one of embodiments 82-93, wherein the binding units each bind different epitopes.

95. The protein of any one of embodiments 82-93, wherein two or more binding units each bind the same epitopes.

96. The protein of any one of embodiments 82-95, wherein the at least one binding units do not bind the first epitope and/or the second epitope.

97. The protein of any one of embodiments 82-95, wherein the at least one binding units do not bind the first epitope and do not bind the second epitope.

98. A composition comprising the protein of any of embodiments 1-97 formulated in a pharmaceutically acceptable carrier.

99. A nucleic acid molecule comprising a nucleotide sequence encoding the protein of any of embodiments 1-97.

100. A nucleic acid composition comprising a first nucleic acid molecule comprising a first nucleotide sequence and a second nucleic acid molecule comprising a second nucleotide sequence;
wherein the protein of any of embodiments 1-97 is encoded by the first and second nucleic acid molecules.

101. A vector comprising the nucleic acid of embodiment 99 or 100.

102. A host cell comprising the vector of embodiment 101.

EXAMPLES

The disclosure is now described with reference to the following examples. These examples are provided for the purpose of illustration only and the disclosure should in no way be construed as being limited to these examples but rather should be construed to encompass any and all variations which become evident as a result of the teachings provided herein. In general terms, the present disclosure employs, unless otherwise indicated, conventional techniques of molecular biology, chemistry, biochemistry, biophysics, recombinant DNA technology, immunology, and antibody engineering. All these techniques are of common knowledge to somebody working in the same field. Of course, it will be appreciated that specific listing or description of particular equipment and reagents used, sizes, manufacturer, etc., is not to be considered limiting on the current disclosure unless specifically stated to be so. It with be further appreciated that other equipment and reagents which perform similarly may be readily substituted.

Example 1

Representative biMabs

FIG. 1 is a schematic diagram of a representative biMab of the disclosure. The biMab is a bispecific binding protein, bivalent for each epitope, in which a Fab domain that binds a first epitope (binding unit 1) is genetically linked to a binding domain that binds a second epitope, shown here as being an scFv (binding unit 2), which is then genetically linked to at least a portion of a Fc domain. The chimeric heavy-chain (shown here with six domains and three interconnecting linker polypeptides; VH1+CH1+upper hinge/linker (also referred to as L1)+scFv (shown here as VL2+linker+VH2)+linker/lower hinge (also referred to as L2)+Fc (shown here comprising $C_H2+C_H3$)) may be expressed as a single-chain molecule. The biMab is also composed of a conventional light chain, which could be of kappa or lambda isotype. Also contemplated is a biMab wherein, binding unit 1 and 2 bind the same epitope which has the monospecificity of a conventional antibody but is tetravalent. The biMab may optionally possess one or more native interchain disulphide bridges, at one or more of the light chain, the heavy chain, or at a hinge region, as shown in this representation. However, a biMab of the present disclosure need not contain any interchain disulphide bridges and, in certain aspects, does not include any interchain disulphide bridges. For simplicity, only one half of the biMab depicted in FIG. 1 is schematically labeled.

For the representative biMab depicted in FIG. 1, also referred to herein as a biMab "core", the binding domain (BD) that binds a second epitope (labeled binding unit 2) is an scFv that binds epitope 2. When a biMab includes an scFv, such as an scFv that binds a second epitope, the scFv can be in the orientation VH-linker-VL, or in the orientation VL-linker-VH. In certain aspects, the scFv that serves as binding unit 2 is in the orientation VL-linker-VH. Generally, the linker that interconnects the VL and VH portions of the scFv is a flexible linker, such as a glycine-serine linker. Suitable linkers, including suitable glycine-serine linkers are well known in the art. The scFv may optionally be structurally-stabilized by introducing stabilizing mutations or by introducing interchain disulphide bond(s) (shown as an open triangle in FIG. 1). However, stabilizing mutations and/or an introduced interchain disulphide bond is not required and, in certain aspects, is not present.

The first binding unit, which is depicted in FIG. 1 as a Fab domain that binds to a first epitope, is interconnected to the scFv via a polypeptide linker. This polypeptide linker is also referred to as an upper hinge/linker or L1. When the term "polypeptide linker" is used to refer to a polypeptide linker that interconnects binding unit 1 to binding unit 2 or binding unit 2 to the Fc domain, the term includes polypeptides that include only linker sequence, only hinge sequence, or both linker and hinge sequence. In certain aspects, the Fab domain is interconnected to the N-terminus of binding unit 2 (here, either the VH or the VL of an scFv), using a polypeptide linker comprising cysteines (at least one cysteine) that may generate interchain disulphide bonds. The C-terminus of binding unit 2 (here, either the VH or the VL of an scFv) is interconnected to the N-terminus of the Ig hinge-Fc using a linker. This linker can be of similar composition of the Ig hinge and may have cysteines. These cysteines may generate interchain disulphide bonds.

The biMab presented in FIG. 1 also comprises an Fc domain comprising at least $C_H2$ and $C_H3$ regions. The Fc domain may be glycosylated, such as at the $C_H2$ domain (shown in FIG. 1 as an open circle), alternatively the Fc domain may be deglycosyalted or aglycosylated. Additionally or alternatively, the Fc domain may optionally contain stabilizing mutations, such as engineered intrachain disulphide bonds. The Fc $C_H3$ domain may or may not contain stabilizing mutations or mutations that favor heterodimerization. Moreover, the Fc domain may be a variant Fc domain, as described herein.

FIG. 2 provides nucleic acid coding sequence and amino acid sequence information for an exemplary biMab chimeric heavy chain. The portions of the chimeric heavy chain are presented in FIGS. 2A and 2B. At the top of FIG. 2A, the DNA and protein sequence of the VH1 region is shown schematically. For any particular biMab, this sequence would correspond to the VH1 of the particular binding unit one, such as the VH1 for a particular Fab. FIG. 2A then provides the DNA and protein sequence for the $C_H1$ domain. This is following by DNA and amino acid sequence for polypeptide linker 1 (L1) which will interconnect the Fab and the BD in a biMab. L1 may comprise a hinge portion and a linker portion (upper hinge/linker), and this is depicted in FIG. 2A. FIG. 2A first depicts the hinge portion of L1 (denoted as upper hinge, in this case human Ig1 upper hinge). Note that FIG. 2A depicts three possible aspects of hinge portions for L1, denoted as human IgG1 upper hinge or modified human IgG1 upper hinge. These hinge portions differ in that the modified hinge portion contains a D to G substitution immediately following the cysteine. FIG. 2A then depicts the linker portion of L1, here a $G_4S$ linker. The sequence of the entire human hinge is provided for comparison (SEQ ID NO: 9 and 10). The upper hinge portion and linker portion together form L1 (also referred to as upper hinge/linker). However, in certain aspects, L1 includes only a linker portion or only a hinge portion. FIG. 2B depicts schematically the DNA and protein sequence of binding unit 2, here an scFv, which may be in VH2-linker-VL2 or VL2-linker-VH2 orientation.

The DNA and amino acid sequence for the second polypeptide linker (L2; also referred to as linker/lower hinge) is depicted on FIG. 2B. The linker portion of L2 is provided on the bottom of FIG. 2B. As depicted, this linker portion is a $G_4S$ linker. The hinge portion of L2 is depicted in the middle of FIG. 2B (note, this hinge portion is depicted as lower hinge or hinge variant). FIG. 2B provides three aspects for the hinge portion of L2, hinge variant of human IgG1 and lower hinge of human IgG1. A lower hinge portion and linker portion together form L2 (also referred to as linker/lower hinge). However, in certain aspect L2 includes only a linker portion or only a hinge portion. FIG. 2C provides DNA and amino acid sequence for Fc $C_H2$ and $C_H3$ domains. As detailed above, the $C_H2$ and $C_H3$ domains depicted in FIG. 2C are from an IgG1 although a biMab could readily be generated using the Fc from any Ig class, including IgM, IgG, IgD, IgA and IgE, and any isotype, including IgG1, IgG2, IgG3 and IgG4.

As depicted in FIG. 2A, one aspect of an upper hinge (present as part of L1) includes the canonical cysteine of the human IgG1 upper hinge which participates in the formation of an interchain disulphide bridge between light and heavy chain in a Fab domain. This cysteine is bolded and underlined in FIG. 2A. This cysteine is also present in the modified upper hinge depicted in FIG. 2A, although not demarcated with an underlined. As depicted in FIG. 2B, one aspect of a lower hinge region (present as part of L2) is a variant having a mutation at EU position C220V to minimize disulphide scrambling at the hinge region. This variant is bolded and underlined in FIG. 2B.

FIG. 3 provides another representation of the amino acid sequence of the chimeric heavy chain for an exemplary schematic depiction of a biMab. Of course, it should be understood that the specific sequence for the VH1 (variable heavy domain 1 of binding unit 1) and the specific sequence for binding domain 2 (depicted as an scFv in the VH2-linker-VL2 orientation) are not provided. These sequences will depend upon the particular binding units that make up a particular biMab. However, the relative position of the portions of the biMab relative to each other is maintained (e.g., the biMab format is the same—although the particular binding units vary).

In FIG. 3, L1 and L2 are underlined and italicized, and the hinge portions of L1 and L2 are bolded. In the top panel, the hinge portion of L1 corresponds to the human IgG1 upper hinge, whereas in the bottom panel the hinge portion of L1 corresponds to the modified human IgG1 upper hinge. In the top panel, the hinge portion of L2 corresponds to the lower hinge variant of human IgG1, whereas in the bottom panel the hinge portion of L2 corresponds to the lower hinge of human IgG1. In either case, L1 interconnects binding unit 1 to binding unit 2, for example, by interconnecting the VH1 of binding unit 1 to the VH2 of binding unit 2. L2 interconnects binding unit 2 to Fc, for example, by interconnecting the VL2 of binding unit 2 to the $C_H2$ domain of an Fc.

Further schematic representations of biMabs are provided in FIGS. 4 and 5. These figures depict the relative position in the molecule of the hinge portions of L1 and L2. For example, in FIGS. 4A, 4B and 4C, the relative position of the hinge portion of L1 is depicted. L1 may further include a linker portion, the sequence of which is not shown in FIG. 4A, 4B or 4C. Examples of L1 further comprising a linker portion are provided in SEQ ID NO:63, 64 and 65). Note, however, that when present, the hinge portion of L1 is interconnected directly to binding unit 1 (e.g., is contiguous with a portion of binding unit 1) and the linker portion is interconnected directly to binding unit 2 (e.g., is contiguous with a portion of binding unit 2). Because of this configuration, L1 is also referred to as upper hinge/linker. The hinge portion depicted in FIG. 4B is a modified hinge portion having a mutation D221 G, introduced to prevent hinge-related spontaneous self-cleavage. The DNA sequence and the amino acid residue mutated are shown bolded, underlined and italicized. The hinge portion depicted in FIG. 4C is a shorted version lacking the last three amino acids of the hinge provided in FIG. 4A. By way of further example, FIGS. 5A, 5B and 5C depict the relative position of the hinge portion of L2. L2 may further include an additional linker portion, the sequence of which is not shown in FIG. 5A or 5B. Note, however, that when present, the hinge portion of L2 is interconnected directly to the Fc domain (e.g., is contiguous with a portion of an Fc domain) and the linker portion is interconnected directly to binding unit 2 (e.g., is contiguous with a portion of binding unit 2). Because of this configuration, L2 is also referred to as linker/lower hinge. The lower hinge portion depicted in FIG. 5A is a modified hinge having a mutation C220V, introduced to minimize disulphide scrambling in the hinge region. Alternative lower hinge domains depicted in FIGS. 5B and 5C may be used (i.e., a truncated hinge region) to prevent hinge-related spontaneous self-cleavage. The specific hinge portions of L1 and L2 depicted in FIGS. 4 and 5 are merely exemplary, and the disclosure contemplates the use of these, in any combination, as well as the use of no hinge portion or other hinge portions.

FIGS. 6A-C show the DNA sequence and the protein sequence of light chain and chimeric heavy chain for a biMab targeting EGFR (Fab domain) and IGF1R (scFv domain), where the EGFR binding unit is derived from the conventional monoclonal antibody Panitumumab and the IGF1R binding unit is derived from the conventional monoclonal antibody Dalotuzumab. This biMab construct is referred to throughout this application as biMab-EI (PaniX/Dalo). This specific biMab contains interconnecting linkers as described in FIG. 4-5. The scFv domain targeting IGF1R is in the orientation VL-linker-VH; the linker connecting the VL and VH domains is 20 amino acids long and is composed of glycine-glycine-glycine-glycine-serine repeated 4 times. The VL and VH domains of the scFv (VL2 and VH2 as represented in the schematic depictions of biMabs) contain mutations VL-Cysteine100 and VH-Cysteine44, which will form an interchain disulphide bond to stabilize the scFv.

FIGS. 7A-C show the DNA sequence and the protein sequence of light chain and chimeric heavy chain for a biMab targeting VEGF (Fab domain) and Ang2 (scFv domain), where the VEGF binding unit is derived from the conventional monoclonal antibody Bevacizumab/Avastin and the Ang2 binding unit is derived from the conventional monoclonal antibody designated LC06. This biMab construct is referred to throughout this application as biMab-VA(Ava/LC06). This biMab contains interconnecting linkers as described in FIG. 4-5. The scFv domain targeting Ang2 is in the orientation VL-linker-VH; the linker connecting the VL and VH domains is 20 amino acids long and is composed of glycine-glycine-glycine-glycine-serine repeated 4 times. The VL and VH domains of the scFv (VL2 and VH2 as represented in the schematic depictions of biMabs) contain mutations VL-Cysteine100 and VH-Cysteine44, which will form an interchain disulphide bonds in order to stabilize the scFv.

FIGS. 8A-D show the DNA sequence and the protein sequence of light chain and chimeric heavy chain for a biMab targeting the *Pseudomonas aeruginosa* (*P. aeruginosa*) PcrV (Fab domain) and Psl exopolysaccharide (scFv domain), where the PcrV binding unit is derived from the conventional monoclonal antibody designated V2L2 and the Psl binding unit is derived from the conventional monoclonal antibody designated W4-RAD. This biMab construct is referred to throughout this application as Bs4-V2L2-2C. This biMab contains interconnecting linkers as described in FIGS. 4 and 5. The scFv domain targeting Psl exopolysaccharide is in the orientation VH-linker-VL; the linker connecting the VL and VH domains is 20 amino acids long and is composed of glycine-glycine-glycine-glycine-serine repeated 4 times. The VL and VH domains of the scFv (VL2 and VH2 as represented in the schematic depictions of biMabs) contain cysteine mutations, which will form an interchain disulphide bonds in order to stabilize the scFv.

These specific examples of biMabs are exemplary of bispecific, bivalent polypeptides presented in the biMab format, as described herein. The remaining examples report the results of experiments performed to evaluate the structural and functional attributes of these exemplary biMabs. In doing so, the properties are often compared to that of the conventional, parental monoclonal antibodies from which each binding unit was derived. In other words, the specific biMab-EI described above may be compared to the conventional parental antibodies panitumumab or dalotuzumab. A specific biMab-EI may also be compared to other conventional antibodies that bind the same target or even the same epitope, but which are not themselves used to generate the binding unit of the biMab. Similarly, the specific biMab-VA described above may be compared to the conventional parental antibodies bevacizumab or LC06. Alternatively, a specific biMab-VA may also be compared to other conventional antibodies that bind the same target or even the same epitope. In addition, the properties of these exemplary biMabs may also be compared to conventional bispecific antibody formats that bind the same target(s) or even the same epitope(s).

Example 2

Stability of Representative biMabs

The transient expression levels, in mg/L, of representative biMabs biMab-EI (PaniX/Dalo) and biMab-VA (Ava/LC06) were analyzed after 10 days of expression in 293 cells (FIG. 9). Expression levels were determined using a protein A binding method. More specifically, DNA encoding biMabs were transfected in HEK293F and/or CHO cells using standard protocols. The transfected cells were cultivated for 10 days in Invitrogen's Freestyle™ media. Recombinant expression was determined using a protein A binding assay. Briefly, the culture media was automatically loaded onto a protein A column using an HPLC system (Agilent 1100 Capillary LC System, Foster City, Calif.). Unbound material was washed with a solution of 100 mM sodium phosphate buffer at pH 6.8, and antibodies were eluted with 0.1% phosphoric acid, pH 1.8. The area corresponding to the eluted peak was integrated and the total antibody concentration was determined by comparing to an immunoglobulin standard. The concentrations of the purified constructs were also determined by reading the absorbance at 280 nm using theoretically determined extinction coefficients. After protein expression, the biMabs were affinity purified using standard protein A affinity chromatography using HiTrap rProteinA FF column that have been equilibrated in PBS 1×. The biMabs were loaded on the column and after loading the column was washed, to eliminate contaminants and unbound material, with PBS 1× until the A280 trace reached baseline. The bound protein was then eluted in 25 mM glycine pH 2.8. Fractions were immediately neutralized by addition of 0.1 volumes 1M Tris-HCl buffer pH 8. Fractions were analyzed for their biMabs content by reading their absorbance at A280. The fraction containing the desired biMabs were pooled together and dialyzed overnight using a dialysis membrane cutoff of 10,000 kiloDalton (kDa), at 4° C. in 10× volume of PBS 1×.

These studies indicate that biMabs are capable of binding to protein A like conventional IgG antibodies. Although expression level of this biMab-EI is lower than expression level of this biMab-VA, the observed expression is consistent with that observed for the conventional antibody from which binding unit two of biMab-EI is derived.

Figure 6D:
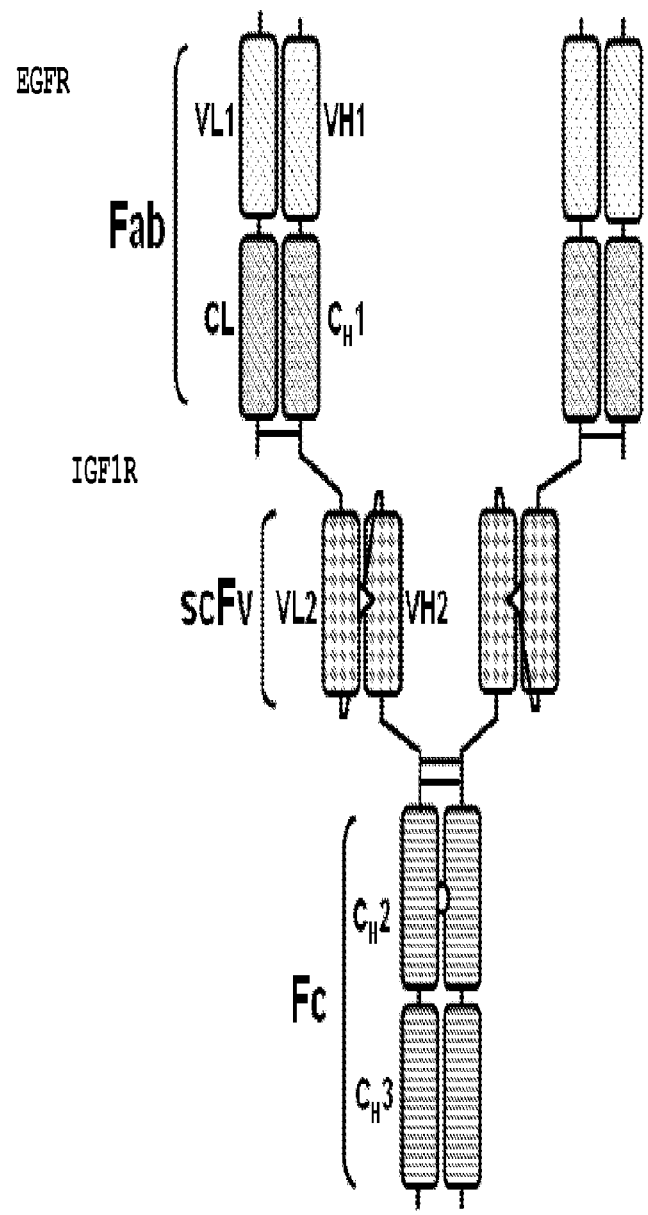
Figure 7D:
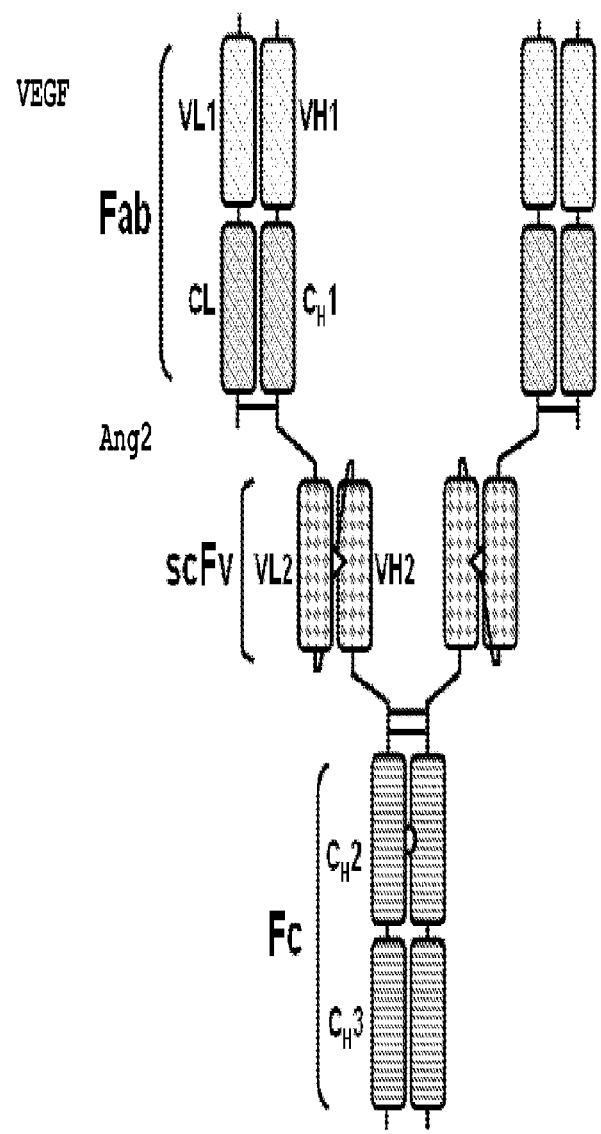
Figure 8D:
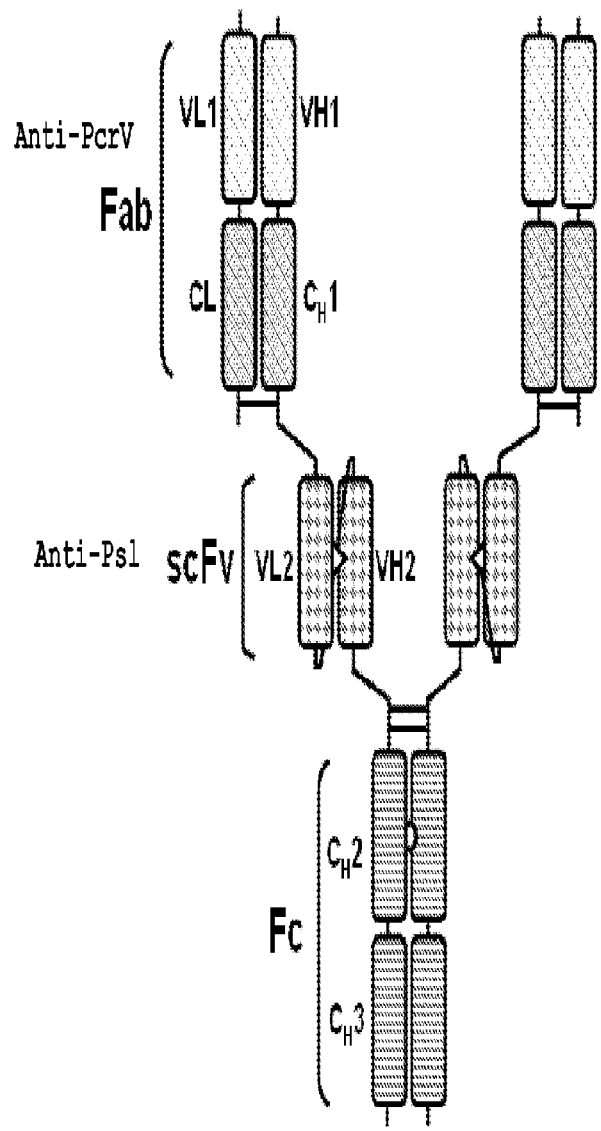

The representative biMabs used in this study, are schematically shown in FIGS. 6D and 7D. The biMab depicted in FIG. 6D is referred to as biMab-EI, and the specific example used is biMab-EI (PaniX/Dalo). The Fab portion of this biMab (binding unit 1) binds to EGFR (EGF receptor) and the binding domain (binding unit 2) is an scFv that binds to the IGF1R (IGF1 receptor). Note that this biMab also includes a polypeptide linker (L1) interconnecting the Fab to the scFv, and a polypeptide linker (L2) interconnecting the scFv to an Fc region. The biMab depicted in FIG. 7D is referred to as biMab-VA, and the specific example used is biMAb (Ava/LC06). The Fab portion of this biMab (binding unit 1) binds to VEGF and the binding domain (binding unit 2) is an scFv that binds to Ang2). Note that this biMab also includes a polypeptide linker (L1) interconnecting the Fab to the scFv, and a polypeptide linker (L2) interconnecting the scFv to an Fc region. Sequence information for these specific examples of biMabs are provided in FIGS. 6A, B, C, 7A, 7B and 7C.

Size-exclusion chromatograghy was used to determine the monomeric content of the representative biMabs and is presented in FIG. 9. FIG. 10 shows the size-exclusion chromatograms (SEC-HPLC) for biMab-EI and biMab-VA after protein A purification and dialysis in 25 mM Histidine-HCl pH 6.

SEC-HPLC was carried out at 280 nm and at 25° C. using a TSK-GEL G3000SWXL column (Tosoh Bioscience LLC, Montgomeryville, Pa.), which separates globular proteins with MW that range from approximately 10 to 500 kDa, with a buffer containing 100 mM sodium phosphate, pH 6.8, and at a flow rate of 1 ml/min. A low molecular weight gel filtration calibration kit from Bio-Rad (Hercules, Calif.) containing vitamin B12 (11,350 Da), equine myoglobin (17,000 Da), chicken ovalbumin (44,000 Da), bovine gamma-globulin (158,000 Da) and thyroglobulin (670,000 Da) was used as molecular mass standards. In addition, a highly purified 99% monomeric IgG was used as immunoglobulin molecular weight standard.

As shown in FIG. 10, a high level of monomeric content (>70%) after protein A purification was obtained. SEC-HPLC analysis clearly shows that after protein A purification, biMab is predominately monomeric and monodisperse similar to traditional antibodies.

Figure 11A:
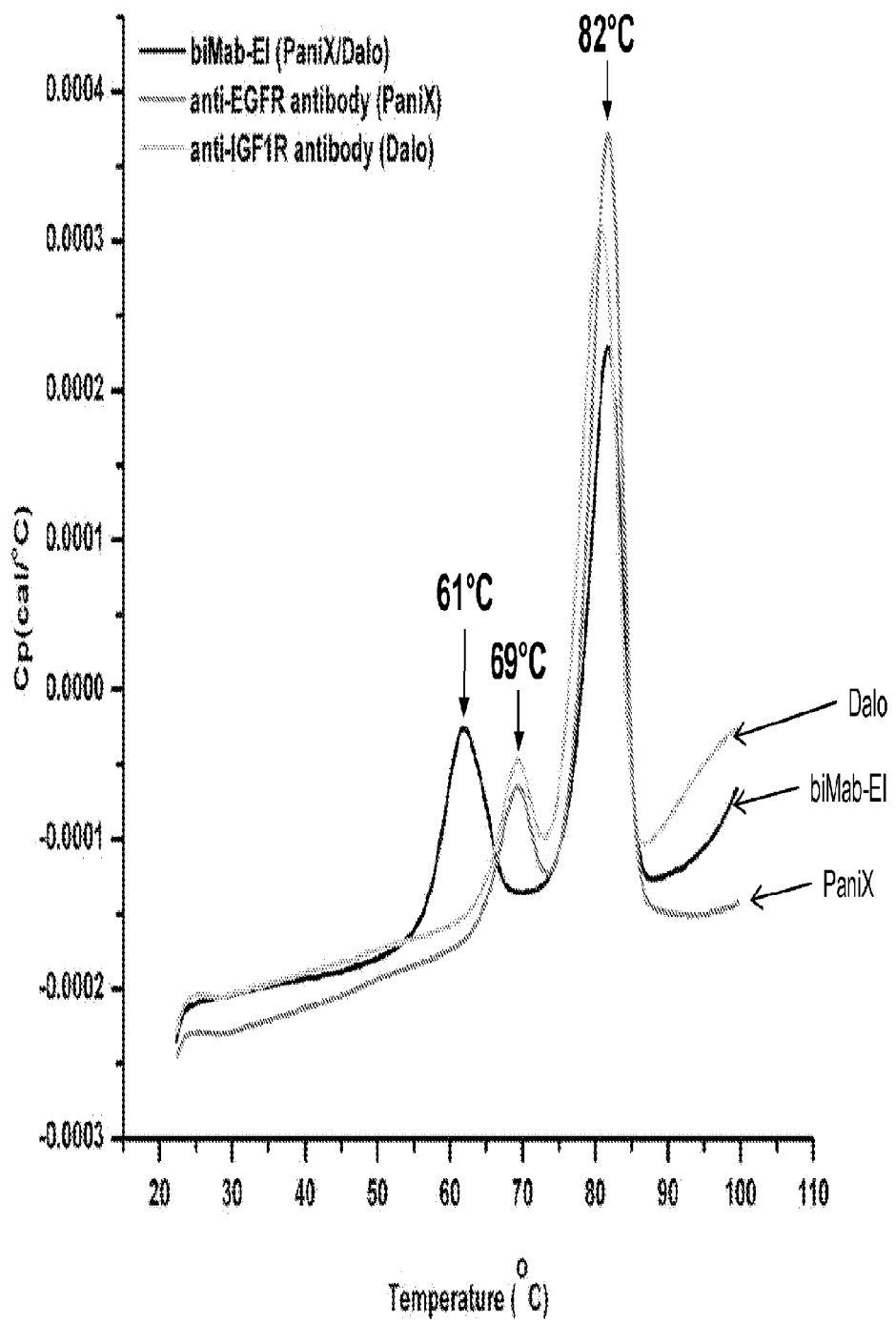
FIG. 11A shows the thermogram obtained using differential scanning calorimetry for biMab-EI and provides comparison to the parental conventional antibodies. Transition temperatures corresponding to the biMab domains are shown and have been identified by overlaying the melting transitions for the parental conventional antibodies (anti-EGFR antibody (PaniX) and the anti-IGF1R antibody (Dalo)). The temperature of the peaks and antibody are indicated for each trace.
Figure 11B:
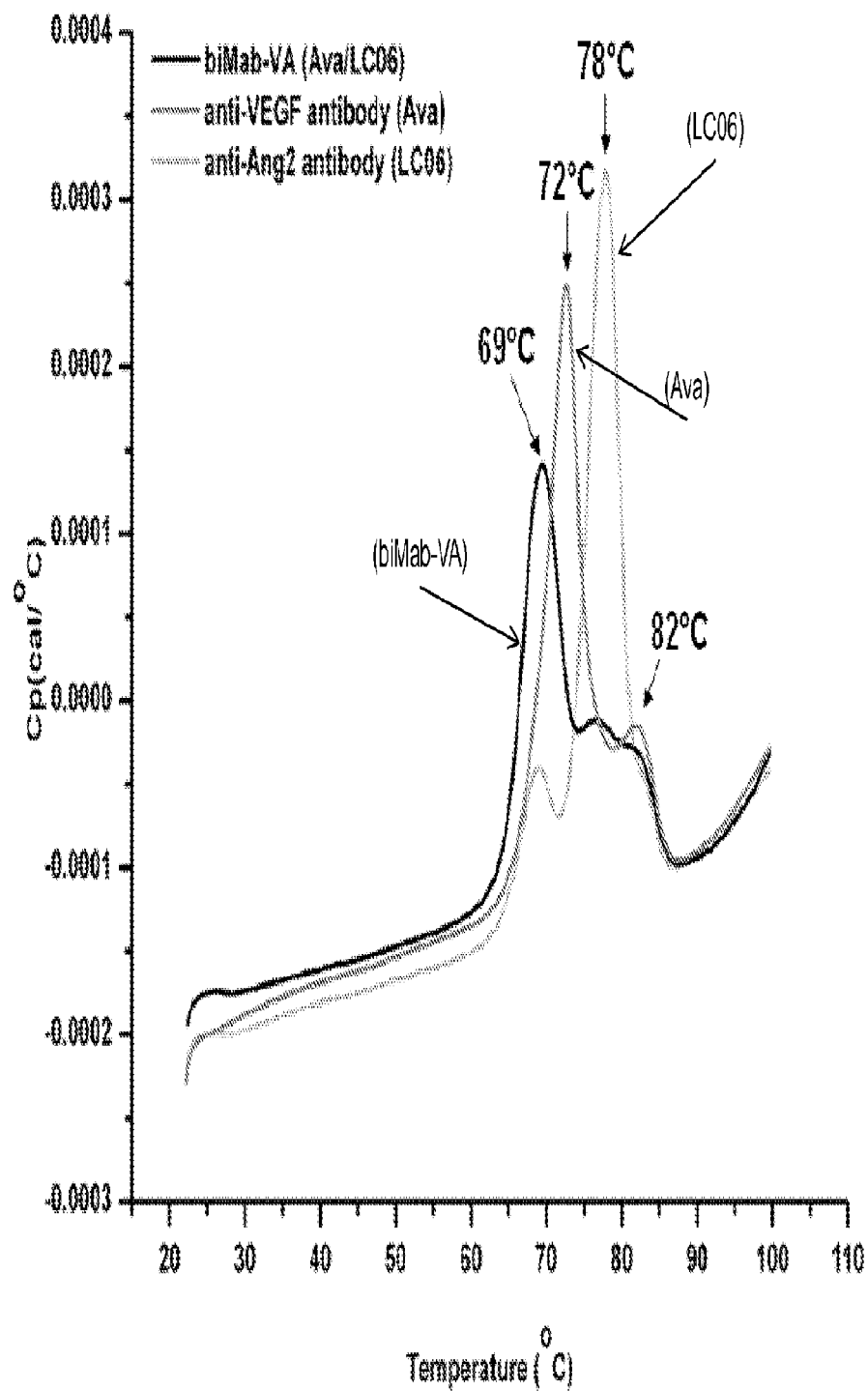
FIG. 11B shows the thermogram obtained using differential scanning calorimetry for biMab-VA and provides comparison to the parental conventional antibodies. Transition temperatures corresponding to the biMab domains are shown (black lines) and have been identified by overlaying the melting transitions for the parental conventional antibodies (anti-VEGF antibody (Ava) and the anti-Ang2 antibody (LC06)). The temperature of the peaks and antibody are indicated for each trace.

These representative biMab-EI and biMab-VA proteins were also analyzed by differential scanning calorimetry (DSC). FIG. 11 shows the thermograms obtained using DSC for biMab-EI (PaniX/Dalo) (FIG. 11A), and for biMab-VA (Ava/LC06) (FIG. 11B). Transition temperatures corresponding to the biMab domains are schematically shown (black lines in both FIGS. 11A and B) and have been identified by overlaying the melting transitions for the respective conventional antibodies from which the binding units of these biMabs were derived (e.g., the conventional anti-EGFR antibody (PaniX) and the conventional anti-IGF1R antibody (Dalo) for biMab-EI; the conventional anti-VEGF antibody (Ava) and the conventional anti-Ang2 antibody (LC06) for biMab-VA). Differential scanning calorimetry (DSC) experiments, as depicted in FIG. 11A-B, at a heating rate of 1° C./min were carried out using a Microcal VP-DSC ultrasensitive scanning microcalorimeter (Microcal, Northampton, Mass.).

DSC experiments were carried out in 25 mM Histidine-HCl, pH 6. All solutions and samples used for DSC were filtered using a 0.22 micron-filter and degassed prior to loading into the calorimeter. The two biMabs and the four parental antibodies that were used for the DSC studies were >99% monomeric as judged by analytical gel filtration chromatography run as described before. For each set of measurement, at least four buffer-versus-baseline runs were first obtained Immediately after, the buffer solution was removed from the sample cell and loaded with approximately 0.75 ml of sample at concentration of 1 mg/ml. For each measurement the reference cell was filled with the sample buffer. In each sample-versus-buffer experiment, the corresponding buffer-versus-buffer baseline run was subtracted. The raw data were normalized for concentration and scan rate. Data analysis and deconvolution was carried out using the Origin™ DSC software provided by Microcal.

This data provided in FIGS. 11A and 11B shows that the exemplary biMabs have high thermostability. In fact the lowest meting transition for these two exemplary biMabs is >60° C. and the domain stability are similar to that of their respective parental, conventional antibody arms.

The experiments described in this example demonstrate that the biMab format is a stable antibody format that can be expressed in reasonable quantities that have high monomeric content and thermostability comparable to conventional antibodies.

Example 3

Binding Activity of Representative biMabs

Figure 12A:
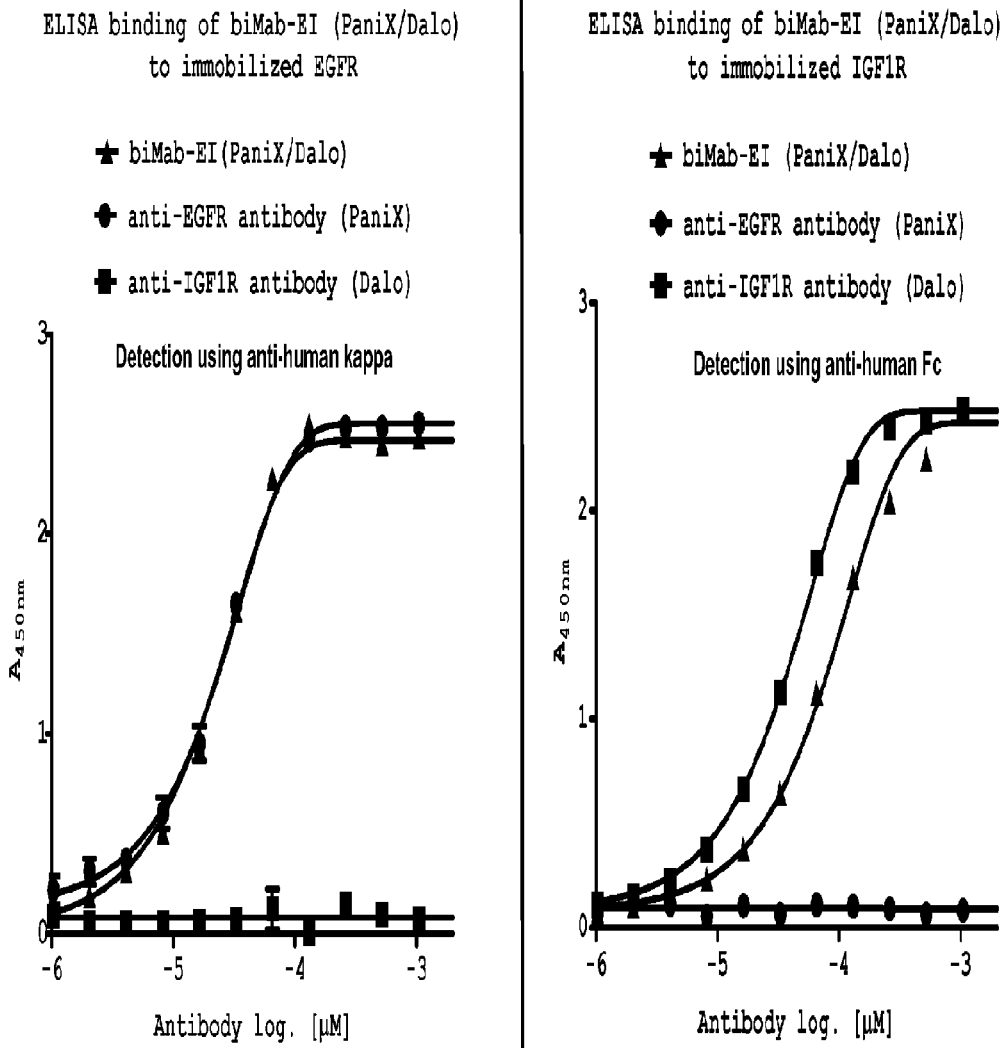
FIG. 12A depicts the results of an ELISA in which the binding of biMab-EI, the parental conventional anti-EGFR mAb (PaniX), or the parental conventional anti-IGF1R mAb (Dalo) is measured. The results in the left hand panel depict binding to immobilized EGFR. The results in the right hand panel depict binding to immobilized IGF1R.

These biMab-EI and biMab-VA proteins were analyzed to confirm that, in biMab format, these binding units retain the ability to bind their target antigens and that this binding is comparable to their respective parental antibodies, in this specific example, EGFR and IGF1R for biMab-EI, and VEGF and Ang2 for biMab-VA. FIG. 12A shows data for the binding, measured by ELISA, of biMab-EI, the conventional parental anti-EGFR antibody (PaniX), and the conventional parental anti-IGF1R antibody (Dalo). In the experiments depicted on the left-hand panel of FIG. 12A, binding to immobilized EGFR was assessed. As expected, biMab-EI and the conventional parental anti-EGFR antibody bound specifically to immobilized EGFR, but the conventional parental anti-IGF1R antibody did not. In fact, binding of the biMab and the conventional parental anti-EGFR antibody were very comparable supporting the conclusion that the biMab retains the binding property of the conventional parental anti-EGFR antibody. In the experiments depicted on the right-hand panel of FIG. 12A, binding to immobilized IGFR1 was assessed. As expected, biMab-EI and the conventional parental anti-IGFR1 antibody bound specifically to immobilized IGFR1, but the conventional parental anti-EGFR antibody did not. In fact, binding of the biMab and the conventional parental anti-IGFR1 antibody were very comparable supporting the conclusion that the biMab retains the binding property of the conventional parental anti-IGFR1 antibody.

Figure 12B:
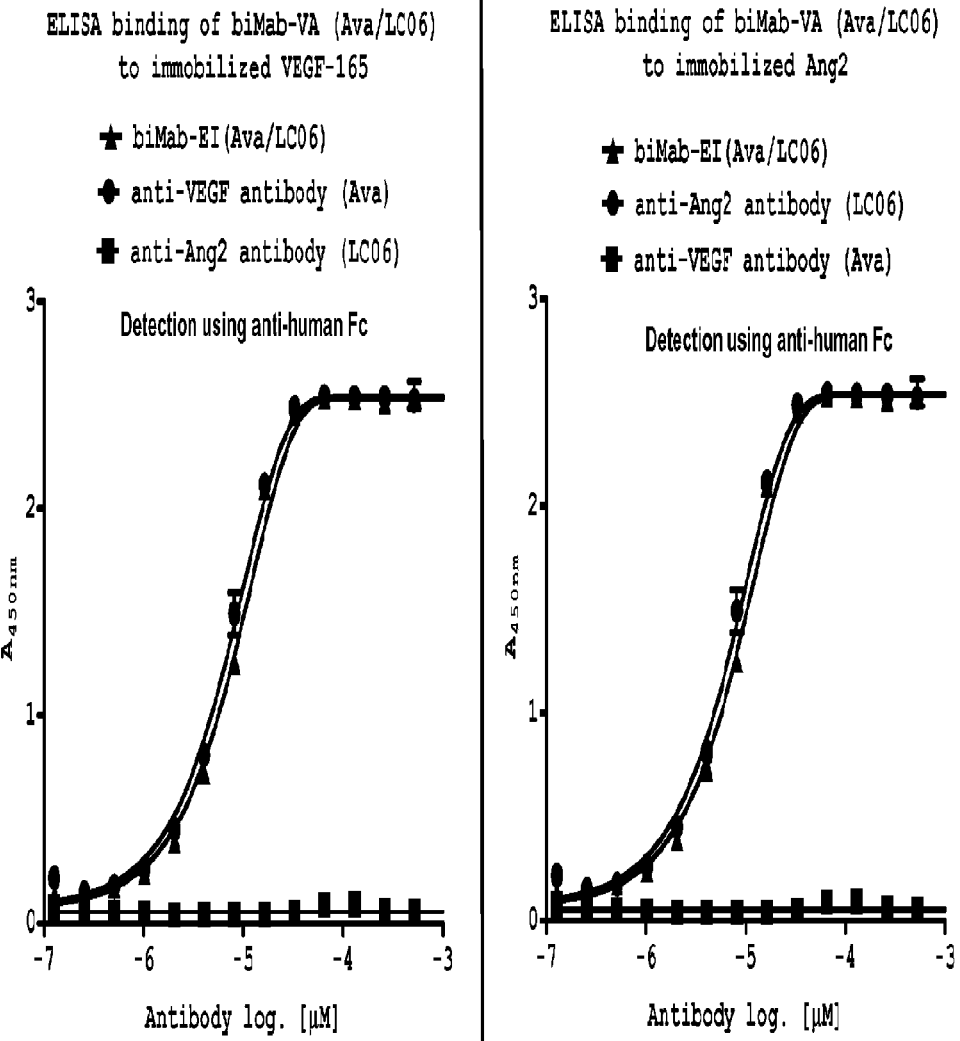
FIG. 12B depicts the results of an ELISA in which the binding of biMab-VA, the parental conventional anti-VEGF mAb (Ava), or the parental conventional anti-Ang2 mAb (LC06) is measured. The results in the left hand panel depict binding to immobilized VEGF-165. The results in the right hand panel depict binding to immobilized Ang2.

FIG. 12B shows data for the binding, measured by ELISA, of biMab-VA, the conventional parental anti-VEGF antibody (Ava), and the conventional parental anti-Ang2 antibody (LC06). In the experiments depicted on the left-hand panel of FIG. 12B, binding to immobilized VEGF-165 was assessed. As expected, biMab-VA and the conventional parental anti-VEGF antibody bound specifically to immobilized VEGF-165, but the conventional parental anti-Ang2 antibody did not. In fact, binding of the biMab and the conventional parental anti-VEGF antibody were very comparable supporting the conclusion that the biMab retains the binding property of the conventional parental anti-VEGF antibody. In the experiments depicted on the right-hand panel of FIG. 12B, binding to immobilized Ang2 was assessed. As expected, biMab-VA and the conventional parental anti-Ang2 antibody bound specifically to immobilized Ang2, but the conventional parental anti-VEGF antibody did not. In fact, binding of the biMab and the conventional parental anti-Ang2 antibody were very comparable supporting the conclusion that the biMab retains the binding property of the conventional parental anti-An2 antibody.

In the above ELISA binding assays, 2 μg/mL of each target antigen (EGFR, IGF1R, VEGF165 and Ang2) in 30 μL of PBS, pH 7.4 was coated on microtiter wells for 1 hour at room temperature. Antigen-coated wells were washed 3 times with PBS containing 0.1% (v/v) Tween-20 and blocked for one hour at room temperature with 3% BSA. biMabs and antibodies were serially diluted in 30 μL of blocking solution and were incubated for 2 hour at 37° C., followed by extensive washes with PBS containing 0.1% (v/v) Tween-20. Bound biMabs and antibodies were detected by HRP-conjugated anti-kappa (FIG. 12A left panel), anti-human-Fc (FIG. 11A right panel and FIG. 12A-B) secondary antibodies and visualized with 30 μL of 3,3',5,5'-tetramethylbenzidine substrate (Pierce). The reaction was stopped by adding 30 μL of 0.18 M sulfuric acid (Pierce). The absorbance at 450 nm was measured using a microtiter plate reader. The resulting data were analyzed using Prism 5 software (GraphPad, San Diego, Calif.).

Example 4

Concurrent Binding Activity of Representative biMabs

Figure 13:
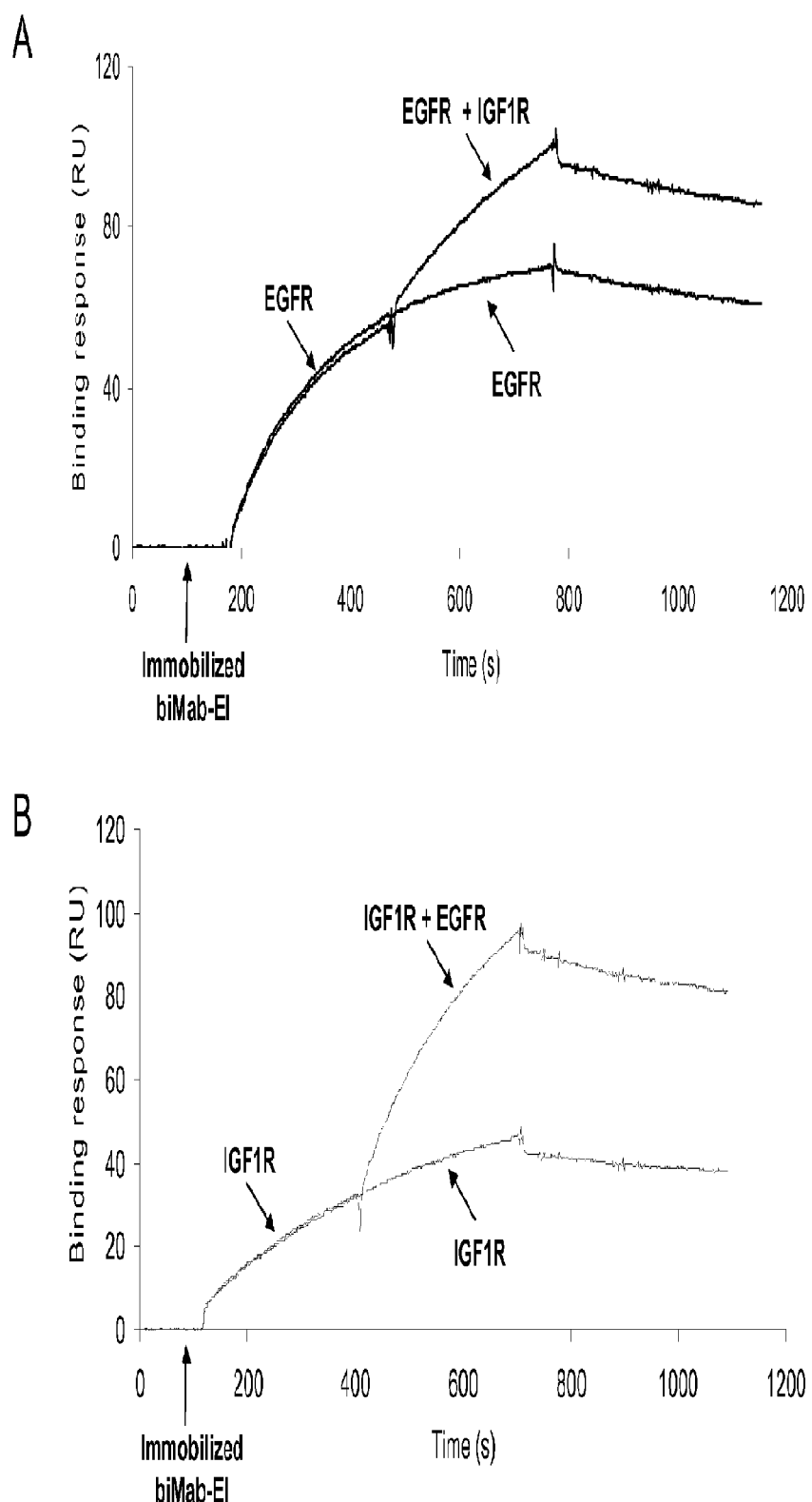
FIGS. 13A-B show the concurrent binding of biMab-EI to its targets EGFR and IGF1R as determined using BIAcore. For the depicted experiments, biMab-EI was immobilized and its respective ligands were run trough. Concurrent binding is observed by increase in the binding response (RU). The concurrent binding is observed regardless of the injection sequence of the targets.

FIG. 13 shows the ability of the biMab-EI (PaniX/Dalo) to concurrently bind its targets EGFR and IGF1R by BIAcore assays. The biMab-EI (PaniX/Dalo) was immobilized on the CM5 BIAcore sensor chip (FIGS. 13A and B). Concurrent binding to both EGFR and IGF1R is represented by the increase in response unit (RU, Y axis in both graphs shown in FIG. 13). Both graphs indicate the EGFR and IGF1R injection, and the co-injection of the two targets. Concurrent binding of the biMab-EI (PaniX/Dalo) to its targets was observed regardless of the injection event (e.g., EGFR injected first and IGFR1 injected second, as shown in the top panel, or vice versa, as shown in the bottom panel) or assay format. Concurrent binding was observed with IGF1R being injected first, followed by a co-injection of EGFR and IGF1R (FIG. 13A), and by reverting those injection events with EGFR injected first, followed by a co-injection of IGF1R and EGFR (FIG. 13B).

Figure 14:
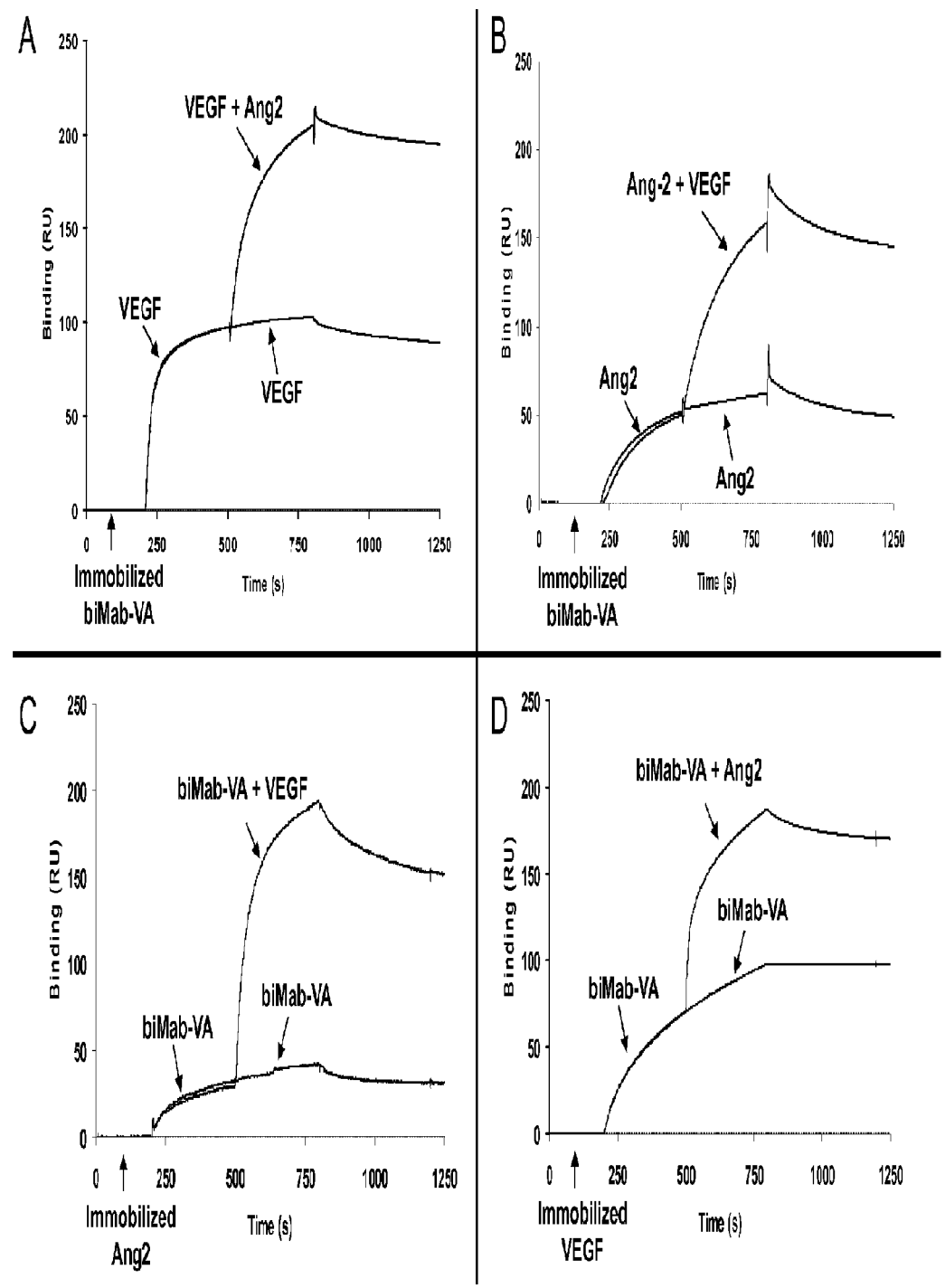
FIGS. 14A-D show the concurrent binding of biMab-VA to its targets VEGF and Ang2 as determined using BIAcore. The immobilized molecule was biMab-VA (panels A and B), Ang2 (panel C), and VEGF (Panel D). Concurrent binding is observed by increase in the binding response (RU). The concurrent binding is observed regardless of the injection sequence of the targets and regardless of what reagent was immobilized on the BIAcore sensor surface.

FIG. 14 shows the ability of the biMab-VA (Ava/LC06) to concurrently bind its targets VEGF and Ang2. For the experiments summarized in FIGS. 14A and 14B, the biMab-VA (Ava/LC06) was immobilized on the CM5 BIAcore sensor chip. Concurrent binding to both VEGF and Ang2 is represented by the increase in response unit (RU, left axis in both graphs shown in FIGS. 14A and B). Both graphs indicate the VEGF and Ang2 injection, and the co-injection of the two ligands. Concurrent binding of the biMab-VA (Ava/LC06) to its targets was observed regardless of the injection event (e.g., VEGF injected first and Ang2 injected second, as shown in panel A, or vice versa, as shown in panel B) or assay format. Concurrent binding was observed with VEGF being injected first, followed by a co-injection of Ang2 and VEGF (FIG. 14A), and by reverting those injection events with Ang2 injected first, followed by a co-injection of Ang2 and VEGF (FIG. 14B).

In addition, as shown in FIGS. 14C and D, concurrent binding is also observed when either one of the target proteins is immobilized on the sensor chip. In the experiments depicted in FIG. 14C, Ang2 was immobilized. In the experiments depicted in FIG. 14D, VEGF was immobilized. In both cases, concurrent binding was observed (represented by the increase in response unit).

For the results described in FIGS. 13 and 14, concurrent binding of the biMabs was measured using BIAcore 3000 instrument (GE Healthcare). Briefly, different flowcells of a CM5 sensor chip were immobilized with different protein samples (in 20 mM acetate buffer pH 4.0 buffer) by amine coupling. An isotype control antibody (IgG1) on flowcell-1, biMab-VA on flowcell-2, VEGF on flowcell-3 and Ang-2 on flowcell-4. Another CM5 sensor chip was prepared by immobilizing the isotype control antibody (IgG1) on flowcell-1, and biMab-EI on flowcell-2. The biMab's and the antigens (VEGF, Ang-2, EGFR-Fc, IGF1R) were diluted in the running buffer (HBS-EP-10 mM Hepes, pH 7.4, 150 mM NaCl, 3 mM ethylenediaminetetraacetic acid (EDTA), and 0.05% P20). Simultaneous binding was determined using the "co-inject" procedure. Concurrent binding for biMab-EI was analyzed using the CM5 sensor chip with immobilized biMab-EI. The analyte injections were composed of EGFR followed by a mixture of EGFR and IGF1R (FIG. 13A). The order of injections of the antigens was reversed in the next set of experiments (i.e IGF1R followed by a mixture of IGF1R and EGFR) (FIG. 13B). Concurrent binding for biMab-VA was performed in all four possible orientations. In the first experiment (FIG. 14A), co-injection of VEGF and a mixture of VEGF and Ang-2 was measured on an immobilized biMab-VA surface, while in the second experiment (FIG. 14B), the order of antigen injections were reversed. In the third experiment (FIG. 14C), co-injection of biMab-VA and a mixture of biMab-VA and VEGF was measured on an immobilized Ang-2 surface. In the fourth experiment (FIG. 14D), co-injection of biMab-VA and a mixture of biMab-VA and Ang-2 was measured on an immobilized VEGF surface.

Example 5

Representative biMabs Bind to FcRn

The ability of representative biMabs to bind to FcRn was assessed by BIAcore analysis. Briefly, the biMabs and control antibody (10 µg/mL in 20 mM acetate buffer pH 4.0) were immobilized on to a CM5 sensor chip by amine coupling to achieve the desired immobilization levels (~600 RU). Human FcRn was buffer exchanged with the running buffer (50 mM Sodium Phosphate, pH 6.0) using a HiTrap desalting column (GE lifesciences). Two-fold dilutions of human FcRn (30 µM-30 nM) were injected over the immobilized antibodies to measure the equilibrium binding for 1 min at 30 µL/min. The analyte was dissociated from the chip for 5 min with running buffer. Any remaining FcRn was removed from the chip with two 60-second injections of PBS pH 7.4. Sensorgrams were generated and analyzed by using BiaEval software version 3.1. The equilibrium RU observed for each injection was plotted against the concentration of FcRn. The equilibrium $K_D$ values were derived by analysis of the plots by using the steady-state affinity model included in the BiaEval software.

FIG. 15 shows the $K_D$ for FcRn binding of biMab-EI (PaniX/Dalo) and biMab-VA (Ava/LC06), as determined by BIAcore. The $K_D$ for FcRn binding for a representative parental antibody (PaniX, anti-EGFR) is also shown. As shown in FIG. 15, both biMabs retain the ability to bind FcRn, and such binding is similar to that of a parental conventional antibody. The differences in the observed $K_D$ are within normal BIAcore standard error.

Example 6

Representative biMabs Bind to C1q

The ability of representative biMabs to bind C1q was assessed by ELISA. Briefly, five micrograms per milliliter (30 µl/well) of biMabs or antibody anti-EGFR or BSA were coated on ELISA plates (Costar 3690) overnight in PBS (Invitrogen catalog number 20012). The ELISA plates were washed 5 times with PBST (1×PBS pH 7.2, 0.1% Tween-20) and blocked with 150 µlof BSB-PBST (3% BSA (Sigma catalog number A2153), 50% Superblock (Thermo Scientfic catalog number 37515) in PBST for 1 hour at 37° C. A two-fold dilution of Human C1q (Cell Sciences catalog number CRC 162B) starting from 100 µg/ml in BSB-PBST was added (30 µl/well) and incubated at room temperature for 1 hour. After the incubation, the ELISA plates were washed 5 times with PBST and 30 µl of 1 µg/ml sheep anti-human C1q (Immunology Consultants Lab catalog number SC1Q-80A) in BSB-PBST was added. The ELISA plates were washed again 5 times with PBST and 30 µl of 1:2500 dilution of Donkey anti-sheep/goat-HRP (SeroTec catalog number Star88P) in BSB-PBST was added. The plates were finally washed 5 times with PBST and developed with (30 µl/well) TMB (KPL catalog number 53-0-03) for 5 minutes; after which, 30 µl of 0.2 N HCl was added to stop the reaction. Data were plotted using Prism5 software.

Figure 16:
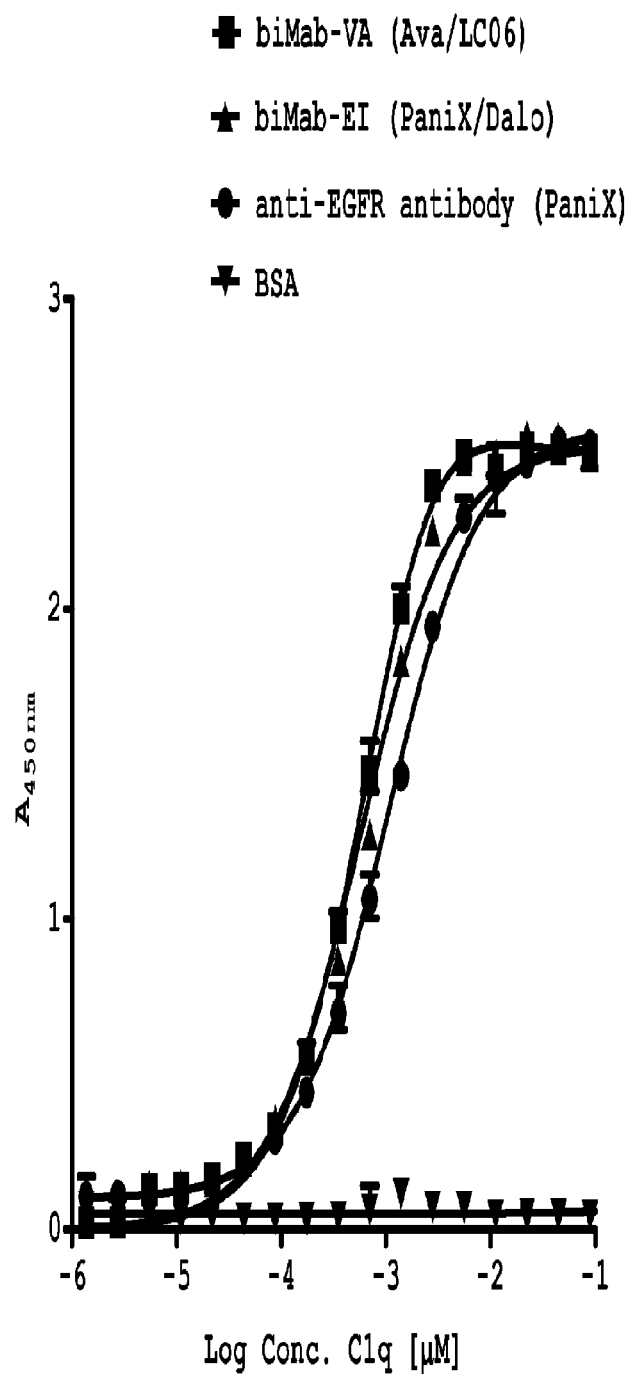
FIG. 16 depicts the results of ELISA analysis in which the binding to human C1q by each of biMab-EI, biMab-VA, the parental conventional anti-EGFR mAb, or BSA are assayed.

As shown in FIG. 16, biMab-EI (PaniX/Dalo) and biMab-VA (Ava/LC06) bind C1q, and the binding is with similar affinity as that of one of the representative parental conventional antibodies anti-EGFR (PaniX), which also serves as a positive control. These data support the conclusion that the biMab format retains the capacity to mediate complement-dependent cytotoxicity (CDC), in a manner similar to conventional antibodies.

Example 7

Figure 17:
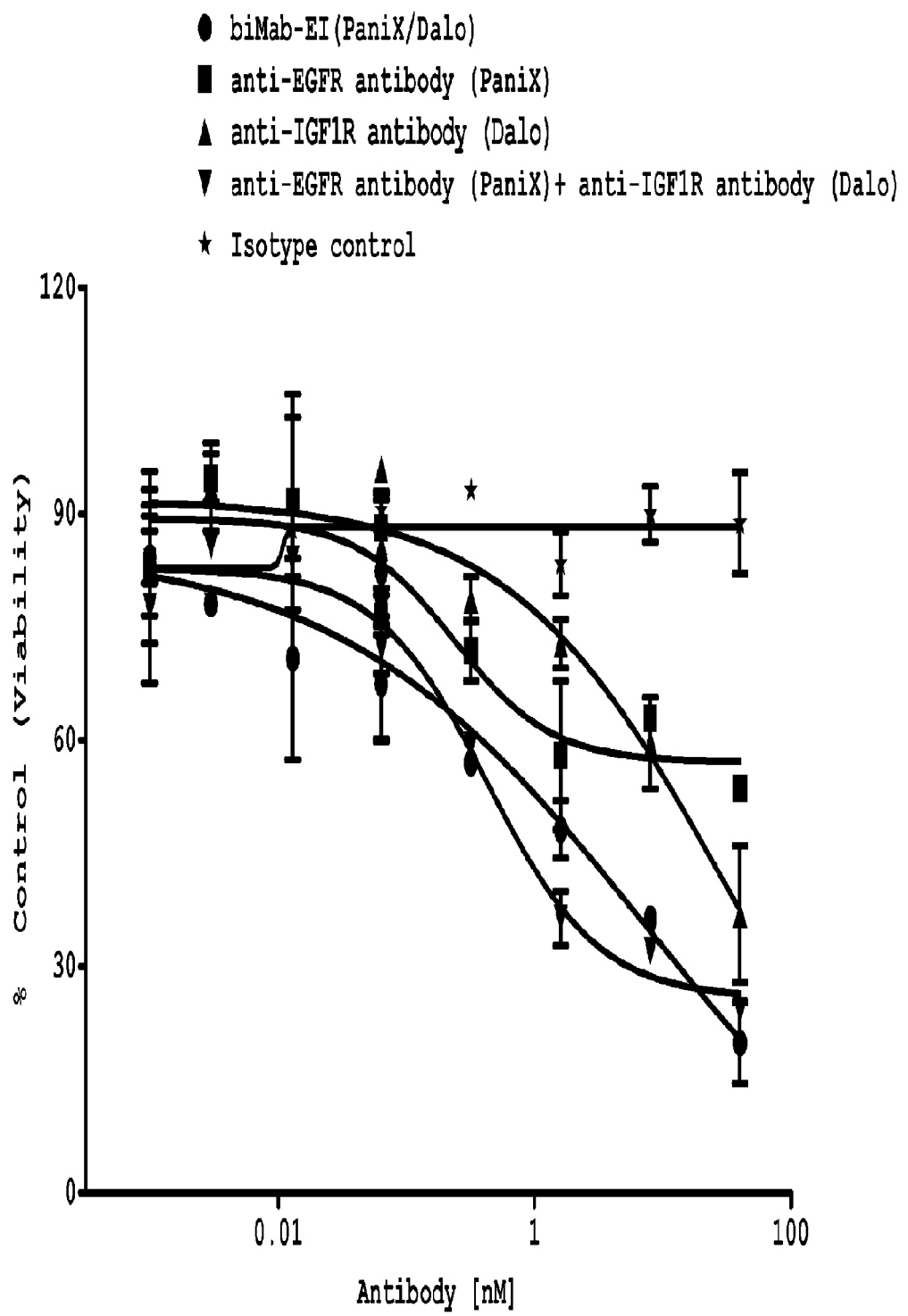
FIG. 17 provides the results of a cell killing assay measuring cell viability in response to: biMab-EI, the parental conventional anti-EGFR mAb, the parental conventional anti-IGR1R mAb, a mixture of the two parental conventional anti-EGFR and anti-IGF1R antibodies used in constructing biMab-EI, and an isotype control antibody.

Representative biMab Retains the Cell Killing Activity Observed for their Parental Conventional Antibodies FIG. 17 shows the results of a cell killing assay involving: (i) biMab-EI (PaniX/Dalo), or (ii) the combination of the parental conventional anti-EGFR antibody (antibody PaniX) and the parental conventional anti-IGF1R antibody (antibody Dalo), or (iii) the parental conventional anti-EGFR antibody (PaniX) alone, or (iv) the parental conventional anti-IGF1R antibody (Dalo) alone, or (v) an isotype negative control antibody. The cells used for this cytotoxicity assay were H358 (human non-small lung adenocarcinoma cells that express both the EGFR and IGF1R receptors; ATCC catalog number CRL-5807). H358 cell were plated at 50,000 cells per well in a 96 well plate (Costar catalog number 3788) in 120 µl complete cell culture medium (1×RPMI 1640 Gibco catalog number 11875+10% Hi FBS Gibco catalog number 25300). Serial dilutions of each antibody were made in cell culture medium at 5× final concentration starting from 200 nM. 30 µl/well of the diluted antibodies were added to the assay plate and incubated at 37° C., 95% humidity for 72 hr. CellTiter-Glo® cell viability assay reagent (Promega catalog number G7571) equilibrated at room temperature was added (120 µl/well) to the assay plates, followed by gently mixing and incubation at room temperature for 15 min. After the incubation, the luminescence of the ATP was measured using Envision 2014 multilabel reader following the manufacture's recommendations. The CellTiter-Glo® Luminescent Cell Viability Assay is a homogeneous method to determine the number of viable cells in culture based on quantitation of the ATP present, which signals the presence of metabolically active cells.

As shown in FIG. 17, biMab-EI (PaniX/Dalo) killed the H358 cells (represented as a decrease in % of viable cells) at a level similar to that of combined treatment with both parental conventional antibodies (PaniX (anti-EGFR)+Dalo (anti-IGF1R)). These results indicate that the biMab format retained the function of each of the conventional antibodies from which it was derived.

Example 8

Representative biMabs Retain Functional Activity to Inhibit Target Ligand

Figure 18A:
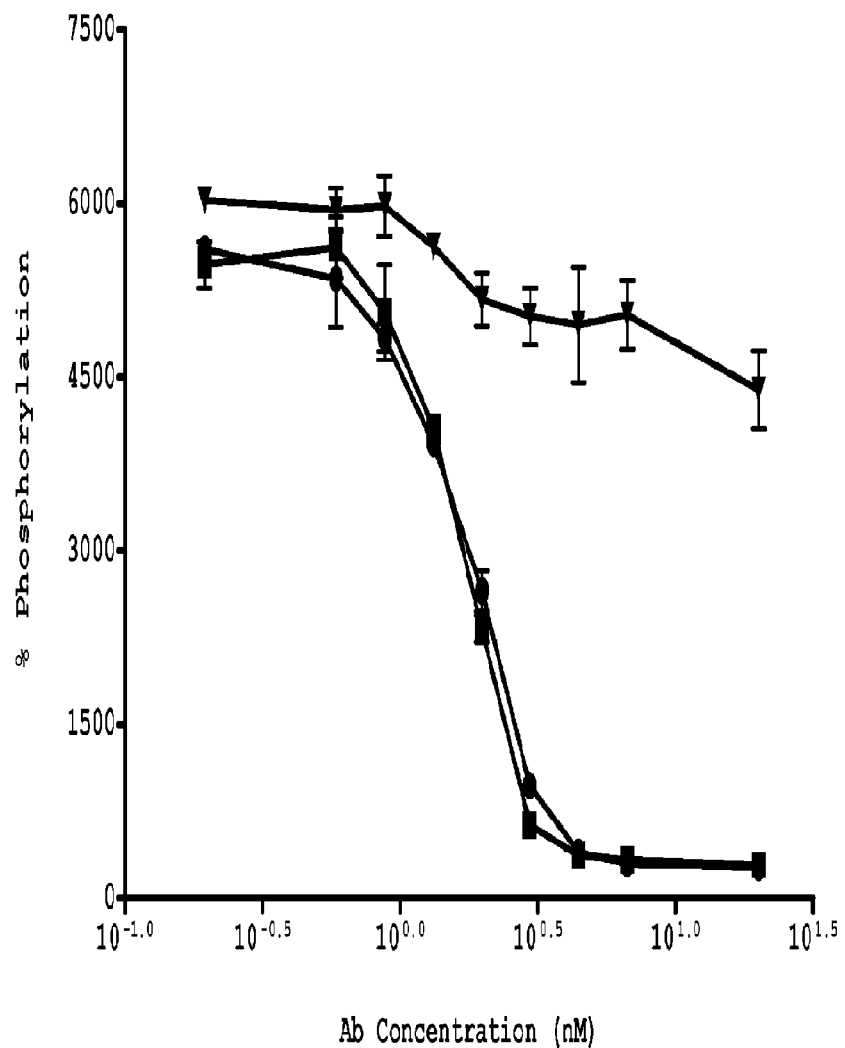
FIG. 18A-B shows the inhibition of pTie2 (natural receptor of Ang2) phosphorylation (FIG. 18A) and inhibition of pVEGFR2 (natural receptor of VEGF) phosphorylation by biMab-VA. The parental antibodies and negative control antibodies were included in these sets of experiments.
Figure 18B:
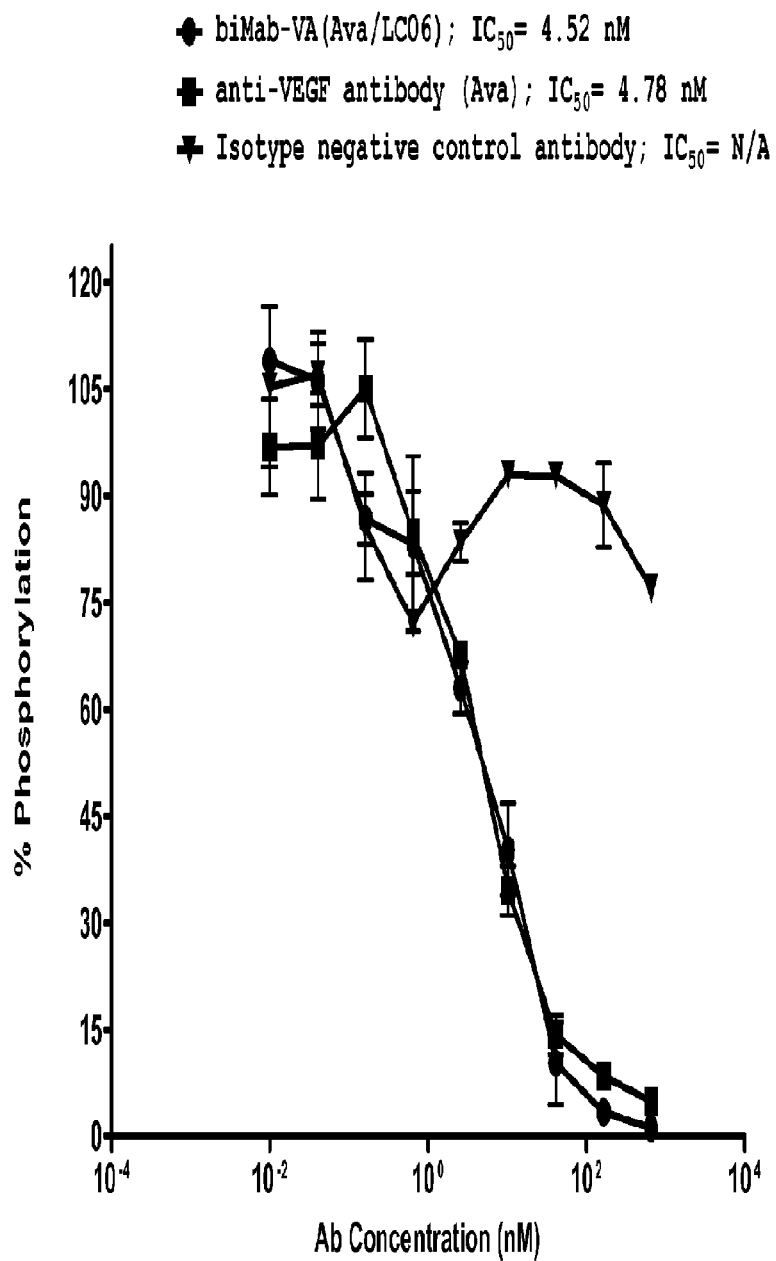

FIG. 18 shows the inhibition of Tie2 (natural receptor of Ang2) phosphorylation (FIG. 18A) and inhibition of VEGFR2 (natural receptor of VEGF) phosphorylation by biMab-VA (FIG. 18B).

The ability of biMab-VA, anti-Ang2 (LC06) and isotype negative control antibodies to bind human Ang2 and block Ang2-mediated Tie2 receptor phosphorylation was determined using the following procedure. Stably transfected HEK293 cell lines expressing the full-length human Tie2 receptor were grown in DMEM supplemented with 10% FBS and 2 µg/mL puromycin at 37° C. and 5% $CO_2$ using 96-well culture plates (Corning Cell-bind tissue culture plates form Sigma-Aldrich) and then serum starved for 18 hours. Cells were stimulated for 25 min in the presence of purified human recombinant Ang2 (R&D Systems catalog number 623-AN-CF; Ang2 reconstituted to 3.6 µg/mL stock solution in PBS), preincubated with either biMab-VA, anti-Ang2 (LC06) or isotype negative control antibodies. The mixtures of antibodies and Ang2 were added to the cells and serial diluted starting from a solution of 120 nM. The cells were then lysed with 40 µL, of ice-cold lysis buffer (7 ml RIPA Lysis Buffer, 1 tube Halt inhibitor, benzonase-Thermo Scientific-), and the phosphorylation levels of Tyrosine 992 of the Tie2 receptor was determined from whole cell lysates by using Meso Scale Discovery with mouse total Tie2 antibody (Abcam catalog number ab24859) for capture and a rabbit specific antibody (R&D Systems catalog number AF2720) for detection.

As shown in FIG. 18A, the inhibition of Tie2 phosphorylation mediated by Ang2 is similar upon addition of biMab-VA (Ava/LC06, IC50 1.79 nM) or its parental conventional anti-Ang2 antibody (LC06, IC50 1.72 nM). The negative isotype control antibody does not inhibit the Ang2-mediated phosphorylation of Tie2. This experiment reveals that the biMab-VA (Ava/LC06) functionally inhibits Ang2. The $IC_{50}$ (half maximal inhibitory concentration) values in nM are schematically reported. As shown, biMab-VA (Ava/LC06) and its parental conventional antibody anti-Ang2 (LC06) have similar $IC_{50}$.

The ability of biMab-VA, anti-VEGF antibody and isotype negative control antibodies to inhibit VEGFR2 phosphorylation mediated by VEGF was determined using the following procedure. Human VEGFR receptor (hVEGFR2) was recombinantly and stably expressed in AD293 cells, which were grown in DMEM medium with 10% FBS (Invitrogen). The cells were seeded at 15000 cells per well in 100 µL of medium, using 96-well flat bottom Corning Cell-bind tissue culture plates (Sigma-Aldrich). After 24 hours of growth, the medium was removed without any wash and "starvation" media, 50 µL/well, composed of DMEM+0.2% FBS+0.1% BSA (Sigma-Aldrich) was added. The cells were then incubated overnight. The medium was removed from each well and 50 µL of 4 nM human VEGF165 (Peprotech catalog number 100-20) prepared in starving medium was added to the cells followed by 30 minutes incubation at 4° C. Concurrently, biMab-VA, anti-VEGF (Ava) and the isotype negative control antibodies were also added and serially diluted starting from 200 µg/mL. The cells were then incubated for 7 minutes at 37° C., the media was removed and no wash step was performed. The cells were then lysed with 40 µL of ice-cold lysis buffer (7 ml RIPA Lysis Buffer, 1 tube Halt inhibitor, benzonase-Thermo Scientific-), and phosphorylation of the VEGFR2 was determined by using Meso Scale Discovery assays kit (MSD catalog number K151DJD-2). This kit provides assay-specific components for the quantitative determination of phospho-VEGFR-2 (Tyr1054) in human whole cell lysates.

As shown in FIG. 18B, the inhibition of VEGFR2 phosphorylation mediated by VEGF is similar upon addition of biMab-VA (Ava/LC06, IC50 4.58 nM) and its parental conventional anti-VEGF antibody (Ava, IC50 4.78 nM). The negative isotype control antibody does not inhibit the VEGF-mediated phosphorylation of pVEGFR2. This experiment reveals that the biMab-VA (Ava/LC06) functionally inhibits VEGF. The $IC_{50}$ (half maximal inhibitory concentration) values in nM are schematically reported. As shown, biMab-VA (Ava/LC06) and its parental conventional antibody anti-VEGF (Ava) have similar $IC_{50}$.

Example 9

Homogeneous Monomer Content of Representative biMabs is Maintained at Increasing Concentrations FIG. 19 demonstrates that representative biMabs can be concentrated without detrimental impact on monomer content. Briefly, the biMab proteins were purified to high monomeric content using protein A and Ceramic Hydroxyapatite Type II Media following the manufacturer's recommendations (BioRad catalog number 158-2200) and analyzed by SEC-HPLC in standard running buffer (0.1 mM sodium phosphate, 0.1 mM sodium sulfate pH 6.8). The purified monomeric proteins were dialyzed overnight in 25 mM Histidine-HCl pH 6 and again analyzed by HPLC-SEC in standard running buffer for the pre-concentration monomeric percentage. The biMabs were then concentrated to less than one milliliter using Vivaspin 20, 100 kDa MWCO (GE healthcare catalog number 28-9323-63) at 1455×g and the concentration was determined by reading the A280 nm absorbance value and by using a molar absorptivity of 1.4. The concentrated material was filtered using 0.22 micron syringe filters and visually inspected for particulate presence and corrected to 25 mg/mL. An aliquot of 250 micrograms of protein from the 25 mg/mL solution was analyzed by HPLC-SEC using the standard buffer to determine monomeric percentage after concentration. SEC-HPLC was carried out as described in Example 2 above.

Initial and final concentrations are shown in mg/mL. The initial concentration of each biMab formulated is presented in the top half of the table presented in FIG. 19, along with the monomer content (%) observed at that initial concentration. At these initial concentrations, monomer content was greater than 99%. The final, more concentrated preparation of each biMab formulated at 20 mg/mL is presented in the bottom half of the table presented in FIG. 19. As can be seen by comparing each row of the top half of the figure to its corresponding row in the bottom half of the figure (e.g., compare the first row in the top half of the figure to the first row in the bottom half of the figure), biMabs can be concentrated with no monomer loss. Monomer content, represented as a %, was determined using SEC-HPLC.

Example 10

Figure 20:
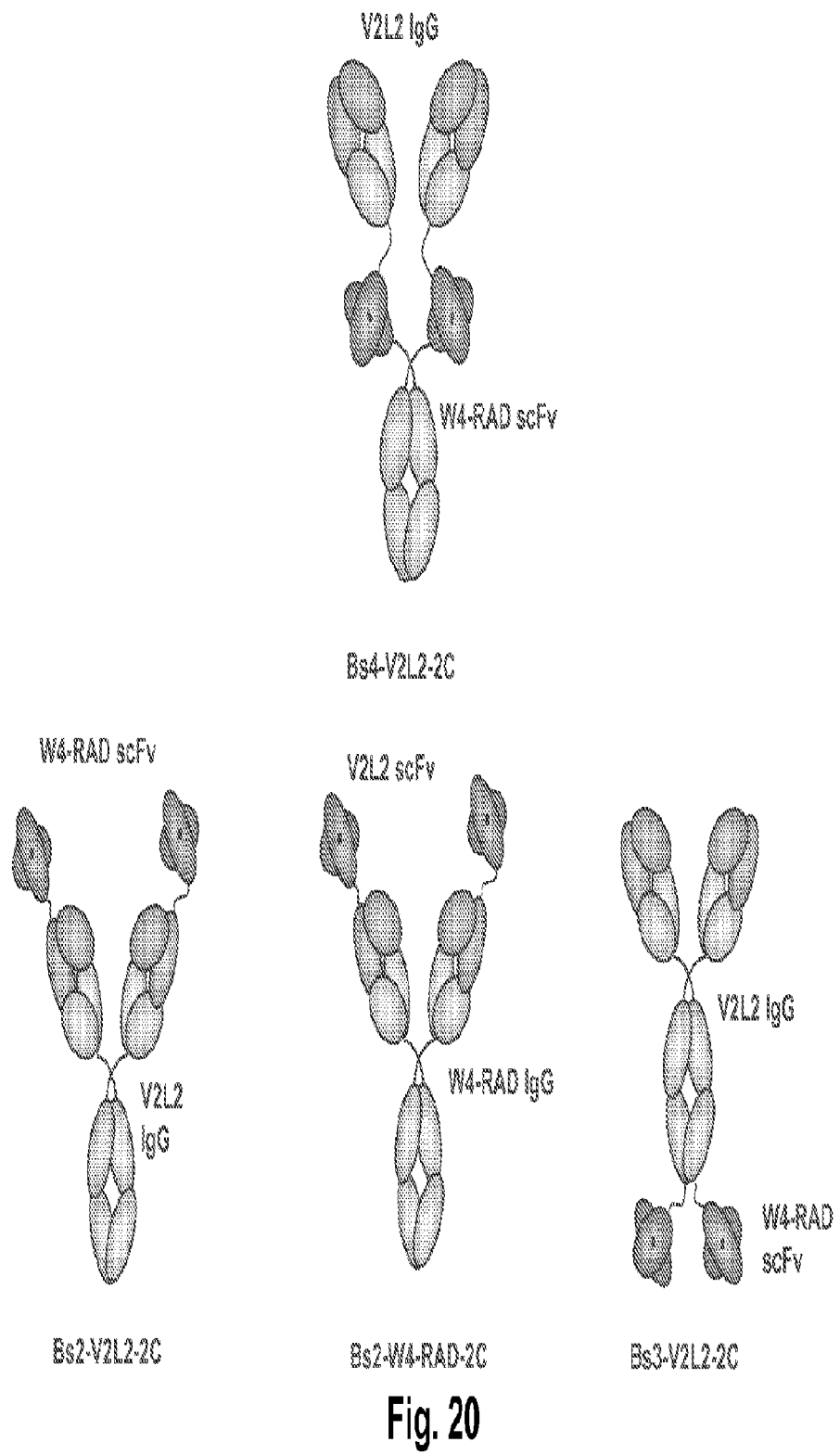
FIG. 20 is a schematic representation of two conventional bispecific antibody formats referred to as Bs2, Bs3 in which an scFv is fused to the amino terminus of the variable region (Bs2) or the carboxy-terminus of CH3 (Bs3) of a heavy chain through a linker (e.g., $(G_4S)_2$). An exemplary biMab of in the instant invention having an scFv inserted in the hinge region, linked by a linker on the N-terminal and C-terminal of the scFv is shown for comparison (also see FIG. 8). Two different Bs2 constructs are shown, for Bs2-V2L2-2C the W4-RAD scFv is fused to the amino-terminus of the V2L2 VH (See, SEQ ID NOS:51 and 53 for the amino acid sequence of the light and heavy chains respectively, and SEQ ID NOS: 50 and 52 for the corresponding nucleotide sequences), for Bs2-W4-RAD-2C the V2L2 scFv is fused to the amino-terminus of W4-RAD VH (See SEQ ID NOS: 55 and 57 for the amino acid sequence of the light and heavy chains, respectively and SEQ ID NOS: 54 and 56 for the corresponding nucleotide sequences). For Bs3-V2L2-2C, the W4-RAD scFv is fused to the carboxy-terminus of CH3 (See SEQ ID NOS:59 and 61 for the amino acid sequence of the light and heavy chains, respectively and SEQ ID NOS: 58 and 60 for the corresponding nucleotide sequences). For the BiMab Bs4-V2L2-2C, the W4-RAD scFv is inserted in the hinge region (See FIG. 8 and SEQ ID NOS:42 and 45 for the amino acid sequence of the light and heavy chains respectively).

Comparison of Representative biMabs to Conventional Bivalent Bispecific Antibody Formats Additional bispecific antibodies were generated using two conventional bivalent bispecific formats (see, e.g., Dimasi et al., J Mol. Biol., 2009 393:627-92) comprising the variable regions from the anti-PcrV antibody V2L2 (SEQ ID NO:43 and 46) and the anti-Psl antibody W4-RAD (SEQ ID NO: 48 and 49). A schematic representation of the conventional Bs2 and Bs3 bispecific antibody formats and an exemplary biMab generated from the same variable regions is provided in FIG. 20. All four antibodies were tested in several in vitro and in vivo assays as follows.

Figure 21:
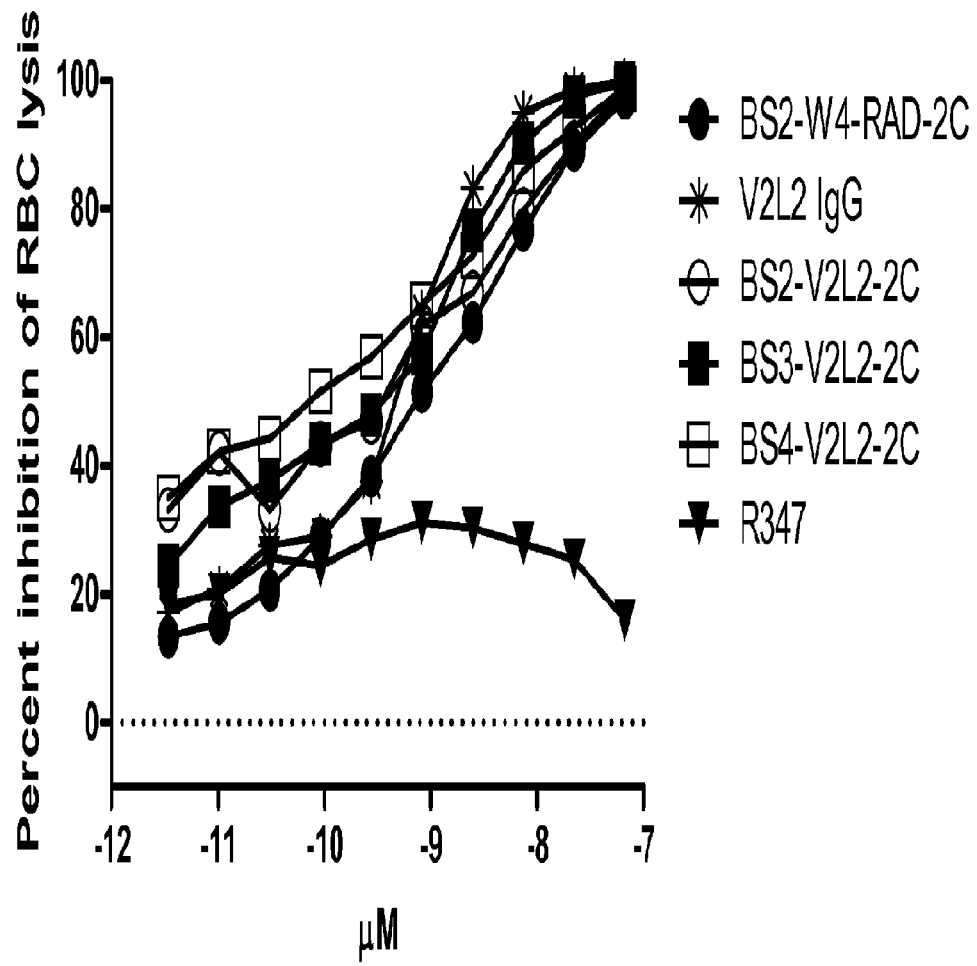
FIG. 21 shows that BS2-V2L2, BS3-V2L2, and BS4-V2L2 all prevented lysis of RBCs similar to the parental control (V2L2). R347 was used as a negative control.

The various bispecific antibodies and R347 (negative control) were evaluated for their ability to prevent lysis of RBCs. Brieflt, the antibodies are mixed with log-phase P. aeruginosa 6077 (exoU$^+$) and washed rabbit red blood cells (RBCs) and incubated for 2 hours at 37°. Intact RBCs are pelleted and the extent of lysis determined by measuring the $OD_{405}$ of the cell-free supernatant. Lysis in the presence of the antibodies is compared to wells without mAb to determine percent inhibition percent inhibition of RBC lysis. As shown in FIG. 21 all bispecific antibodies inhibited RBC lysis at levels similar to the parental V2L2 antibody.

Figure 22:
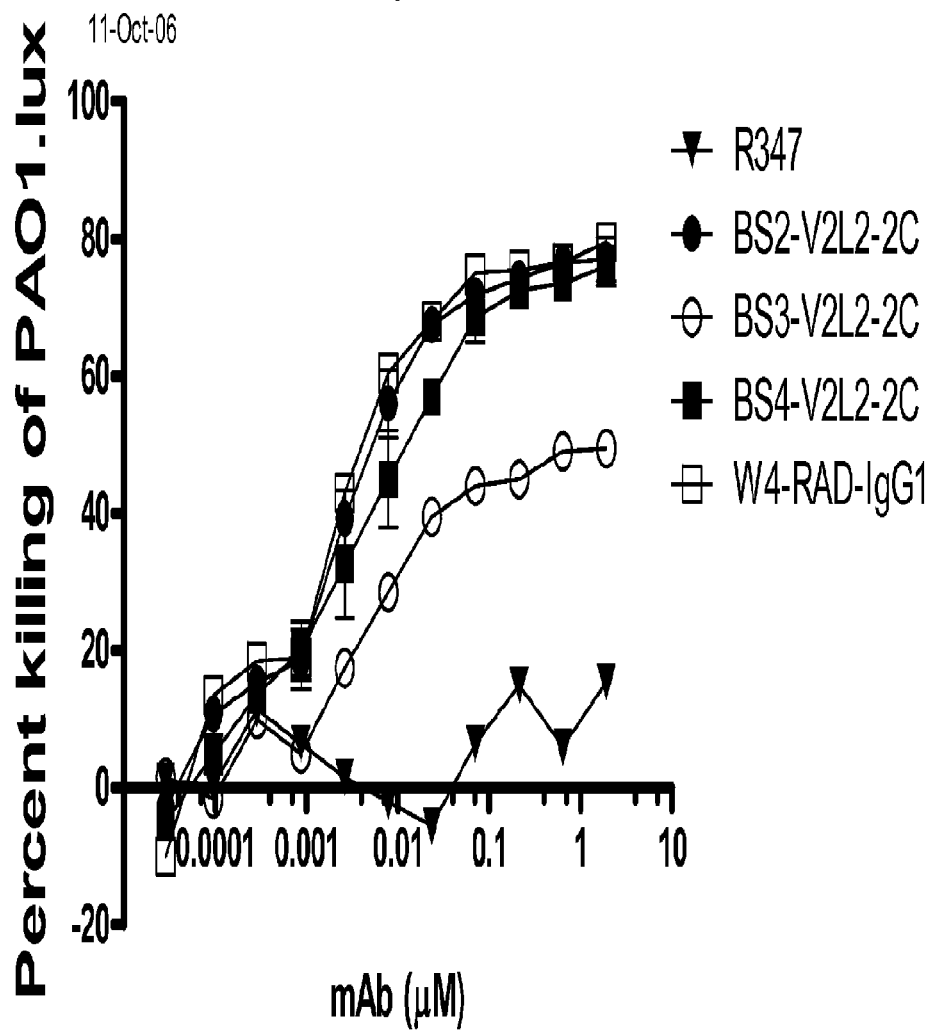
FIG. 22 shows an opsonophagocytosis assay with luminescent P. aeruginosa serogroup O5 strain (PAO1.lux), with dilutions of purified the W4-RAD parental antibody; the Psl/PcrV bispecific antibodies Bs2-V2L2-2C, Bs3-V2L2-2C, Bs4-V2L2-2C. The Bs2-V2L2-2C and Bs4-V2L2-2C antibodies showed similar killing compared to the parental W4-RAD antibody, the killing for the Bs3-V2L2-2C antibody was decreased. R347 was used as a negative control in all experiments.
Figure 23A:
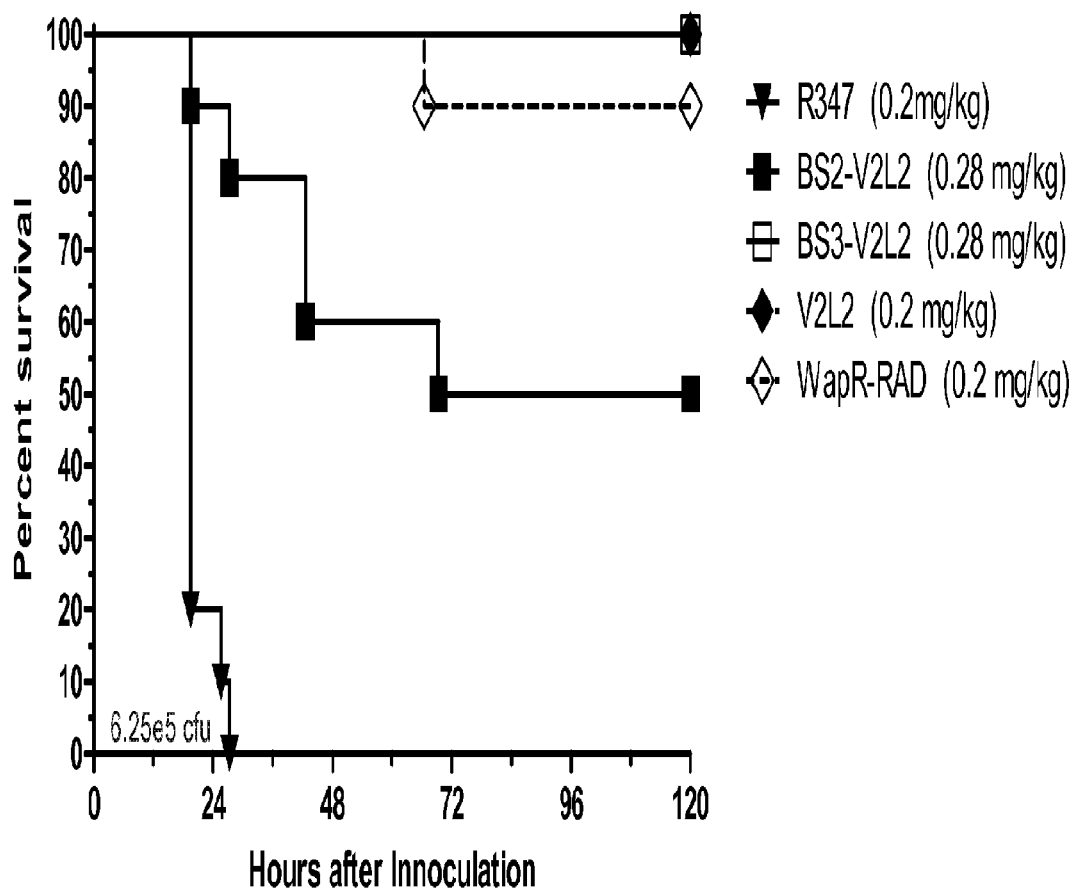
FIG. 23A-D shows In vivo survival study of mice treated with different anti-Psl/anti-PcrV bispecific antibodies in a 6206 acute pneumonia model system. In all studies the control mice succumbed to infection by ~30-48 hours post infection. Studies A-D are show in panels A-D, respectively. (A) All of the Bs3-V2L2 animals survived, along with those which received the V2L2 control. Approximately 90% of the W4-RAD immunized animals survived. In contrast, approximately 50% of the Bs2-V2L2 animals succumbed to infection by 120 hours. (B): Bs4-V2L2-2C had greater activity in comparison to Bs2-V2L2 at both 1.0 and 0.5 mg/kg. (C): Bs4-V2L2-2C appeared to have greater activity in comparison to Bs2-V2L2 at 1.0 mg/kg. (D): Bs4-V2L2-2C had greater activity in comparison to Bs3-V2L2 at 0.5 mg/kg.
Figure 23B:
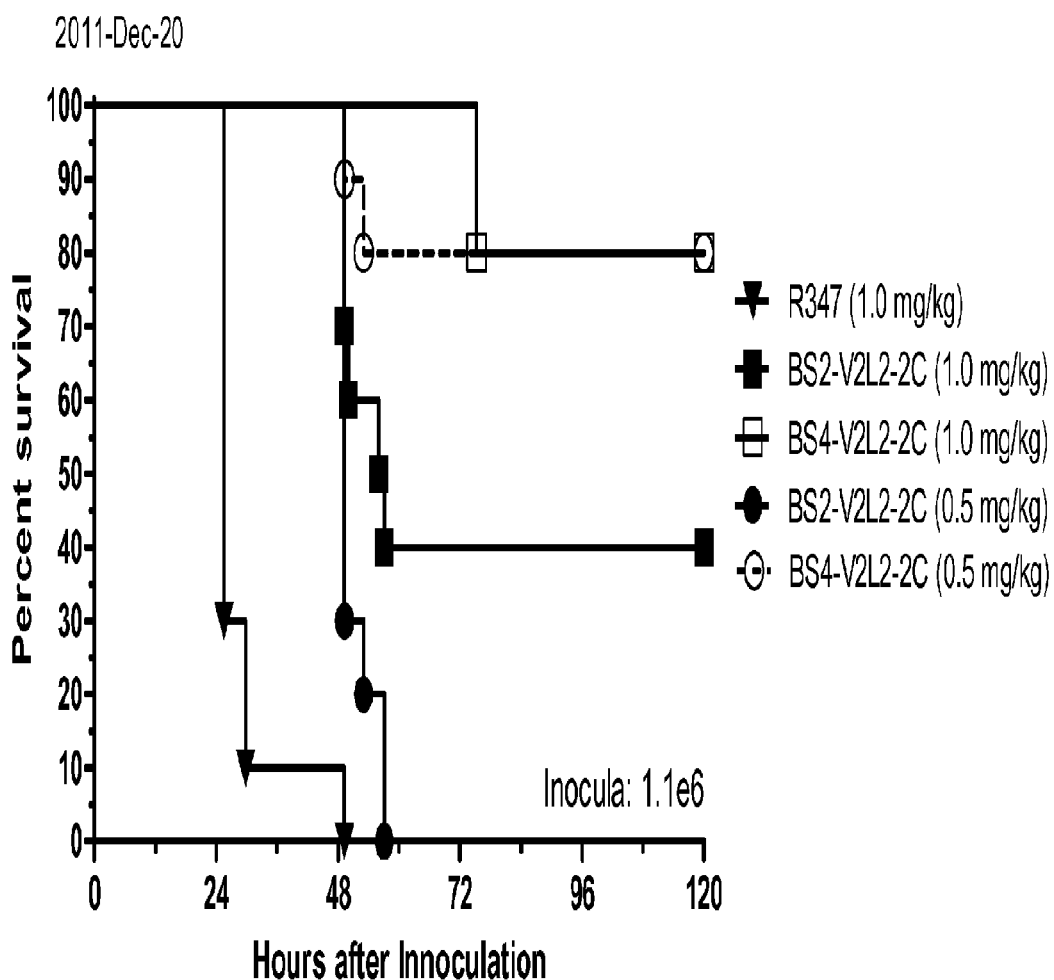
Figure 23C:
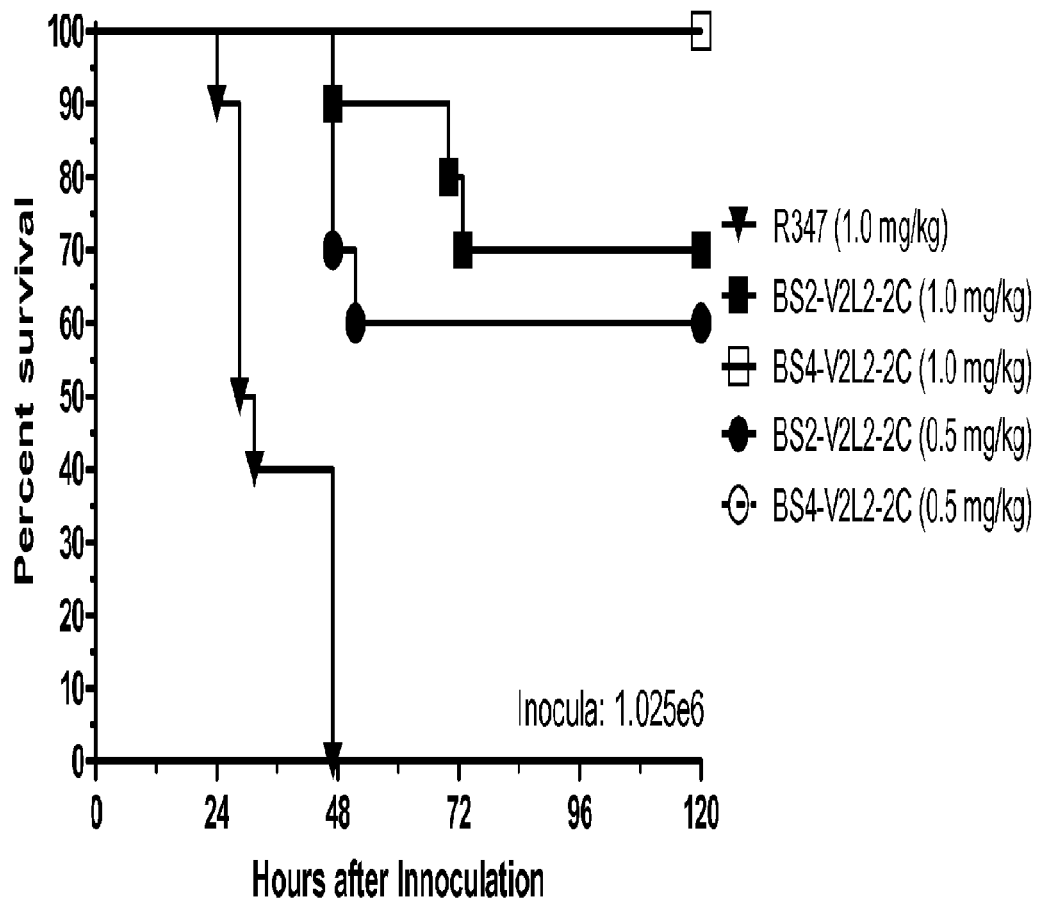
Figure 23D:
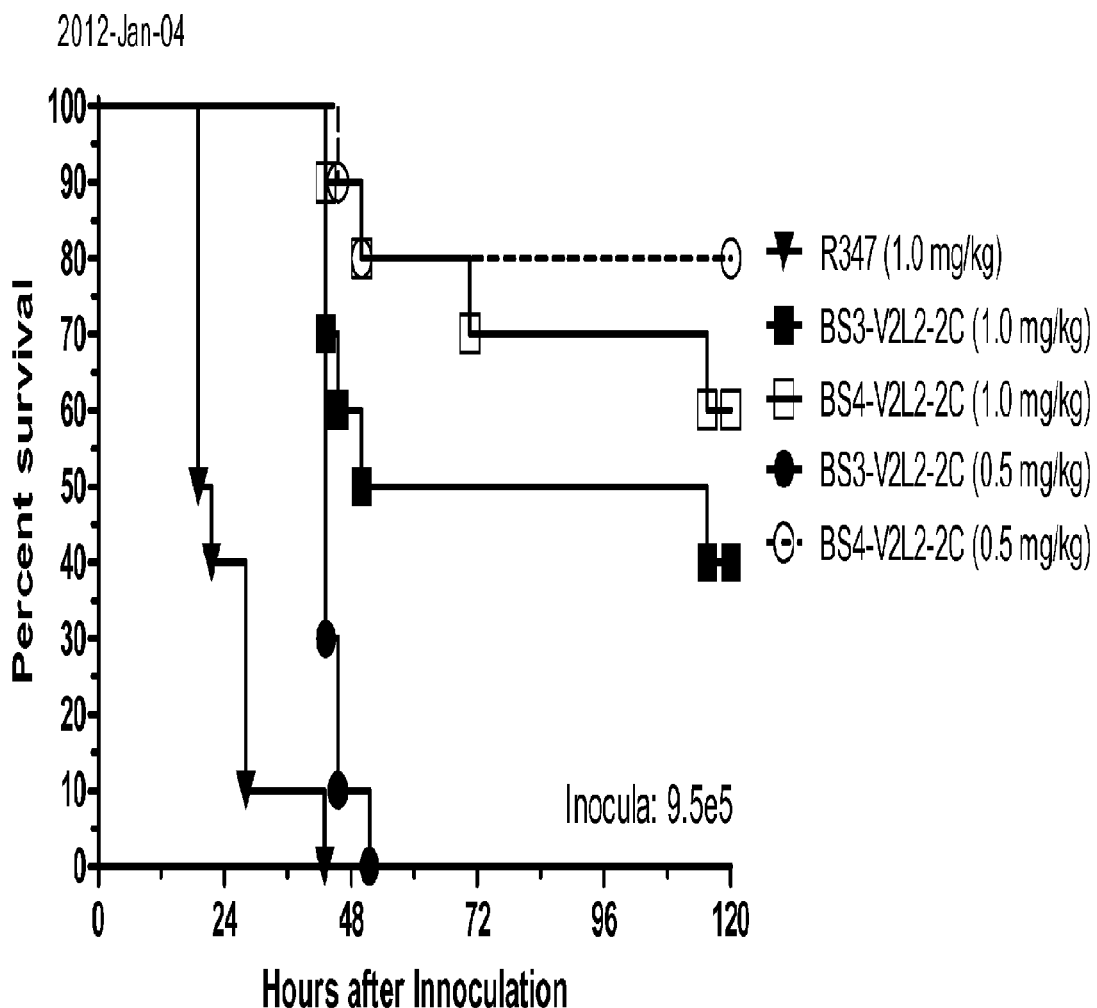
Figure 25:
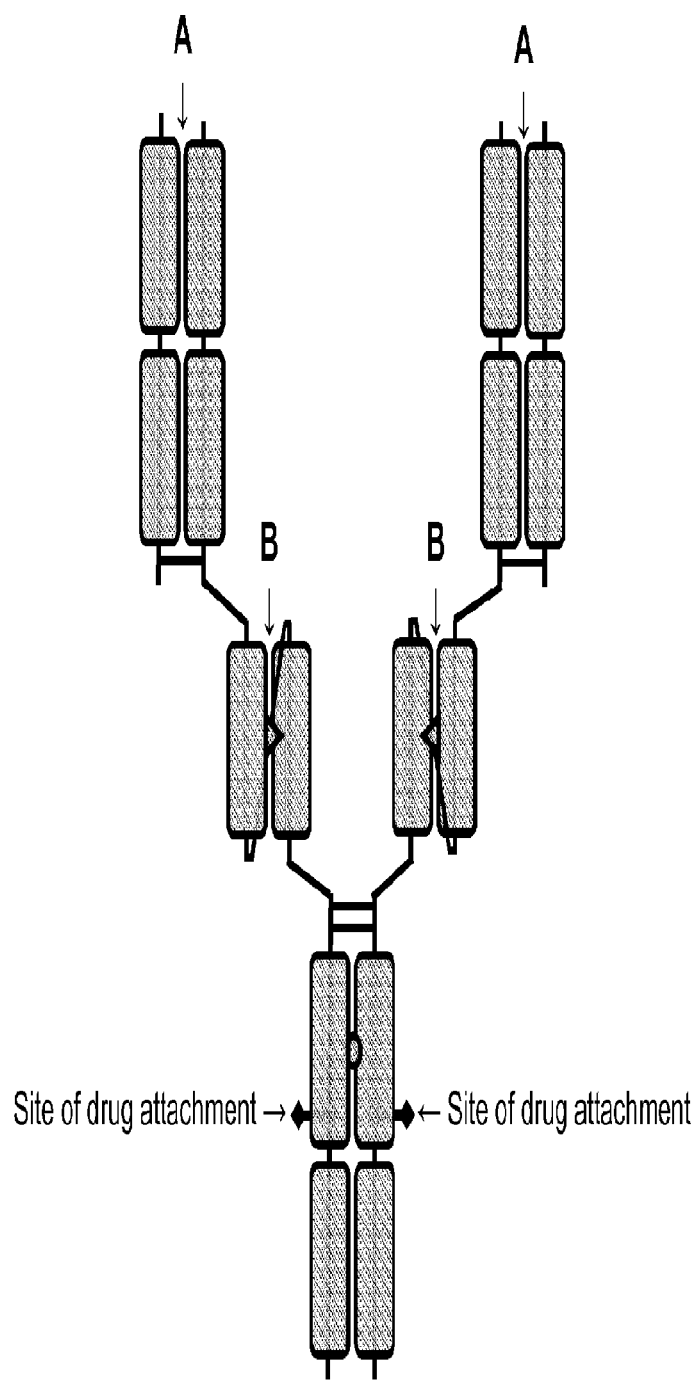
FIG. 25 illustrates a biMab that carries site-specific modifications for points of attachment of drugs or toxins. The modifications are shown on the $C_H2$ Fc domain of the biMab for illustration purposes only. Modifications can be introduced in any domain of the biMab or can be introduced in multiple domains of the biMab. The drug or toxin can be conjugated to the biMab using chemical- or protein-mediated conjugation methods. Site-specific protease cleavage sites can be engineered in or around the linkers that connect the active drug or toxin to the biMab if the release of the drug or toxin is needed. The binding units of the biMab modified for site-specific drug conjugation are labeled with the letters A and B. This biMab modified for site-specific drug conjugation is bispecific bivalent for each target. Of note, the biMab targets can be different or can be the same. When the targets are the same, the biMab binding units may bind to non-overlapping regions (e.g., bispecific, bivalent), or may bind the same epitope (e.g., monospecific, tetravalent).

A single Bs2 (BS2-V2L2-2C) the Bs3 and the biMab antibodies were also tested in an in vitro opsonophagocytosis (OPK) killing assay performed as described in (DiGiandomenico, A., et al., *Infect Immun* 72, 7012-7021 (2004)), with modifications. Briefly, assays were performed in 96-well plates using 0.025 ml of each OPK component; *P. aeruginosa* strains; diluted baby rabbit serum; differentiated HL-60 cells; and monoclonal antibody. In some OPK assays, luminescent *P. aeruginosa* strains, which were constructed as described (Choi, K. H., et al., *Nat Methods* 2, 443-448 (2005)), were used. Luminescent OPK assays were performed as described above but with determination of relative luciferase units (RLUs) using a Perkin Elmer ENVISION Multilabel plate reader (Perkin Elmer). As shown in FIG. 22 the Bs2-V2L2-2C and Bs4-V2L2-2C antibodies showed similar killing compared to the parental W4-RAD antibody. However, the killing for the Bs3-V2L2-2C antibody was decreased. In this assay the biMab format had comparable activity to both the parental and the Bs2 bispecific antibody format.

The Bs2-V2L2, Bs3-V2L2 and Bs4-V2L2 constructs were assessed for survival from acute pneumonia infections in several studies using an in vivo *P. aeruginosa* 6202 acute pneumonia model. Mice (n=10) were treated as follows: (Study A) R347 (negative control, 0.2 mg/kg), Bs2-V2L2 (0.28 mg/kg), Bs3-V2L2 (0.28 mg/kg), V2L2 (0.2 mg/kg) or W4-RAD (0.2 mg/kg); (Studies B and C) R347 (negative control, 1 mg/kg), Bs2-V2L2 (0.5 mg/kg or 1 mg/kg), or Bs4-V2L2-2C (0.5 mg/kg or 1 mg/kg); (Study D): R347 (negative control, 1 mg/kg), Bs3-V2L2 (0.5 mg/kg or 1 mg/kg), or Bs4-V2L2-2C (0.5 mg/kg or 1 mg/kg). Twenty-four hours post-treatment, all mice were infected with ~($6.25\times10^5$-$1\times10^6$ CFU/animal) 6206 (011-ExoU+). All mice were monitored for 120 hours. The results for the studies are shown in FIG. 23A-D, respectively, (A) all of the control mice succumbed to infection by approximately 30 hours post-infection. All of the Bs3-V2L2 animals survived, along with those which received the V2L2 control. Approximately 90% of the W4-RAD immunized animals survived. In contrast, approximately 50% of the Bs2-V2L2 animals succumbed to infection by 120 hours. (B-D): All of the control mice succumbed to infection by approximately 48 hours post-infection. (B): Bs4-V2L2-2C had greater activity in comparison to Bs2-V2L2 at both 1.0 and 0.5 mg/kg. (C): Bs4-V2L2-2C appeared to have greater activity in comparison to Bs2-V2L2 at 1.0 mg/kg (results are not statistically significant). (D): Bs4-V2L2-2C had greater activity in comparison to Bs3-V2L2 at 0.5 mg/kg. To analyze the efficacy of each antibody construct, mice were treated with 0.1 mg/kg, 0.2 mg/kg, 0.5 mg/kg, 1 mg/kg, 2 mg/kg, 5 mg/kg, 10 mg/kg or 15 mg/kg and analyzed for survival in a 6206 lethal pneumonia model. The percent survival is indicated in Table shown in FIG. 24 with the number of animals for each comparison indicated in parentheses.

These data show that Bs4-V2L2-2C biMab antibody format is as effective as the mixture of the parental W4-RAD+V2L2 antibodies and is at least as effective, or even more effective than the conventional Bs2 and Bs3 bispecific antibody formats in protection against lethal pneumonia in mice challenged with *P. aeruginosa* strain 6206 (ExoU+).

INCORPORATION BY REFERENCE

All publications and patents mentioned herein are hereby incorporated by reference in their entirety as if each individual publication or patent was specifically and individually indicated to be incorporated by reference. In addition, U.S. Provisional Application Nos. 61/556,645 filed Nov. 7, 2011; 61/624,651 filed Apr. 16, 2012; 61/625,299 filed Apr. 17, 2012; 61/697,585 filed Sep. 6, 2012 and International Application No: PCT/US2012/41538, filed Nov. 6, 2012, entitled "COMBINATION THERAPIES USING ANTI-PSEUDOMONAS PSL AND PCRV BINDING MOLECULES") are incorporated by reference in their entirety for all purposes.

While specific aspects of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

We claim:

1. A protein, comprising:
   (a) a Fab arm that binds to a first epitope,
   (b) a binding domain (BD) that binds to a second epitope, and
   (c) an Fc region comprising CH2 and CH3 domains;
   wherein the protein comprises a chimeric heavy chain comprising the following polypeptide domains, from N-terminus to C-terminus VH1-CH1-L1-BD-L2-Fc;

wherein VH1 comprises the heavy chain variable domain of the Fab, CH1 comprises the heavy chain constant domain 1 of the Fab, L1 comprises the first linker polypeptide, BD comprises an scFV, L2 comprises the second linker polypeptide, and Fc comprises a CH2 and a CH3 domain and wherein the protein is bivalent for binding to each of the first and second epitopes, and wherein the L1 comprises the amino acid sequence EPKSCDKT (SEQ ID NO: 4) or EPKSCGKT (SEQ ID NO: 6) or EPKSC (SEQ ID NO: 38) wherein the L2 comprises the amino acid sequence EPKSVDKTHTCPPCP (SEQ ID NO: 12), CPPCP (SEQ ID NO: 14) or DKTHTCPPCP (SEQ ID NO: 40), and wherein the first epitope is selected from the group consisting of EGFR, IGFR1, VEGF, angiopoietin-2 (Ang2), exopolysaccharide (Psl) and *Pseudomonas aeruginosa* (Per V) and wherein the second epitope is selected from the group consisting of EGFR, IGFR1, VEGF, angiopoietin-2 (Ang2), exopolysaccharide (Psl) and *Pseudomonas aeruginosa* (Per V).

2. The protein of claim 1, wherein the L1 further comprises a Gly-Ser peptide and/or wherein the L2 further comprises a linker portion comprising a Gly-Ser peptide.

3. The protein of claim 1, wherein the scFv comprises a VH domain, a polypeptide linker and a VL domain.

4. The protein of claim 1, wherein the Fc region is selected from the group consisting of an Fc region from an IgG1, IgG2, IgG3, IgG4, IgA, IgM, IgE, and IgD.

5. The protein of claim 4, wherein the Fc region is aglycosylated.

6. The protein of claim 4, wherein the Fc region is deglycosylated.

7. The protein of claim 4, wherein the Fc region has reduced fucosylation or is afucosylated.

8. The protein of claim 4, wherein the Fc region comprises a substitution at position 297.

9. The protein of claim 8, wherein the substitution at position 297 is 297Q.

10. The protein of claim 1, wherein the first and second epitopes are different or wherein the first and second epitopes are the same.

11. The protein of claim 1, wherein the CH1 domain of the Fab arm comprises a substitution at one or more of positions 131, 132, 134, 135, 136 and 139, as numbered by the EU index and wherein the substitution is selected from the group consisting of amino acid cysteine, lysine, tyrosine, histidine, selenocysteine and selenomethionine.

12. The protein of claim 11, wherein the substitution is a cysteine.

13. The protein of claim 1, wherein the scFv comprises, from N-terminus to C-terminus VH2-polypeptide linker-VL2 or VL2-polypeptide linker-VH2;

wherein VH2 comprises the heavy chain variable domain of the scFv and VL2 comprises the light chain variable domain of the scFv.

14. The protein of claim 13, wherein the VL2 has a cysteine at Kabat position 100.

15. The protein of claim 13, wherein the VH domain of the scFv has a cysteine at Kabat position 44.

16. The protein of claim 1, wherein the first and second epitopes are different.

17. The protein of claim 1, wherein the first and second epitopes are the same.

18. A composition comprising the protein of claim 1 formulated in a pharmaceutically acceptable carrier.

* * * * *

SEQUENCE LISTING

```
<160> NUMBER OF SEQ ID NOS: 70

<210> SEQ ID NO 1
<211> LENGTH: 294
<212> TYPE: DNA
<213> ORGANISM: Homo sapiens

<400> SEQUENCE: 1
gcgtcgacca agggcccatc cgtcttcccc ctggcaccct cctccaagag cacctctggg      60
ggcacagcgg ccctgggctg cctggtcaag gactacttcc ccgaaccggt gacggtgtcc     120
tggaactcag gcgctctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagag agtt           294

<210> SEQ ID NO 2
<211> LENGTH: 98
<212> TYPE: PRT
<213> ORGANISM: Homo sapiens

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 3
<211> LENGTH: 24
<212> TYPE: DNA
<213> ORGANISM: Artificial
<220> FEATURE:
<223> OTHER INFORMATION: synthetic construct

<400> SEQUENCE: 3
gagcccaaat cttgtgacaa aact                                             24

<210> SEQ ID NO 4
<211> LENGTH: 8
<212> TYPE: PRT
```

```
<213> ORGANISM: Artificial
<220> FEATURE:
<223> OTHER INFORMATION: synthetic construct

<400> SEQUENCE: 4

Glu Pro Lys Ser Cys Asp Lys Thr
1               5

<210> SEQ ID NO 5
<211> LENGTH: 24
<212> TYPE: DNA
<213> ORGANISM: Artificial
<220> FEATURE:
<223> OTHER INFORMATION: synthetic construct

<400> SEQUENCE: 5
gagcccaaat cttgtggaaa aact                                          24

<210> SEQ ID NO 6
<211> LENGTH: 8
<212> TYPE: PRT
<213> ORGANISM: Artificial
<220> FEATURE:
<223> OTHER INFORMATION: synthetic construct

<400> SEQUENCE: 6

Glu Pro Lys Ser Cys Gly Lys Thr
1               5

<210> SEQ ID NO 7
<211> LENGTH: 30
<212> TYPE: DNA
<213> ORGANISM: Artificial
<220> FEATURE:
<223> OTHER INFORMATION: synthetic construct

<400> SEQUENCE: 7
ggcggagggg gatccggcgg aggggctct                                     30

<210> SEQ ID NO 8
<211> LENGTH: 10
<212> TYPE: PRT
<213> ORGANISM: Artificial
<220> FEATURE:
<223> OTHER INFORMATION: synthetic construct

<400> SEQUENCE: 8

Gly Gly Gly Gly Ser Gly Gly Gly Gly Ser
1               5                   10

<210> SEQ ID NO 9
<211> LENGTH: 45
<212> TYPE: DNA
<213> ORGANISM: Homo sapiens

<400> SEQUENCE: 9
gagcccaaat cttgtgacaa aactcacaca tgcccaccgt gccca                   45

<210> SEQ ID NO 10
<211> LENGTH: 15
<212> TYPE: PRT
<213> ORGANISM: Homo sapiens

<400> SEQUENCE: 10

Glu Pro Lys Ser Cys Asp Lys Thr His Thr Cys Pro Pro Cys Pro
1               5                   10                  15
```

<210> SEQ ID NO 11
<211> LENGTH: 45
<212> TYPE: DNA
<213> ORGANISM: Artificial
<220> FEATURE:
<223> OTHER INFORMATION: synthetic construct

<400> SEQUENCE: 11
gagcccaaat ctgtagacaa aactcacaca tgcccaccgt gccca                    45

<210> SEQ ID NO 12
<211> LENGTH: 15
<212> TYPE: PRT
<213> ORGANISM: Artificial
<220> FEATURE:
<223> OTHER INFORMATION: synthetic construct

<400> SEQUENCE: 12

Glu Pro Lys Ser Val Asp Lys Thr His Thr Cys Pro Pro Cys Pro
1               5                   10                  15

<210> SEQ ID NO 13
<211> LENGTH: 15
<212> TYPE: DNA
<213> ORGANISM: Artificial
<220> FEATURE:
<223> OTHER INFORMATION: synthetic construct

<400> SEQUENCE: 13
tgcccaccgt gccca                                                     15

<210> SEQ ID NO 14
<211> LENGTH: 5
<212> TYPE: PRT
<213> ORGANISM: Artificial
<220> FEATURE:
<223> OTHER INFORMATION: synthetic construct

<400> SEQUENCE: 14

Cys Pro Pro Cys Pro
1               5

<210> SEQ ID NO 15
<211> LENGTH: 330
<212> TYPE: DNA
<213> ORGANISM: Homo sapiens

<400> SEQUENCE: 15
gcacctgaac tcctgggggg accgtcagtc ttcctcttcc ccccaaaacc caaggacacc    60
ctcatgatct cccggacccc tgaggtcaca tgcgtggtgg tggacgtgag ccacgaagac   120
cctgaggtca agttcaactg gtacgtggac ggcgtggagg tgcataatgc caagacaaag   180
ccgcgggagg agcagtacaa cagcacgtac cgtgtggtca gcgtcctcac cgtcctgcac   240
caggactggc tgaatggcaa ggagtacaag tgcaaggtct ccaacaaagc cctcccagcc   300
cccatcgaga aaaccatctc caaagccaaa                                    330

<210> SEQ ID NO 16
<211> LENGTH: 110
<212> TYPE: PRT
<213> ORGANISM: Homo sapiens

<400> SEQUENCE: 16

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65              70                  75                  80

Gln Asp Trp Leu Asn Gly Lys Glu Tyr Lys Cys Lys Val Ser Asn Lys
            85                  90                  95

Ala Leu Pro Ala Pro Ile Glu Lys Thr Ile Ser Lys Ala Lys
            100                 105                 110

<210> SEQ ID NO 17
<211> LENGTH: 321
<212> TYPE: DNA
<213> ORGANISM: Homo sapiens

<400> SEQUENCE: 17
gggcagcccc gagaaccaca ggtctacacc ctgcccccat cccgggagga gatgaccaag      60
aaccaggtca gcctgacctg cctggtcaaa ggcttctatc ccagcgacat cgccgtggag     120
tgggagagca atgggcagcc ggagaacaac tacaagacca cgcctcccgt gctggactcc     180
gacggctcct tcttcctcta tagcaagctc accgtggaca agagcaggtg gcagcagggg     240
aacgtcttct catgctccgt gatgcatgag gctctgcaca accactacac gcagaagagc     300
ttaagcctgt ctccgggtaa a                                                321

<210> SEQ ID NO 18
<211> LENGTH: 107
<212> TYPE: PRT
<213> ORGANISM: Homo sapiens

<400> SEQUENCE: 18

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65              70                  75                  80

Asn Val Phe Ser Cys Ser Val Met His Glu Ala Leu His Asn His Tyr
            85                  90                  95

Thr Gln Lys Ser Leu Ser Leu Ser Pro Gly Lys
            100                 105

<210> SEQ ID NO 19
<211> LENGTH: 648
<212> TYPE: DNA
<213> ORGANISM: artificial
<220> FEATURE:
<223> OTHER INFORMATION: synthetic construct

<400> SEQUENCE: 19
```

-continued

```
gacatccaga tgacccagag ccccagcagc ctgagcgcca gcgtgggcga cagagtgacc      60
atcacctgcc aggccagcca ggacatcagc aactacctga actggtatca gcagaagccc     120
ggcaaggccc ccaagctgct gatctacgac gccagcaacc tggagacagg cgtgcccagc     180
agattcagcg gcagcggctc cggcaccgac ttcaccttca ccatcagcag cctccagccc     240
gaggatatcg ccacctactt ttgccagcac ttcgaccacc tgcccctggc ctttggcggc     300
ggaacaaagg tggagatcaa gcgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga aaacacaaa gtctacgcct gcgaagtcac ccatcagggc     600
ctgagctcgc ccgtcacaaa gagcttcaac aggggagagt gttagtga                 648
```

<210> SEQ ID NO 20
<211> LENGTH: 214
<212> TYPE: PRT
<213> ORGANISM: artificial
<220> FEATURE:
<223> OTHER INFORMATION: synthetic construct

<400> SEQUENCE: 20

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 21
<211> LENGTH: 107
<212> TYPE: PRT

<213> ORGANISM: artificial
<220> FEATURE:
<223> OTHER INFORMATION: synthetic construct

<400> SEQUENCE: 21

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys
            100                 105
```

<210> SEQ ID NO 22
<211> LENGTH: 2148
<212> TYPE: DNA
<213> ORGANISM: artificial
<220> FEATURE:
<223> OTHER INFORMATION: synthetic construct

<400> SEQUENCE: 22

| | | | | | |
|---|---|---|---|---|---|
| caggtgcagc | tccaggagag | cggccctggc | ctggtgaagc | ccagcgagac | actgagcctg | 60 |
| acctgcaccg | tgtccggcgg | cagcgtgtcc | agcggcgact | actactggac | ctggatcaga | 120 |
| cagagccccg | gcaagggcct | ggagtggatc | ggccacatct | actacagcgg | caacaccaac | 180 |
| tacaacccca | gcctgaagtc | cagactgacc | atcagcatcg | acaccagcaa | gacccagttc | 240 |
| agcctgaagc | tgtccagcgt | gacagccgcc | gacaccgcca | tctactactg | cgtgagagac | 300 |
| agagtgaccg | gcgctttcga | catctggggc | cagggcacca | tggtgaccgt | gtccagcgcg | 360 |
| tcgaccaagg | gacctagcgt | gttccctctg | gcccccagca | gcaagtctac | atctggcgga | 420 |
| acagccgccc | tgggctgcct | cgtgaaggac | tactttcccg | agcccgtgac | cgtgtcctgg | 480 |
| aacagcggag | cactgaccag | cggcgtgcac | acctttccag | ccgtgctgca | gagcagcggc | 540 |
| ctgtactctc | tgagcagcgt | cgtgacagtg | cccagcagct | ctctgggcac | ccagacctac | 600 |
| atctgcaacg | tgaaccacaa | gcccagcaac | accaaggtgg | acaagcgggt | ggaacccaag | 660 |
| agctgcggca | aaacaggcgg | cggaggatcc | ggcgaggcg | ctctgatat | cgtgatgacc | 720 |
| cagagccccg | tgagcctgcc | tgtgacacct | ggcgaacctg | ccagcatcag | ctgcagatcc | 780 |
| agccagagca | tcgtgcacag | caacggcaac | acctacctgc | agtggtatct | gcagaagccc | 840 |
| ggccagagcc | ctcagctgct | gatctacaag | gtgtccaacc | ggctgtacgg | cgtgcccgac | 900 |
| agatttctg | gcagcggctc | cggcaccgac | ttcaccctga | gatctcccg | gtggaagcc | 960 |
| gaggacgtgg | gcgtgtacta | ctgttttcaa | ggcagccacg | tgccctggac | cttcggctgt | 1020 |
| ggcacaaagg | tggaaatcaa | gggcggaggg | ggatctgggg | gcggaggctc | tggcggggga | 1080 |
| ggaagtgggg | gaggcggatc | tcaggtgcag | ctgcaggaat | ctggccctgg | cctcgtgaaa | 1140 |
| cccagcgaga | cactgagcct | gacatgcacc | gtgtccggct | acagcatcac | cggcggctac | 1200 |
| ctgtggaact | ggatcagaca | gcccccctggc | aagtgcctgg | aatggatcgg | ctacatcagc | 1260 |

```
tacgacggca ccaacaacta caagccctcc ctgaaggaca gagtgaccat cagccgggac   1320
accagcaaga accagttcag cctgaagctg tccagcgtga cagccgccga taccgccgtg   1380
tactattgcg ccagatacgg ccgggtgttc ttcgactatt ggggccaggg caccctcgtg   1440
actgtgtcat ctgggggagg gggaagcgga ggcggaggaa gttgtcctcc ttgtcctgcc   1500
cccgaactgc tgggcggacc ttccgtgttc ctgttccccc caaagcccaa ggacaccctg   1560
atgatcagcc ggaccccgga agtgacctgc gtggtggtgg atgtgtccca cgaggaccct   1620
gaagtgaagt tcaattggta cgtggacggc gtggaagtgc acaacgccaa gaccaagcct   1680
agagaggaac agtacaacag cacctaccgg gtggtgtccg tgctgacagt gctgcaccag   1740
gactggctga acggcaaaga gtacaagtgc aaagtgtcca acaaggccct gcctgccccc   1800
atcgagaaaa ccatcagcaa ggccaaggga cagccccgcg agccccaagt gtataccctg   1860 cccccctagcc gggaagagat gaccaagaat caggtgtccc tgacctgtct cgtgaaaggc   1920
ttctacccca gcgacattgc cgtggaatgg gagagcaacg gccagcccga gaacaattac   1980
aagaccaccc cccctgtgct ggactccgac ggctcattct tcctgtactc caagctgacc   2040
gtggacaaga ccggtggca gcagggcaac gtgttcagct gctccgtgat gcacgaggcc   2100
ctgcacaacc actacaccca gaagtccctg tccctgagcc ccggcaaa             2148

<210> SEQ ID NO 23
<211> LENGTH: 716
<212> TYPE: PRT
<213> ORGANISM: artificial
<220> FEATURE:
<223> OTHER INFORMATION: synthetic construct

<400> SEQUENCE: 23

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

```
Ser Asn Thr Lys Val Asp Lys Arg Val Glu Pro Lys Ser Cys Gly Lys
    210                 215                 220

Thr Gly Gly Gly Gly Ser Gly Gly Gly Ser Asp Ile Val Met Thr
225                 230                 235                 240

Gln Ser Pro Leu Ser Leu Pro Val Thr Pro Gly Glu Pro Ala Ser Ile
                    245                 250                 255

Ser Cys Arg Ser Ser Gln Ser Ile Val His Ser Asn Gly Asn Thr Tyr
            260                 265                 270

Leu Gln Trp Tyr Leu Gln Lys Pro Gly Gln Ser Pro Gln Leu Leu Ile
        275                 280                 285

Tyr Lys Val Ser Asn Arg Leu Tyr Gly Val Pro Asp Arg Phe Ser Gly
    290                 295                 300

Ser Gly Ser Gly Thr Asp Phe Thr Leu Lys Ile Ser Arg Val Glu Ala
305                 310                 315                 320

Glu Asp Val Gly Val Tyr Tyr Cys Phe Gln Gly Ser His Val Pro Trp
                325                 330                 335

Thr Phe Gly Cys Gly Thr Lys Val Glu Ile Lys Gly Gly Gly Gly Ser
            340                 345                 350

Gly Gly Gly Gly Ser Gly Gly Gly Ser Gly Gly Gly Gly Ser Gln
        355                 360                 365

Val Gln Leu Gln Glu Ser Gly Pro Gly Leu Val Lys Pro Ser Glu Thr
    370                 375                 380

Leu Ser Leu Thr Cys Thr Val Ser Gly Tyr Ser Ile Thr Gly Gly Tyr
385                 390                 395                 400

Leu Trp Asn Trp Ile Arg Gln Pro Pro Gly Lys Cys Leu Glu Trp Ile
                405                 410                 415

Gly Tyr Ile Ser Tyr Asp Gly Thr Asn Asn Tyr Lys Pro Ser Leu Lys
            420                 425                 430

Asp Arg Val Thr Ile Ser Arg Asp Thr Ser Lys Asn Gln Phe Ser Leu
        435                 440                 445

Lys Leu Ser Ser Val Thr Ala Ala Asp Thr Ala Val Tyr Tyr Cys Ala
    450                 455                 460

Arg Tyr Gly Arg Val Phe Phe Asp Tyr Trp Gly Gln Gly Thr Leu Val
465                 470                 475                 480

Thr Val Ser Ser Gly Gly Gly Ser Gly Gly Gly Gly Ser Cys Pro
                485                 490                 495

Pro Cys Pro Ala Pro Glu Leu Leu Gly Gly Pro Ser Val Phe Leu Phe
            500                 505                 510

Pro Pro Lys Pro Lys Asp Thr Leu Met Ile Ser Arg Thr Pro Glu Val
        515                 520                 525

Thr Cys Val Val Val Asp Val Ser His Glu Asp Pro Glu Val Lys Phe
    530                 535                 540

Asn Trp Tyr Val Asp Gly Val Glu Val His Asn Ala Lys Thr Lys Pro
545                 550                 555                 560

Arg Glu Glu Gln Tyr Asn Ser Thr Tyr Arg Val Val Ser Val Leu Thr
                565                 570                 575

Val Leu His Gln Asp Trp Leu Asn Gly Lys Glu Tyr Lys Cys Lys Val
            580                 585                 590

Ser Asn Lys Ala Leu Pro Ala Pro Ile Glu Lys Thr Ile Ser Lys Ala
        595                 600                 605

Lys Gly Gln Pro Arg Glu Pro Gln Val Tyr Thr Leu Pro Pro Ser Arg
    610                 615                 620

Glu Glu Met Thr Lys Asn Gln Val Ser Leu Thr Cys Leu Val Lys Gly
```

```
                625                 630                 635                 640

Phe Tyr Pro Ser Asp Ile Ala Val Glu Trp Glu Ser Asn Gly Gln Pro
            645                 650                 655

Glu Asn Asn Tyr Lys Thr Thr Pro Pro Val Leu Asp Ser Asp Gly Ser
                660                 665                 670

Phe Phe Leu Tyr Ser Lys Leu Thr Val Asp Lys Ser Arg Trp Gln Gln
            675                 680                 685

Gly Asn Val Phe Ser Cys Ser Val Met His Glu Ala Leu His Asn His
        690                 695                 700

Tyr Thr Gln Lys Ser Leu Ser Leu Ser Pro Gly Lys
705                 710                 715

<210> SEQ ID NO 24
<211> LENGTH: 119
<212> TYPE: PRT
<213> ORGANISM: artificial
<220> FEATURE:
<223> OTHER INFORMATION: synthetic construct

<400> SEQUENCE: 24

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser
        115

<210> SEQ ID NO 25
<211> LENGTH: 249
<212> TYPE: PRT
<213> ORGANISM: artificial
<220> FEATURE:
<223> OTHER INFORMATION: synthetic construct

<400> SEQUENCE: 25

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Gln Trp Tyr Leu Gln Lys Pro Gly Gln Ser
        35                  40                  45

Pro Gln Leu Leu Ile Tyr Lys Val Ser Asn Arg Leu Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95
```

```
Ser His Val Pro Trp Thr Phe Gly Cys Gly Thr Lys Val Glu Ile Lys
            100                 105                 110

Gly Gly Gly Gly Ser Gly Gly Gly Ser Gly Gly Gly Gly Ser Gly
        115                 120                 125

Gly Gly Gly Ser Gln Val Gln Leu Gln Glu Ser Gly Pro Gly Leu Val
        130                 135                 140

Lys Pro Ser Glu Thr Leu Ser Leu Thr Cys Thr Val Ser Gly Tyr Ser
145                 150                 155                 160

Ile Thr Gly Gly Tyr Leu Trp Asn Trp Ile Arg Gln Pro Pro Gly Lys
                165                 170                 175

Cys Leu Glu Trp Ile Gly Tyr Ile Ser Tyr Asp Gly Thr Asn Asn Tyr
                180                 185                 190

Lys Pro Ser Leu Lys Asp Arg Val Thr Ile Ser Arg Asp Thr Ser Lys
                195                 200                 205

Asn Gln Phe Ser Leu Lys Leu Ser Ser Val Thr Ala Ala Asp Thr Ala
            210                 215                 220

Val Tyr Tyr Cys Ala Arg Tyr Gly Arg Val Phe Phe Asp Tyr Trp Gly
225                 230                 235                 240

Gln Gly Thr Leu Val Thr Val Ser Ser
                245

<210> SEQ ID NO 26
<211> LENGTH: 112
<212> TYPE: PRT
<213> ORGANISM: artificial
<220> FEATURE:
<223> OTHER INFORMATION: synthetic construct

<400> SEQUENCE: 26

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Gln Trp Tyr Leu Gln Lys Pro Gly Gln Ser
        35                  40                  45

Pro Gln Leu Leu Ile Tyr Lys Val Ser Asn Arg Leu Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Cys Gly Thr Lys Val Glu Ile Lys
            100                 105                 110

<210> SEQ ID NO 27
<211> LENGTH: 117
<212> TYPE: PRT
<213> ORGANISM: artificial
<220> FEATURE:
<223> OTHER INFORMATION: synthetic construct

<400> SEQUENCE: 27

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Gly Gly
            20                  25                  30

Tyr Leu Trp Asn Trp Ile Arg Gln Pro Pro Gly Lys Cys Leu Glu Trp
        35                  40                  45
```

```
Ile Gly Tyr Ile Ser Tyr Asp Gly Thr Asn Asn Tyr Lys Pro Ser Leu
        50                  55                  60

Lys Asp Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Tyr Gly Arg Val Phe Phe Asp Tyr Trp Gly Gln Gly Thr Leu
                100                 105                 110

Val Thr Val Ser Ser
            115

<210> SEQ ID NO 28
<211> LENGTH: 642
<212> TYPE: DNA
<213> ORGANISM: artificial
<220> FEATURE:
<223> OTHER INFORMATION: synthetic construct

<400> SEQUENCE: 28
gacatccaga tgacccagag ccccagcagc ctgagcgcca gcgtgggcga cagagtgacc      60
atcacctgta gcgccagcca ggacatcagc aactacctga actggtatca gcagaagccc    120
ggcaaggccc ccaaggtgct gatctacttc accagctccc tgcacagcgg cgtgcccagc    180
agattttctg gcagcggcag cggcaccgac ttcaccctga ccatcagcag cctgcagccc    240
gaggacttcg ccacctacta ctgccagcag tacagcaccg tgccttggac cttcggccag    300
ggcaccaagg tggaaatcaa gcgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                      642

<210> SEQ ID NO 29
<211> LENGTH: 214
<212> TYPE: PRT
<213> ORGANISM: artificial
<220> FEATURE:
<223> OTHER INFORMATION: synthetic construct

<400> SEQUENCE: 29

Asp Ile Gln Met Thr Gln Ser Pro Ser Ser Leu Ser Ala Ser Val Gly
  1               5                  10                  15

Asp Arg Val Thr Ile Thr Cys Ser Ala Ser Gln Asp Ile Ser Asn Tyr
                 20                  25                  30

Leu Asn Trp Tyr Gln Gln Lys Pro Gly Lys Ala Pro Lys Val Leu Ile
             35                  40                  45

Tyr Phe Thr Ser Ser Leu His Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val Ala Ala
                100                 105                 110
```

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 30
<211> LENGTH: 107
<212> TYPE: PRT
<213> ORGANISM: artificial
<220> FEATURE:
<223> OTHER INFORMATION: synthetic construct

<400> SEQUENCE: 30

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
            100                 105
```

<210> SEQ ID NO 31
<211> LENGTH: 2184
<212> TYPE: DNA
<213> ORGANISM: artificial
<220> FEATURE:
<223> OTHER INFORMATION: synthetic construct

<400> SEQUENCE: 31

| | | | | | |
|---|---|---|---|---|---|
| gaggtgcagc | tggtggaaag | cggcggagga | ctggtgcagc | ctggcggcag | cctgagactg | 60 |
| tcttgtgccg | ccagcggcta | caccttcacc | aactacggca | tgaactgggt | gcgccaggcc | 120 |
| cctggcaagg | gactggaatg | ggtgggatgg | atcaacacct | acaccggcga | gcccacctac | 180 |
| gccgccgact | tcaagcggcg | gttcaccttc | agcctggaca | ccagcaagag | caccgcctac | 240 |
| ctgcagatga | acagcctgcg | ggccgaggac | accgccgtgt | actactgcgc | caagtacccc | 300 |
| cactactacg | gcagcagcca | ctggtacttc | gacgtgtggg | gccagggcac | cctggtgaca | 360 |
| gtgtccagcg | cgtcgaccaa | gggaccuagc | gtgttccctc | tggcccccag | cagcaagtct | 420 |
| acatctggcg | gaacagccgc | cctgggctgc | ctcgtgaagg | actactttcc | cgagcccgtg | 480 |
| accgtgtcct | ggaacagcgg | agcactgaca | agcggcgtgc | acaccttttcc | agccgtgctg | 540 |

```
cagagcagcg gcctgtactc tctgagcagc gtcgtgacag tgcccagcag ctctctgggc    600
acccagacct acatctgcaa cgtgaaccac aagcccagca acaccaaggt ggacaagcgg    660
gtggaaccca agagctgcgg caaaacaggc ggcggaggat ccggcggagg cggatctcag    720
gtgcagctgg tggaaagcgg cgctgaagtg aagaaacctg gggccagcgt gaaggtgtcc    780
tgcaaggcca gcggctacac ctttaccggc tactacatgc actgggtgcg ccaggcccct    840
ggccagtgtc tggaatggat gggctggatc aaccccaaca gcggcggcac caactacgcc    900
cagaaattcc agggcagagt gaccatgacc cgggacacca gcatcagcac cgcctacatg    960
gaactgagcc ggctgagaag cgacgacacc gccgtgtact actgcgccag aagccccaac   1020
ccctactact acgacagcag cggctattac taccctgggg ccttcgacat ctggggacag   1080
ggcacaatgg tcaccgtgtc tagcggaggg ggaggatctg ggggcggagg ctctggcggg   1140
ggaggaagtg ggggaggcgg aagccagcct ggactgacac agcctccaag cgtgtcagtg   1200
gcccctggac agaccgccag aatcacctgt ggcggcaaca acatcggcag caagagcgtg   1260
cactggtatc agcagaagcc cggacaggcc ccagtgctgg tggtgtacga cgacagcgat   1320
agacccagcg gcatccccga gagattcagc ggcagcaact ccggcaatac cgccaccctg   1380
accatcagca gagtggaagc cggcgacgag gccgactact actgccaagt gtgggacagc   1440
agcagcgacc actacgtgtt cggctgtggc accaaagtga ccgtgctggg aggcggggga   1500
tcagggggag gggggtcttg tcctccttgt cctgctcccg aactgctggg cggaccttcc   1560
gtgttcctgt tcccccccaa agcccaaggac accctgatga tcagccggac ccccgaagtg   1620
acctgcgtgg tggtggatgt gtcccacgag gacccagaag tgaagttcaa ttggtacgtg   1680
gacggcgtgg aagtgcacaa cgccaagacc aagcctagag aggaacagta caacagcacc   1740
taccgggtgg tgtccgtgct gacagtgctg caccaggact ggctgaacgg caaagagtac   1800
aagtgcaagg tgtccaacaa agccctgcct gcccccatcg agaaaaccat ctccaaggcc   1860
aagggccagc cccgcgagcc tcaagtgtat accctgcccc ctagccggga agagatgacc   1920
aagaaccagg tgtccctgac ctgtctcgtg aaaggcttct accctccga tatcgccgtg   1980 gaatgggaga gcaacggcca gcccgagaac aactacaaga ccacccccc tgtgctggac   2040 agcgacggct cattcttcct gtactccaag ctgaccgtgg acaagagccg gtggcagcag   2100
ggcaacgtgt tcagctgcag cgtgatgcac gaggccctgc acaaccacta cacacagaag   2160
tccctgagcc tgagccccgg caaa                                          2184
```

<210> SEQ ID NO 32
<211> LENGTH: 728
<212> TYPE: PRT
<213> ORGANISM: artificial
<220> FEATURE:
<223> OTHER INFORMATION: synthetic construct

<400> SEQUENCE: 32

```
Glu Val Gln Leu Val Glu Ser Gly Gly Gly Leu Val Gln Pro Gly Gly
1               5                  10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60
```

```
Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
210                 215                 220

Ser Cys Gly Lys Thr Gly Gly Gly Ser Gly Gly Gly Ser Gln
225                 230                 235                 240

Val Gln Leu Val Glu Ser Gly Ala Glu Val Lys Lys Pro Gly Ala Ser
                245                 250                 255

Val Lys Val Ser Cys Lys Ala Ser Gly Tyr Thr Phe Thr Gly Tyr Tyr
            260                 265                 270

Met His Trp Val Arg Gln Ala Pro Gly Gln Cys Leu Glu Trp Met Gly
        275                 280                 285

Trp Ile Asn Pro Asn Ser Gly Gly Thr Asn Tyr Ala Gln Lys Phe Gln
        290                 295                 300

Gly Arg Val Thr Met Thr Arg Asp Thr Ser Ile Ser Thr Ala Tyr Met
305                 310                 315                 320

Glu Leu Ser Arg Leu Arg Ser Asp Asp Thr Ala Val Tyr Tyr Cys Ala
                325                 330                 335

Arg Ser Pro Asn Pro Tyr Tyr Tyr Asp Ser Ser Gly Tyr Tyr Tyr Pro
            340                 345                 350

Gly Ala Phe Asp Ile Trp Gly Gln Gly Thr Met Val Thr Val Ser Ser
        355                 360                 365

Gly Gly Gly Gly Ser Gly Gly Gly Ser Gly Gly Gly Gly Ser Gly
        370                 375                 380

Gly Gly Gly Ser Gln Pro Gly Leu Thr Gln Pro Ser Val Ser Val
385                 390                 395                 400

Ala Pro Gly Gln Thr Ala Arg Ile Thr Cys Gly Gly Asn Asn Ile Gly
                405                 410                 415

Ser Lys Ser Val His Trp Tyr Gln Gln Lys Pro Gly Gln Ala Pro Val
            420                 425                 430

Leu Val Val Tyr Asp Asp Ser Asp Arg Pro Ser Gly Ile Pro Glu Arg
        435                 440                 445

Phe Ser Gly Ser Asn Ser Gly Asn Thr Ala Thr Leu Thr Ile Ser Arg
        450                 455                 460

Val Glu Ala Gly Asp Glu Ala Asp Tyr Tyr Cys Gln Val Trp Asp Ser
465                 470                 475                 480

Ser Ser Asp His Tyr Val Phe Gly Cys Gly Thr Lys Val Thr Val Leu
```

```
            485                 490                 495
Gly Gly Gly Gly Ser Gly Gly Gly Ser Cys Pro Cys Pro Ala
            500                 505                 510

Pro Glu Leu Leu Gly Gly Pro Ser Val Phe Leu Phe Pro Pro Lys Pro
            515                 520                 525

Lys Asp Thr Leu Met Ile Ser Arg Thr Pro Glu Val Thr Cys Val Val
530                 535                 540

Val Asp Val Ser His Glu Asp Pro Glu Val Lys Phe Asn Trp Tyr Val
545                 550                 555                 560

Asp Gly Val Glu Val His Asn Ala Lys Thr Lys Pro Arg Glu Glu Gln
                565                 570                 575

Tyr Asn Ser Thr Tyr Arg Val Val Ser Val Leu Thr Val Leu His Gln
                580                 585                 590

Asp Trp Leu Asn Gly Lys Glu Tyr Lys Cys Lys Val Ser Asn Lys Ala
            595                 600                 605

Leu Pro Ala Pro Ile Glu Lys Thr Ile Ser Lys Ala Lys Gly Gln Pro
            610                 615                 620

Arg Glu Pro Gln Val Tyr Thr Leu Pro Pro Ser Arg Glu Glu Met Thr
625                 630                 635                 640

Lys Asn Gln Val Ser Leu Thr Cys Leu Val Lys Gly Phe Tyr Pro Ser
                645                 650                 655

Asp Ile Ala Val Glu Trp Glu Ser Asn Gly Gln Pro Glu Asn Asn Tyr
            660                 665                 670

Lys Thr Thr Pro Pro Val Leu Asp Ser Asp Gly Ser Phe Phe Leu Tyr
            675                 680                 685

Ser Lys Leu Thr Val Asp Lys Ser Arg Trp Gln Gln Gly Asn Val Phe
690                 695                 700

Ser Cys Ser Val Met His Glu Ala Leu His Asn His Tyr Thr Gln Lys
705                 710                 715                 720

Ser Leu Ser Leu Ser Pro Gly Lys
                725

<210> SEQ ID NO 33
<211> LENGTH: 123
<212> TYPE: PRT
<213> ORGANISM: artificial
<220> FEATURE:
<223> OTHER INFORMATION: synthetic construct

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120
```

-continued

```
            115                 120
```

<210> SEQ ID NO 34
<211> LENGTH: 257
<212> TYPE: PRT
<213> ORGANISM: artificial
<220> FEATURE:
<223> OTHER INFORMATION: synthetic construct

<400> SEQUENCE: 34

```
Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Cys Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Gly Gly Gly Gly Ser Gly Gly Gly Gly Ser Gly Gly Gly Gly Ser
    130                 135                 140

Gly Gly Gly Gly Ser Gln Pro Gly Leu Thr Gln Pro Pro Ser Val Ser
145                 150                 155                 160

Val Ala Pro Gly Gln Thr Ala Arg Ile Thr Cys Gly Gly Asn Asn Ile
                165                 170                 175

Gly Ser Lys Ser Val His Trp Tyr Gln Gln Lys Pro Gly Gln Ala Pro
            180                 185                 190

Val Leu Val Val Tyr Asp Asp Ser Asp Arg Pro Ser Gly Ile Pro Glu
        195                 200                 205

Arg Phe Ser Gly Ser Asn Ser Gly Asn Thr Ala Thr Leu Thr Ile Ser
    210                 215                 220

Arg Val Glu Ala Gly Asp Glu Ala Asp Tyr Tyr Cys Gln Val Trp Asp
225                 230                 235                 240

Ser Ser Ser Asp His Tyr Val Phe Gly Cys Gly Thr Lys Val Thr Val
                245                 250                 255

Leu
```

<210> SEQ ID NO 35
<211> LENGTH: 108
<212> TYPE: PRT
<213> ORGANISM: artificial
<220> FEATURE:
<223> OTHER INFORMATION: synthetic construct

<400> SEQUENCE: 35

```
Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
```

```
                35                  40                  45
Asp Asp Ser Asp Arg Pro Ser Gly Ile Pro Glu Arg Phe Ser Gly Ser
         50                  55                  60
Asn Ser Gly Asn Thr Ala Thr Leu Thr Ile Ser Arg Val Glu Ala Gly
 65                  70                  75                  80
Asp Glu Ala Asp Tyr Tyr Cys Gln Val Trp Asp Ser Ser Asp His
                 85                  90                  95
Tyr Val Phe Gly Cys Gly Thr Lys Val Thr Val Leu
            100                 105

<210> SEQ ID NO 36
<211> LENGTH: 129
<212> TYPE: PRT
<213> ORGANISM: artificial
<220> FEATURE:
<223> OTHER INFORMATION: synthetic construct

<400> SEQUENCE: 36

Gln Val Gln Leu Val Glu Ser Gly Ala Glu Val Lys Lys Pro Gly Ala
  1               5                  10                  15
Ser Val Lys Val Ser Cys Lys Ala Ser Gly Tyr Thr Phe Thr Gly Tyr
             20                  25                  30
Tyr Met His Trp Val Arg Gln Ala Pro Gly Gln Cys Leu Glu Trp Met
         35                  40                  45
Gly Trp Ile Asn Pro Asn Ser Gly Gly Thr Asn Tyr Ala Gln Lys Phe
     50                  55                  60
Gln Gly Arg Val Thr Met Thr Arg Asp Thr Ser Ile Ser Thr Ala Tyr
 65                  70                  75                  80
Met Glu Leu Ser Arg Leu Arg Ser Asp Asp Thr Ala Val Tyr Tyr Cys
                 85                  90                  95
Ala Arg Ser Pro Asn Pro Tyr Tyr Asp Ser Ser Gly Tyr Tyr Tyr
            100                 105                 110
Pro Gly Ala Phe Asp Ile Trp Gly Gln Gly Thr Met Val Thr Val Ser
        115                 120                 125
Ser

<210> SEQ ID NO 37
<211> LENGTH: 15
<212> TYPE: DNA
<213> ORGANISM: Artificial
<220> FEATURE:
<223> OTHER INFORMATION: synthetic construct

<400> SEQUENCE: 37
gagcccaaat cttgt                                                    15

<210> SEQ ID NO 38
<211> LENGTH: 5
<212> TYPE: PRT
<213> ORGANISM: Artificial
<220> FEATURE:
<223> OTHER INFORMATION: synthetic construct

<400> SEQUENCE: 38

Glu Pro Lys Ser Cys
  1               5

<210> SEQ ID NO 39
<211> LENGTH: 30
<212> TYPE: DNA
```

<213> ORGANISM: Artificial
<220> FEATURE:
<223> OTHER INFORMATION: synthetic construct

<400> SEQUENCE: 39

```
gacaaaactc acacatgccc accgtgccca                                        30
```

<210> SEQ ID NO 40
<211> LENGTH: 10
<212> TYPE: PRT
<213> ORGANISM: Artificial
<220> FEATURE:
<223> OTHER INFORMATION: synthetic construct

<400> SEQUENCE: 40

Asp Lys Thr His Thr Cys Pro Pro Cys Pro
1               5                   10

<210> SEQ ID NO 41
<211> LENGTH: 642
<212> TYPE: DNA
<213> ORGANISM: artificial
<220> FEATURE:
<223> OTHER INFORMATION: synthetic construct

<400> SEQUENCE: 41

```
gccatccaga tgacccagtc tccatcctcc ctgtctgcat ctgtaggaga cagagtcacc        60
atcacttgcc gggcaagtca gggcattaga aatgatttag gctggtatca acagaagcca       120
gggaaagccc ctaaactcgt gatctattct gcatccactt tacaaagtgg ggtcccatca       180
aggttcagcg gcagtggatc tggcacagat ttcactctct ccatcagcag cctgcagcct       240
gacgattttg caacttatta ctgtctacaa gattacaatt accgtggac gttcggccaa        300
gggaccaagg ttgaaatcaa acgtacggtg gctgcaccat ctgtcttcat cttcccgcca       360
tctgatgagc agttgaaatc tggaactgcc tctgttgtgt gcctgctgaa taacttctat       420
cccagagagg ccaaagtaca gtggaaggtg gataacgccc tccaatcggg taactcccag       480
gagagtgtca cagagcagga cagcaaggac agcacctaca gcctcagcag cacccctgacg      540
ctgagcaaag cagactacga gaaacacaaa gtctacgcct gcgaagtcac ccatcagggc       600
ctgagctcgc ccgtcacaaa gagcttcaac aggggagagt gt                          642
```

<210> SEQ ID NO 42
<211> LENGTH: 214
<212> TYPE: PRT
<213> ORGANISM: artificial
<220> FEATURE:
<223> OTHER INFORMATION: synthetic construct

<400> SEQUENCE: 42

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Leu Val Ile
            35                  40                  45

Tyr Ser Ala Ser Thr Leu Gln Ser Gly Val Pro Ser Arg Phe Ser Gly
        50                  55                  60

Ser Gly Ser Gly Thr Asp Phe Thr Leu Ser Ile Ser Ser Leu Gln Pro
65                  70                  75                  80

Asp Asp Phe Ala Thr Tyr Tyr Cys Leu Gln Asp Tyr Asn Tyr Pro Trp

```
                    85                  90                  95
Thr Phe Gly Gln Gly Thr Lys Val Glu Ile Lys Arg Thr Val Ala Ala
               100                 105                 110

Pro Ser Val Phe Ile Phe Pro Pro Ser Asp Glu Gln Leu Lys Ser Gly
           115                 120                 125

Thr Ala Ser Val Val Cys Leu Leu Asn Asn Phe Tyr Pro Arg Glu Ala
       130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 43
<211> LENGTH: 107
<212> TYPE: PRT
<213> ORGANISM: artificial
<220> FEATURE:
<223> OTHER INFORMATION: synthetic construct

<400> SEQUENCE: 43

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Val Ile
        35                  40                  45

Tyr Ser Ala Ser Thr Leu Gln Ser Gly Val Pro Ser Arg Phe Ser Gly
    50                  55                  60

Ser Gly Ser Gly Thr Asp Phe Thr Leu Ser Ile Ser Ser Leu Gln Pro
65                  70                  75                  80

Asp Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys
            100                 105

<210> SEQ ID NO 44
<211> LENGTH: 2160
<212> TYPE: DNA
<213> ORGANISM: artificial
<220> FEATURE:
<223> OTHER INFORMATION: synthetic construct

<400> SEQUENCE: 44
gagatgcagc tgttggagtc tgggggaggc ttggtacagc ctgggggtc  cctgagactc      60 tcctgtgcag cctctggatt cacctttagc agctatgcca tgaactgggt ccgccaggct     120 ccagggggagg ggctgagtg gtctcagct attactatta gtggtattac cgcatactac     180
accgactccg tgaagggccg gttcaccatc tccagagaca attccaagaa cacgctatat     240
ctgcaaatga acagcctgag ggccggggac acggccgtat attactgtgc gaaggaagaa     300
tttttacctg gaacgcacta ctactacggt atggacgtct ggggccaagg gaccacggtc     360
```

```
accgtctcct cagcgtcgac caagggccca tccgtcttcc ccctggcacc ctcctccaag    420
agcacctctg ggggcacagc ggccctgggc tgcctggtca aggactactt ccccgaaccg    480
gtgacggtgt cctggaactc aggcgctctg accagcggcg tgcacacctt cccggctgtc    540
ctacagtcct caggactcta ctccctcagc agcgtggtga ccgtgccctc agcagcttg     600 ggcacccaga cctacatctg caacgtgaat cacaagccca gcaacaccaa ggtggacaag    660
agagttgagc ccaaatcttg tggcggaggg ggctctggcg aggggggatc cgaggtgcag    720
ctgttggagt cgggcccagg actggtgaag ccttcggaga ccctgtccct cacctgcaat    780
gtcgctggtg gctccatcag tccttactac tggacctgga tccggcagcc cccagggaag    840
tgcctggagt tgattggtta tatccactcc agtgggtaca ccgactacaa ccctccctc     900 aagagtcgag tcaccatatc aggagacacg tccaagaagc agttctccct gcacgtgagc    960
tctgtgaccg ctgcggacac ggccgtgtac ttctgtgcga gagccgattg ggacctgctt   1020
catgctcttg atatctgggg ccaagggacc ctggtcaccg tctcgagtgg cggagggggc   1080 tctggggag gggcagcgg cggcggagga tctggggag gggcagcga aattgtgttg       1140 acacagtctc catcctccct gtctacatct gtaggagaca gagtcaccat cacttgccgg   1200
gcaagtcaga gcattaggag ccatttaaat tggtatcagc agaaaccagg aaagccccct   1260
aaactcctga tctatggtgc atccaatttg caaagtgggg tcccatcaag gttcagtggc   1320
agtggatctg ggacagattt cactctcacc attagtagtc tgcaacctga agattttgca   1380
acttactact gtcaacagag ttacagtttc cccctcactt tcggctgtgg gaccaagctg   1440
gagatcaaag cgaggtgg ctctggcgga gggggatccg acaaaactca cacatgccca    1500
ccgtgcccag cacctgaact cctgggggga ccgtcagtct tcctcttccc cccaaaaccc   1560
aaggacaccc tcatgatctc ccggacccct gaggtcacat gcgtggtggt ggacgtgagc   1620
cacgaagacc ctgaggtcaa gttcaactgg tacgtggacg gcgtggaggt gcataatgcc   1680
aagacaaagc cgcgggagga gcagtacaac agcacgtacc gtgtggtcag cgtcctcacc   1740
gtcctgcacc aggactggct gaatggcaag gagtacaagt gcaaggtctc caacaaagcc   1800
ctcccagccc ccatcgagaa aaccatctcc aaagccaaag gcagccccg agaaccacag    1860 gtctacaccc tgcccccatc ccgggaggag atgaccaaga accaggtcag cctgacctgc   1920
ctggtcaaag gcttctatcc cagcgacatc gccgtggagt gggagagcaa tgggcagccg   1980
gagaacaact acaagaccac gcctcccgtg ctggactccg acggctcctt cttcctctat   2040
agcaagctca ccgtggacaa gagcaggtgg cagcagggga acgtcttctc atgctccgtg   2100
atgcatgagg ctctgcacaa ccactacacg cagaagagct aagcctgtc tccgggtaaa    2160
```

<210> SEQ ID NO 45
<211> LENGTH: 720
<212> TYPE: PRT
<213> ORGANISM: artificial
<220> FEATURE:
<223> OTHER INFORMATION: synthetic construct

<400> SEQUENCE: 45

```
Glu Met Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Glu Gly Leu Glu Trp Val
        35                  40                  45
```

```
Ser Ala Ile Thr Ile Ser Gly Ile Thr Ala Tyr Tyr Thr Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Gly Asp Thr Ala Val Tyr Tyr Cys
                 85                  90                  95

Ala Lys Glu Glu Phe Leu Pro Gly Thr His Tyr Tyr Gly Met Asp
            100                 105                 110

Val Trp Gly Gln Gly Thr Thr Val Thr Val Ser Ser Ala Ser Thr Lys
             115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                 165                 170                 175

Phe Pro Ala Val Leu Gln Ser Ser Gly Leu Tyr Ser Leu Ser Ser Val
             180                 185                 190

Val Thr Val Pro Ser Ser Ser Leu Gly Thr Gln Thr Tyr Ile Cys Asn
             195                 200                 205

Val Asn His Lys Pro Ser Asn Thr Lys Val Asp Lys Arg Val Glu Pro
210                 215                 220

Lys Ser Cys Gly Gly Gly Ser Gly Gly Gly Ser Glu Val Gln
225                 230                 235                 240

Leu Leu Glu Ser Gly Pro Gly Leu Val Lys Pro Ser Glu Thr Leu Ser
                 245                 250                 255

Leu Thr Cys Asn Val Ala Gly Gly Ser Ile Ser Pro Tyr Tyr Trp Thr
             260                 265                 270

Trp Ile Arg Gln Pro Pro Gly Lys Cys Leu Glu Leu Ile Gly Tyr Ile
         275                 280                 285

His Ser Ser Gly Tyr Thr Asp Tyr Asn Pro Ser Leu Lys Ser Arg Val
     290                 295                 300

Thr Ile Ser Gly Asp Thr Ser Lys Lys Gln Phe Ser Leu His Val Ser
305                 310                 315                 320

Ser Val Thr Ala Ala Asp Thr Ala Val Tyr Phe Cys Ala Arg Ala Asp
                 325                 330                 335

Trp Asp Leu Leu His Ala Leu Asp Ile Trp Gly Gln Gly Thr Leu Val
             340                 345                 350

Thr Val Ser Ser Gly Gly Gly Ser Gly Gly Gly Ser Gly Gly
             355                 360                 365

Gly Gly Ser Gly Gly Gly Ser Glu Ile Val Leu Thr Gln Ser Pro
370                 375                 380

Ser Ser Leu Ser Thr Ser Val Gly Asp Arg Val Thr Ile Thr Cys Arg
385                 390                 395                 400

Ala Ser Gln Ser Ile Arg Ser His Leu Asn Trp Tyr Gln Gln Lys Pro
             405                 410                 415

Gly Lys Ala Pro Lys Leu Leu Ile Tyr Gly Ala Ser Asn Leu Gln Ser
             420                 425                 430

Gly Val Pro Ser Arg Phe Ser Gly Ser Gly Ser Gly Thr Asp Phe Thr
             435                 440                 445

Leu Thr Ile Ser Ser Leu Gln Pro Glu Asp Phe Ala Thr Tyr Tyr Cys
             450                 455                 460

Gln Gln Ser Tyr Ser Phe Pro Leu Thr Phe Gly Cys Gly Thr Lys Leu
```

```
                            465                 470                 475                 480
        Glu Ile Lys Gly Gly Gly Ser Gly Gly Gly Ser Asp Lys Thr
                            485                 490                 495
        His Thr Cys Pro Pro Cys Pro Ala Pro Glu Leu Leu Gly Gly Pro Ser
                            500                 505                 510
        Val Phe Leu Phe Pro Pro Lys Pro Lys Asp Thr Leu Met Ile Ser Arg
                            515                 520                 525
        Thr Pro Glu Val Thr Cys Val Val Val Asp Val Ser His Glu Asp Pro
                            530                 535                 540
        Glu Val Lys Phe Asn Trp Tyr Val Asp Gly Val Glu Val His Asn Ala
        545                 550                 555                 560
        Lys Thr Lys Pro Arg Glu Glu Gln Tyr Asn Ser Thr Tyr Arg Val Val
                            565                 570                 575
        Ser Val Leu Thr Val Leu His Gln Asp Trp Leu Asn Gly Lys Glu Tyr
                            580                 585                 590
        Lys Cys Lys Val Ser Asn Lys Ala Leu Pro Ala Pro Ile Glu Lys Thr
                            595                 600                 605
        Ile Ser Lys Ala Lys Gly Gln Pro Arg Glu Pro Gln Val Tyr Thr Leu
                            610                 615                 620
        Pro Pro Ser Arg Glu Glu Met Thr Lys Asn Gln Val Ser Leu Thr Cys
        625                 630                 635                 640
        Leu Val Lys Gly Phe Tyr Pro Ser Asp Ile Ala Val Glu Trp Glu Ser
                            645                 650                 655
        Asn Gly Gln Pro Glu Asn Asn Tyr Lys Thr Thr Pro Pro Val Leu Asp
                            660                 665                 670
        Ser Asp Gly Ser Phe Phe Leu Tyr Ser Lys Leu Thr Val Asp Lys Ser
                            675                 680                 685
        Arg Trp Gln Gln Gly Asn Val Phe Ser Cys Ser Val Met His Glu Ala
                            690                 695                 700
        Leu His Asn His Tyr Thr Gln Lys Ser Leu Ser Leu Ser Pro Gly Lys
        705                 710                 715                 720

<210> SEQ ID NO 46
<211> LENGTH: 124
<212> TYPE: PRT
<213> ORGANISM: artificial
<220> FEATURE:
<223> OTHER INFORMATION: synthetic construct

<400> SEQUENCE: 46

Glu Met Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
                20                  25                  30
Ala Met Asn Trp Val Arg Gln Ala Pro Gly Glu Gly Leu Glu Trp Val
            35                  40                  45
Ser Ala Ile Thr Ile Ser Gly Ile Thr Ala Tyr Tyr Thr Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Gly Asp Thr Ala Val Tyr Tyr Cys
                85                  90                  95
Ala Lys Glu Glu Phe Leu Pro Gly Thr His Tyr Tyr Tyr Gly Met Asp
                100                 105                 110
Val Trp Gly Gln Gly Thr Thr Val Thr Val Ser Ser
```

```
            115                 120

<210> SEQ ID NO 47
<211> LENGTH: 246
<212> TYPE: PRT
<213> ORGANISM: artificial
<220> FEATURE:
<223> OTHER INFORMATION: synthetic construct

<400> SEQUENCE: 47

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Cys Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Ser Gly Gly Gly
        115                 120                 125

Ser Gly Gly Gly Ser Gly Gly Gly Ser Glu Ile Val Leu Thr
130                 135                 140

Gln Ser Pro Ser Ser Leu Ser Thr Ser Val Gly Asp Arg Val Thr Ile
145                 150                 155                 160

Thr Cys Arg Ala Ser Gln Ser Ile Arg Ser His Leu Asn Trp Tyr Gln
                165                 170                 175

Gln Lys Pro Gly Lys Ala Pro Lys Leu Leu Ile Tyr Gly Ala Ser Asn
            180                 185                 190

Leu Gln Ser Gly Val Pro Ser Arg Phe Ser Gly Ser Gly Ser Gly Thr
        195                 200                 205

Asp Phe Thr Leu Thr Ile Ser Ser Leu Gln Pro Glu Asp Phe Ala Thr
    210                 215                 220

Tyr Tyr Cys Gln Gln Ser Tyr Ser Phe Pro Leu Thr Phe Gly Cys Gly
225                 230                 235                 240

Thr Lys Leu Glu Ile Lys
                245

<210> SEQ ID NO 48
<211> LENGTH: 107
<212> TYPE: PRT
<213> ORGANISM: artificial
<220> FEATURE:
<223> OTHER INFORMATION: synthetic construct

<400> SEQUENCE: 48

Glu Ile Val Leu Thr Gln Ser Pro Ser Ser Leu Ser Thr Ser Val Gly
1               5                   10                  15

Asp Arg Val Thr Ile Thr Cys Arg Ala Ser Gln Ser Ile Arg Ser His
            20                  25                  30

Leu Asn Trp Tyr Gln Gln Lys Pro Gly Lys Ala Pro Lys Leu Leu Ile
        35                  40                  45
```

Tyr Gly Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Leu
                85                  90                  95

Thr Phe Gly Cys Gly Thr Lys Leu Glu Ile Lys
            100                 105

<210> SEQ ID NO 49
<211> LENGTH: 119
<212> TYPE: PRT
<213> ORGANISM: artificial
<220> FEATURE:
<223> OTHER INFORMATION: synthetic construct

<400> SEQUENCE: 49

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Cys Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser
        115

<210> SEQ ID NO 50
<211> LENGTH: 642
<212> TYPE: DNA
<213> ORGANISM: artificial
<220> FEATURE:
<223> OTHER INFORMATION: synthetic construct

<400> SEQUENCE: 50
gccatccaga tgacccagtc tccatcctcc ctgtctgcat ctgtaggaga cagagtcacc      60
atcacttgcc gggcaagtca gggcattaga aatgatttag gctggtatca acagaagcca     120
gggaaagccc ctaaactcgt gatctattct gcatccactt tacaaagtgg ggtcccatca     180
aggttcagcg gcagtggatc tggcacagat ttcactctct ccatcagcag cctgcagcct     240
gacgattttg caacttatta ctgtctacaa gattacaatt accgtggac gttcggccaa      300 gggaccaagg ttgaaatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                        642

-continued

```
<210> SEQ ID NO 51
<211> LENGTH: 214
<212> TYPE: PRT
<213> ORGANISM: artificial
<220> FEATURE:
<223> OTHER INFORMATION: synthetic construct

<400> SEQUENCE: 51

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Val Ile
        35                  40                  45

Tyr Ser Ala Ser Thr Leu Gln Ser Gly Val Pro Ser Arg Phe Ser Gly
50                  55                  60

Ser Gly Ser Gly Thr Asp Phe Thr Leu Ser Ile Ser Ser Leu Gln Pro
65                  70                  75                  80

Asp Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 52
<211> LENGTH: 2130
<212> TYPE: DNA
<213> ORGANISM: artificial
<220> FEATURE:
<223> OTHER INFORMATION: synthetic construct

<400> SEQUENCE: 52
gaggtgcagc tgttggagtc gggcccagga ctggtgaagc cttcggagac cctgtccctc      60
acctgcaatg tcgctggtgg ctccatcagt ccttactact ggacctggat ccggcagccc     120
ccagggaagt gcctggagtt gattggttat atccactcca gtgggtacac cgactacaac     180 ccctcccttca agagtcgagt caccatatca ggagacacgt ccaagaagca gttctccctg     240
cacgtgagct ctgtgaccgc tgcggacacg gccgtgtact tctgtgcgag agccgattgg     300
gacctgcttc atgctcttga tatctggggc caagggaccc tggtcaccgt ctcgagtggc     360
ggagggggct ctgggggagg gggcagcggc ggcggaggat ctgggggagg gggcagcgaa     420
attgtgttga cacagtctcc atcctccctg tctacatctg taggagacag agtcaccatc     480
acttgccggg caagtcagag cattaggagc catttaaatt ggtatcagca gaaaccaggg     540
```

```
aaagccccta aactcctgat ctatggtgca tccaatttgc aaagtggggt cccatcaagg    600
ttcagtggca gtggatctgg gacagatttc actctcacca ttagtagtct gcaacctgaa    660
gattttgcaa cttactactg tcaacagagt tacagtttcc ccctcacttt cggctgtggg    720
accaagctgg agatcaaagg cggaggggga tccggcggag ggggctctga gatgcagctg    780
ttggagtctg ggggaggctt ggtacagcct gggggggtcc tgagactctc ctgtgcagcc    840
tctggattca cctttagcag ctatgccatg aactgggtcc gccaggctcc agggaagggg    900
ctggagtggg tctcagctat tactattagt ggtattaccg catactacac cgactccgtg    960
aagggccggt tcaccatctc cagagacaat tccaagaaca cgctatatct gcaaatgaac   1020
agcctgaggg ccggggacac ggccgtatat tactgtgcga aggaagaatt tttacctgga   1080
acgcactact actacggtat ggacgtctgg ggccaaggga ccacggtcac cgtctcctca   1140
gcgtcgacca agggcccatc cgtcttcccc ctggcaccct cctccaagag cacctctggg   1200
ggcacagcgg ccctgggctg cctggtcaag gactacttcc ccgaaccggt gacggtgtcc   1260
tggaactcag gcgctctgac cagcggcgtg cacaccttcc cggctgtcct acagtcctca   1320
ggactctact ccctcagcag cgtggtgacc gtgccctcca gcagcttggg cacccagacc   1380
tacatctgca acgtgaatca caagcccagc aacaccaagg tggacaagag agttgagccc   1440
aaatcttgtg acaaaactca cacatgccca ccgtgcccag cacctgaact cctgggggga   1500
ccgtcagtct tcctcttccc cccaaaaccc aaggacaccc tcatgatctc ccggacccct   1560
gaggtcacat gcgtggtggt ggacgtgagc cacgaagacc ctgaggtcaa gttcaactgg   1620
tacgtggacg gcgtggaggt gcataatgcc aagacaaagc cgcgggagga gcagtacaac   1680
agcacgtacc gtgtggtcag cgtcctcacc gtcctgcacc aggactggct gaatggcaag   1740
gagtacaagt gcaaggtctc caacaaagcc ctcccagccc ccatcgagaa aaccatctcc   1800
aaagccaaag ggcagccccg agaaccacag gtctacaccc tgcccccatc ccgggaggag   1860
atgaccaaga accaggtcag cctgacctgc ctggtcaaag gcttctatcc cagcgacatc   1920
gccgtggagt gggagagcaa tgggcagccg gagaacaact acaagaccac gcctcccgtg   1980
ctggactccg acggctcctt cttcctctat agcaagctca ccgtggacaa gagcaggtgg   2040
cagcagggga acgtcttctc atgctccgtg atgcatgagg ctctgcacaa ccactacacg   2100
cagaagagct taagcctgtc tccgggtaaa                                    2130
```

```
<210> SEQ ID NO 53
<211> LENGTH: 710
<212> TYPE: PRT
<213> ORGANISM: artificial
<220> FEATURE:
<223> OTHER INFORMATION: synthetic construct

<400> SEQUENCE: 53
```

```
Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Cys Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80
```

-continued

```
His Val Ser Ser Val Thr Ala Ala Asp Thr Ala Val Tyr Phe Cys Ala
             85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
            115                 120                 125

Ser Gly Gly Gly Gly Ser Gly Gly Gly Gly Ser Glu Ile Val Leu Thr
            130                 135                 140

Gln Ser Pro Ser Ser Leu Ser Thr Ser Val Gly Asp Arg Val Thr Ile
145                 150                 155                 160

Thr Cys Arg Ala Ser Gln Ser Ile Arg Ser His Leu Asn Trp Tyr Gln
            165                 170                 175

Gln Lys Pro Gly Lys Ala Pro Lys Leu Leu Ile Tyr Gly Ala Ser Asn
            180                 185                 190

Leu Gln Ser Gly Val Pro Ser Arg Phe Ser Gly Ser Gly Ser Gly Thr
            195                 200                 205

Asp Phe Thr Leu Thr Ile Ser Ser Leu Gln Pro Glu Asp Phe Ala Thr
            210                 215                 220

Tyr Tyr Cys Gln Gln Ser Tyr Ser Phe Pro Leu Thr Phe Gly Cys Gly
225                 230                 235                 240

Thr Lys Leu Glu Ile Lys Gly Gly Gly Ser Gly Gly Gly Gly Ser
            245                 250                 255

Glu Met Gln Leu Leu Glu Ser Gly Gly Gly Leu Val Gln Pro Gly Gly
            260                 265                 270

Ser Leu Arg Leu Ser Cys Ala Ala Ser Gly Phe Thr Phe Ser Ser Tyr
            275                 280                 285

Ala Met Asn Trp Val Arg Gln Ala Pro Gly Glu Gly Leu Glu Trp Val
            290                 295                 300

Ser Ala Ile Thr Ile Ser Gly Ile Thr Ala Tyr Tyr Thr Asp Ser Val
305                 310                 315                 320

Lys Gly Arg Phe Thr Ile Ser Arg Asp Asn Ser Lys Asn Thr Leu Tyr
            325                 330                 335

Leu Gln Met Asn Ser Leu Arg Ala Gly Asp Thr Ala Val Tyr Tyr Cys
            340                 345                 350

Ala Lys Glu Glu Phe Leu Pro Gly Thr His Tyr Tyr Gly Met Asp
            355                 360                 365

Val Trp Gly Gln Gly Thr Thr Val Thr Val Ser Ser Ala Ser Thr Lys
            370                 375                 380

Gly Pro Ser Val Phe Pro Leu Ala Pro Ser Ser Lys Ser Thr Ser Gly
385                 390                 395                 400

Gly Thr Ala Ala Leu Gly Cys Leu Val Lys Asp Tyr Phe Pro Glu Pro
            405                 410                 415

Val Thr Val Ser Trp Asn Ser Gly Ala Leu Thr Ser Gly Val His Thr
            420                 425                 430

Phe Pro Ala Val Leu Gln Ser Ser Gly Leu Tyr Ser Leu Ser Ser Val
            435                 440                 445

Val Thr Val Pro Ser Ser Ser Leu Gly Thr Gln Thr Tyr Ile Cys Asn
            450                 455                 460

Val Asn His Lys Pro Ser Asn Thr Lys Val Asp Lys Arg Val Glu Pro
465                 470                 475                 480

Lys Ser Cys Asp Lys Thr His Thr Cys Pro Pro Cys Pro Ala Pro Glu
            485                 490                 495

Leu Leu Gly Gly Pro Ser Val Phe Leu Phe Pro Pro Lys Pro Lys Asp
```

```
                      500                 505                 510
Thr Leu Met Ile Ser Arg Thr Pro Glu Val Thr Cys Val Val Asp
                515                 520                 525
Val Ser His Glu Asp Pro Glu Val Lys Phe Asn Trp Tyr Val Asp Gly
            530                 535                 540
Val Glu Val His Asn Ala Lys Thr Lys Pro Arg Glu Glu Gln Tyr Asn
545                 550                 555                 560
Ser Thr Tyr Arg Val Val Ser Val Leu Thr Val Leu His Gln Asp Trp
                565                 570                 575
Leu Asn Gly Lys Glu Tyr Lys Cys Lys Val Ser Asn Lys Ala Leu Pro
            580                 585                 590
Ala Pro Ile Glu Lys Thr Ile Ser Lys Ala Lys Gly Gln Pro Arg Glu
        595                 600                 605
Pro Gln Val Tyr Thr Leu Pro Pro Ser Arg Glu Glu Met Thr Lys Asn
    610                 615                 620
Gln Val Ser Leu Thr Cys Leu Val Lys Gly Phe Tyr Pro Ser Asp Ile
625                 630                 635                 640
Ala Val Glu Trp Glu Ser Asn Gly Gln Pro Glu Asn Asn Tyr Lys Thr
                645                 650                 655
Thr Pro Pro Val Leu Asp Ser Asp Gly Ser Phe Phe Leu Tyr Ser Lys
            660                 665                 670
Leu Thr Val Asp Lys Ser Arg Trp Gln Gln Gly Asn Val Phe Ser Cys
        675                 680                 685
Ser Val Met His Glu Ala Leu His Asn His Tyr Thr Gln Lys Ser Leu
    690                 695                 700
Ser Leu Ser Pro Gly Lys
705                 710

<210> SEQ ID NO 54
<211> LENGTH: 642
<212> TYPE: DNA
<213> ORGANISM: artificial
<220> FEATURE:
<223> OTHER INFORMATION: synthetic construct

<400> SEQUENCE: 54
gaaattgtgt tgacacagtc tccatcctcc ctgtctacat ctgtaggaga cagagtcacc        60
atcacttgcc gggcaagtca gagcattagg agccatttaa attggtatca gcagaaacca       120
gggaaagccc ctaaactcct gatctatggt gcatccaatt tgcaaagtgg ggtcccatca       180
aggttcagtg gcagtggatc tgggacagat ttcactctca ccattagtag tctgcaacct       240
gaagattttg caacttacta ctgtcaacag agttacagtt ccccctcac tttcggcgga       300 gggaccaagc tggagatcaa acgtacggtg gctgcaccat ctgtcttcat cttcccgcca       360
tctgatgagc agttgaaatc tggaactgcc tctgttgtgt gcctgctgaa taacttctat       420
cccagagagg ccaaagtaca gtggaaggtg gataacgccc tccaatcggg taactcccag       480
gagagtgtca cagagcagga cagcaaggac agcacctaca gcctcagcag caccctgacg       540
ctgagcaaag cagactacga gaaacacaaa gtctacgcct gcgaagtcac ccatcagggc       600
ctgagctcgc ccgtcacaaa gagcttcaac aggggagagt gt                         642

<210> SEQ ID NO 55
<211> LENGTH: 214
<212> TYPE: PRT
<213> ORGANISM: artificial
<220> FEATURE:
```

<223> OTHER INFORMATION: synthetic construct

<400> SEQUENCE: 55

```
Glu Ile Val Leu Thr Gln Ser Pro Ser Ser Leu Ser Thr Ser Val Gly
1               5                   10                  15

Asp Arg Val Thr Ile Thr Cys Arg Ala Ser Gln Ser Ile Arg Ser His
            20                  25                  30

Leu Asn Trp Tyr Gln Gln Lys Pro Gly Lys Ala Pro Lys Leu Leu Ile
        35                  40                  45

Tyr Gly Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Leu
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 56
<211> LENGTH: 2130
<212> TYPE: DNA
<213> ORGANISM: artificial
<220> FEATURE:
<223> OTHER INFORMATION: synthetic construct

<400> SEQUENCE: 56

| gccatccaga tgacccagtc tccatcctcc ctgtctgcat ctgtaggaga cagagtcacc | 60 |
| atcacttgcc gggcaagtca gggcattaga aatgatttag gctggtatca acagaagcca | 120 |
| gggaaagccc ctaaactcgt gatctattct gcatccactt tacaaagtgg ggtcccatca | 180 |
| aggttcagcg gcagtggatc tggcacagat ttcactctct ccatcagcag cctgcagcct | 240 |
| gacgattttg caacttatta ctgtctacaa gattacaatt acccgtggac gttcggctgt | 300 |
| gggaccaagg ttgaaatcaa aggcggagga ggctccggcg gaggagggtc tggaggcggg | 360 |
| ggaagtggag gaggaggctc cgagatgcag ctgttggagt ctgggggagg cttggtacag | 420 |
| cctgggggt ccctgagact ctcctgtgca gcctctggat tcacctttag cagctatgcc | 480 |
| atgaactggg tccgccaggc tccaggggag tgtctggagt gggtctcagc tattactatt | 540 |
| agtggtatta ccgcatacta caccgactcc gtgaagggcc ggttcaccat ctccagagac | 600 |
| aattccaaga acacgctata tctgcaaatg aacagcctga ggccggggga cacggccgta | 660 |
| tattactgtg cgaaggaaga atttttacct ggaacgcact actactacgg tatggacgtc | 720 |

```
tggggccaag ggaccacggt caccgtctcc tcaggcggag ggggatccgg cggcggcggc    780
agcgaggtgc agctgttgga gtcgggccca ggactggtga agccttcgga ccctgtcc     840 ctcacctgca atgtcgctgg tggctccatc agtccttact actggacctg gatccggcag    900
cccccaggga agggcctgga gttgattggt tatatccact ccagtgggta caccgactac    960
aacccctccc tcaagagtcg agtcaccata tcaggagaca cgtccaagaa gcagttctcc   1020
ctgcacgtga gctctgtgac cgctgcggac acggccgtgt acttctgtgc gagagccgat   1080
tgggacctgc ttcatgctct tgatatctgg ggccaaggga ccctggtcac cgtctcgagt   1140
gcgtcgacca agggcccatc cgtcttcccc ctggcaccct cctccaagag cacctctggg   1200
ggcacagcgg ccctgggctg cctggtcaag gactacttcc ccgaaccggt gacggtgtcg   1260
tggaactcag gcgccctgac cagcggcgtg cacaccttcc cggctgtcct acagtcctca   1320
ggactctact ccctcagcag cgtggtgacc gtgccctcca gcagcttggg cacccagacc   1380
tacatctgca acgtgaatca caagcccagc aacaccaagg tggacaagag agttgagccc   1440
aaatcttgtg acaaaactca cacatgccca ccgtgcccag cacctgaact cctgggggga   1500
ccgtcagtct tcctcttccc cccaaaaccc aaggacaccc tcatgatctc ccggacccct   1560
gaggtcacat gcgtggtggt ggacgtgagc cacgaagacc ctgaggtcaa gttcaactgg   1620
tacgtggacg gcgtggaggt gcataatgcc aagacaaagc cgcgggagga gcagtacaac   1680
agcacgtacc gtgtggtcag cgtcctcacc gtcctgcacc aggactggct gaatggcaag   1740
gagtacaagt gcaaggtctc caacaaagcc ctcccagccc ccatcgagaa aaccatctcc   1800
aaagccaaag ggcagccccg agaaccacag gtctacaccc tgcccccatc ccgggaggag   1860
atgaccaaga accaggtcag cctgacctgc ctggtcaaag gcttctatcc cagcgacatc   1920
gccgtggagt gggagagcaa tgggcagccg gagaacaact acaagaccac gcctcccgtg   1980
ctggactccg acggctcctt cttcctctat agcaagctca ccgtggacaa gagcaggtgg   2040
cagcagggga acgtcttctc atgctccgtg atgcatgagg ctctgcacaa ccactacacg   2100
cagaagagcc tctccctgtc tccgggtaaa                                    2130
```

<210> SEQ ID NO 57
<211> LENGTH: 710
<212> TYPE: PRT
<213> ORGANISM: artificial
<220> FEATURE:
<223> OTHER INFORMATION: synthetic construct

<400> SEQUENCE: 57

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Val Ile
        35                  40                  45

Tyr Ser Ala Ser Thr Leu Gln Ser Gly Val Pro Ser Arg Phe Ser Gly
    50                  55                  60

Ser Gly Ser Gly Thr Asp Phe Thr Leu Ser Ile Ser Ser Leu Gln Pro
65                  70                  75                  80

Asp Asp Phe Ala Thr Tyr Tyr Cys Leu Gln Asp Tyr Asn Tyr Pro Trp
                85                  90                  95

Thr Phe Gly Cys Gly Thr Lys Val Glu Ile Lys Gly Gly Gly Gly Ser
                100                 105                 110
```

```
Gly Gly Gly Gly Ser Gly Gly Gly Ser Gly Gly Gly Ser Glu
            115                 120                 125
Met Gln Leu Leu Glu Ser Gly Gly Leu Val Gln Pro Gly Gly Ser
    130                 135                 140
Leu Arg Leu Ser Cys Ala Ala Ser Gly Phe Thr Phe Ser Ser Tyr Ala
145                 150                 155                 160
Met Asn Trp Val Arg Gln Ala Pro Gly Glu Cys Leu Glu Trp Val Ser
                165                 170                 175
Ala Ile Thr Ile Ser Gly Ile Thr Ala Tyr Tyr Thr Asp Ser Val Lys
            180                 185                 190
Gly Arg Phe Thr Ile Ser Arg Asp Asn Ser Lys Asn Thr Leu Tyr Leu
                195                 200                 205
Gln Met Asn Ser Leu Arg Ala Gly Asp Thr Ala Val Tyr Tyr Cys Ala
210                 215                 220
Lys Glu Glu Phe Leu Pro Gly Thr His Tyr Tyr Gly Met Asp Val
225                 230                 235                 240
Trp Gly Gln Gly Thr Thr Val Thr Val Ser Ser Gly Gly Gly Gly Ser
                245                 250                 255
Gly Gly Gly Gly Ser Glu Val Gln Leu Leu Glu Ser Gly Pro Gly Leu
            260                 265                 270
Val Lys Pro Ser Glu Thr Leu Ser Leu Thr Cys Asn Val Ala Gly Gly
    275                 280                 285
Ser Ile Ser Pro Tyr Tyr Trp Thr Trp Ile Arg Gln Pro Pro Gly Lys
    290                 295                 300
Gly Leu Glu Leu Ile Gly Tyr Ile His Ser Ser Gly Tyr Thr Asp Tyr
305                 310                 315                 320
Asn Pro Ser Leu Lys Ser Arg Val Thr Ile Ser Gly Asp Thr Ser Lys
                325                 330                 335
Lys Gln Phe Ser Leu His Val Ser Ser Val Thr Ala Ala Asp Thr Ala
            340                 345                 350
Val Tyr Phe Cys Ala Arg Ala Asp Trp Asp Leu Leu His Ala Leu Asp
        355                 360                 365
Ile Trp Gly Gln Gly Thr Leu Val Thr Val Ser Ser Ala Ser Thr Lys
    370                 375                 380
Gly Pro Ser Val Phe Pro Leu Ala Pro Ser Ser Lys Ser Thr Ser Gly
385                 390                 395                 400
Gly Thr Ala Ala Leu Gly Cys Leu Val Lys Asp Tyr Phe Pro Glu Pro
                405                 410                 415
Val Thr Val Ser Trp Asn Ser Gly Ala Leu Thr Ser Gly Val His Thr
            420                 425                 430
Phe Pro Ala Val Leu Gln Ser Ser Gly Leu Tyr Ser Leu Ser Ser Val
        435                 440                 445
Val Thr Val Pro Ser Ser Ser Leu Gly Thr Gln Thr Tyr Ile Cys Asn
    450                 455                 460
Val Asn His Lys Pro Ser Asn Thr Lys Val Asp Lys Arg Val Glu Pro
465                 470                 475                 480
Lys Ser Cys Asp Lys Thr His Thr Cys Pro Pro Cys Pro Ala Pro Glu
                485                 490                 495
Leu Leu Gly Gly Pro Ser Val Phe Leu Phe Pro Pro Lys Pro Lys Asp
            500                 505                 510
Thr Leu Met Ile Ser Arg Thr Pro Glu Val Thr Cys Val Val Val Asp
        515                 520                 525
```

```
Val Ser His Glu Asp Pro Glu Val Lys Phe Asn Trp Tyr Val Asp Gly
        530                 535                 540

Val Glu Val His Asn Ala Lys Thr Lys Pro Arg Glu Glu Gln Tyr Asn
545                 550                 555                 560

Ser Thr Tyr Arg Val Val Ser Val Leu Thr Val Leu His Gln Asp Trp
                565                 570                 575

Leu Asn Gly Lys Glu Tyr Lys Cys Lys Val Ser Asn Lys Ala Leu Pro
            580                 585                 590

Ala Pro Ile Glu Lys Thr Ile Ser Lys Ala Lys Gly Gln Pro Arg Glu
        595                 600                 605

Pro Gln Val Tyr Thr Leu Pro Pro Ser Arg Glu Glu Met Thr Lys Asn
610                 615                 620

Gln Val Ser Leu Thr Cys Leu Val Lys Gly Phe Tyr Pro Ser Asp Ile
625                 630                 635                 640

Ala Val Glu Trp Glu Ser Asn Gly Gln Pro Glu Asn Asn Tyr Lys Thr
                645                 650                 655

Thr Pro Pro Val Leu Asp Ser Asp Gly Ser Phe Phe Leu Tyr Ser Lys
            660                 665                 670

Leu Thr Val Asp Lys Ser Arg Trp Gln Gln Gly Asn Val Phe Ser Cys
        675                 680                 685

Ser Val Met His Glu Ala Leu His Asn His Tyr Thr Gln Lys Ser Leu
690                 695                 700

Ser Leu Ser Pro Gly Lys
705                 710

<210> SEQ ID NO 58
<211> LENGTH: 642
<212> TYPE: DNA
<213> ORGANISM: artificial
<220> FEATURE:
<223> OTHER INFORMATION: synthetic construct

<400> SEQUENCE: 58
gccatccaga tgacccagtc tccatcctcc ctgtctgcat ctgtaggaga cagagtcacc    60
atcacttgcc gggcaagtca gggcattaga aatgatttag ctggtatcaa cagaagcca   120 gggaaagccc ctaaactcgt gatctattct gcatccactt tacaaagtgg ggtcccatca   180
aggttcagcg gcagtggatc tggcacagat ttcactctct ccatcagcag cctgcagcct   240
gacgattttg caacttatta ctgtctacaa gattacaatt acccgtggac gttcggccaa   300
gggaccaagg ttgaaatcaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                      642

<210> SEQ ID NO 59
<211> LENGTH: 214
<212> TYPE: PRT
<213> ORGANISM: artificial
<220> FEATURE:
<223> OTHER INFORMATION: synthetic construct

<400> SEQUENCE: 59

Ala Ile Gln Met Thr Gln Ser Pro Ser Ser Leu Ser Ala Ser Val Gly
```

```
            1               5                  10                 15
Asp Arg Val Thr Ile Thr Cys Arg Ala Ser Gln Gly Ile Arg Asn Asp
            20                 25                 30

Leu Gly Trp Tyr Gln Gln Lys Pro Gly Lys Ala Pro Lys Leu Val Ile
            35                 40                 45

Tyr Ser Ala Ser Thr Leu Gln Ser Gly Val Pro Ser Arg Phe Ser Gly
            50                 55                 60

Ser Gly Ser Gly Thr Asp Phe Thr Leu Ser Ile Ser Ser Leu Gln Pro
65                 70                 75                 80

Asp Asp Phe Ala Thr Tyr Tyr Cys Leu Gln Asp Tyr Asn Tyr Pro Trp
                85                 90                 95

Thr Phe Gly Gln Gly Thr Lys Val Glu Ile Lys Arg Thr Val Ala Ala
                100                105                110

Pro Ser Val Phe Ile Phe Pro Pro Ser Asp Glu Gln Leu Lys Ser Gly
            115                120                125

Thr Ala Ser Val Val Cys Leu Leu Asn Asn Phe Tyr Pro Arg Glu Ala
            130                135                140

Lys Val Gln Trp Lys Val Asp Asn Ala Leu Gln Ser Gly Asn Ser Gln
145                150                155                160

Glu Ser Val Thr Glu Gln Asp Ser Lys Asp Ser Thr Tyr Ser Leu Ser
                165                170                175

Ser Thr Leu Thr Leu Ser Lys Ala Asp Tyr Glu Lys His Lys Val Tyr
            180                185                190

Ala Cys Glu Val Thr His Gln Gly Leu Ser Ser Pro Val Thr Lys Ser
            195                200                205

Phe Asn Arg Gly Glu Cys
            210

<210> SEQ ID NO 60
<211> LENGTH: 2130
<212> TYPE: DNA
<213> ORGANISM: artificial
<220> FEATURE:
<223> OTHER INFORMATION: synthetic construct

<400> SEQUENCE: 60
gagatgcagc tgttggagtc tgggggaggc ttggtacagc ctgggggtc cctgagactc      60 tcctgtgcag cctctggatt caccttagc agctatgcca tgaactgggt ccgccaggct     120
ccaggggagg ggctggagtg ggtctcagct attactatta gtggtattac cgcatactac    180
accgactccg tgaagggccg gttcaccatc tccagagaca attccaagaa cacgctatat    240
ctgcaaatga acagcctgag ggccgggac acggccgtat attactgtgc gaaggaagaa    300
ttttaacctg gaacgcacta ctactacggt atggacgtct ggggccaagg gaccacggtc    360
accgtctcct cagcgtcgac caagggccca tccgtcttcc ccctggcacc ctcctccaag    420
agcacctctg gggcacagc ggccctgggc tgcctggtca aggactactt ccccgaaccg     480
gtgacggtgt cctggaactc aggcgctctg accagcggcg tgcacacctt cccggctgtc    540
ctacagtcct caggactcta ctccctcagc agcgtggtga ccgtgccctc agcagcttg     600 ggcacccaga cctacatctg caacgtgaat cacaagccca gcaaccacaa ggtggacaag    660
agagttgagc ccaaatcttg tgacaaaact cacacatgcc caccgtgccc agcacctgaa    720
ctcctggggg gaccgtcagt cttcctcttc cccccaaaac ccaaggacac cctcatgatc    780
tcccggaccc ctgaggtcac atgcgtggtg gtggacgtga gccacgaaga ccctgaggtc    840
```

```
aagttcaact ggtacgtgga cggcgtggag gtgcataatg ccaagacaaa gccgcgggag    900
gagcagtaca acagcacgta ccgtgtggtc agcgtcctca ccgtcctgca ccaggactgg    960
ctgaatggca aggagtacaa gtgcaaggtc tccaacaaag ccctcccagc ccccatcgag    1020
aaaaccatct ccaaagccaa agggcagccc cgagaaccac aggtctacac cctgccccca    1080
tcccgggagg agatgaccaa gaaccaggtc agcctgacct gcctggtcaa aggcttctat    1140
cccagcgaca tcgccgtgga gtgggagagc aatgggcagc cggagaacaa ctacaagacc    1200
acgcctcccg tgctggactc cgacggctcc ttcttcctct atagcaagct caccgtggac    1260
aagagcaggt ggcagcaggg gaacgtcttc tcatgctccg tgatgcatga ggctctgcac    1320
aaccactaca cgcagaagag cttaagcctg tctccgggta aaggcggagg gggatccggc    1380
ggagggggct ctgaggtgca gctgttggag tcgggcccag gactggtgaa gccttcggag    1440
accctgtccc tcacctgcaa tgtcgctggt ggctccatca gtccttacta ctggacctgg    1500
atccggcagc ccccagggaa gtgcctggag ttgattggtt atatccactc cagtgggtac    1560
accgactaca accctccct caagagtcga gtcaccatat caggagacac gtccaagaag    1620
cagttctccc tgcacgtgag ctctgtgacc gctgcggaca cggccgtgta cttctgtgcg    1680
agagccgatt gggacctgct tcatgctctt gatatctggg gccaagggac cctggtcacc    1740
gtctcgagtg gcggaggggg ctctggggga ggggcagcg gcggcggagg atctggggga    1800
gggggcagcg aaattgtgtt gacacagtct ccatcctccc tgtctacatc tgtaggagac    1860
agagtcacca tcacttgccg ggcaagtcag agcattagga gccatttaaa ttggtatcag    1920
cagaaaccag ggaaagcccc taaactcctg atctatggtg catccaattt gcaaagtggg    1980
gtcccatcaa ggttcagtgg cagtggatct gggacagatt tcactctcac cattagtagt    2040
ctgcaacctg aagattttgc aacttactac tgtcaacaga gttacagttt cccccctcact    2100 ttcggctgtg ggaccaagct ggagatcaaa                                    2130
```

<210> SEQ ID NO 61
<211> LENGTH: 710
<212> TYPE: PRT
<213> ORGANISM: artificial
<220> FEATURE:
<223> OTHER INFORMATION: synthetic construct

<400> SEQUENCE: 61

Glu Met Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Glu Gly Leu Glu Trp Val
        35                  40                  45

Ser Ala Ile Thr Ile Ser Gly Ile Thr Ala Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Gly Asp Thr Ala Val Tyr Tyr Cys
                85                  90                  95

Ala Lys Glu Glu Phe Leu Pro Gly Thr His Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly

```
              130                 135                 140
Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys Gly Gly Gly Ser Gly Gly Gly Gly Ser
    450                 455                 460

Glu Val Gln Leu Leu Glu Ser Gly Pro Gly Leu Val Lys Pro Ser Glu
465                 470                 475                 480

Thr Leu Ser Leu Thr Cys Asn Val Ala Gly Gly Ser Ile Ser Pro Tyr
                485                 490                 495

Tyr Trp Thr Trp Ile Arg Gln Pro Pro Gly Lys Cys Leu Glu Leu Ile
            500                 505                 510

Gly Tyr Ile His Ser Ser Gly Tyr Thr Asp Tyr Asn Pro Ser Leu Lys
        515                 520                 525

Ser Arg Val Thr Ile Ser Gly Asp Thr Ser Lys Lys Gln Phe Ser Leu
    530                 535                 540

His Val Ser Ser Val Thr Ala Ala Asp Thr Ala Val Tyr Phe Cys Ala
545                 550                 555                 560
```

-continued

```
Arg Ala Asp Trp Asp Leu Leu His Ala Leu Asp Ile Trp Gly Gln Gly
                565                 570                 575

Thr Leu Val Thr Val Ser Ser Gly Gly Gly Ser Gly Gly Gly
            580                 585                 590

Ser Gly Gly Gly Ser Gly Gly Gly Ser Glu Ile Val Leu Thr
        595                 600                 605

Gln Ser Pro Ser Ser Leu Ser Thr Ser Val Gly Asp Arg Val Thr Ile
    610                 615                 620

Thr Cys Arg Ala Ser Gln Ser Ile Arg Ser His Leu Asn Trp Tyr Gln
625                 630                 635                 640

Gln Lys Pro Gly Lys Ala Pro Lys Leu Leu Ile Tyr Gly Ala Ser Asn
                645                 650                 655

Leu Gln Ser Gly Val Pro Ser Arg Phe Ser Gly Ser Gly Ser Gly Thr
            660                 665                 670

Asp Phe Thr Leu Thr Ile Ser Ser Leu Gln Pro Glu Asp Phe Ala Thr
        675                 680                 685

Tyr Tyr Cys Gln Gln Ser Tyr Ser Phe Pro Leu Thr Phe Gly Cys Gly
    690                 695                 700

Thr Lys Leu Glu Ile Lys
705                 710

<210> SEQ ID NO 62
<211> LENGTH: 18
<212> TYPE: PRT
<213> ORGANISM: artificial
<220> FEATURE:
<223> OTHER INFORMATION: synthetic construct

<400> SEQUENCE: 62

Glu Pro Lys Ser Cys Asp Lys Thr Gly Gly Gly Ser Gly Gly Gly
1               5                   10                  15

Gly Ser

<210> SEQ ID NO 63
<211> LENGTH: 18
<212> TYPE: PRT
<213> ORGANISM: artificial
<220> FEATURE:
<223> OTHER INFORMATION: synthetic construct

<400> SEQUENCE: 63

Glu Pro Lys Ser Cys Gly Lys Thr Gly Gly Gly Ser Gly Gly Gly
1               5                   10                  15

Gly Ser

<210> SEQ ID NO 64
<211> LENGTH: 15
<212> TYPE: PRT
<213> ORGANISM: artificial
<220> FEATURE:
<223> OTHER INFORMATION: synthetic construct

<400> SEQUENCE: 64

Glu Pro Lys Ser Cys Gly Gly Gly Ser Gly Gly Gly Gly Ser
1               5                   10                  15

<210> SEQ ID NO 65
<211> LENGTH: 75
<212> TYPE: DNA
<213> ORGANISM: artificial
```

<220> FEATURE:
<223> OTHER INFORMATION: synthetic construct

<400> SEQUENCE: 65
ggtggcggtg gctctggtgg cggtggctct gagcccaaat ctgtagacaa aactcacaca    60
tgcccaccgt gccca                                                     75

<210> SEQ ID NO 66
<211> LENGTH: 25
<212> TYPE: PRT
<213> ORGANISM: artificial
<220> FEATURE:
<223> OTHER INFORMATION: synthetic construct

<400> SEQUENCE: 66

Gly Gly Gly Gly Ser Gly Gly Gly Gly Ser Glu Pro Lys Ser Val Asp
1               5                   10                  15

Lys Thr His Thr Cys Pro Pro Cys Pro
            20                  25

<210> SEQ ID NO 67
<211> LENGTH: 45
<212> TYPE: DNA
<213> ORGANISM: artificial
<220> FEATURE:
<223> OTHER INFORMATION: synthetic construct

<400> SEQUENCE: 67
ggaggcggag gatctggcgg aggcggatct tgcccaccgt gccca                    45

<210> SEQ ID NO 68
<211> LENGTH: 15
<212> TYPE: PRT
<213> ORGANISM: artificial
<220> FEATURE:
<223> OTHER INFORMATION: synthetic construct

<400> SEQUENCE: 68

Gly Gly Gly Gly Ser Gly Gly Gly Gly Ser Cys Pro Pro Cys Pro
1               5                   10                  15

<210> SEQ ID NO 69
<211> LENGTH: 60
<212> TYPE: DNA
<213> ORGANISM: artificial
<220> FEATURE:
<223> OTHER INFORMATION: synthetic construct

<400> SEQUENCE: 69
ggtggcggtg gctctggtgg cggtggctct gacaaaactc acacatgccc accgtgccca    60

<210> SEQ ID NO 70
<211> LENGTH: 20
<212> TYPE: PRT
<213> ORGANISM: artificial
<220> FEATURE:
<223> OTHER INFORMATION: synthetic construct

<400> SEQUENCE: 70

Gly Gly Gly Gly Ser Gly Gly Gly Gly Ser Asp Lys Thr His Thr Cys
1               5                   10                  15

Pro Pro Cys Pro
            20